US011591400B2

(12) United States Patent
Loo et al.

(10) Patent No.: US 11,591,400 B2
(45) Date of Patent: *Feb. 28, 2023

(54) B7-H3 DIRECTED ANTIBODY DRUG CONJUGATES

(71) Applicant: MacroGenics, Inc., Rockville, MD (US)

(72) Inventors: Deryk T. Loo, Belmont, CA (US); Ling Huang, Bethesda, MD (US); Leslie S. Johnson, Darnestown, MD (US); Thomas Son, San Francisco, CA (US); Juniper A. Scribner, Burlingame, CA (US); Ezio Bonvini, Potomac, MD (US)

(73) Assignee: MacroGenics, Inc., Rockville, MD (US)

( * ) Notice: Subject to any disclaimer, the term of this patent is extended or adjusted under 35 U.S.C. 154(b) by 150 days.

This patent is subject to a terminal disclaimer.

(21) Appl. No.: 17/124,972

(22) Filed: Dec. 17, 2020

(65) Prior Publication Data

US 2021/0171641 A1 Jun. 10, 2021

Related U.S. Application Data

(63) Continuation of application No. 16/092,740, filed as application No. PCT/US2017/027317 on Apr. 13, 2017, now Pat. No. 10,961,311.

(Continued)

(51) Int. Cl.
*C07K 16/28* (2006.01)
*A61K 47/68* (2017.01)
(Continued)

(52) U.S. Cl.
CPC ........ *C07K 16/2827* (2013.01); *A61K 39/395* (2013.01); *A61K 47/6803* (2017.08);
(Continued)

(58) Field of Classification Search
None
See application file for complete search history.

(56) References Cited

U.S. PATENT DOCUMENTS 3,842,067 A 10/1974 Sarantakis
3,862,925 A 1/1975 Sarantakis et al.
(Continued)

FOREIGN PATENT DOCUMENTS

CL 2018002895 A1 2/2019
CN 103458930 A 12/2013
(Continued)

OTHER PUBLICATIONS

US 6,331,391 B1, 12/2001, Wittrup et al. (withdrawn)
(Continued)

*Primary Examiner* — Karl J Puttlitz
(74) *Attorney, Agent, or Firm* — Medler, Ferro, Woodhouse & Mills PLLC

(57) ABSTRACT

The present invention is directed to novel B7-H3-binding molecules capable of binding to human and non-human B7-H3, and in particular to such molecules that are cross-reactive with B7-H3 of a non-human primate (e.g., a cynomolgus monkey). The invention additionally pertains to B7-H3-binding molecules that comprise Variable Light Chain and/or Variable Heavy Chain (VH) Domains that have been humanized and/or deimmunized so as to exhibit a reduced immunogenicity upon administration to recipient subjects. The invention particularly pertains to bispecific, trispecific or multispecific B7-H3-binding molecules, including bispecific diabodies, BiTEs, bispecific antibodies, trivalent binding molecules, etc. that comprise: (i) such B7-H3-binding Variable Domains and (ii) a domain capable of binding to an epitope of a molecule present on the surface of an effector cell. The invention is also directed to pharmaceutical compositions that contain any of such B7-H3-

(Continued)

binding molecules, and to methods involving the use of any of such B7-H3-binding molecules in the treatment of cancer and other diseases and conditions. The invention also particularly pertains to a molecule that comprises the human B7-H3 binding domain of a humanized anti-human B7-H3 antibody conjugated to at least one drug moiety (a "B7-H3-ADC"). The invention is also directed to pharmaceutical compositions that contain such B7-H3-ADCs, and to methods involving the use of any of such B7-H3-ADCs in the treatment of cancer and other diseases and conditions.

27 Claims, 39 Drawing Sheets

Specification includes a Sequence Listing.

Related U.S. Application Data

(60) Provisional application No. 62/323,228, filed on Apr. 15, 2016, provisional application No. 62/323,249, filed on Apr. 15, 2016, provisional application No. 62/432,314, filed on Dec. 9, 2016.

(51) Int. Cl.
  *A61K 39/395* (2006.01)
  *A61P 35/00* (2006.01)
  *A61K 39/00* (2006.01)

(52) U.S. Cl.
  CPC ...... *A61K 47/6811* (2017.08); *A61K 47/6851* (2017.08); *A61K 47/6879* (2017.08); *A61P 35/00* (2018.01); *A61K 2039/505* (2013.01); *C07K 2317/24* (2013.01); *C07K 2317/55* (2013.01); *C07K 2317/77* (2013.01)

(56) References Cited

U.S. PATENT DOCUMENTS

| | | |
|---|---|---|
| 3,896,111 A | 7/1975 | Kupchan et al. |
| 3,972,859 A | 8/1976 | Fujino et al. |
| 4,105,603 A | 8/1978 | Vale, Jr. et al. |
| 4,137,230 A | 1/1979 | Hashimoto et al. |
| 4,151,042 A | 4/1979 | Higashide et al. |
| 4,179,337 A | 12/1979 | Davis et al. |
| 4,248,870 A | 2/1981 | Miyashita et al. |
| 4,752,601 A | 6/1988 | Hahn |
| 4,816,567 A | 3/1989 | Cabilly et al. |
| 4,880,078 A | 11/1989 | Inoue et al. |
| 5,024,835 A | 6/1991 | Rao et al. |
| 5,116,964 A | 5/1992 | Capon et al. |
| 5,169,933 A | 12/1992 | Anderson et al. |
| 5,185,432 A | 2/1993 | Hellstrom et al. |
| 5,208,020 A | 5/1993 | Chari et al. |
| 5,225,539 A | 7/1993 | Winter |
| 5,290,540 A | 3/1994 | Prince et al. |
| 5,348,876 A | 9/1994 | Michaelsen et al. |
| 5,416,064 A | 5/1995 | Chari et al. |
| 5,547,667 A | 8/1996 | Angelucci et al. |
| 5,565,332 A | 10/1996 | Hoogenboom et al. |
| 5,576,184 A | 11/1996 | Better et al. |
| 5,580,717 A | 12/1996 | Dower et al. |
| 5,585,089 A | 12/1996 | Queen et al. |
| 5,624,821 A | 4/1997 | Winter et al. |
| 5,648,260 A | 7/1997 | Winter et al. |
| 5,656,444 A | 8/1997 | Webb et al. |
| 5,663,149 A | 9/1997 | Pettit et al. |
| 5,693,761 A | 12/1997 | Queen et al. |
| 5,693,762 A | 12/1997 | Queen et al. |
| 5,698,449 A | 12/1997 | Baumann et al. |
| 5,711,944 A | 1/1998 | Gilbert et al. |
| 5,712,374 A | 1/1998 | Kuntsmann et al. |
| 5,714,586 A | 2/1998 | Kunstmann et al. |
| 5,723,584 A | 3/1998 | Schatz |
| 5,731,168 A | 3/1998 | Carter et al. |
| 5,733,743 A | 3/1998 | Johnson et al. |
| 5,736,135 A | 4/1998 | Goeddel et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,807,706 A | 9/1998 | Carter et al. |
| 5,807,715 A | 9/1998 | Morrison et al. |
| 5,821,333 A | 10/1998 | Carter et al. |
| 5,837,243 A | 11/1998 | Deo et al. |
| 5,855,913 A | 1/1999 | Hanes et al. |
| 5,866,692 A | 2/1999 | Shitara et al. |
| 5,874,064 A | 2/1999 | Edwards et al. |
| 5,874,239 A | 2/1999 | Schatz |
| 5,877,296 A | 3/1999 | Hamann et al. |
| 5,877,396 A | 3/1999 | Ravetch et al. |
| 5,885,573 A | 3/1999 | Bluestone et al. |
| 5,888,533 A | 3/1999 | Dunn |
| 5,932,433 A | 8/1999 | Schatz |
| 5,934,272 A | 8/1999 | Lloyd et al. |
| 5,945,115 A | 8/1999 | Dunn et al. |
| 5,985,309 A | 11/1999 | Edwards et al. |
| 5,985,320 A | 11/1999 | Edwards et al. |
| 5,985,599 A | 11/1999 | Mckenzie et al. |
| 5,997,867 A | 12/1999 | Waldmann et al. |
| 6,019,968 A | 2/2000 | Platz et al. |
| 6,025,485 A | 2/2000 | Kamb et al. |
| 6,054,297 A | 4/2000 | Carter et al. |
| 6,054,561 A | 4/2000 | Ring |
| 6,114,147 A | 9/2000 | Frenken et al. |
| 6,132,764 A | 10/2000 | Li et al. |
| 6,132,992 A | 10/2000 | Ledbetter et al. |
| 6,165,745 A | 12/2000 | Ward et al. |
| 6,180,370 B1 | 1/2001 | Queen et al. |
| 6,180,377 B1 | 1/2001 | Morgan et al. |
| 6,194,551 B1 | 2/2001 | Idusogie et al. |
| 6,214,345 B1 | 4/2001 | Firestone et al. |
| 6,218,149 B1 | 4/2001 | Morrison et al. |
| 6,242,195 B1 | 6/2001 | Presta et al. |
| 6,265,150 B1 | 7/2001 | Terstappen et al. |
| 6,277,375 B1 | 8/2001 | Ward |
| 6,300,065 B1 | 10/2001 | Kieke et al. |
| 6,331,415 B1 | 12/2001 | Cabilly et al. |
| 6,339,069 B1 | 1/2002 | Meers et al. |
| 6,420,149 B1 | 7/2002 | Fukuda et al. |
| 6,423,538 B1 | 7/2002 | Wittrup et al. |
| 6,455,263 B2 | 9/2002 | Payan |
| 6,472,511 B1 | 10/2002 | Leung et al. |
| 6,492,123 B1 | 12/2002 | Holliger et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,623,940 B1 | 9/2003 | Ledbetter et al. |
| 6,696,550 B2 | 2/2004 | LaRosa et al. |
| 6,737,056 B1 | 5/2004 | Presta |
| 6,821,505 B2 | 11/2004 | Ward |
| 6,884,869 B2 | 4/2005 | Senter et al. |
| 6,891,030 B2 | 5/2005 | Chen |
| 6,965,018 B2 | 11/2005 | Mikesell et al. |
| 6,982,321 B2 | 1/2006 | Winter |
| 7,083,784 B2 | 8/2006 | Dall'Acqua et al. |
| 7,122,637 B2 | 10/2006 | Presta |
| 7,183,387 B1 | 2/2007 | Presta |
| 7,217,797 B2 | 5/2007 | Hinton et al. |
| 7,261,890 B2 | 8/2007 | Krah et al. |
| 7,276,586 B2 | 10/2007 | Goddard et al. |
| 7,279,567 B2 | 10/2007 | Mikesell et al. |
| 7,315,786 B2 | 1/2008 | Dahiyat et al. |
| 7,317,091 B2 | 1/2008 | Lazar et al. |
| 7,332,581 B2 | 2/2008 | Presta |
| 7,335,742 B2 | 2/2008 | Presta |
| 7,351,803 B2 | 4/2008 | Johnson et al. |
| 7,355,008 B2 | 4/2008 | Stavenhagen et al. |
| 7,358,354 B2 | 4/2008 | Mikesell et al. |
| 7,368,554 B2 | 5/2008 | Mikesell et al. |

(56) References Cited

U.S. PATENT DOCUMENTS

| | | |
|---|---|---|
| 7,371,826 B2 | 5/2008 | Presta |
| 7,416,727 B2 | 8/2008 | Presta |
| 7,425,619 B2 | 9/2008 | Koenig et al. |
| 7,425,620 B2 | 9/2008 | Koenig et al. |
| 7,429,652 B2 | 9/2008 | Wang et al. |
| 7,521,542 B2 | 4/2009 | Johnson et al. |
| 7,527,969 B2 | 5/2009 | Mather et al. |
| 7,585,491 B2 | 9/2009 | Govindan |
| 7,618,628 B2 | 11/2009 | Johnson et al. |
| 7,632,497 B2 | 12/2009 | Stavenhagen |
| 7,642,228 B2 | 1/2010 | Carter et al. |
| 7,655,229 B2 | 2/2010 | Chan et al. |
| 7,662,926 B2 | 2/2010 | Chan et al. |
| 7,695,936 B2 | 4/2010 | Carter et al. |
| 7,700,100 B2 | 4/2010 | Johnson et al. |
| 7,718,774 B2 | 5/2010 | Mather et al. |
| 7,754,681 B2 | 7/2010 | Feng |
| 7,776,814 B2 | 8/2010 | Doemling et al. |
| 7,786,270 B2 | 8/2010 | Johnson et al. |
| 7,838,635 B2 | 11/2010 | Johnson et al. |
| 7,960,512 B2 | 6/2011 | Stavenhagen et al. |
| 7,964,566 B2 | 6/2011 | Doronina et al. |
| 8,003,774 B2 | 8/2011 | Stavenhagen et al. |
| 8,039,592 B2 | 10/2011 | Lazar et al. |
| 8,044,180 B2 | 10/2011 | Koenig et al. |
| 8,080,250 B1 | 12/2011 | Govindan et al. |
| 8,088,376 B2 | 1/2012 | Chamberlain et al. |
| 8,124,731 B2 | 2/2012 | Lazar et al. |
| 8,133,982 B2 | 3/2012 | Johnson et al. |
| 8,137,668 B2 | 3/2012 | Li |
| 8,183,357 B2 | 5/2012 | Mather et al. |
| 8,187,593 B2 | 5/2012 | Koenig et al. |
| 8,187,594 B2 | 5/2012 | Mather et al. |
| 8,188,231 B2 | 5/2012 | Lazar et al. |
| 8,192,737 B2 | 6/2012 | Stavenhagen et al. |
| 8,193,318 B2 | 6/2012 | Koenig et al. |
| 8,216,570 B2 | 7/2012 | Mather et al. |
| 8,216,574 B2 | 7/2012 | Stavenhagen et al. |
| 8,216,578 B2 | 7/2012 | Mather et al. |
| 8,216,579 B2 | 7/2012 | Johnson et al. |
| 8,216,800 B2 | 7/2012 | Fabrega et al. |
| 8,217,147 B2 | 7/2012 | Stavenhagen et al. |
| 8,461,117 B2 | 6/2013 | Sufi et al. |
| 8,779,098 B2 | 7/2014 | Mather et al. |
| 8,802,091 B2 | 8/2014 | Johnson et al. |
| 9,150,656 B2 | 10/2015 | Johnson et al. |
| 10,683,364 B2 | 6/2020 | Johnson et al. |
| 10,961,311 B2 | 3/2021 | Loo et al. |
| 2001/0036459 A1 | 11/2001 | Ravetch |
| 2002/0028486 A1 | 3/2002 | Morrison et al. |
| 2002/0127227 A1 | 9/2002 | Holmes et al. |
| 2002/0147311 A1 | 10/2002 | Gillies et al. |
| 2002/0168762 A1 | 11/2002 | Chen |
| 2003/0077282 A1 | 4/2003 | Bigler et al. |
| 2003/0103963 A1 | 6/2003 | Cheung |
| 2003/0103976 A1 | 6/2003 | Serizawa et al. |
| 2003/0115614 A1 | 6/2003 | Kanda et al. |
| 2003/0158389 A1 | 8/2003 | Idusogie et al. |
| 2003/0185827 A1 | 10/2003 | Rodriguez et al. |
| 2003/0190319 A1 | 10/2003 | Adolf et al. |
| 2003/0207346 A1 | 11/2003 | Arathoon et al. |
| 2004/0002587 A1 | 1/2004 | Watkins et al. |
| 2004/0038339 A1 | 2/2004 | Kufer et al. |
| 2004/0058400 A1 | 3/2004 | Holliger et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0191244 A1 | 9/2004 | Presta |
| 2004/0220388 A1 | 11/2004 | Mertens et al. |
| 2004/0235065 A1 | 11/2004 | Hansen et al. |
| 2004/0236078 A1 | 11/2004 | Carter et al. |
| 2005/0025764 A1 | 2/2005 | Watkins et al. |
| 2005/0037000 A1 | 2/2005 | Stavenhagen et al. |
| 2005/0054832 A1 | 3/2005 | Lazar et al. |
| 2005/0064514 A1 | 3/2005 | Stavenhagen et al. |
| 2005/0079170 A1 | 4/2005 | Le Gall et al. |
| 2005/0090648 A1 | 4/2005 | Tsurushita et al. |
| 2005/0202536 A1 | 9/2005 | Chen |
| 2005/0215767 A1 | 9/2005 | Koenig et al. |
| 2005/0260213 A1 | 11/2005 | Koenig et al. |
| 2006/0013810 A1 | 1/2006 | Johnson et al. |
| 2006/0018899 A1 | 1/2006 | Kao et al. |
| 2006/0024298 A1 | 2/2006 | Lazar et al. |
| 2006/0073142 A1 | 4/2006 | Chan et al. |
| 2006/0134709 A1 | 6/2006 | Stavenhagen et al. |
| 2006/0154313 A1 | 7/2006 | Anderson et al. |
| 2006/0177439 A1 | 8/2006 | Koenig et al. |
| 2006/0193849 A1 | 8/2006 | Krauss et al. |
| 2007/0004909 A1 | 1/2007 | Johnson et al. |
| 2007/0031436 A1 | 2/2007 | Little et al. |
| 2007/0036799 A1 | 2/2007 | Stavenhagen et al. |
| 2007/0077246 A1 | 4/2007 | Koenig et al. |
| 2007/0135338 A1 | 6/2007 | O'Neil et al. |
| 2007/0140966 A1 | 6/2007 | Chang et al. |
| 2007/0148164 A1 | 6/2007 | Farrington et al. |
| 2007/0244303 A1 | 10/2007 | Johnson et al. |
| 2007/0253948 A1 | 11/2007 | Chan et al. |
| 2008/0044417 A1 | 2/2008 | Johnson et al. |
| 2008/0044429 A1 | 2/2008 | Johnson et al. |
| 2008/0050371 A1 | 2/2008 | Johnson et al. |
| 2008/0051563 A1 | 2/2008 | Lazar et al. |
| 2008/0081346 A1 | 4/2008 | Moretta et al. |
| 2008/0085277 A1 | 4/2008 | Cho et al. |
| 2008/0095766 A1 | 4/2008 | Koenig et al. |
| 2008/0112961 A1 | 5/2008 | Stavenhagen et al. |
| 2008/0116219 A1 | 5/2008 | Lawrence |
| 2008/0131435 A1 | 6/2008 | Stavenhagen et al. |
| 2008/0138344 A1 | 6/2008 | Stavenhagen et al. |
| 2008/0138349 A1 | 6/2008 | Stavenhagen et al. |
| 2008/0177045 A1 | 7/2008 | Lee et al. |
| 2008/0286819 A1 | 11/2008 | Ravetch et al. |
| 2009/0017023 A1 | 1/2009 | Koenig et al. |
| 2009/0017026 A1 | 1/2009 | Koenig et al. |
| 2009/0017027 A1 | 1/2009 | Koenig et al. |
| 2009/0018315 A1 | 1/2009 | Chen |
| 2009/0022747 A1 | 1/2009 | Chen |
| 2009/0053218 A1 | 2/2009 | Koenig et al. |
| 2009/0060910 A1 | 3/2009 | Johnson et al. |
| 2009/0074771 A1 | 3/2009 | Koenig et al. |
| 2009/0076251 A1 | 3/2009 | Koenig et al. |
| 2009/0087416 A1 | 4/2009 | Chen |
| 2009/0092610 A1 | 4/2009 | Koenig et al. |
| 2009/0098124 A1 | 4/2009 | Stavenhagen |
| 2009/0191195 A1 | 7/2009 | Tuaillon et al. |
| 2009/0202537 A1 | 8/2009 | Johnson et al. |
| 2009/0252732 A1 | 10/2009 | Siadak et al. |
| 2009/0262732 A1 | 10/2009 | Wood |
| 2010/0015142 A1 | 1/2010 | Koenig |
| 2010/0086969 A1 | 4/2010 | Mather et al. |
| 2010/0099853 A1 | 4/2010 | Little et al. |
| 2010/0174053 A1 | 7/2010 | Johnson et al. |
| 2010/0183605 A1 | 7/2010 | Mather et al. |
| 2010/0196362 A1 | 8/2010 | Stavenhagen et al. |
| 2010/0196372 A1 | 8/2010 | Johnson et al. |
| 2010/0322851 A1 | 12/2010 | Liang et al. |
| 2010/0322924 A1 | 12/2010 | Johnson et al. |
| 2011/0020667 A1 | 1/2011 | Deeman et al. |
| 2011/0045006 A1 | 2/2011 | Mather et al. |
| 2011/0081347 A1 | 4/2011 | Gorlatov |
| 2011/0097323 A1 | 4/2011 | Johnson et al. |
| 2011/0117089 A1 | 5/2011 | Johnson et al. |
| 2011/0152504 A1 | 6/2011 | Johnson et al. |
| 2011/0243941 A1 | 10/2011 | Stavenhagen et al. |
| 2011/0305714 A1 | 12/2011 | Stavenhagen et al. |
| 2012/0009186 A1 | 1/2012 | Koenig et al. |
| 2012/0034221 A1 | 2/2012 | Bonvini et al. |
| 2012/0141476 A1 | 6/2012 | Johnson et al. |
| 2012/0294796 A1 | 11/2012 | Johnson et al. |
| 2013/0078234 A1 | 3/2013 | Takahashi et al. |
| 2013/0149236 A1 | 6/2013 | Johnson et al. |
| 2013/0189263 A1 | 7/2013 | Little et al. |
| 2013/0295121 A1 | 11/2013 | Johnson et al. |
| 2014/0099318 A1 | 4/2014 | Huang et al. |
| 2014/0255407 A1 | 9/2014 | Koenig |

(56) References Cited

U.S. PATENT DOCUMENTS

| | | |
|---|---|---|
| 2014/0322129 A1 | 10/2014 | Leong et al. |
| 2014/0328750 A1 | 11/2014 | Johnson et al. |
| 2015/0175697 A1 | 6/2015 | Bonvini et al. |
| 2015/0259434 A1 | 9/2015 | Johnson et al. |
| 2015/0274838 A1 | 10/2015 | Johnson et al. |
| 2015/0297748 A1 | 10/2015 | Masuda et al. |
| 2015/0314017 A1 | 11/2015 | Zhao |
| 2015/0352224 A1 | 12/2015 | Naito et al. |
| 2019/0012747 A1 | 1/2019 | Antonelli et al. |
| 2019/0127471 A1 | 5/2019 | Loo et al. |

FOREIGN PATENT DOCUMENTS

| | | |
|---|---|---|
| CO | 6630123 A2 | 3/2013 |
| CO | 6811812 A2 | 12/2013 |
| CO | 7471165 A2 | 12/2015 |
| EP | 0 332 865 A2 | 9/1989 |
| EP | 0 403 156 A1 | 12/1990 |
| EP | 0 519 596 A1 | 12/1992 |
| EP | 0 629 703 A2 | 12/1994 |
| EP | 0 425 235 B1 | 9/1996 |
| EP | 0 327 378 B1 | 12/1996 |
| EP | 0 359 096 B1 | 11/1997 |
| EP | 0 953 639 A1 | 11/1999 |
| EP | 1 006 183 A1 | 6/2000 |
| EP | 0 343 950 B1 | 10/2000 |
| EP | 1 293 514 A1 | 3/2003 |
| EP | 1 327 638 A1 | 7/2003 |
| EP | 1 354 600 A1 | 10/2003 |
| EP | 1 514 933 A1 | 3/2005 |
| EP | 1 078 004 B1 | 10/2007 |
| EP | 1 868 650 A2 | 12/2007 |
| EP | 1 292 619 B1 | 2/2008 |
| EP | 1 892 251 A2 | 2/2008 |
| EP | 2 158 221 A2 | 3/2010 |
| EP | 2 361 936 A1 | 8/2011 |
| EP | 2 371 866 A2 | 10/2011 |
| EP | 2 376 109 A1 | 10/2011 |
| EP | 2 601 216 A1 | 6/2013 |
| EP | 2 714 079 A2 | 4/2014 |
| EP | 2 907 824 A1 | 8/2015 |
| FR | 2 894 982 A1 | 6/2007 |
| JP | 2015-524387 A | 8/2015 |
| WO | 88/07089 A1 | 9/1988 |
| WO | 89/07142 A1 | 8/1989 |
| WO | 91/03493 A1 | 3/1991 |
| WO | 92/16562 A1 | 10/1992 |
| WO | 92/19244 A2 | 11/1992 |
| WO | 92/22583 A2 | 12/1992 |
| WO | 93/22332 A2 | 11/1993 |
| WO | 94/18330 A1 | 8/1994 |
| WO | 94/29351 A2 | 12/1994 |
| WO | 95/05468 A1 | 2/1995 |
| WO | 96/40878 A1 | 12/1996 |
| WO | 97/28267 A1 | 8/1997 |
| WO | 97/32572 A2 | 9/1997 |
| WO | 97/34631 A1 | 9/1997 |
| WO | 97/44013 A1 | 11/1997 |
| WO | 97/44362 A1 | 11/1997 |
| WO | 98/02463 A1 | 1/1998 |
| WO | 98/05787 A1 | 2/1998 |
| WO | 98/23289 A1 | 6/1998 |
| WO | 98/31346 A1 | 7/1998 |
| WO | 98/52975 A1 | 11/1998 |
| WO | 99/19362 A1 | 4/1999 |
| WO | 99/41285 A1 | 8/1999 |
| WO | 99/43713 A1 | 9/1999 |
| WO | 99/46281 A2 | 9/1999 |
| WO | 99/51642 A1 | 10/1999 |
| WO | 99/57150 A2 | 11/1999 |
| WO | 99/58572 A1 | 11/1999 |
| WO | 99/66903 A2 | 12/1999 |
| WO | 00/09560 A2 | 2/2000 |
| WO | 00/12507 A2 | 3/2000 |
| WO | 00/42072 A2 | 7/2000 |
| WO | 00/47625 A2 | 8/2000 |
| WO | 00/68266 A1 | 11/2000 |
| WO | 01/18021 A1 | 3/2001 |
| WO | 01/18204 A1 | 3/2001 |
| WO | 01/43869 A2 | 6/2001 |
| WO | 01/79299 A1 | 10/2001 |
| WO | 01/94413 A2 | 12/2001 |
| WO | 02/02781 A1 | 1/2002 |
| WO | 02/10187 A1 | 2/2002 |
| WO | 02/32375 A2 | 4/2002 |
| WO | 02/060919 A2 | 8/2002 |
| WO | 02/083180 A1 | 10/2002 |
| WO | 02/086070 A2 | 10/2002 |
| WO | 02/088172 A2 | 11/2002 |
| WO | 03/012069 A2 | 2/2003 |
| WO | 03/025018 A2 | 3/2003 |
| WO | 03/035835 A2 | 5/2003 |
| WO | 03/066095 A2 | 8/2003 |
| WO | 03/074679 A2 | 9/2003 |
| WO | 03/094859 A2 | 11/2003 |
| WO | 03/101485 A1 | 12/2003 |
| WO | 2004/001381 A2 | 12/2003 |
| WO | 2004/016750 A2 | 2/2004 |
| WO | 2004/029207 A2 | 4/2004 |
| WO | 2004/063351 A2 | 7/2004 |
| WO | 2004/065423 A2 | 8/2004 |
| WO | 2004/074455 A2 | 9/2004 |
| WO | 2004/080979 A1 | 9/2004 |
| WO | 2004/093894 A2 | 11/2004 |
| WO | 2004/099249 A2 | 11/2004 |
| WO | 2005/018669 A1 | 3/2005 |
| WO | 2005/040170 A2 | 5/2005 |
| WO | 2005/061547 A2 | 7/2005 |
| WO | 2005/070963 A1 | 8/2005 |
| WO | 2005/070966 A2 | 8/2005 |
| WO | 2005/085251 A1 | 9/2005 |
| WO | 2005/110423 A2 | 11/2005 |
| WO | 2005/110474 A2 | 11/2005 |
| WO | 2005/115452 A2 | 12/2005 |
| WO | 2005/118635 A2 | 12/2005 |
| WO | 2005/121179 A2 | 12/2005 |
| WO | 2006/016276 A2 | 2/2006 |
| WO | 2006/020114 A2 | 2/2006 |
| WO | 2006/028956 A2 | 3/2006 |
| WO | 2006/053301 A2 | 5/2006 |
| WO | 2006/066078 A2 | 6/2006 |
| WO | 2006/076584 A2 | 7/2006 |
| WO | 2006/083852 A2 | 8/2006 |
| WO | 2006/084075 A2 | 8/2006 |
| WO | 2006/084092 A2 | 8/2006 |
| WO | 2006/084226 A2 | 8/2006 |
| WO | 2006/088494 A2 | 8/2006 |
| WO | 2006/107617 A2 | 10/2006 |
| WO | 2006/107786 A2 | 10/2006 |
| WO | 2006/110593 A2 | 10/2006 |
| WO | 2006/113665 A2 | 10/2006 |
| WO | 2006/125668 A2 | 11/2006 |
| WO | 2007/009064 A2 | 1/2007 |
| WO | 2007/009065 A2 | 1/2007 |
| WO | 2007/021841 A2 | 2/2007 |
| WO | 2007/024249 A2 | 3/2007 |
| WO | 2007/024715 A2 | 3/2007 |
| WO | 2007/039752 A1 | 4/2007 |
| WO | 2007/046893 A2 | 4/2007 |
| WO | 2007/075270 A2 | 7/2007 |
| WO | 2007/080277 A1 | 7/2007 |
| WO | 2007/106707 A2 | 9/2007 |
| WO | 2007/110205 A2 | 10/2007 |
| WO | 2007/117600 A2 | 10/2007 |
| WO | 2007/146968 A2 | 12/2007 |
| WO | 2007/147090 A2 | 12/2007 |
| WO | 2008/002933 A2 | 1/2008 |
| WO | 2008/003103 A2 | 1/2008 |
| WO | 2008/003116 A2 | 1/2008 |
| WO | 2008/009545 A1 | 1/2008 |
| WO | 2008/019199 A2 | 2/2008 |
| WO | 2008/024188 A2 | 2/2008 |
| WO | 2008/027236 A2 | 3/2008 |
| WO | 2008/066691 A2 | 6/2008 |

(56) References Cited

FOREIGN PATENT DOCUMENTS

| | | |
|---|---|---|
| WO | 2008/070593 A2 | 6/2008 |
| WO | 2008/091908 A2 | 7/2008 |
| WO | 2008/105886 A2 | 9/2008 |
| WO | 2008/116219 A2 | 9/2008 |
| WO | 2008/119566 A2 | 10/2008 |
| WO | 2008/140603 A2 | 11/2008 |
| WO | 2008/157379 A2 | 12/2008 |
| WO | 2009/018386 A1 | 2/2009 |
| WO | 2009/021754 A2 | 2/2009 |
| WO | 2009/058492 A2 | 5/2009 |
| WO | 2009/073533 A2 | 6/2009 |
| WO | 2009/083009 A2 | 7/2009 |
| WO | 2009/123894 A2 | 10/2009 |
| WO | 2009/132876 A1 | 11/2009 |
| WO | 2009/151717 A2 | 12/2009 |
| WO | 2010/027797 A1 | 3/2010 |
| WO | 2010/028795 A1 | 3/2010 |
| WO | 2010/028796 A1 | 3/2010 |
| WO | 2010/028797 A1 | 3/2010 |
| WO | 2010/033279 A2 | 3/2010 |
| WO | 2010/062171 A2 | 6/2010 |
| WO | 2010/080538 A1 | 7/2010 |
| WO | 2010/108127 A1 | 9/2010 |
| WO | 2010/136172 A1 | 12/2010 |
| WO | 2011/044368 A1 | 4/2011 |
| WO | 2011/086091 A1 | 7/2011 |
| WO | 2011/109400 A2 | 9/2011 |
| WO | 2011/133039 A2 | 10/2011 |
| WO | 2011/133886 A2 | 10/2011 |
| WO | 2011/143545 A1 | 11/2011 |
| WO | 2012/009544 A2 | 1/2012 |
| WO | 2012/018687 A1 | 2/2012 |
| WO | 2012/019123 A1 | 2/2012 |
| WO | 2012/058768 A1 | 5/2012 |
| WO | 2012/156430 A1 | 11/2012 |
| WO | 2012/162068 A2 | 11/2012 |
| WO | 2012/162583 A1 | 11/2012 |
| WO | 2013/003652 A1 | 1/2013 |
| WO | 2013/006544 A1 | 1/2013 |
| WO | 2013/006867 A1 | 1/2013 |
| WO | 2013/013700 A1 | 1/2013 |
| WO | 2013/070565 A1 | 5/2013 |
| WO | 2013/119903 A1 | 8/2013 |
| WO | 2013/163427 A1 | 10/2013 |
| WO | 2013/174873 A1 | 11/2013 |
| WO | 2014/006217 A1 | 1/2014 |
| WO | 2014/022540 A1 | 2/2014 |
| WO | 2014/057119 A1 | 4/2014 |
| WO | 2014/057687 A1 | 4/2014 |
| WO | 2014/061277 A1 | 4/2014 |
| WO | 2015/026894 A2 | 2/2015 |
| WO | 2015/031698 A1 | 3/2015 |
| WO | 2015/104359 A2 | 7/2015 |
| WO | 2015/104385 A2 | 7/2015 |
| WO | 2015/123241 A1 | 8/2015 |
| WO | 2015/151078 A2 | 10/2015 |
| WO | 2015/151081 A2 | 10/2015 |
| WO | 2015/157594 A1 | 10/2015 |
| WO | 2015/184203 A1 | 12/2015 |
| WO | 2015/184207 A1 | 12/2015 |
| WO | 2015/185142 A1 | 12/2015 |
| WO | 2016/037119 A1 | 3/2016 |
| WO | 2016/044383 A1 | 3/2016 |
| WO | 2017/062615 A2 | 4/2017 |
| WO | 2017/062619 A2 | 4/2017 |
| WO | 2017/180813 A1 | 10/2017 |
| WO | 2018/156740 A1 | 8/2018 |

OTHER PUBLICATIONS

Yang, et al. "Development of Antibody-Drug Conjugates as Targeted Cancer Therapeutics", International Journal of Pharmaceutical Research, Feb. 28, 2014, 41(1):45-50 (Abstract only).

Clinical Trials (8H9), National Institutes of Health, "Radiolabeled Monoclonal Antibody Therapy in Treating Patients with Refractory, Recurrent, or Advanced CNS or Leptomeningeal Cancer," 3 pages.

Clinical Trials (MGA271), National Institutes of Health, "Safety Study of MGA271 in Refractory Center," 4 pages.

Clinical Trials (MGD009), National Institutes of Health, "Safety Study of MGD009 in B7-H3-expressing Tumors," 4 pages.

International Preliminary Report on Patentability dated Oct. 16, 2018 for International Application No. PCT/US2017/027317, filed on Apr. 13, 2017 and published as WO 2017/180813 on Oct. 19, 2017, 8 pages.

International Search Report and Written Opinion dated Sep. 15, 2017 for International Application No. PCT/US2017/027317, filed on Apr. 13, 2017 and published as WO 2017/180813 on Oct. 19, 2017, 13 pages.

Office Action dated Aug. 27, 2020 in U.S. Appl. No. 16/092,740, filed Oct. 10, 2018 and published as US-2019-0127471-A1 on May 2, 2019, 15 pages.

Office Action dated Nov. 12, 2020 in U.S. Appl. No. 16/092,740, filed Oct. 10, 2018 and published as US-2019-0127471-A1 on May 2, 2019, 7 pages.

Office Action Received dated Mar. 9, 2020 in U.S. Appl. No. 16/092,740, filed Oct. 10, 2018 and published as US-2019-0127471-A1 on May 2, 2019, 24 pages.

Abra et al., "The Next Generation of Liposome Delivery Systems: Recent Experience with Tumor-Targeted, Sterically-Stabilized Immunoliposomes And Active-Loading Gradients", J Liposome Res., 2002, 12(1-2):1-3.

Abrams et al., "CTLA4Ig-Mediated Blockade of T-Cell Costimulation In Patients with Psoriasis Vulgaris", J. Clin Invest., 1999, 103(9):1243-1252.

Agarwal et al., "The Role of Positive Costimulatory Molecules in Transplantation and Tolerance", Curr. Opin. Organ Transplant., 2008, 13:366-372.

Ahmed et al., "Humanized Affinity-Matured Monoclonal Antibody 8H9 Has Potent Anti-Tumor Activity and Binds to FG Loop of B7-H3", J. Biol. Chem., 2015, 290: 30018-30029.

Al Hussaini et al., "Targeting CD123 In AML Using A T-Cell Directed Dual-Affinity Re-Targeting (DART®) Platform", Blood, Nov. 2015, 127(1):122-131.

Alegre et al., "A Non-Activating "Humanized" Anti-CD3 Monoclonal Antibody Retains Immunosuppressive Properties In Vivo", Transplantation, 1994, 57:1537-1543.

Alison et al., "Stem Cells and Lung Cancer: Future Therapeutic Targets?", Expert Opin. Biol. Ther., 2009, 9(9):1127-1141.

Almagro et al., "Humanization of Antibodies", Frontiers in Bioscience, Jan. 1, 2008, 13:1619-1633.

Alt et al., "Novel Tetravalent and Bispecific IgG-Like Antibody Molecules Combining Single-Chain Diabodies With the Immunoglobulin γ1 Fc or CH3 Region", FEBS Letters, 1999, 454(1-2):90-94.

Altman et al., "Phenotypic Analysis of Antigen-Specific T Lymphocytes", Science, 1996, 274:94-96.

Amit et al., "Three-Dimensional Structure of An Antigen-Antibody Complex At 2.8 A Resolution", Science, 1986, 233:747-753.

Angal et al., "A Single Amino Acid Substitution Abolishes the Heterogeneity of Chimeric Mouse/Human (Igg4) Antibody", Mol. Immunol., 1993, 30:105-108.

Anonymous, "New Products for Molecular Biotechnology", Molec. Biol., 2000, 16:293-294.

Armour et al., "Differential Binding to Human FcgammaRIIa And FcgammaRIIB Receptors by Human IgG Wildtype and Mutant Antibodies", Mol. Immunol., 2003, 40:585-593.

Armour et al., "Recombinant Human IgG Molecules Lacking Fcγ Receptor I Binding and Monocyte Triggering Activities", European Journal of Immunology, 1999, 29:2613-2624.

Armour et al., "The Contrasting IgG-Binding Interactions of Human and Herpes Simplex Virus Fc Receptors", Biochemical Society Transactions, 2002, 30:495-500.

Armstrong et al., "Conformational Changes and Flexibility in T-Cell Receptor Recognition of Peptide-MHC Complexes", Biochemical Journal, Oct. 15, 2008, 415(2):183-196.

(56) References Cited

OTHER PUBLICATIONS

Armstrong et al., "Heterogeneity of IgG1 Monoclonal Anti-Rh(D): An Investigation Using ADCC And Macrophage Binding Assays", Br. J. Haematol., 1987, 66:257-262.
Aruffo et al., "Molecular Cloning of A CD28 cDNA By A High-Efficiency COS Cell Expression System", Proc. Natl. Acad. Sci. (U.S.A.), 1987, 84:8573-8577.
Asano et al., "A Diabody for Cancer Immunotherapy and its Functional Enhancement by Fusion of Human Fc Domain", Abstract 3P-683, Journal of Biochemistry, 2004, 76(8):992.
Asano et al., "Construction and Humanization of a Functional Bispecific EGFR CD16 Diabody Using A Refolding System", FEBS Journal, 2012, 279:223-233.
Atwell et al., "Stable Heterodimers from Remodeling the Domain Interface of a Homodimer Using a Phage Display Library", Journal of Molecular Biology, 1997, 270:26-35.
Bachanova et al., "NK Cells in Therapy of Cancer", Critical Reviews in Oncogenesis, 2014, 19(1-2):133-141.
Bachmann et al., "Recall Proliferation of Memory CD8+ T Cells and Antiviral Protection", J. Immunol., 2008, 175:4677-4685.
Baeuerle et al., "Bispecific T-Cell Engaging Antibodies for Cancer Therapy", Cancer Research, 2009, 69(12):4941-4944.
Baeuerle et al., "BiTE: A New Class of Antibodies That Recruit T Cells", Drugs of the Future, 2008, 33:137-147.
Baggiolini et al., "Cellular Models for The Detection and Evaluation of Drugs That Modulate Human Phagocyte Activity", Experientia., Oct. 15, 1988;44(10):841-848.
Bargou et al., "Tumor Regression in Cancer Patients by Very Low Doses of a T Cell-Engaging Antibody", Science, 2008, 321:974-977.
Bauer et al., "Activation of NK Cells and T Cells by NKG2D, a Receptor for Stress-Inducible MICA", Science, Jul. 1999, 285(5428):727-729.
Bedzyk et al., "Comparison of Variable Region Primary Structures Within an Anti-Fluorescein Idiotype Family", Journal of Biological Chemistry, 1989, 264(3):1565-1569.
Behrens et al., "Methods for Site-Specific Drug Conjugation to Antibodies", mAbs, 2014, 6(1):46-53.
Beier et al., "Master Switches of T-Cell Activation and Differentiation", European Respiratory Journal, Apr. 2007, 29(4):804-812.
Bendas Gerd, "Immunoliposomes: A Promising Approach to Targeting Cancer Therapy", BioDrugs., 2001, 15(4):215-224.
Bendig MaryM., "Humanization of Rodent Monoclonal Antibodies", Methods: A Companion to Methods in Enzymology, 1995, 8:83-93.
Bernard et al., "A Unique Epitope on The CD2 Molecule Defined by The Monoclonal Antibody 9-1: Epitope-Specific Modulation of the E-Rosette Receptor and Effects On T-Cell Functions", Hum. Immunol., 1986, 17(4):388-405.
Bernard et al., "T and B Cell Cooperation: A Dance of Life and Death", Transplantation, 2005, 79: S8-S11.
Berntzen et al., "Identification of a High Affinity FcRIIA-binding Peptide That Distinguishes FcRIIA from FcRIIB and Exploits FcgammaRIIA-mediated Phagocytosis and Degradation", J. Biol. Chem., 2009, 284(2):1126-1135.
Bertram et al., "Role of T cell Costimulation in anti-viral immunity", Semin. Immunol., 2004, 16:185-198.
Bewarder et al., "In Vivo And In Vitro Specificity of Protein Tyrosine Kinases for Immunoglobulin G Receptor (FcgammaRII) Phosphorylation", Mol. Cell. Biol., 1996, 16(9):4735-43.
Billadeau et al., "ITAMs Versus ITIMs: Striking A Balance During Cell Regulation", J. Clin. Invest., 2002, 109(2):161-168.
Bird et al., "Single-Chain Antigen-Binding Proteins", Science, 1988, 242:423-426.
Blazar et al., "Opposing Roles of CD28:B7 and CTLA-4: B7 Pathways in Regulating In Vivo Alloresponses In Murine Recipients of MHC Disparate T Cells", J. Immunol, 1999, 162(11):6368-6377.
Boder et al., "Directed Evolution of Antibody Fragments with Monovalent Femtomolar Antigen-Binding Affinity", Proc. Natl. Acad. Sci. U.S.A., 2000, 97:10701-10705.
Boder et al., "Optimal Screening of Surface-Displayed Polypeptide Libraries", Biotechnology. Prog., 1998, 14:55-62.
Boder et al., "Yeast Surface Display for Directed Evolution of Protein Expression, Affinity, And Stability", Methods in Enzymology, 2000, 328:430-444.
Boder et al., "Yeast Surface Display for Screening Combinatorial Polypeptide Libraries", Nature Biotechnology, 1997, 15:553-557.
Boger et al., "CC-1065 And the Duocarmycins: Unraveling the Keys to A New Class of Naturally Derived DNA Alkylating Agents", Proc. Natl. Acad. Sci. (U.S.A.), 1995, 92(9):3642-3649.
Boger et al., "DNA alkylation properties of enhanced functional analogs of CC-1065 incorporating the 1,2,9,9a-tetrahydrocyclopropa[1,2-c]benz[1,2-e]indol-4-one (CBI) alkylation subunit", J. Am. Chem. Soc., 1992, 114:5487-5496.
Boger et al., "Duocarmycins—A New Class of Sequence Selective DNA Minor Groove Alkylating Agents", Chemtracts: Organic Chemistry, 1991, 4 (5): 329-349.
Boger et al., "Total synthesis and evaluation of (.+-.)-N-(tert-butoxy carbonyl)-CBI, (.+-.)-CBI-CDPI1, and (+-.)-CBI-CDPI2: CC-1065 functional agents incorporating the equivalent 1,2,9,9a-tetrahydrocyclopropa[1,2-c]benz[1,2-e]indol-4-one (CBI) left-hand subunit", J. Am. Chem. Soc., 1989, 111:6461-6463.
Boland et al., "Tumor B7-H1 and B7-H3 Expression in Squamous Cell Carcinoma of the Lung", Clinical Lung Cancer, Mar. 213, pp. 157-163.
Bolland et al., "Genetic Modifiers of Systemic Lupus Erythematosus in Fc.gamma.RIIB(-/-) Mice", J. Exp. Med., 2002, 195(9):1167-1174.
Bolland et al., "Inhibitory pathways triggered by ITIM-containing receptors", Adv. Immunol., 1999, 72:149-177.
Boorjian et al., "T-Cell Co-Regulatory Molecule Expression in Renal Angiomyolipoma and Pulmonary Lymphangioleiomyomatosis", Urology, 2009, 74(6):1359-1364.
Boruchov et al., "Activating and Inhibitory IgG Fc Receptors on Human DCs Mediate Opposing Functions", J. Clin. Invest., 2005, 115(10):2914-2923.
Boruchov et al., "Expression and Modulation of the Inhibitory Fcγ Receptor, FcγRIIB (CD32B), on Human Dendritic Cells (DCs)", Blood, 2003, 102(11): Abstract #1908.
Bouchard et al., "Antibody-Drug Conjugates—A New Wave of Cancer Drugs", Bioorganic & Medicinal Chem. Lett, 2014, 24:5357-5363.
Boyer et al., "Relative Cytotoxic Activity of Immunotoxins Reactive with Different Epitopes on The Extracellular Domain of the c-erbB-2 (HER-2/neu) Gene Product p185", Int. J. Cancer., 1999, 82(4):525-531.
Brandsma et al., "Fc Receptor Inside-Out Signaling and Possible Impact on Antibody Therapy", Immunological Reviews, Nov. 2015, 268(1):74-87.
Brauweiler et al., "Partially Distinct Molecular Mechanisms Mediate Inhibitory Fc.gamma.RIIB Signaling in Resting and Activated B Cells", J. Immunol., 2001, 167:204-211.
Bredius et al., "Role of Neutrophil Fc gamma RIIa (CD32) and Fc gamma RIIIb (CD16) Polymorphic Forms in Phagocytosis of Human IgG1- and IgG3-Opsonized Bacteria and Erythrocytes", Immunology, 1994, 83:624-630.
Brekke et al., "Human IgG Isotype-Specific Amino Acid Residues Affecting Complement-Mediated Cell Lysis and Phagocytosis", Eur. J. Immunol., 1994, 24:2542-2547.
Brown et al., "Tolerance of single, but not multiple, amino acid replacements in antibody VH CDR 2: a means of minimizing B cell wastage from somatic hypermutation?", The Journal of Immunology, 1996, 156(9): 3285-3291.
Brown et al., "Tumor-Specific Genetically Engineered Murine-Human Chimeric Monoclonal Antibody", Cancer Research, 1987, 47(13):3577-3583.
Brown EricJ., "In Vitro Assays of Phagocytic Function of Human Peripheral Blood Leukocytes: Receptor Modulation and Signal Transduction", Microbes as Tools for Cell Biology, vol. 45, in Methods in Cell Biology, Russell ed., Academic Press Inc., NY, 1994, pp. 147-164.

(56) References Cited

OTHER PUBLICATIONS

Brown KA., "Factors Modifying the Migration of Lymphocytes Across the Blood-Brain Barrier", Int. Immunopharmacology., 2001, 1(12):2043-2062.

Bruhns et al., "Specificity and Affinity of Human Fcγ Receptors and Their Polymorphic Variants for Human IgG Subclasses", Blood, Apr. 16, 2009, 113(16):3716-3725.

Brunet et al., "A New Member of the Immunoglobulin Superfamily-CTLA-4", Nature, 1987, 328:267-270.

Budde et al., "Specificity of CD32 mAB for Fc.gamma.RIIa, Fc.gamma.RIIb1, and Fc.gamma.RIIb2 Expressed in Transfected Mouse B cells and BHK-21 Cells", Leukocyte Typing V: White Cell Differentiation Antigens. (Schlossman, et al., eds.), 1995, pp. 828-832.

Burgess et al., "Possible Dissociation of The Heparin-Binding and Mitogenic Activities of The Heparin-Binding (Acidic Fibroblast) Growth Factor-1 From Its Receptor Binding Activities by Site Directed Mutagenesis of a Single Lysine Residue", J. Cell Biol., 1990, 111:2129-2138.

Burmeister et al., "Crystal Structure of The Complex of Rat Neonatal Fc Receptor with Fc", Nature, 1994, 372:379-383.

Burton et al., "Human Antibody Effector Function", Advances in Immunology, 1992, 51:1-64.

Burton et al., "Molecular Recognition of Antibody (IgG) by Cellular Fc Receptor (FcRI)", Mol. Immunol., 1988, 25:1175-1181.

Burton DennisR., "Immunoglobulin G: Functional Sites", Mol Immunol, 1985, 22:161-206.

Cacciari et al., "CC-1065 And the Duocarmycins: Recent Developments", Expert Opinion on Therapeutic Patents, 2000, 10(12):1853-1871.

Callanan et al., "The IgG Fc Receptor, Fc.Gamma.RIIB Is A Target for Deregulation by Chromosomal Translocation in Malignant Lymphoma", Proc. Natl. Acad. Sci. (U.S.A.), 2000, 97(1):309-314.

Cameron et al., "Differentiation of the Human Monocyte Cell Line, U937, with Dibutyryl Cyclicamp Induces the Expression of the Inhibitory Fc Receptor, Fc.gamma.RIIb", Immunol. Lett., 2002, 83(3):171-179.

Camilleri-Broet et al., "Fc.gamma.RIIB is Differentially Expressed During B Cell Maturation and in B-Cell Lymphomas", Br. J. Haematol., 2004, 124(1):55-62.

Campbell et al., "Monoclonal Antibody Therapy for Lymphoma", Blood Rev., 2003, 17(3):143-152.

Canafax et al., "Monoclonal Antilymphocyte Antibody (OKT3) Treatment of Acute Renal Allograft Rejection", Pharmacotherapy, Aug. 1987, 7(4):121-124.

Canfield et al., "The Binding Affinity of Human IgG For Its High Affinity Fc Receptor Is Determined by Multiple Amino Acids in The CH2 Domain and Is Modulated by The Hinge Region", J. Exp. Med., 1991, 173:1483-1491.

Caron et al., "Engineered Humanized Dimeric Forms of IgG Are More Effective Antibodies", Journal of Experimental Medicine, 1992, 176:1191-1195.

Carter et al., "Humanization of an Anti-p185her2 Antibody for Human Cancer Therapy", Proceedings of the National Academy of Sciences, 1992, 89:4285-4289.

Cartron et al., "Therapeutic Activity of Humanized Anti-CD20 Monoclonal Antibody and Polymorphism in IgG Fc Receptor FcgammaRIIIa Gene", Blood, 2002, 99:754-758.

Cassard et al., "Modulation of Tumor Growth by Inhibitory Fc.Gamma. Receptor Expressed by Human Melanoma Cells", J. Clin. Invest., 2002, 110(10):1549-1557.

Casset et al., "A Peptide Mimetic of An Anti-CD4 Monoclonal Antibody by Rational Design", Biochem. Biophs. Res. Commun., 2003, 307:198-205.

Castriconi et al., "Identification Of 4Ig-B7-H3 As A Neuroblastoma-Associated Molecule That Exerts A Protective Role from An NK Cell-Mediated Lysis", Proc. Natl. Acad. Sci. (U.S.A.), 2004, 101(34):12640-12645.

Cavacini et al., "Influence of Heavy Chain Constant Regions on Antigen Binding And HIV-1 Neutralization by A Human Monoclonal Antibody", J. Immunol., 1995, 155(7):3638-3644.

Chan et al., "The Use of Antibodies in the Treatment of Infectious Diseases", Singapore Medical Journal, 2009, 50(7):663-666.

Chapoval et al., "B7-H3", Chapter 8, The B7-CD28 Family Molecules, Kluwer Academic, NY; 2003, pp. 91-99.

Chapoval et al., "B7-H3: A Costimulatory Molecule for T Cell Activation and IFN-γ Production", Nature Immunology, 2001, 2:269-274.

Chappel et al., "Identification of a Secondary FcγRI Binding Site within a Genetically Engineered Human IgG Antibody", Journal of Biological Chemistry, 1993, 268(33):25124-25131.

Chappel et al., "Identification of the Fcγ Receptor Class I Binding Site in Human IgG Through the use of Recombinant IgG1/IgG2 Hybrid and Point-Mutated Antibodies", Proc. Natl. Acad. Sci U.S.A., 1991, 88:9036-9040.

Charafe-Jauffret et al., "Breast Cancer Stem Cells: Tools and Models to Rely On", BMC Cancer, 2009, 9:202 (10 pages).

Chari et al., "Immunoconjugates Containing Novel Maytansinoids: Promising Anticancer Drugs", Cancer Research, 1992, 52:127-131.

Chattergee et al., "Idiotypic Antibody Immunotherapy of Cancer", Cancer Immunol. Immunotherapy., 1994, 38:75-82.

Chen et al., "Cloning and Characterization of Porcine 41g-B7-H3: A Potent Inhibitor of Porcine T-Cell Activation", PLOS One, 2011, 6(6): E21341.

Chen et al., "Selection and Analysis of an Optimized Anti-VEGF Antibody: Crystal Structure of an Affinity-Matured Fab in Complex with Antigen", J. Molec. Biol., 1999, 293:865-881.

Chen et al., "Surface Antigen Expression and Complement Susceptibility of Differentiated Neuroblastoma Clones", Amer. J. Pathol., 2000, 156(3):1085-1091.

Chen et al., "The Immunoregulatory Protein Human B7H3 is a Tumor-Associated Antigen that Regulates Tumor Cell Migration and Invasion", Curr. Cancer Drug Targets, 2008, 8:404-413.

Cheung et al., "Immunology and Targeted Immunotherapy of Human Neuroblastoma", In: Neuroblastoma: Tumor Biology and Therapy, CRC Press, Boca Raton, 1990, pp. 52-68.

Cheung et al., "Immunotherapy of Neuroblastoma", In: Neuroblastoma, Elsevier, NY, 2000, 10 pages.

Cheung et al., "Oral (1□73), (1□D4)-beta-D-Glucan Synergizes with Antiganglioside GD2 Monoclonal Antibody 3F8 in the Therapy of Neuroblastoma", Clin. Canc. Res., 2002, 8:1217-1223.

Chichili et al., "A CD3xCD123 Bispecific DART for Redirecting Host T Cells to Myelogenous Leukemia: Preclinical Activity and Safety in Nonhuman Primates", Science Translational Medicine, 2015, 7(289):14 pages.

Chothia et al., "Canonical Structures for The Hypervariable Regions of Immunoglobulins", Journal of Molecular Biology, 1987, 196:901-917.

Chu et al., "CD79: A Review", Appl. Immunohistochem. Molec. Morphol., 2001, 9(2):97-106.

Ciccimarra et al., "Localization of The IgG Effector Site for Monocyte Receptors", Proc. Natl. Acad. Sci. U.S.A., 1975, 72:2081-2083.

Clynes et al., "Cytotoxic Antibodies Trigger Inflammation Through Fc Receptors", Immunity, 1995, 3:21-26.

Clynes et al., "Fc Receptors are Required in Passive and Active Immunity to Melanoma", Proc. Natl. Acad. Sci U.S.A., 1998, 95:652-656.

Clynes et al., "Inhibitory Fc Receptors Modulate In Vivo Cytoxicity Against Tumor Targets", Nature Medicine, 2000, 6:443-446.

Clynes et al., "Modulation of Immune Complex-Induced Inflammation In Vivo By the Coordinate Expression of Activation and Inhibitory Fc Receptors", J. Exp. Med., 1999, 189:179-185.

Clynes et al., "Uncoupling of Immune Complex Formation and Kidney Damage in Autoimmune Glomerulonephritis", Science, 1998, 279:1052-1054.

Co et al., "Chimeric and Humanized Antibodies with Specificity for the CD33 Antigen", The Journal of Immunology, 1992, 148(4):1149-1154.

Co et al., "Humanized Antibodies for Antiviral Therapy", Proceedings of the National Academy of Sciences, 1991, 88:2869-2873.

(56) References Cited

OTHER PUBLICATIONS

Collins et al., "The B7 Family of Immune-Regulatory Ligands", Genome Biology, 2005, 6(6):223.1-223.7.
Colman PM., "Effects of Amino Acid Sequence Changes on Antibody-Antigen Interactions", Res. Immunol., 1994, 145:33-36.
Comerci et al., "CD2 Promotes Human Natural Killer Cell Membrane Nanotube Formation", PLoS One, Oct. 2012, 7(10): e47664:1-12.
Coudert et al., "Altered NKG2D Function in NK Cells Induced by Chronic Exposure to NKG2D Ligand-expressing Tumor Cells", Blood, Oct. 2005, 106:1711-1717.
Coyle et al., "The Expanding B7 Superfamily: Increasing Complexity in Costimulatory Signals Regulating T Cell Function", Nature Immunol., 2001, 2(3):203-209.
Crispen et al., "Tumor Cell and Tumor Vasculature Expression of B7-H3 Predict Survival in Clear Cell Renal Cell Carcinoma", Clin Cancer Res., 2008, 14(16):5150-5157.
Daeron et al., "The Same Tyrosine Based Inhibition Motif, in the Intracytoplasmic Domain of Fc.gamma.RIIB, Regulates Negatively BCR, TCR– and FcR Dependent Cell Activation", Immunity, 1995, 3:635-646.
Daeron Marc, "Fc Receptor Biology", Annu. Rev. Immunol., 1997, 15:203-234.
Damle et al., "B-Cell Chronic Lymphocytic Leukemia Cells Express A Surface Membrane Phenotype of Activated, Antigen-Experienced B Lymphocytes", Blood, 2002, 99(11):4087-4093.
Daugherty et al., "Polymerase Chain Reaction Facilitates the Cloning, CDR-Grafting, and Rapid Expression of a Murine Monoclonal Antibody Directed Against the CD18 Component of Leukocyte Integrins", Nucleic Acids Research, 1991, 19(9):2471-2476.
Davies et al., "Affinity Improvement of Single Antibody VH Domains: Residues in all Three Hypervariable Regions Affect Antigen Binding", Immunotechnology, 1996, 2(3):169-179.
Davies et al., "Antibody VH Domains as Small Recognition Units", Bio/Technology, 1995, 13:475-479.
Davies et al., "Expression of GnTIII In A Recombinant Anti-CD20 CHO Production Cell Line: Expression of Antibodies with Altered Glycoforms Leads to An Increase in ADCC Through Higher Affinity for FCgamma. RIII", Biotechnol. Bioeng., 2001, 74(4):288-294.
De Groot et al., "Design, Synthesis, and Biological Evaluation of a Dual Tumor-Specific Motive Containing Integrin-Targeted Plasmin-Cleavable Doxorubicin Prodrug", Molecular Cancer Therapeutics, 2002, 1: 901-911.
De Groot et al., "Elongated Multiple Electronic Cascade and Cyclization Spacer Systems in Activatible Anticancer Prodrugs for Enhanced Drug.", Journal of Organic Chemistry, 2001, 66(26):8815-8830.
De Haas et al., "IgG-Fc Receptors and The Clinical Relevance of Their Polymorphisms", Wien Klin Wochenscha, 2001, 113:825-831.
De Pascalis et al., "Grafting of Abbreviated Complementarity Determining Regions Containing Specificity Determining Residues Essential for Ligand Contact to Engineer A Less Immunogenic Humanized Monoclonal Antibody", J. Immunol., 2002, 169:3076-3084.
De Santes et al., "Radiolabeled Antibody Targeting of the Her-2/neu Oncoprotein", Cancer Res., 1992, 52:1916-1923.
Deisenhofer Johann, "Crystallographic Refinement and Atomic Models of a Human Fc Fragment and Its Complex with Fragment B of Protein A from *Staphylococcus aureus* at 2.9- and 2.8-A Resolution", Biochem., 1981, 20:2361-2370.
Deo et al., "Clinical Significance of IgG Fc Receptors and Fc gamma R-Directed Immunotherapies", Immunology Today, 1997, 18:127-135.
Dermer GeraldB. , "Another Anniversary for the War on Cancer", Biotechnology, 1994, 12:320 (1 page).
Ding et al., "Inhibition of the Function of the Fc.gamma.RIIB by a Monoclonal Antibody to Thymic Shared Antigen-1, a Ly-6 Family Antigen", Immunology, 2001, 104(1):28-36.
Doemling et al., "Myxobacterial Epothilones And Tubulysins As Promising Anticancer Agents", Mol. Diversity, 2005, 9:141-147.
Dokter et al., "Preclinical Profile of the HER2-Targeting ADC SYD983/SYD985: Introduction of a New Duocarmycin-Based Linker-Drug Platform", Mol. Cancer Ther., 2014, 13(11):2618-2629.
Dong et al., "B7-H1, a Third Member of the B7 Family, Co-Stimulates T-cell Proliferation and interleukin-10 Secretion", Nature Medicine, Dec. 1999, 5(12):1365-1369.
Dong et al., "Immune Regulation by Novel Costimulatory Molecules", Immunologic Research, 2003, 28(1):39-48.
Doronina et al., "Development of Potent Monoclonal Antibody Auristatin Conjugates for Cancer Therapy", Nat. Biotechnol., 2003, 21:778-784.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem., 2002, 13:855-869.
Dubowchik et al., "Doxorubicin Immunoconjugates Containing Bivalent, Lysosomally-Cleavable Dipeptide Linkages", Bioorganic & Medicinal Chemistry Letters, 2002, 12:1529-1532.
Ducry et al., "Antibody-Drug Conjugates: Linking Cytotoxic Payloads to Monoclonal Antibodies", Bioconjugate Chemistry, 2010, 21:5-13.
Dumoulin et al., "Single-Domain Antibody Fragments with High Conformational Stability", Protein Science, 2002, 11:500-512.
Duncan et al., "Localization of The Binding Site for The Human High-Affinity Fc Receptor on IgG", Nature, 1988, 332:563-564.
Duncan et al., "The Binding Site for C1q on IgG", Nature, 1988, 332:738-740.
Edberg et al., "Modulation of Fcgamma and Complement Receptor Function by the Glycosyl-Phosphatidylinositol-Anchored Form of FcgammaRIII", J. Immunol., 1994, 152:5826-5835.
Efferson et al., "Stimulation of Human T Cells by an Influenza A Vector Expressing a CTL Epitope from the HER-2/neu Protooncogene Results in Higher Numbers of Antigen Specific TCRhi Cells than Stimulation with Peptide", Anticancer Research, 2005, 25:715-724.
Elgersma et al., "Design, Synthesis, and Evaluation of Linker-Duocarmycin Payloads: Toward Selection of HER2-Targeting Antibody-Drug Conjugate SYD985", Mol. Pharmaceut., 2014, 12:1813-1835.
Elkabetz et al., "Cysteines in CH1 Underlie Retention of Unassembled Ig Heavy Chains", J. Biol. Chem., 2005, 280:14402-14412.
Ellman et al., "Biosynthetic Method for Introducing Unnatural Amino Acids Site-Specifically into Proteins", Methods Enzymol., 1991, 202:301-336.
Emamaullee et al., "Costimulatory Blockade with Belatacept In Clinical and Experimental Transplantation—A Review", Expert Opin. Biol. Ther., 2009, 9(6):789-796.
Eppstein et al., "Biological Activity of Liposome-Encapsulated Murine Interferon .Gamma. Is Mediated by A Cell Membrane Receptor", Proc. Natl. Acad. Sci. (U.S.A.), 1985, 82(11):3688-3689.
Fanger et al., "Production and Use of Anti-FcR Bispecific Antibodies", Immunomethods., 1994, 4(1):72-81.
Farag et al., "Fc.gamma.RIIIa and Fc.gamma.RIIIa Polymorphisms Do Not Predict Response to Rituximab In B-Cell Chronic Lymphocytic Leukemia", Blood, 2003, 15 pages.
Fidler IsaiahJ. , "Macrophages and Metastasis—A Biological Approach to Cancer Therapy", Cancer Res., 1985, 45(10):4714-4726.
Fieger et al., "The Anti-B7-H3-4Ig Antibody TES7 Recognized Cancer Stem Cell Lines, Modulates Angiogenic Factor Secretion, And Exhibits Potent Anti-Tumor Activity in vivo", Proc. Amer. Assoc. Cancer Re. Annual Meeting (99th Annual Meeting of The American Association for Cancer Research; San Diego, CA, USA, Apr. 12-16, 2008, 49:606; Abstract 2555 (1 page).
Fitzgerald et al., "Improved Tumour Targeting by Disulphide Stabilized Diabodies Expressed in Pichia pastoris", Protein Engineering, 1997, 10(10):1221-1225.
Fleit et al., "Cross-Linking of mAb to FC.gamma.RII Results in Tyrosine Phosphorylation of Multiple Polypeptides Including FC.gamma.RII Itself", Leukocyte Typing V: White cell differentiation antigens, 1995, 826-827.
Flesch et al., "Functions of the Fc Receptors for Immunoglobulin G", Journal of Clinical Laboratory Analysis, 2000, 14:141-156.

(56) References Cited

OTHER PUBLICATIONS

Flies et al., "The New B7s: Playing a Pivotal Role in Tumor Immunity", Journal of Immunotherapy, 2007, 30(3):251-260.
Fukushima et al., "B7-H3 Regulates the Development of Experimental Allergic Conjunctivitis in Mice", Immunology Letters, 2007, 113:52-573.
Gamberale et al., "To the Editor: Expression of Fc.gamma. Receptors Type II (FC.gamma.RII) in Chronic Lymphocytic Leukemia B Cells", Blood (Correspondence), 2003, 102(7):2698-2699.
Ganesan A, "Solid-Phase Synthesis in the Twenty-First Century", Mini-Reviews in Medicinal Chemistry, 2006, 6(1):3-10.
Gao et al., "Molecular Interactions of Coreceptor CD8 and MHC Class I: The Molecular Basis for Functional Coordination With the T-Cell Receptor", Immunology Today, Dec. 2000, 21(12):630-636.
Gerber et al., "Stimulatory and Inhibitory Signals Originating from The Macrophage Fc.Gamma. Receptors", Microbes Infect., 2001, 3(2):131-139.
Gergely et al., "Fc Receptors on Lymphocytes and K Cells", Biochem. Soc. Trans., 1984, 12:739-743.
Gergely et al., "The Two Binding-Site Models of Human IgG Binding Fc Gamma Receptors", FASEB J., 1990, 4:3275-3283.
Ghotra et al., "The Cancer Stem Cell Microenvironment and Anti-Cancer Therapy", Int. J. Radiat. Biol., 2009, 85(11):955-962.
Gill et al., "Efficacy Against Human Acute Myeloid Leukemia and Myeloablation of Normal Hematopoiesis in a Mouse Model Using Chimeric Antigen Receptor-Modified T Cells", Blood, Mar. 2014, 123(15): 2343-2354.
Giusti et al., "Someatic Diversification of S107 from an Antiphosphocholine to an anti-DNA Autoanitbody Is Due to a Single Base Change in its Heavy Chain Variable Region", Proc. Natl. Acad. Sci. (U.S.A.), 1987, 84:2926-2930.
Gorman et al., "Reshaping A Therapeutic CD4 Antibody", Proceedings of the National Academy of Sciences, 1991, 88:4181-4185.
Gouw et al., "Sarcoma Immunotherapy", Cancers, 2011, 3:4139-4150.
Greenwald et al., "The B7 Family Revisited", Annual Review of Immunology, 2005, 23:515-548.
Greenwood et al., "Effector Functions of Matched Sets of Recombinant Human IgG Subclass Antibodies", Final Version Edited Feb. 11, 1993, 24 pages.
Greenwood et al., "Engineering Multiple-Domain Forms of the Therapeutic Antibody CAMPATH-1H: Effects on Complement Lysis", Therapeutic Immunology, 1994, 1:247-255.
Greenwood et al., "Structural Motifs Involved in Human IgG Antibody Effector Functions", Eur. J. Immunol., 1993, 23:1098-1104.
Gregorio et al., "Small Round Blue Cell Tumours: Diagnostic and Prognostic Usefulness of the Expression of B7-H3 Surface Molecule", Histopathology, 2008, 53:73-80.
Groh et al., "Costimulation of CD8αβ T Cells by NKG2D via Engagement by MIC Induced on Virus-Infected Cells", Nature Immunology, Mar. 2001, 2(3):255-260.
Gruber et al., "Efficient Tumor Cell Lysis Mediated by a Bispecific Single Chain Antibody Expressed in *Escherichia coli*", Journal of Immunology, 1994, 152(11):5368-5374.
Guery et al., "B7-H3 Protein Expression in Acute Myeloid Leukemia", Cancer Medicine, 2015, 4(12):1879-1883.
Gupta et al., "Cancer Stem Cells: Mirage or Reality?", Nature Medicine, 2009, 15(9):1010-1012.
Gura Trisha, "Systems for Identifying New Drugs are Often Faulty", Science, 1997, 278:1041-1042.
Guy et al., "Organization of Proximal Signal Initiation at the TCR:CD3 Complex", Immunological Reviews, Nov. 2009, 232(1):7-21.
Hadley et al., "The Functional Activity of Fc Gamma RII and Fc Gamma RIII on Subsets of Human Lymphocytes", Immunology, 1992, 76:446-451.

Hashiguchi et al., "Triggering Receptor Expressed on Myeloid Cell-Like Transcript 2 (TLT-2) Is A Counter-Receptor for B7-H3 And Enhances T Cell Responses", Proc. Natl. Acad. Sci. (U.S.A.), 2008, 105(30):10495-10500.
Hatta et al., "Association of Fc Gamma Receptor IIIB, but Not of Fc Gamma Receptor IIA and IIIA Polymorphisms with Systemic Lupus Erythematosus in Japanese", Genes Immunity, 1999, 1:53-60.
Hayes Robert, "Fc Engineering to Enhance Monoclonal Antibody Effector Functions", Xencor Presentation, 2003, 6 pages.
Henry et al., "A Prostate-Specific Membrane Antigen-Targeted Monoclonal Antibody-Chemotherapeutic Conjugate Designed for The Treatment of Prostate Cancer", Cancer Res., 2004, 64(21):7995-8001.
Henry et al., "Structure and Evolution of The Extended B7 Family", Immunol Today, 1999, 20(6):285-288.
Hermann et al., "Pancreatic Cancer Stem Cells—Insights and Perspectives", Expert Opin. Biol. Ther., 2003, 9(10):1271-1278.
Herzenberg et al., "The History and Future of The Fluorescence Activated Cell Sorter and Flow Cytometry: A View from Stanford", Clin. Chem., 2002, 48:1819-1827.
Heyman Birgitta, "Regulation of Antibody Responses Via Antibodies, Complement, and Fc Receptors", Annu. Rev. Immunol., 2000, 18:709-737.
Hinman et al., "Preparation and Characterization of Monoclonal Antibody Conjugates of The Calicheamicins: A Novel and Potent Family of Antitumor Antibiotics", Cancer Research, 1993, 53:3336-3342.
Hofmeyer et al., "The Contrasting Role of B7-H3", Proceedings of the National Academy of Sciences of the United States of America, Jul. 29, 2008, 105(30):10277-10278.
Hogarth et al., "Characterization of Fcr Ig-Binding Sites and Epitope Mapping", Immunomethods, 1994, 4:17-24.
Holler et al., "In Vitro Evolution of A T Cell Receptor with High Affinity for Peptide/MHC", Proc. Natl. Acad. Sci. (U.S.A.), 2000, 97:5387-5392.
Holliger et al., "'Diabodies': Small Bivalent and Bispecific Antibody Fragments", Proceedings of the National Academy of Sciences, 1993, 90:6444-6448.
Holliger et al., "Engineered Antibody Fragments and The Rise of Single Domains", Nature Biotechnology, Oct. 2005, 23(9):1126-1135.
Holliger et al., "Specific Killing of Lymphoma Cells by Cytotoxic T-Cells Mediated by a Bispecific Diabody", Protein Engineering, 1996, 9(3):299-305.
Holm et al., "Functional Mapping and Single Chain Construction of the Anti-Cytokeratin 8 Monoclonal Antibody TS1", Molecular Immunology, 2007, 44:1075-1084.
Holmes et al., "Alleles of the Ly-17 Alloantigen Define Polymorphisms of The Murine IgG Fc Receptor", Proc. Natl. Acad. Sci. (U.S.A.), 1985, 82(22):7706-7710.
Holt et al., "Domain Antibodies: Proteins for Therapy", Trends in Biotechnology, 2003, 21(11):484-490.
Houghten et al., "Monoclonal Antibody Therapies—A 'Constant' Threat to Cancer", Nature Medicine, 2000, 6(4):373-374.
Houghten et al., "General Method for The Rapid Solid-Phase Synthesis of Large Numbers of Peptides: Specificity of Antigen-Antibody Interaction at The Level of Individual Amino Acids", Proceedings of the National Academy of Sciences, 1985, 82(15):5131-5135.
Hu et al., "Expression of Costimulatory Molecule B7-H3 and its Prognostic Implications in Human Acute Leukemia", Hematology, 2015, 16(20):187-195.
Hulett et al., "Chimeric Fc Receptors Identify Functional Domains of The Murine High Affinity Receptor for IgG", J. Immunol., 1991, 147:1863-1868.
Hulett et al., "Identification of The IgG Binding Site of The Human Low Affinity Receptor for IgG Fc Gamma RII. Enhancement and Ablation of Binding by Site-Directed Mutagenesis", Journal of Biological Chemistry, 1994, 269:15287-15293.
Hulett et al., "Multiple Regions of Human Fc Gamma RII (CD32) Contribute to The Binding of IgG", Journal of Biological Chemistry, 1995, 270:21188-21194.

(56) References Cited

OTHER PUBLICATIONS

Hutchins et al., "Improved Biodistribution, Tumor Targeting, and Reduced Immunogenicity in Mice with a Gamma 4 Variant of Campath-1H", Proc. Natl. Acad. Sci. (U.S.A.), 1995, 92:11980-11984.
Hwang et al., "Hepatic Uptake and Degradation of Unilamellar Sphingomyelin/Cholesterol Liposomes: A Kinetic Study", Proc. Natl. Acad. Sci. (U.S.A.), 1980, 77(7):4030-4034.
Ibragimova,"Stability of the β-Sheet of The WW Domain: A Molecular Dynamics Simulation Study", Biophys. J., 1999, 77(4):2191-2198.
Idusogie et al., "Engineered Antibodies with Increased Activity to Recruit Complement", Journal of Immunology, 2001, 166:2571-2575.
Idusogie et al., "Mapping of The C1q Binding Site on Rituxan, A Chimeric Antibody with A Human IgG1 Fc", Journal of Immunology, 2000, 164: 4178-4184.
Indik et al., "The Molecular Dissection of Fcgamma Receptor Mediated Phagocytosis", Blood, 1995, 86(12):4389-4399.
Isaacs et al., "A Therapeutic Human IgG4 Monoclonal Antibody That Depletes Target Cells in Humans", Clinical and Experimental Immunology, 1996, 106:427-433.
Isaacs et al., "Therapy with Monoclonal Antibodies. An in Vivo Model for The Assessment of Therapeutic Potential", Journal of Immunology, 1992, 148:3062-3071.
Isaacs et al., "Therapy with Monoclonal Antibodies. II. The Contribution of Fc Gamma Receptor Binding and The Influence of C(H)1 and C(H)3 Domains On In vivo Effector Function", Journal of Immunology, 1998, 161:3862-3869.
Jain et al., "Current ADC Linker Chemistry", Pharmaceutical Research, 2015, 32:3526-3540.
Jain et al., "Barriers to Drug Delivery in Solid Tumors", Scientific American, 1994, Jul. 1994:58-65.
Jamieson et al., "The Role of the NKG2D Immunoreceptor in Immune Cell Activation and Natural Killing", Immunity, Jul. 2002, 17(1):19-29.
Jassal et al., "Remodeling Glycans On IgG By Genetic Re-Engineering", Biochemical Society Transactions, 1998, 26:S113.
Jefferis et al., "IgG-Fc-Mediated Effector Functions: Molecular Definition of Interaction Sites for Effector Ligands and The Role of Glycosylation", Immunol. Rev., 1998, 163:59-76.
Jefferis et al., "Interaction Sites on Human IgG-Fc for FcγR: Current Models", Immunology Letters, 2002, 82:57-65.
Jefferis et al., "Modulation of FcγR and Human Complement Activation by IgG3-core Oligosaccharide Interactions", Immunology Letters, 1996, 54:101-104.
Jefferis et al., "Molecular Definition of Interaction Sites on Human IgG for Fc Receptors (Hufcγ R)", Mol. Immunol., 1990, 27:1237-1240.
Jefferis et al., "Recognition Sites on Human IgG for Fcγ Receptors: The Role of Glycosylation", Immunology Letters, 1995, 44:111-117.
Jeger et al., "Site-Specific and Stoichiometric Modification of Antibodies by Bacterial Transglutaminase", Angewandte Chemie, 2010, 49:9995-9997.
Jendeberg et al., "Engineering of Fc(1) and Fc(3) From Human Immunoglobulin G to Analyse Subclass Specificity for Staphylococcal Protein A", Journal of Immunological Methods, 1997, 201:25-34.
Jennings Veronica M., "Review of Selected Adjuvants Used in Antibody Production", ILAR Journal, 1995, 37(3):119-125.
Jiang et al., "A Novel Peptide Isolated from A Phage Display Peptide Library with Trastuzumab Can Mimic Antigen Epitope of HER-2", Journal of Biological Chemistry, 2004, 280(6):4656-4662.
Johansson et al., "Structure, Specificity, and Mode of Interaction for Bacterial Albumin-binding Modules", Journal of Biological Chemistry, Mar. 2002, 277(10):8114-8120.
Johnson et al., "Effector Cell Recruitment with Novel Fv-Based Dual-Affinity Re-Targeting Protein Leads to Potent Tumor Cytolysis And In vivo B-Cell Depletion", Journal of Molecular Biology, 2010, 399(3):436-449.
Jones et al., "Replacing the Complementarity-Determining Regions in a Human Antibody with Those from A Mouse", Nature, 1986, 321:522-525.
Junutula et al., "Engineered Thio-Trastuzumab-DM1 Conjugate with An Improved Therapeutic Index to Target Human Epidermal Growth Factor Receptor 2-Positive Breast Cancer", Clin, Cancer Res., 2010, 16:4769-4778.
Kadar et al., "Modulatory Effect of Synthetic Human IgG Fc Peptides on The in Vitro Immune Response of Murine Spleen Cells", Int. J. Immunopharmacology., 1991, 13:1147-55.
Kadar et al., "Synthetic Peptides Comprising Defined Sequences of CH-2 and CH-3 Domains of Human IgG1 Induce Prostaglandin E2 Production from Human Peripheral Blood Mononuclear Cells", Immunol Lett, 1992, 32:59-63.
Kagari et al., "Essential Role of Fc.Gamma. Receptors in Anti-Type II Collagen Antibody Induced Arthritis", Journal of Immunology, 2003, 170:4318-4324.
Kalergis et al., "Inducing Tumor Immunity through the Selective Engagement of Activating Fcgamma Receptors on Dendritic Cells", Journal of Experimental Medicine, 2002, 195(12):1653-1659.
Kang et al., "Inhibition of Self-Binding Antibodies (Autobodies) by a VH-Derived Peptide", Science, 1988, 240(4855):1034-1036.
Katayama et al., "Expression of B7-H3 in Hypopharyngeal Squamous Cell Carcinoma as A Predictive Indicator for Tumor Metastasis and Prognosis", International Journal of Oncology, 2011, 38:1219-1226.
Kato et al., "Structural Basis of The Interaction Between IgG and Fcγ Receptors", Journal of Molecular Biology, 2000, 295:213-224.
Kaur et al., "Biological Evaluation of Tubulysin A: A Potential Anticancer and Antiangiogenic Natural Product", Biochemical Journal, 2006, 396: 235-242.
Keler et al., "Differential Effect of Cytokine Treatment on Fc Alpha Receptor I- and Fc Gamma Receptor I-Mediated Tumor Cytotoxicity by Monocyte-Derived Macrophages", Journal of Immunology, 2000, 164:5746-5752.
Kelsey et al., "Epidemiologic Studies of Risk Factors for Cancer in Pet Dogs", Epidemiologic Reviews, 1998, 20(2):204-217.
Kepley et al., "Co-aggregation of FcgammaRII with FcepsilonRI On Human Mast Cells Inhibits Antigeninduced Secretion and Involves SHIP-Grb2-Dok Complexes", Journal of Biological Chemistry, 2004, 279(34) 35139-35149.
Kettleborough et al., "Humanization of a Mouse Monoclonal Antibody by CDR-Grafting: The Importance of Framework Residues on Loop Conformation", Protein Engineering, 1991, 4(7):773-783.
Khalil et al., "Mechanism of Action of Tubulysin, An Antimitotic Peptide From Myxobacteria", ChemBioChem, 2006, 7:678-683.
Khawli et al., "Cytokine, Chemokine, and Co-Stimulatory Fusion Proteins for the Immunotherapy of Solid Tumors", Handbook of Experimental Pharmacology, 2008, 181:291-328.
Kieke et al., "Selection of Functional T Cell Receptor Mutants from A Yeast Surface-Display Library", Proc. Natl. Acad. Sci. (U.S.A.), 1999, 96:5651-5656.
Kiick et al., "Identification of An Expanded Set of Translationally Active Methionine Analogues in *Escherichia*", FEBS Letters, 2001, 502(1-2):25-30.
Kim et al., "Analysis of FcγRIII and IgG Fc Polymorphism Reveals Functional and Evolutionary Implications of Protein-Protein Interaction", Journal of Molecular Evolution, 2001, 53:1-9.
Kim et al., "Both the Epitope Specificity and Isotype Are Important in The Antitumor Effect of Monoclonal Antibodies Against Her-2/Neu Antigen", International Journal of Cancer, 2002, 102(4):428-434.
Kimura et al., "A New Mouse Cell-Surface Antigen (Ly-M20) Controlled by A Gene Linked to Mls Locus and Defined by Monoclonal Antibodies", Immunogenetics., 1981, 14(1-2):3-14.
King et al., "Trem-Like Transcript 2 Is Expressed on Cells of The Myeloid/Granuloid and B Lymphoid Lineage and Is Up-Regulated in Response to Inflammation", Journal of Immunology, 2006, 176:6012-6021.

(56) References Cited

OTHER PUBLICATIONS

Kipps et al., "Importance of Immunoglobin Isotype in Human Antibody-Dependent, Cell-Mediated Cytotoxicity Directed by Murine Monoclonal Antibodies", Journal of Experimental Medicine, 1985, 161:1-17.
Kirk et al., "CTLA4-Ig and Anti-CD40 Ligand Prevent Renal Allograft Rejection in Primates", Proc. Natl. Acad. Sci. (U.S.A.), 1997, 94(16):8789-8794.
Klein et al., "Expression of Biological Effector Functions by Immunoglobulin G Molecules Lacking the Hinge Region", Proc. Natl. Acad. Sci. (U.S.A.), 1981, 78:524-528.
Klesney-Tait et al., "The TREM Receptor Family and Signal Integration", Nature Immunology, 2006, 7:1266-1273.
Koene et al., "Fc gammaRIIIa-158V/F Polymorphism Influences the Binding of IgG By Natural Killer Cell FcgammaRIIIa, Independently of The FcGammaRIIIa-48L/R/H Phenotype", Blood, 1997, 90:1109-1114.
Kohler et al., "Continuous Cultures of Fused Cells Secreting Antibody of Predefined Specificity", Nature, 1975, 256:495-497.
Korman et al., "Checkpoint Blockade in Cancer Immunotherapy", Advances in Immunology, 2007, 90:297-339.
Kovtun et al., "Antibody-Drug Conjugates Designed to Eradicate Tumors with Homogeneous and Heterogeneous Expression of The Target Antigen", Cancer Research, 2006, 66:3214-3221.
Kranz et al., "Mechanisms of Ligand Binding by Monoclonal Anti-Fluorescyl Antibodies", Journal of Biological Chemistry, 1982, 257:6987-6995.
Kristiansen et al., "CTLA-4 in Autoimmune Diseases—A General Susceptibility Gene to Autoimmunity?", Genes & Immunity, 2000, 1(3):170-184.
Kudo et al., "A Novel Human Monoclonal Antibody Directed to a Tumor-associated Antigen", Japanese Journal of Cancer Research, 1993, 84:760-769.
Kuhns et al., "Deconstructing the Form and Function of the TCR/CD3 Complex", Immunity, Feb. 2006, 24(2):133-139.
Kumpel et al., "Human Monoclonal Anti-D Antibodies", British Journal of Haematology, 1989, 71:415-420.
Kurlander et al., "Comparison of Intravenous Gamma Globulin and A Monoclonal Anti-Fc Receptor Antibody as Inhibitors of Immune Clearance in Vivo in Mice", Journal of Clinical Investigation, 1986, 77(6):2010-2018.
Kurrle et al., "BMA 031—A TCR-Specific Monoclonal Antibody for Clinical Application", Transplantation Proceedings, 1989, 21(1 Pt 1):1017-1019.
Kussie et al., "A Single Engineered Amino Acid Substitution Changes Antibody Fine Specificity", Journal of Immunology, 1994, 152:146-152.
Kwong et al., "Generation, Affinity Maturation, and Characterization of a Human Anti-Human NKG2D Monoclonal Antibody with Dual Antagonistic and Agonistic Activity", Journal of Molecular Biology, Dec. 2008, 384(5):1143-1156.
Langer Robert, "New Methods of Drug Delivery", Science, 1990, 249:1527-1533.
Larsen et al., "Long-Term Acceptance of Skin and Cardiac Allografts After Blocking CD40 and CD28 Pathways", Nature, 1996, 381(6581):434-438.
Law et al., "Expression and Characterization of Recombinant Soluble Human CD3 Molecules" Presentation of Antigenic Epitopes Defined on The Native TCR-CD3 Complex, International Immunology, 2002, 14(4):389-400.
Lawson et al., "Cancer Stem Cells in Breast Cancer and Metastasis", Breast Cancer Research and Treatment, 2009, 118(2):241-254.
Lazar et al., "Transforming Growth Factor α: Mutation of Aspartic Acid 47 and Leucine 48 Results in Different Biological Activities", Molecular and Cellular Biology, Mar. 1988, 8(3):1247-1252.
Le Gall et al., "Effect of Linker Sequences Between the Antibody Variable Domains on The Formation, Stability and Biological Activity of a Bispecific Tandem Diabody", Protein Engineering Design & Selection, 2004, 17(4):357-366.

Leach et al., "Enhancement of Antitumor Immunity By CTLA-4 Blockade", Science, 1996, 271(5256):1734-1736.
Leahy D. J., "A Structural View of CD4 and CD8", The FASEB Journal, Jan. 1995, 9(1):17-25.
Lee et al., "Calicheamicins, A Novel Family of Antitumor Antibiotics. 3. Isolation, Purification and Characterization of Calicheamicins Beta 1Br, Gamma 1Br, Alpha 2I, Alpha 3I, Beta 1I, Gamma 1I and Delta 1I.", The Journal of Antibiotics, 1989, 42(7):1070-1087.
Lefranc et al., "Gm, Am and Km immunoglobulin allotypes of two populations in Tunisia", Human Genetics, 1979, 50:199-211.
Lefranc et al., "Molecular Genetics of Immunoglobulin Allotype Expression", The Human IgG Subclasses: Molecular Analysis of Structure, Function and Regulation, Pergamon Press, 1990, 43-78.
Lehmann et al., "Phagocytosis: Measurement by Flow Cytometry", Journal of Immunological Methods, 2000, 243(1-2):229-242.
Lehrnbecher et al., "Variant Genotypes of The Low-Affinity Fcgamma Receptors in Two Control Populations and A Review of Low-Affinity Fcgamma Receptor Polymorphisms in Control and Disease Populations", Blood, 1999, 94:4220-4232.
Leitner et al., "B7-H3 Is A Potent Inhibitor of Human T-Cell Activation: No Evidence for B7-H3 and TREML2 Interaction", European Journal of Immunology, 2009, 39:1754-1764.
Lenschow et al., "CD28/B7 System of T Cell Costimulation", Ann. Rev. Immunol., 1996, 14:233-258.
Lewis et al., "Differential Responses of Human Tumor Cell Lines to Anti-p185HER2 Monoclonal Antibodies", Cancer Immunology, Immunotherapy, 1993, 37(4):255-263.
Li et al., "Monocyte Surface Expression of Fcγ Receptor RI (CD64), A Biomarker Reflecting Type-I Interferon Levels in Systemic Lupus Erythematosus", Arthritis Research & Therapy, 2010, 12:R90 :12 pages.
Li et al., "Paraphyaryngeal Liposarcoma: A Case Report", Diagnostic Pathology, 2013, 8:42-45.
Li et al., "Reconstitution of Human Fc Gamma RIII Cell Type Specificity in Transgenic Mice", Journal of Experimental Medicine, 1996, 183:1259-1263.
Liang et al., "TES7, A Monoclonal Antibody Targeting B7-H3, Potently Inhibits Hs-700T Growth in Vivo", The FASEB Journal, 2008, 22:321.11.
Lifely et al., "Glycosylation and Biological Activity of CAMPATH-1H Expressed in Different Cell Lines and Grown Under Different Culture Conditions", Glycobiology, 1995, 5(8):813-822.
Lim et al., "Fc Gamma Receptor IIb On Target B Cells Promotes Rituximab Internalization and Reduces Clinical Efficacy", Blood, 2011, 118(9):2530-2540.
Lin et al., "Colony-Stimulating Factor 1 Promotes Progression of Mammary Tumors to Malignancy", Journal of Experimental Medicine, 2001, 193(6):727-739.
Lin et al., "The Macrophage Growth Factor CSF-1 in Mammary Gland Development and Tumor Progression", Journal of Mammary Gland Biology and Neoplasia, 2002, 7(2):147-162.
Linsley et al., "Extending the B7 (CD80) Gene Family", Protein Science, 1994, 3:1341-1343.
Linsley et al., "The Clinical Utility of Inhibiting CD28-Mediated Costimulation", Immunological Reviews, 2009, 229:307-321.
Liu et al., "Eradication of Large Colon Tumor Xenografts by Targeted Delivery of Maytansinoids", Proc. Natl. Acad. Sci. (U.S. A.), 1996, 93:8618-8623.
Liu et al., "Fine Mapping of the Antigen-Antibody Interaction of scFv215, A Recombinant Antibody Inhibiting RNA Polymerase II from *Drosophia melangogaster*", Journal of Molecular Recognition, 1999, 12:103-111.
Liu et al., "Production of A Mouse-Human Chimeric Monoclonal Antibody to CD20 with Potent Fc-Dependent Biologic Activity", Journal of Immunology, 1987, 139:3521-3526.
Lobuglio et al., "Mouse-Human Chimeric Monoclonal Antibody in Man: Kinetics and Immune Response", Proceedings of the National Academy of Sciences, 1989, 86:4220-4224.
Lode et al., "Targeted Therapy with A Novel Enediyene Antibiotic Calicheamicin Theta(l)1 Effectively Suppresses Growth and Dissemination of Liver Metastases in A Syngeneic Model of Murine Neuroblastoma", Cancer Research, 1998, 58:2925-2928.

(56) References Cited

OTHER PUBLICATIONS

Loke et al., "Emerging Mechanisms of Immune Regulation: The Extended B7 Family and Regulatory T Cells", Arthritis Res. Ther., 2004, 6:208-214.
Lonberg et al., "Human Antibodies from Transgenic Mice", International Reviews of Immunology, 1995, 13:65-93.
Loo et al., "Development of an Fc-Enhanced Anti-B7-H3 Monoclonal Antibody with Potent Antitumor Activity", Clinical Cancer Research, Jul. 15, 2012, 18(14):3834-3845.
Loo et al., "The Glycotope-Specific RAV12 Monoclonal Antibody Induces Oncosis In Vitro and Has Antitumor Activity Against Gastrointestinal Adenocarcinoma Tumor Xenografts In Vivo", Molecular Cancer Therapeutics, 2007, 6:856-65.
Looney et al., "Human Monocytes and U937 Cells Bear Two Distinct Fc Receptors for IgG", Journal of Immunology, 1986, 136(5):1641-1647.
Lorusso et al., "Trastuzumab Emtansine: A Unique Antibody-Drug Conjugate in Development for Human Epidermal Growth Factor Receptor 2-Positive Cancer", Clinical Cancer Research, 2011, 20:6437-6447.
Lu et al., "A Fully Human Recombinant IgG-Like Bispecific Antibody to Both the Epidermal Growth Factor Receptor and The Insulin-Like Growth Factor Receptor for Enhanced Antitumor Activity", Journal of Biological Chemistry, 2005, 280(20):19665-19672.
Lu et al., "Di-Diabody: A Novel Tetravalent Bispecific Antibody Molecule by Design", Journal of Immunological Methods, 2003, 279: 219-232.
Lu et al., "Structural Mechanism of High Affinity FcγRI Recognition of Immunoglobulin G", Immunological Review, Nov. 2015, 268(1):192-200.
Lu et al., "The Effect of Variable Domain Orientation and Arrangement on The Antigen-Binding Activity of a Recombinant Human Bispecific Diabody", Bioscience Biotechnology Research Communications, 2004, 318: 507-513.
Lund et al., "Expression and Characterization of Truncated Forms of Humanized L243 IgG1. Architectural Features Can Influence Synthesis of Its Oligosaccharide Chains and Affect Superoxide Production Triggered Through Human Fcgamma Receptor I", European Journal of Biochemistry, 2000, 267:7246-7257.
Lund et al., "Human FcγRI and FcγRII Interact with Distinct but Overlapping Sites on Human IgG", Journal of Immunology, 1991, 147:2657-2662.
Lund et al., "Multiple Binding Sites on The CH2 Domain of IgG for Mouse FcγR11", Molecular Immunology, 1992, 29:53-59.
Lund et al., "Multiple Interactions of IgG with Its Core Oligosaccharide Can Modulate Recognition by Complement and Human Fcγ Receptor I and Influence the Synthesis of Its Oligosaccharide Chains", Journal of Immunology, 1996, 157:4963-4969.
Lund et al., "Oligosaccharide-Protein Interactions in IgG Can Modulate Recognition by Fcγ Receptors", The FASEB Journal, 1995, 9:115-119.
Luo et al., "B7-H3 Enhances Tumor Immunity in Vivo by Costimulating Rapid Clonal Expansion of Antigen-Specific CD8+ Cytolytic T Cells", Journal of Immunology, 2004, 173:5445-5450.
Lyden et al., "The Fc Receptor for IgG Expressed in The Villus Endothelium of Human Placenta Is Fc.Gamma.RIIB2", Journal of Immunology, 2001, 166(6):3882-3889.
MacCallum et al., "Antibody-Antigen Interactions: Contact Analysis and Binding Site Topography", J. Molec. Biol., 1996, 262:732-745.
Mace et al., "Cell Biological Steps and Checkpoints in Accessing NK Cell Cytotoxicity", Immunology & Cell Biology, Mar. 2014, 92(3):245-255.
Maeda et al., "Construction of Reshaped Human Antibodies With HIV-Neutralizing Activity", Human Antibodies Hybridoma, 1991, 2:124-134.
Maenaka et al., "The Human Low Affinity Fcgamma Receptors Iia, Iib, and III Bind IgG with Fast Kinetics and Distinct Thermodynamic Properties", Journal of Biological Chemistry, 2001, 48:44898-904.

Mahato et al., "Cationic Lipid-Based Gene Delivery Systems: Pharmaceutical Perspectives", Pharmaceutical Research, 1997, 14:853-859.
Mahnke et al., "Induction of Immunosuppressive Functions of Dendritic Cells in Vivo By CD4+CD25+ Regulatory T Cells: Role of B7-H3 Expressions and Antigen Presentation", European Journal of Immunology, 2007, 37(8):2117-26.
Malbec et al., "Fcs Receptor I-Associated Lyn-Dependent Phosphorylation of Fc.Gamma. Receptor IIB During Negative Regulation of Mast Cell Activation", Journal of Immunology, 1998, 160(4):1647-1658.
Mallone et al., "Targeting T Lymphocytes for Immune Monitoring and Intervention in Autoimmune Diabetes", American Journal of Therapeutics, 2005, 12(6):534-550.
Mangham et al., "A Novel Immunohistochemical Detection System Using Mirror Image Complementary Antibodies (MICA)", Histopathology, 1999, 35(2):129-33.
Mardiros et al., "T Cells Expressing CD123-specific Chimeric Antigen Receptors Exhibit Specific Cytolytic Effector Functions and Antitumor Effects Against Human Acute Myeloid Leukemia", Blood, Oct. 2013, 122(18):3138-3148.
Maresco et al., "The SH2-Containing 5'-Inositol Phosphatase (SHIP) Is Tyrosine Phosphorylated after Fc.gamma. Receptor Clustering in Monocytes", Journal of Immunology, 1999, 162:6458-6465.
Martin et al., "Structure of CC-1065 (NSC 298223), A New Antitumor Antibiotic", The Journal of Antibiotics, 1980, 33:902-903.
Martin-Orozco et al., "Inhibitory Costimulation And Anti-Tumor Immunity", Seminars in Cancer Biology, 2007, 17(4):288-298.
Maruyama Kazuo, "In Vivo Targeting by Liposomes", Biological and Pharmaceutical Bulletin, 2000, 23(7):791-799.
Marvin et al., "Recombinant Approaches to IgG-Like Bispecific Antibodies", Acta Pharmacologica Sinica, 2005, 26:649-658.
Masui et al., "Mechanism of Antitumor Activity in Mice for Anti-Epidermal Growth Factor Receptor Monoclonal Antibodies with Different Isotypes", Cancer Research, 1986, 46:5592-5598.
Maynard et al., "Anitbody Engineering", Annual Review of Biomedical Engineering, 2000, 2:339-76.
McDevitt et al., "An Alpha-Particle Emitting Antibody ([213Bi]J591) for Radioimmunotherapy of Prostate Cancer", Cancer Research, 2000, 60(21):6095-6100.
Melero et al., "The Frequent Expansion of a Subpopulation of B Cells That Express RF-Associated Cross-Reactive Idiotypes: Evidence from Analysis of a Panel Autoreactive Monoclonal Antibodies", Scandinavian Journal of Immunology, 1998, 48:152-158.
Merino et al., "Immunomagnetic Purging of Ewing's Sarcoma from Blood and Bone Marrow: Quantitation by Real-Time Polymerase Chain Reaction", Journal of Clinical Oncology, 2001, 19(16):3649-3659.
Merrifield et al., "Solid Phase Synthesis", Science, 1986, 232(4748):341-347.
Mertens et al., "New Recombinant Bi- and Trispecific Antibody Derivatives", Novel Frontiers in the Production of Compounds for Biomedical Use, 2001, 1:195.208.
Metcalfe et al., "Mast Cells", Physiological Reviews, 1997, 77(4):1033-1079.
Michaelsen et al., "One Disulfide Bond in Front of The Second Heavy Chain Constant Region Is Necessary and Sufficient for Effector Functions of Human IgG3 Without A Genetic Hinge", Immunology, 1994, 91:9243-9247.
Micklem et al., "Different isoforms of human FcRII distinguished by CDw32 antibodies", Journal of Immunology, 1990, 144:2295-2303.
Miller JeffreyS., "Therapeutic Applications: Natural Killer Cells in the Clinic", Hematology, Dec. 2013, 2013(1):247-253.
Mittal et al., "Cancer Stem Cells: The Other Face of Janus", The American Journal of the Medical Sciences, 2009, 338(2):107-112.
Modak et al., "Disialoganglioside Directed Immunotherapy of Neuroblastoma", Cancer Investigation, 2007, 25:67-77.
Modak et al., "Disialoganglioside GD2 and a Novel Tumor Antigen: Potential Targets for Immunotherapy of Desmoplastic Small Round Cell Tumor", Medical and Pediatric Oncology, 2002, 39:547-551.

(56) References Cited

OTHER PUBLICATIONS

Modak et al., "Disialoganglioside GD2 and Antigen 8H9: Potential Targets for Antibody-Based Immunotherapy Against Desmoplastic Small Round Cell Tumor (DSRCT) and Rhabdomyosarcoma (RMS)", Proceedings of The American Association for Cancer Research, 90th Annual Meeting; Philadelphia, Pennsylvania, US, 1999, 40:474.
Modak et al., "Monoclonal Antibody 8H9 Targets A Novel Cell Surface Antigen Expressed by A Wide Spectrum of Human Solid Tumors", Cancer Research, 2001, 61(10):4048-4054.
Modak et al., "Novel Tumor-Associated Surface Antigen: Broad Distribution among Neuroectodermal, Mesenchymal and Epithelial Tumors, with Restricted Expression among Normal Tissues", Pediatric Research, 1998, 43(4):136.
Modak et al., "Radioimmunotargeting of Human Rhabdomyosarcom Using Monoclonal Antibody 8H9", Cancer Biotherapy & Radiopharmaceuticals, 2005, 20:534-546.
Modak et al., "Radioimmunotargeting to Human Rhabdomyosarcoma Using Monoclonal Antibody 8H9", Proceedings. American Association for Cancer Research. Annual Meeting, 2000, 41:724.
Moore et al., "Application of Dual Affinity Retargeting Molecules to Achieve Optimal Redirected T-Cell Killing Of B-Cell Lymphoma", Blood, 2011, 117(17):4542-4551.
Morgan et al., "The N-Terminal End of The CH2 Domain of Chimeric Human IgG1 Anti-HLA-DR Is Necessary for C1q, FcγRI and FcγRIII Binding", Immunology, 1995, 86:319-324.
Morrison et al., "Structural Determinants of IgG Structure", Immunologist, 1994, 2:119-124.
Munn et al., "Phagocytosis of Tumor Cells by Human Monocytes Cultured in Recombinant Macrophage Colony-Stimulating Factor", Journal of Experimental Medicine, 1990, 172(1):231-237.
Nagarajan et al., "Ligand Binding and Phagocytosis by CD16 (Fc γ Receptor III) Isoforms. Phagocytic Signaling by Associated Zeta and Gamma Subunits in Chinese Hamster Ovary Cells", Journal of Biological Chemistry, 1995, 270:25762-25770.
Nagase-Zembutsu et al., "Development of DS-5573a: A Novel Afucosylated Monoclonal Antibody Directed at B7-H3 with Potent Antitumor Activity", Cancer Science, 2016, 107:674-681.
Nakamura et al., "Fc Receptor Targeting in The Treatment of Allergy, Autoimmune Diseases and Cancer", Expert Opinion on Therapeutic Targets, 2005, 9(1):169-190.
Nakamura et al., "Fcγ Receptor IIB-Deficient Mice Develop Goodpasture's Syndrome Upon Immunization with Type IV Collagen: A Novel Murine Model for Autoimmune Glomerular Basement Membrane Disease", Journal of Experimental Medicine, 2000, 191(5):899-905.
Nakamura et al., "Heterogeneity of Immunoglobulin-Associated Molecules on Human B Cells Identified by Monoclonal Antibodies", Proceedings of the National Academy of Sciences of the United States of America, 1992, 89:8522-8526.
Nashan et al., "Fine Specificity of a Panel of Antibodies Against the TCR/CD3 Complex", Transplantation Proceedings, Oct. 1987, 19(5):4270-4272.
Neuberger et al., "Recombinant Antibodies Possessing Novel Effector Functions", Nature, 1984, 312:604-608.
Norderhaug et al., "Chimeric Mouse Human IgG3 Antibodies with An IgG4-Like Hinge Region Induce Complement-Mediated Lysis More Efficiently Than IgG3 with Normal Hinge", European Journal of Immunology, 1991, 21:2379-2384.
Nordstrom et al., "Anti-Tumor Activity and Toxicokinetics Analysis of MGAH22, An Anti-HER2 Monoclonal Antibody with Enhanced Fcγ Receptor Binding Properties", Breast Cancer Research, 2011, 13:R123, 14 pages.
Noren et al., "A General Method for Site-Specific Incorporation of Unnatural Amino Acids into Proteins", Science, 1989, 244:182-188.
Norman DouglasJ. , "Mechanisms of Action and Overview of OKT3", Therapeutic Drug Monitoring, Dec. 1995, 17(6):615-620.
Norris et al., "A Naturally Occurring Mutation in FcγRIIA: A Q to K.Sup.127 Change Confers Unique IgG Binding Properties to the R.Sup.131 Allelic Form of The Receptor", Blood, 1998, 91(2):656-662.
Nose et al., "Substitution of Asparagine324 with Aspartic Acid in The Fc Portion of Mouse Antibodies Reduces Their Capacity for C1q Binding", European Journal of Immunology, 1989, 19:2179-2181.
Okazaki et al., "Fucose Depletion from Human IgG1 Oligosaccharide Enhances Binding Enthalpy and Association Rate Between IgG1 and FcgammaRIIIA", Journal of Molecular Biology, 2004, 336:1239-1249.
Olafsen et al., "Covalent Disulfide-Linked Anti-CEA Diabody Allows Site-Specific Conjugation and Radiolabeling for Tumor Targeting Applications", Protein Engineering, Design and Selection, 2004, 17(1):21-27.
Onda et al., "In Vitro and in Vivo Cytotoxic Activities of Recombinant Immunotoxin 8H9(Fv)-PE38 against Breast Cancer, Osteosarcoma, and Neuroblastoma", Cancer Research, 2004, 64:1419-1424.
Orfao et al., "General Concepts About Cell Sorting Techniques", Clinical Biochemistry, 1996, 29:5-9.
Ott et al., "Downstream of Kinase, P62.Sup.Dok, Is A Mediator of FcγRIIB Inhibition of FcεRI Signaling", Journal of Immunology, 2002, 168:4430-4439.
Ott et al., "FcγRIIB As A Potential Molecular Target for Intravenous Gamma Globulin Therapy", The Journal of Allergy and Clinical Immunology, 2001, 108(4):S95-S98.
Panchal RekhaG. , "Novel Strategies to Selectively Kill Cancer Cells", Biochemical Pharmacology, 1998, 55:247-252.
Panka et al., "Variable Region Framework Differences Result in Decreased or Increased Affinity of Variant Anti-Digoxin Antibodies", Proceedings of the National Academy of Sciences of the United States of America, 1988, 85:3080-3084.
Panowski et al., "Site-Specific Antibody Drug Conjugates for Cancer Therapy", mAbs, 2014, 6(1):34-45.
Pardridge et al., "Blood-Brain Barrier Drug Targeting: The Future of Brain Drug Development", Molecular Interventions, 2003, 3(2):90-105.
Park et al., "Immunoliposomes for Cancer Treatment", Advances in Pharmacology, 1997, 40:399-435.
Park YongS. , "Tumor-Directed Targeting of Liposomes", Bioscience Reports, 2002, 22(2):267-281.
Partridge et al., "The Use of Anti-IgG Monoclonal Antibodies in Mapping the Monocyte Receptor Site on IgG", Molecular Immunology, 1986, 23(12):1365-1372.
Pasternack et al., "Bacterial Pro-Transglutaminase from Streptoverticillium mobaraense—Purification, Characterisation and Sequence of The Zymogen", European Journal of Biochemistry, 1998, 257(3):570-576.
Paul WilliamE. , "Protein and Polypeptide Antigenic Determinants", Fundamental Immunology, 1993, 242:292-296.
Peeters et al., "Production of Antibodies and Antibody Fragments in Plants", Vaccine, 2001, 19:2756-2761.
Peipp et al., "Bispecific Antibodies Targeting Cancer Cells", Biochemical Society Transactions, 2002, 30(4):507-511.
Peltz et al., "Human FcARIII: Cloning, Expression, and Identification of the Chromosomal Locus of Two Fc Receptors for IgG", Proc. Natl. Acad. Sci. (U.S.A.), Feb. 1989, 86(3):1013-1017.
Pereira et al., "Cardiolipin Binding A Light Chain from Lupus-Prone Mice", Biochemistry, 1998, 37:1460-1437.
Perussia et al., "Assays for Antibody-Dependent Cell-Mediated Cytotoxicity (ADCC) and Reverse ADCC (Redirected Cytotoxicity) in Human Natural Killer Cells", Methods in Molecular Biology, Natural Killer Cell Protocols: Cellular and Molecular Methods, 2000, 121:179-192.
Pettersen et al., "CD47 Signals T Cell Death", Journal of Immunology, 1999, 162(12):7031-7040.
Pini et al., "Design and Use of a Phage Display Library Human Antibodies with Subnanomolar Affinity Against a Marker of Angiogensis Eluted from a Two-Dimensional Gel", Journal of Biological Chemistry, 1998, 272(34):21769-21779.
Pizzitola et al., "Chimeric Antigen Receptors Against CD33/CD123 Antigens Efficiently Target Primary Acute Myeloid Leukemia Cells in vivo", Leukemia, Aug. 2014, 28(8):1596-605.

(56) References Cited

OTHER PUBLICATIONS

Pluckthun et al., "New Protein Engineering Approaches to Multivalent and Bispecific Antibody Fragments", Immunotechnology, 1997, 3(2):83-105.
Pollock et al., "Transgenic Milk as A Method for The Production of Recombinant Antibodies", Journal of Immunological Methods, 1999, 231:147-157.
Polson et al., "Antibody-Drug Conjugates Targeted to CD79 for The Treatment of Non-Hodgkin Lymphoma", Blood, 2007, 110(2):616-623.
Poul et al., "Selection of Tumor-Specific Internalizing Human Antibodies from Phage Libraries", Journal of Molecular Biology, 2000, 301:1149-1161.
Prasad et al., "Murine B7-H3 Is A Negative Regulator of T Cells", The Journal of Immunology, 2004, 173:2500-2506.
Presta et al., "Engineering Therapeutic Antibodies for Improved Function", Biochemical Society Transactions, 2002, 30(4):487-490.
Presta et al., "Selection, Design and Engineering of Therapeutic Antibodies", The Journal of Allergy and Clinical Immunology, 2005, 116(4):731-736.
Presta LeonardG., "Engineering Antibodies for Therapy", Current Pharmaceutical Biotechnology, 2002, 3(3):237-256.
Pricop et al., "Differential Modulation of Stimulatory and Inhibitory Fcγ Receptors on Human Monocytes by Th1 and Th2 Cytokines", Journal of Immunology, 2001, 166(1):531-537.
Pulford et al., "A New Monoclonal Antibody (KB61) Recognizing A Novel Antigen Which Is Selectively Expressed on A Subpopulation of Human B Lymphocytes", Immunology, 1986, 57(1):71-76.
Pulford et al., "M6.5: The Immunocytochemical Distribution of CD16, CD32, and CD64 Antigens", Leukocyte Typing V: White cell differentiation antigens, 1995, 817-821.
Qin et al., "Fcγ Receptor IIB On Follicular Dendritic Cells Regulates the B Cell Recall Response", Journal of Immunology, 2000, 164:6268-6275.
Radaev et al., "Recognition of Immunoglobulins by Fcγ Receptors", Molecular Immunology, 2001, 38:1073-1083.
Rader et al., "A Phage Display Approach for Rapid Antibody Humanization: Designed Combinatorial V Gene Libraries", Proceedings of the National Academy of Sciences of the United States of America, 1998, 95:8910-8915.
Rankin et al., "CD32B, The Human Inhibitory Fc-Y Receptor IIB, As A Target for Monoclonal Antibody Therapy of B-Cell Lymphoma", Blood, 2006, 108(7):2384-2391.
Raulet DavidH., "Roles of The NKG2D Immunoreceptor and Its Ligands", Nature Reviews Immunology, Oct. 2003, 3:781-790.
Ravetch et al., "Divergent Roles for Fc Receptors and Complement in Vivo", Annual Review of Immunology, 1998, 16:421-432.
Ravetch et al., "Fc Receptors", Annual Review of Immunology, 1991, 9:457-492.
Ravetch et al., "Fc Receptors: Rubor Redux", Cell, 1994, 78(4):553-560.
Ravetch et al., "IgG Fc receptors", Annual Review of Immunology, 2001, 19:275-290.
Ravetch et al., "Immune Inhibitory Receptors", Science, 2000, 290:84-89.
Reali et al., "IgEs Targeted on Tumor Cells: Therapeutic Activity and Potential in The Design of Tumor Vaccines", Cancer Research, 2001, 61(14):5517-5522.
Reddy et al., "Elimination of Fc Receptor-Dependent Effector Functions of a Modified IgG4 Monoclonal Antibody to Human CD4", Journal of Immunology, 2000, 164:1925-1933.
Redpath et al., "The Influence of The Hinge Region Length in Binding of Human IgG to Human Fcgamma Receptors", Human Immunology, 1998, 59:720-727.
Reff et al., "A Review of Modifications to Recombinant Antibodies: Attempt to Increase Efficacy in Oncology Applications", Critical Reviews in Oncology/Hematology, 2001, 40:25-35.
Reff et al., "Depletion of B Cells in Vivo By A Chimeric Mouse Human Monoclonal Antibody to CD20", Blood, Jan. 15, 1994, 83(2):435-445.
Renders et al., "Engineered CD3 Antibodies for Immunosuppression", Clinical & Experimental Immunology, 2003, 133(3):307-309.
Ridgway et al., "Knobs-Into-Holes Engineering of Antibody CH3 Domains for Heavy Chain Heterodimerization", Protein Engineering, 1996, 9(7):617-621.
Riechmann et al., "Reshaping Human Antibodies for Therapy", Nature, 1988, 332(6162):323-327.
Riemer et al., "Matching of Trastuzumab (Herceptin) Epitope Mimics Onto the Surface of Her-2/Neu—A New Method of Epitope Definition", Molecular Immunology, 2005, 42(9):1121-1124.
Rouard et al., "Fc Receptors as Targets for Immunotherapy", International Reviews of Immunology, 1997, 16(1-2):147-185.
Routledge et al., "The Effect of Aglycosylation On the Immunogenicity of a Humanized Therapeutic CD3 Monoclonal Antibody", Transplantation, 1995, 60(8):847-853.
Rudikoff et al., "Single Amino Acid Substitution Altering Antigen-Binding Specificity", Proceedings of the National Academy of Sciences, 1982, 79:1979-1983.
Saatian et al., "Expression of Genes for B7-H3 and Other T Cell Ligands by Nasal Epithelial Cells During Differentiation and Activation", AJP Lung Cellular and Molecular Physiology, Aug. 2004, 287(1):L217-L225.
Samsom et al., "FcγRIIB Regulates Nasal and Oral Tolerance: A Role for Dendritic Cells", Journal of Immunology, 2005, 174:5279-5287.
Samuelsson et al., "Anti-Inflammatory Activity of IVIG Mediated Through the Inhibitory Fc Receptor", Science, 2001, 291:484-486.
Sarkar et al., "Negative Signaling via FcγRIIB1 in B Cells Blocks Phospholipase Cγ2 Tyrosine Phosphorylation but not Syk or Lyn Activation", Journal of Biological Chemistry, 1996, 271(33):20182-20186.
Sarmay et al., "Ligand Inhibition Studies on the Role of Fc Receptors in Antibody-Dependent Cell-Mediated Cytotoxicity", Molecular Immunology, 1984, 21:43-51.
Sarmay et al., "Mapping and Comparison of the Interaction Sites on the Fc Region of IgG Responsible for Triggering Antibody Dependent Cellular Cytotoxicity (ADCC) Through Different Types of Human Fc Gamma Receptor", Molecular Immunology, 1992, 29:633-639.
Sarmay et al., "The Effect of Synthetic Peptides Corresponding to Fc Sequences in Human IgG1 on Various Steps in the B Cell Activation Pathway", European Journal of Immunology, 1988, 18:289-294.
Sasse et al., "Tubulysins, New Cytostatic Peptides from Myxobacteria Acting on Microtubuli. Production, Isolation, Physico-Chemical and Biological Properties", The Journal of Antibiotics, 2000, 53:879-885.
Sato et al., "Reshaping a Human Antibody to Inhibit the Interleukin 6-dependent Tumor Cell Growth", Cancer Research, 1993, 53:851-856.
Sautes-Fridman et al., "Fc Gamma Receptors: A Magic Link with the Outside World", ASHI Quarterly, 4th Quarter: 2003, 148-151.
Schaffner et al., "Chimeric Interleukin 2 Receptor Alpha Chain Antibody Derivatives with Fused Mu and Gamma Chains Permit Improved Recruitment of Effector Functions", Molecular Immunology, 1995, 32(1):9-20.
Schatton et al., "Identification and Targeting of Cancer Stem Cells", Bioessays, 2009, 31(10):1038-1049.
Schatz et al., "Use of Peptide Libraries to Map the Substrate Specificity of a Peptide-Modifying Enzyme: A 13 Residue Consensus Peptide Specifies Biotinylation in *Escherichia coli*", Bio/Technology, 2000, 11:1138-1143.
Schildbach et al., "Contribution of a Single Heavy Chain Residue to Specificity of an Anti-Digoxin Monoclonal Antibody", Protein Science, 1994, 3:737-749.
Schildbach et al., "Heavy Chain Position 50 is a Determinism of Affinity and Specificity for the Anti-digoxin Antibody 26-10", The Journal of Biological Chemistry, 1993, 268(29):21739-21747.
Schoenfeld et al., "Immunohistochemical Analysis of Chordoma Targeting B7H3 and HMW-MAA", Orthopaedic Journal at Harvard Medical School, 2009, 11:136-140.

(56) References Cited

OTHER PUBLICATIONS

Scholl et al., "Is Colony-Stimulating Factor-1 A Key Mediator of Breast Cancer Invasion and Metastasis?", Molecular Carcinogenesis, 1993, 7(4):207-211.
Schuna et al., "New Drugs for The Treatment of Rheumatoid Arthritis", American Journal of Health—System Pharmacy, 2000, 57:225-237.
Scopelliti et al., "Therapeutic Implications of Cancer Initiating Cells", Expert Opinion on Biological Therapy, 2009, 9(8):1005-1016.
Seaver SallyS., "Monoclonal Antibodies in Industry: More Difficult than Originally Thought", Genetic Engineering News, 1994, 14(14):2 pages.
Sedmak et al., "Expression of IgG Fc Receptor Antigens in Placenta and on Endothelial Cells in Humans", The American Journal of Pathology, 1991, 138(1):175-181.
Selvaraj et al., "Functional Regulation of Human Neutrophil Fc γ Receptors", Immunologic Research, 2004, 29(1-3):219-230.
Sensel et al., "Amino Acid Differences in the N-Terminus of C(H)2 Influence the Relative Abilities of IgG2 and IgG3 to Activate Complement", Molecular Immunology, 1997, 34:1019-1029.
Senter et al., "The Discovery and Development of Brentuximab Vedotin for Use in Relapsed Hodgkin Lymphoma and Systemic Anaplastic Large Cell Lymphoma", Nature Biotechnology, 2012, 30:631-637.
Sharpe et al., "The B7-CD28 Superfamily", Nature Reviews Immunology, 2002, 2:116-126.
Shaw et al., "Characterization of A Mouse-Human Chimeric Monoclonal Antibody (17-1A) To A Colon Cancer Tumor-Associated Antigen", Journal of Immunology, 1987, 138(12):4534-4538.
Shearman et al., "Construction, Expression and Characterization of Humanized Antibodies Directed Against the Human α/β T Cell Receptor", The Journal of Immunology, Dec. 1991, 147(12):4366-4373.
Shearman et al., "Construction, Expression, and Biologic Activity of Murine/human Chimeric Antibodies with Specificity for the Human α/β T Cell Receptor", The Journal of Immunology, Feb. 1991, 146(3):928-935.
Shields et al., "High Resolution Mapping of the Binding Site on Human IgG1 for FcγRI, FcγRII, FcγRIII, and FcRn and Design of IgG1 Variants with Improved Binding to the FcγR", Journal of Biological Chemistry, 2001, 276:6591-6604.
Shields et al., "Lack of Fucose On Human IgG1 N-Linked Oligosaccharide Improves Binding to Human Fc.Gamma. RIII and Antibody-Dependent Cellular Toxicity", Journal of Biological Chemistry, 2002, 277(30):26733-26740.
Shopes et al., "Recombinant Human IgG1-Murine Ige Chimeric Ig. Construction, Expression, and Binding to Human Fc Gamma Receptors", Journal of Immunology, 1990, 145:3842-3848.
Shopes Bob, "A Genetically Engineered Human IgG Mutant with Enhanced Cytolytic Activity", Journal of Immunology, 1992, 148:2918-2922.
Shopes Bob, "A Genetically Engineered Human IgG with Limited Flexibility Fully Initiates Cytolysis via Complement", Molecular Immunology, 1993, 30:603-609.
Shusta et al., "Directed Evolution of a Stable Scaffold for T-Cell Receptor Engineering", Nature Biotechnology, 2000, 18:754-759.
Shusta et al., "Increasing the Secretory Capacity of *Saccharomyces cerevisiae* for Production of Single-Chain Antibody Fragments", Nature Biotechnology, 1998, 16:773-777.
Shusta et al., "Yeast Polypeptide Fusion Surface Display Levels Predict Thermal Stability and Soluble Secretion Efficiency", Journal of Molecular Biology, 1999, 292:949-956.
Siberil et al., "Molecular Aspects of Human FcgammaR Interactions with IgG Functional and Therapeutic Consequences", Immunology Letters, 2006, 106:111-118.
Skolnick et al., "From Genes to Protein Structure and Function: Novel Aspects of Computational Approaches in the Genomic Era", Trends in Biotechnology, 2000, 18:34-39.

Sleister et al., "Subtractive Immunization; A Tool for The Generation of Discriminatory Antibodies to Proteins of Similar Sequence", Journal of Immunological Methods, 2002, 261:213-220.
Sloan et al., "Targeting HIV Reservoir in Infected CD4 T Cells by Dual-Affinity Re-targeting Molecules (DARTs) that Bind HIV Envelope and Recruit Cytotoxic T Cells", PLOS Pathogens, doi: 10.1371-journal.ppat.1005233, 2015, 11(11):e1005233.
Smith et al., "Recombinant Polymeric IgG: An Approach to Engineering More Potent Antibodies", Bio/Technology, 1994, 12:683-688.
Smith-Garvin et al., "T Cell Activation", Annual Review of Immunology, 2009, 27:591-619.
Sondermann et al., "Crystal Structure of The Soluble Form of The Human Fcgamma-Receptor IIb: A New Member of The Immunoglobulin Superfamily At 1.7 A Resolution", The EMBO Journal, 1999, 18:1095-1103.
Sondermann et al., "Molecular Basis for Immune Complex Recognition: A Comparison of Fc-Receptor Structures", Journal of Molecular Biology, 2001, 309:737-749.
Sondermann et al., "The 3.2-A Crystal Structure of The Human IgG1 Fc Fragment-FcγRIII Complex", Nature, 2000, 406:267-273.
Sondermann et al., "The Structure of Fc Receptor/Ig Complexes: Considerations on Stoichiometry and Potential Inhibitors", Immunology Letters, 2002, 82:51-56.
St. Clair EW., "Novel Targeted Therapies for Autoimmunity", Current Opinion in Immunology, Dec. 2009, 21(6):648-657.
Staerz et al., "Hybrid Antibodies Can Target Sites for Attack by T Cells", Nature, 1985, 314:628-631.
Stammers et al., "BTL-II: A Polymorphic Locus with Homology to The Butyrophilin Gene Family, Located at The Border of The Major Histocompatibility Complex Class II and Class III Regions in Human and Mouse", Immunogenetics, 2000, 51:373-382.
Stancovski et al., "Mechanistic Aspects of The Opposing Effects of Monoclonal Antibodies to The ERBB2 Receptor on Tumor Growth", Proceedings of the National Academy of Sciences of the United States of America, 1991, 88(19):8691-8695.
Stavenhagen et al., "Enhancing the Potency of Therapeutic Antibodies via Fc Optimization", Advances in Enzyme Regulation, 2008, 48:152-164.
Stavenhagen et al., "Fc Optimization of Therapeutic Antibodies Enhances Their Ability to Kill Tumor Cells In Vitro And Controls Tumor Expansion In Vivo Via Low-Affinity Activating Fcγ Receptors", Cancer Research, 2007, 67(18):8882-8890.
Stefanescu et al., "Inhibitory Fc Gamma Receptors: From Gene to Disease", Journal of Clinical Immunology, 2004, 24(4):315-326.
Steinberger et al., "Molecular Characterization of Human 4Ig-B7-H3, A Member of The B7 Family with Four Ig-Like Domains", Journal of Immunology, 2004, 172(4):2352-2359.
Steinmetz et al., "Isolation, Crystal and Solution Structure Determination, and Biosynthesis of Tubulysins—Powerful Inhibitors of Tubulin Polymerization from Myxobacteria", Angewandte Chemie International Edition, 2004, 43:4888-4892.
Stephan et al., "Distribution and Function of The Adhesion Molecule BEN During Rat Development", Developmental Biology, 1999, 212:264-277.
Stephan et al., "Selective Cloning of Cell Surface Proteins Involved in Organ Development: Epithelial Glycoprotein Is Involved in Normal Epithelial Differentiation", Endocrinology, 1999, 140:5841-5854.
Steplewski et al., "Biological Activity of Human-Mouse IgG1, IgG2, IgG3, and IgG4 Chimeric Monoclonal Antibodies with Antitumor Specificity", Proceedings of the National Academy of Sciences of the United States of America, 1988, 85:4852-4856.
Stopforth et al., "Regulation of Monoclonal Antibody Immunotherapy by FcγRIIB", Journal of Clinical Immunology, Feb. 27, 2016, 36(Suppl 1):S88-S94.
Strohmeier et al., "Role of The FcγR Subclasses FcγRII and FcγRIII in The Activation of Human Neutrophils by Low and High Valency Immune Complexes", Journal of Leukocyte Biology, 1995, 58:415-422.
Su et al., "Expression Profile of FcγRIIB On Leukocytes and Its Dysregulation in Systemic Lupus Erythematosus", Journal of Immunology, 2007, 178:3272-3280.

(56) References Cited

OTHER PUBLICATIONS

Subudhi et al., "The Balance of Immune Responses: Costimulation Verse Coinhibition", Journal of Molecular Medicine, 2005, 83:193-202.
Suh et al., "The B7 Family Member B7-H3 Preferentially Down-Regulates T Helper Type 1-Mediated Immune Responses", Nature Immunology, 2005, 4(9):899-906.
Sun et al., "B7-H3 and B7-H4 Expression in Non-small-cell Lung Cancer", Lung Cancer, 2006, 53(2):143-151.
Sun et al., "Characterization of Mouse and Human B7-H3 Genes", Journal of Immunology, 2002, 168:6294-6297.
Sun et al., "Mechanisms Contributing to T Cell Receptor Signaling and Assembly Revealed by The Solution Structure of An Ectodomain Fragment of The CD3ε:γ Heterodimer", Cell, Jun. 29, 2001, 105(7):913-923.
Swinnen et al., "OKT3 Monoclonal Antibodies Induce Interleukin-6 and Interleukin-10: A Possible Cause of Lymphoproliferative Disorders Associated with Transplantation", Current Opinion in Nephrology and Hypertension, Jul. 1993, 2(4):670-678.
Swisher et al., "The Many Faces of FcγRI: Implications for Therapeutic Antibody Function", Immunological Review, Nov. 2015, 268(1):160-174.
Sylvestre et al., "A Dominant Role for Mast Cell Fc Receptors in The Arthus Reaction", Immunity, 1996, 5:387-390.
Sylvestre et al., "Fc Receptors Initiate the Arthus Reaction: Redefining the Inflammatory Cascade", Science, 1994, 265:1095-1098.
Takai et al., "Augmented Humoral and Anaphylactic Responses in Fc Gamma RII-Deficient Mice", Nature, 1996, 379:346-349.
Takai et al., "Fc Receptors as Potential Targets for the Treatment of Allergy, Autoimmune Disease and Cancer", Current Drug Targets—Immune, Endocrine & Metabolic Disorders, 2003, 3:187-197.
Takai et al., "FcR Gamma Chain Deletion Results in Pleiotrophic Effector Cell Defects", Cell, 1994, 76:519-529.
Takai Toshiyuki, "Roles of Fc Receptors in Autoimmunity", Nature Reviews, 2002, 2:580-592.
Takemura et al., "Construction of A Diabody (Small Recombinant Bispecific Antibody) Using A Refolding System", Protein Engineering, 2000, 13(8):583-588.
Tam et al., "A Bispecific Antibody Against Human IgE and Human FC.gamma.RII That Inhibits Antigen-Induced Histamine Release by Human Mast Cells and Basophils", Allergy, 2004, 59:772-780.
Tamm et al., "The IgG Binding Site of Human FcγRIIIb Receptor Involves CC' and FG Loops of The Membrane-Proximal Domain", Journal of Biological Chemistry, 1996, 271:3659-3666.
Tang et al., "Biosynthesis of A Highly Stable Coiled-Coil Protein Containing Hexafluoroleucine in An Engineered Bacterial Host", Journal of the American Chemical Society, 2001, 123(44):11089-11090.
Tao et al., "Structural Features of Human Immunoglobulin G That Determine Isotype-Specific Differences in Complement Activation", Journal of Experimental Medicine, 1993, 178:661-667.
Tao et al., "Studies of Aglycosylated Chimeric Mouse-Human IgG. Role of Carbohydrate in The Structure and Effector Functions Mediated by The Human IgG Constant Region", Journal of Immunology, 1989, 143(8):2595-2601.
Tao et al., "The Differential Ability of Human IgG1 and IgG4 to Activate Complement Is Determined by the COOH-Terminal Sequence of The CH2 Domain", Journal of Experimental Medicine, 1991, 173:1025-1028.
Tekle et al., "B7-H3 Contributes to The Metastatic Capacity of Melanoma Cells by Modulation of Known Metastasis-Associated Genes", International Journal of Cancer, 2012, 130:2282-2290.
Tempest et al., "Reshaping A Human Monoclonal Antibody to Inhibit Human Respiratory Syncytial Virus Infection in Vivo", Bio-Technology, 1991, 9:266-271.
Tercel et al., "The Cytotoxicity of Duocarmycin Analogues Is Mediated Through Alkylation of DNA, Not Aldehyde Dehydrogenase 1: A Comment", Angewandte Chemie International Edition, 2013, 52(21):5442-5446.

Tettamanti et al., "Targeting of Acute Myeloid Leukaemia By Cytokine-induced Killer Cells Redirected with A Novel CD123-specific Chimeric Antigen Receptor", British Journal of Haematology, May 2013, 161(3):389-401.
Thepen et al., "Fcγ Receptor 1 (CD64), a Target Beyond Cancer", Current Pharmaceutical Design, Aug. 2009, 15(23):2712-2718.
Thomas et al., "Molecular Immunology Lessons from Therapeutic T-Cell Receptor Gene Transfer", Immunology, 2010, 129(2):170-177.
Tivol et al., "Loss of CTLA-4 Leads to Massive Lymphoproliferation and Fatal Multiorgan Tissue Destruction, Revealing A Critical Negative Regulatory Role of CTLA-4", Immunity, 1995, 3(5):541-547.
Todorovska et al., "Design and Application of Diabodies, Triabodies and Tetrabodies for Cancer Targeting", Journal of Immunological Methods, 2001, 248(1-2):47-66.
Tran et al., "Interactions of T Cells with Fibroblast-Like Synoviocytes: Role of The B7 Family Costimulatory Ligand B7-H3", Journal of Immunology, 2008, 180(5):2989-2998.
Trindandapani et al., "Regulated Expression and Inhibitory Function of FcγRIIB in Human Monocytic Cells", Journal of Biological Chemistry, 2002, 277(7):5082-5089.
Umana et al., "Engineered Glycoforms of An Antineuroblastoma Igg1 with Optimized Antibody-Dependent Cellular Cytotoxic Activity", Nature Biotechnology, 1999, 17(2):176-180.
Vaccaro et al., "Divergent Activities of An Engineered Antibody in Murine and Human Systems Have Implications for Therapeutic Antibodies", Proceedings of the National Academy of Sciences of the United States of America, 2006, 103(49):18709-18714.
Vajdos et al., "Comprehensive Functional Maps of the Antigen-Binding Site of an Anti-ErbB2 Antibody Obtained with Shotgun Scanning Mutagenesis", Journal of Molecular Biology, 2002, 320:415-428.
Van Antwerp et al., "Fine Affinity Discrimination by Yeast Surface Display and Flow Cytometry", Biotechnology Progress, 2000, 16:31-37.
Van De Donk et al., "Brentuximab Vedotin", MAbs, 2012, 4:458-465.
Van De Winkel et al., "CD32 Cluster Workshop Report", Leukocyte Typing V: White Cell Differentiation Antigens, 1995, 823-825.
Van Den Beuken et al., "Building Novel Binding Ligands to B7.1 and B7.2 Based on Human Antibody Single Variable Light Chain Domains", Journal of Molecular Biology, 2001, 310:591-601.
Van Hest et al., "Protein-Based Materials, Toward A New Level of Structural Control", Chemical Communications, 2001, 19:1897-1904.
Van Nguyen et al., "Colony Stimulating Factor-1 is Required to Recruit Macrophages into the Mammary Gland to Facilitate Mammary Ductal Outgrowth", Developmental Biology, 2002, 247(1):11-25.
Van Sorge et al., "FcγR Polymorphisms: Implications for Function, Disease Susceptibility and Immunotherapy", Tissue Antigens, Mar. 2003, 61(3):189-202.
Vandenborre et al., "Interaction of CTLA-4 (CD152) with CD80 Or CD86 Inhibits Human T-Cell Activation", Immunology, 1999, 98(3):413-421.
Veenstra et al., "B7-H3 expression in Donor T Cells and Host Cells Negatively Regulates Acute Graft-Versus-Host Disease Lethality", Blood, 2015, 125:3335-3346.
Vely et al., "A New Set of Monoclonal Antibodies Against Human FcγRII (CD32) and FcγRIII (CD16): Characterization and Use in Various Assays", Hybridoma, 1997, 16(6):519-528.
Verhoeyen et al., "Reshaping Human Antibodies: Grafting an Antilysozyme Activity", Science, 1988, 239:1534-1536.
Veri et al., "Monoclonal Antibodies Capable of Discriminating the Human Inhibitory Fcgamma-Receptor IIB (CD32B) From the Activating Fcgamma-Receptor IIA (CD32A): Biochemical, Biological and Functional Characterization", Immunology, 2007, 121(3):392-404.
Veri et al., "Therapeutic Control of B Cell Activation Via Recruitment of Fcγ Receptor IIb (CD32B) Inhibitory Function with A Novel Bispecific Antibody Scaffold", Arthritis & Rheumatology, 2010, 62(7):1933-1943.

(56) References Cited

OTHER PUBLICATIONS

Vidarte et al., "Serine 132 is the C3 Covalent Attachment Point on the CH1 Domain of Human Igg1", Journal of Biological Chemistry, 2001, 276:38217-38233.
Viglietta et al., "Modulating Co-Stimulation", Neurotherapeutics, 2007, 4:666-675.
Vingerhoeds et al., "Immunoliposomes in Vivo", Immunomethods, 1994, 4(3):259-272.
Vitetta et al., "Immunology. Considering Therapeutic Antibodies", Science, 2006, 313:308-309.
Von Koskull et al., "Identification of Cells from Fetal Bladder Epithelium in Human Amniotic Fluid", Human Genetics, 1984, 65:262-267.
Vuist et al., "Two Distinct Mechanisms of Antitumor Activity Mediated by the Combination of Interleukin 2 and Monoclonal Antibodies", Cancer Research, 1990, 50:5767-5772.
Wallick et al., "Glycosylation of a VH Residue of a Monoclonal Antibody Against a(1→6) Dextran Increases Its Affinity for Antigen", Journal of Experimental Medicine, 1988, 168(3):1099-1109.
Wang et al., "B7-H3 is Overexpressed in Patients Suffering Osteosarcoma and Associated Tumor Aggressiveness and Metastasis", PLOS One, 2013, 8(8):8 pages.
Wang et al., "B7-H3 Mediated Tumor Immunology: Friend or Foe?", International Journal of Cancer, 2013, 134(12):2764-2771.
Wang et al., "Co-Signaling Molecules of The B7-CD28 Family in Positive and Negative Regulation of T Lymphocyte Responses", Microbes and Infection, 2004, 6:759-766.
Wang et al., "Expanding the Genetic Code", Chemical Communications, 2002, 1:1-11.
Wang et al., "Expanding the Genetic Code of *Escherichia coli*", Science, 2001, 292:498-500.
Ward et al., "Building Activities of a Repertoire of Single Immunoglobulin Variable Domains Secreted from *Escherichia coli*", Nature, 1989, 341:544-546.
Ward et al., "The Effector Functions of Immunoglobulins: Implications for Therapy", Therapeutic Immunology, 1995, 2:77-94.
Warmerdam et al., "Molecular Basis for A Polymorphism of Human Fcγ Receptor II (CD32)", Journal of Experimental Medicine, 1990, 172(1):19-25.
Warren et al., "NK Cells and Apoptosis", Immunology and Cell Biology, 1999, 77(1):64-75.
Weinrich et al., "Epitope Mapping of New Monoclonal Antibodies Recognizing Distinct Human FCRII (CD32) Isoforms", Hybridoma, 1996, 15(2):109-116.
Weng et al., "Two Immunoglobulin G Fragment C Receptor Polymorphisms Independently Predict Response to Rituximab in Patients with Follicular Lymphoma", Journal of Clinical Oncology, 2003, 21:3940-3947.
Wheeler CosetteM., "Preventive Vaccines for Cervical Cancer", Salud Pública de México, 1997, 39:1-9.
White et al., "FcγRIIB as a Key Determinant of Agonistic Antibody Efficacy", Current Topics in Microbiology and Immunology, 2014, 382:355-372.
Wiener et al., "Differences Between the Activities of Human Monoclonal Igg1 and Igg3 Anti-D Antibodies of the Rh Blood Group System in their Abilities to Mediate Effector Functions of Monocytes", Immunology, 1988, 65:159-163.
Willemsen et al., "Selection of Human Antibody Fragments Directed Against Tumor T-cell Epitopes for Adoptive T-cell Therapy", Cytometry A., Nov. 2008, 73(11):1093-1099.
Wing et al., "Mechanism of First-Dose Cytokine-Release Syndrome by CAMPATH 1-H: Involvement of CD16 (FcγRIII) and CD11a/CD18 (LFA-1) on NK Cells", Journal of Clinical Investigation, 1996, 98:2819-2826.
Wingren et al., "Comparison of Surface Properties of Human IgA, IgE, IgG and IgM Antibodies with Identical and Different Specificities", Scandinavian Journal of Immunology, 1996, 44:430-436.
Winter et al., "Making Antibodies by Phage Display Technology", Annual Review of Immunology, 1994, 12:433-455.
Winter et al., "Man-made Antibodies", Nature, 1991, 349:293-299.
Wittrup KD., "Protein Engineering by Cell-Surface Display", Current Opinion in Biotechnology, 2001, 12:395-399.
Wittrup KD., "The Single Cell as A Microplate Well", Nature Biotechnology, 2000, 18:1039-1040.
Wolff et al., "Monoclonal Antibody Homodimers: Enhanced Antitumor Activity in Nude Mice", Cancer Research, 1993, 53:2560-2565.
Woof et al., "Localisation of The Monocyte-Binding Region on Human Immunoglobulin G", Molecular Immunology, 1986, 23:319-330.
Woyke et al., "Effect of Auristatin PHE on Microtubule Integrity and Nuclear Localization in Cryptococcus Neoformans", Antimicrobial Agents and Chemotherapy, 2001, 45:3580-3584.
Wright et al., "Effect of Glycosylation on Antibody Function: Implications for Genetic Engineering", Trends in Biotechnology, 1997, 15(1):26-32.
Wu et al., "A Novel Polymorphism of FcγRIIIA (CD16) Alters Receptor Function and Predisposes to Autoimmune Disease", Journal of Clinical Investigation, 1997, 100:1059-1070.
Wu et al., "Humanization of a Murine Monoclonal Antibody by Simultaneous Optimization of Framework and CDR Residues", Journal of Molecular Biology, 1999, 294:151-162.
Wu et al., "Multimerization of a Chimeric Anti-CD20 Single Chain Fv-Fv Fusion Protein Is Mediated Through Variable Domain Exchange", Protein Engineering, 2001, 14(12):1025-1033.
Wu et al., "Receptor-Mediated In Vitro Gene Transformation by A Soluble DNA Carrier System", Journal of Biological Chemistry, 1987, 262(10):4429-4432.
Wucherpfennig et al., "Structural Biology of the T-cell Receptor: Insights into Receptor Assembly, Ligand Recognition, and Initiation of Signaling", Cold Spring Harbor Perspectives in Biology, Apr. 2010, 2(4):14 pages.
Xiang et al., "Study of B72.3 Combining Sites by Molecular Modeling and Site-Directed Mutagenesis", Protein Engineering, 2000, 13(5):339-344.
Xie et al., "A New Format of Bispecific Antibody: Highly Efficient Heterodimerization, Expression and Tumor Cell Lysis", Journal of Immunological Methods, 2005, 296:95-101.
Xu et al., "Antibody-Induced Growth Inhibition Is Mediated Through Immunochemically and Functionally Distinct Epitopes on The Extracellular Domain of the c-erbB-2 (HER-2/neu) Gene product p185", International Journal of Cancer, 1993, 53(3):401-408.
Xu et al., "FcγRs Modulate Cytotoxicity of Anti-Fas Antibodies: Implications for Agonistic Antibody Based Therapeutics", The Journal of Immunology, 2003, 171:562-568.
Xu et al., "In Vitro Characterization of Five Humanized OKT3 Effector Function Variant Antibodies", Cellular Immunology, 2000, 200:16-26.
Xu et al., "MicroRNA miR-29 Modulates Expression of Immunoinhibitory Molecule B7-H3: Potential Implications for Immune Based Therapy of Human Solid Tumors", Cancer Research, 2009, 69(15):5275-6281.
Xu et al., "Residue at Position 331 in The IgG1 and IgG4 CH2 Domains Contributes to Their Differential Ability to Bind and Activate Complement", Journal of Biological Chemistry, 1994, 269:3469-3474.
Xu et al., "Soluble Mouse B7-H3 Down-Regulates Dendritic Cell Stimulatory Capacity to Allogenic T Cell Proliferation and Production of IL-2 and IFN-γ", Cellular & Molecular Immunology, 2006, 3(3):235-240.
Yao et al., "Methods to Design and Synthesize Antibody-Drug Conjugates (ADCs)", International Journal of Molecular Sciences, Feb. 2, 2016, 17(2):16 pages.
Yeung et al., "Quantitative Screening of Yeast Surface-Displayed Polypeptide Libraries by Magnetic Bead Capture", Biotechnology Progress, 2002, 18:212-220.
Yi et al., "Fine Tuning the Immune Response Through B7-H3 and B7-H4", Immunological reviews, 2009, 229:145-151.
Yokoyama et al., "Properties and Applications of Microbial Transglutaminase", Applied Microbiology and Biotechnology, 2004, 64:447-454.

(56) References Cited

OTHER PUBLICATIONS

Youinou et al., "Pathogenic Effects of anti-Fc Gamma Receptor IIIb (CD16) on Polymorphonuclear Neutrophils in Non-Organ-Specific Autoimmune Diseases", Autoimmunity Reviews, Feb. 2002, 1(1-2):13-19.

Zang et al., "B7-H3 and B7x Are Highly Expressed in Human Prostate Cancer and Associated with Disease Spread and Poor Outcome", Proceedings of the National Academy of Sciences of the United States of America, 2007, 104(49):19458-19463.

Zang et al., "B7x: A Widely Expressed B7 Family Member That Inhibits T Cell Activation", Proceedings of the National Academy of Sciences of the United States of America, 2003, 100:10388-10392.

Zang et al., "The B7 Family and Cancer Therapy: Costimulation and Coinhibition", Clinical Cancer Research, Sep. 15, 2007, 13(18):5271-5279.

Zang et al., "Tumor Associated Endothelial Expression of B7-H3 Predicts Survival in Ovarian Carcinomas", Modern Pathology, 2010, 23(8):1104-1112.

Zeidler et al., "The Fc-Region of A New Class of Intact Bispecific Antibody Mediates Activation of Accessory Cells and NK Cells and Induces Direct Phagocytosis of Tumour Cells", British Journal of Cancer, 2000, 83:261-266.

Zhang et al., "B7-H3: Another Molecule Marker for Mo-DCs?", Cellular and Molecular Immunology, 2005, 2(4):307-311.

Zhang et al., "Soluble CD276 (B7-H3) Is Released from Monocytes, Dendritic Cells and Activated T Cells and Is Detectable in Normal Human Serum", Immunology, 2008, 123:538-546.

Zhao et al., "Relation of B7-H3 Molecule Expression in Multiple Myeloma with Poor Prognosis and Bone Destruction", Zhongguo Shi Yan Xue Ye Xue Za Zhi., Jun. 2013, 21(3):637-42.

Zhou et al., "CD32B Is Highly Expressed on Clonal Plasma Cells from Patients with Systemic Light-Chain Amyloidosis and Provides A Target for Monoclonal Antibody-Based Therapy", Blood doi:10.1182/blood-2007-11-125526, 2008, 5 pages.

Zhu et al., "Remodeling domain interfaces to enhance heterodimer formation", Protein Science, 1997, 6:781-788.

Zola et al., "CD32 (FcgammaRII)", Journal of Biological Regulators & Homeostatic Agents, 2000, 14(4):311-316.

Zuckier et al., "Chimeric Human-Mouse IgG Antibodies with Shuffled Constant Region Exons Demonstrate That Multiple Domains Contribute to in Vivo Half-Life", Cancer Research, 1998, 58:3905-3908.

hmAb-C-DUBA - Calu-6 Cells Single Dose *in vivo* Efficacy Study hmAb-C-DUBA – PA-1 Cells Single Dose *in vivo* Efficacy Study hmAb-C-DUBA — A375.S2 Melanoma Cells Single Dose *in vivo* Efficacy Study MDA-MB-468 Mammary Fat Pad Xenografts for Anti-B7-H3-DUBA (6 mg/kg Single Dose Data)

MDA-MB-468 Mammary Fat Pad Xenografts for Anti-B7-H3-DUBA
(3 mg/kg Single Dose Data)

MDA-MB-468 Mammary Fat Pad Xenografts for Anti-B7-H3-DUBA
(3 mg/kg Triplicate Dose Data)

SEQUENCE LISTING

```
<160> NUMBER OF SEQ ID NOS: 106

<210> SEQ ID NO 1
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Human IgG CL Kappa Domain

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

-continued

```
<210> SEQ ID NO 2
<211> LENGTH: 104
<212> TYPE: PRT
<213> ORGANISM: Homo sapiens
<220> FEATURE:
<221> NAME/KEY: MISC_FEATURE
<222> LOCATION: (1)..(104)
<223> OTHER INFORMATION: Human IgG CL Lambda Domain

<400> SEQUENCE: 2

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 3
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG1 CH1 Domain

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 4
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG2 CH1 Domain

<400> SEQUENCE: 4

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 5
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG3 CH1 Domain

<400> SEQUENCE: 5

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 6
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG4 CH1 Domain

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

Arg Val

<210> SEQ ID NO 7
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Human IgG1 Hinge Domain

<400> SEQUENCE: 7

Glu Pro Lys Ser Cys Asp Lys Thr His Thr Cys Pro Pro Cys Pro
1               5                   10                  15

<210> SEQ ID NO 8
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human IgG2 Hinge Domain

<400> SEQUENCE: 8

Glu Arg Lys Cys Cys Val Glu Cys Pro Pro Cys Pro
1               5                   10

<210> SEQ ID NO 9
<211> LENGTH: 62
<212> TYPE: PRT
<213> ORGANISM: Homo sapiens
<220> FEATURE:
<221> NAME/KEY: MISC_FEATURE
<222> LOCATION: (1)..(62)
<223> OTHER INFORMATION: Human IgG3 Hinge Domain

<400> SEQUENCE: 9

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro Glu
            35                  40                  45

Pro Lys Ser Cys Asp Thr Pro Pro Pro Cys Pro Arg Cys Pro
        50                  55                  60

<210> SEQ ID NO 10
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human IgG4 Hinge Domain

<400> SEQUENCE: 10

Glu Ser Lys Tyr Gly Pro Pro Cys Pro Ser Cys Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: S228P-Stabilized Human IgG4 Hinge Domain

```
<400> SEQUENCE: 11

Glu Ser Lys Tyr Gly Pro Pro Cys Pro Pro Cys Pro
1               5                   10

<210> SEQ ID NO 12
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Human IgG1 CH2-CH3 Domain
<220> FEATURE:
<221> NAME/KEY: MISC_FEATURE
<222> LOCATION: (217)..(217)
<223> OTHER INFORMATION: X is Lysine or Absent

<400> SEQUENCE: 12

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 13
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: Human IgG2 CH2-CH3 Domain
<220> FEATURE:
<221> NAME/KEY: MISC_FEATURE
<222> LOCATION: (216)..(216)
<223> OTHER INFORMATION: X is Lysine or Absent

<400> SEQUENCE: 13
```

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val His Gln
65              70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Xaa
    210                 215

<210> SEQ ID NO 14
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Human IgG3 CH2-CH3 Domain
<220> FEATURE:
<221> NAME/KEY: MISC_FEATURE
<222> LOCATION: (217)..(217)
<223> OTHER INFORMATION: X is Lysine or Absent

<400> SEQUENCE: 14

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65              70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

```
Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
            195                 200                 205

Lys Ser Leu Ser Leu Ser Pro Gly Xaa
            210                 215

<210> SEQ ID NO 15
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Human IgG4 CH2-CH3 Domain
<220> FEATURE:
<221> NAME/KEY: MISC_FEATURE
<222> LOCATION: (217)..(217)
<223> OTHER INFORMATION: X is Lysine or Absent

<400> SEQUENCE: 15

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Xaa
            210                 215
```

<210> SEQ ID NO 16
<211> LENGTH: 534
<212> TYPE: PRT
<213> ORGANISM: Homo sapiens
<220> FEATURE:
<221> NAME/KEY: MISC_FEATURE
<222> LOCATION: (1)..(534)
<223> OTHER INFORMATION: Human 4Ig Form of B7-H3

<400> SEQUENCE: 16

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
```

```
            355                 360                 365
Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530

<210> SEQ ID NO 17
<211> LENGTH: 316
<212> TYPE: PRT
<213> ORGANISM: Homo sapiens
<220> FEATURE:
<221> NAME/KEY: MISC_FEATURE
<222> LOCATION: (1)..(316)
<223> OTHER INFORMATION: Human 2Ig Form of B7-H3

<400> SEQUENCE: 17

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175
```

```
Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
                260                 265                 270

Lys Ile Lys Gln Ser Cys Glu Glu Asn Ala Gly Ala Glu Asp Gln
                275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315
```

```
<210> SEQ ID NO 18
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: VL Domain of Murine Anti-B7-H3 Antibody "mAb-C"

<400> SEQUENCE: 18
```

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Ser Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Thr Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Arg Tyr Tyr Cys Gln His His Tyr Gly Thr Pro Pro
                85                  90                  95

Trp Thr Phe Gly Gly Gly Thr Asn Leu Glu Ile Lys
            100                 105
```

```
<210> SEQ ID NO 19
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: VH Domain of Murine Anti-B7-H3 Antibody "mAb-C"

<400> SEQUENCE: 19
```

```
Glu Val Gln Gln Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30
```

```
Gly Met Ser Trp Val Arg Gln Thr Pro Asp Lys Arg Leu Glu Trp Val
            35                  40                  45

Ala Thr Ile Asn Ser Gly Gly Ser Asn Thr Tyr Tyr Pro Asp Ser Leu
 50                      55                  60

Lys Gly Arg Phe Thr Ile Ser Arg Asp Asn Ala Lys Asn Thr Leu Tyr
 65                  70                  75                  80

Leu Gln Met Arg Ser Leu Lys Ser Glu Asp Thr Ala Met Tyr Tyr Cys
                 85                  90                  95

Ala Arg His Asp Gly Gly Ala Met Asp Tyr Trp Gly Gln Gly Thr Ser
                100                 105                 110

Val Thr Val Ser Ser
            115
```

<210> SEQ ID NO 20
<211> LENGTH: 108
<212> TYPE: PRT
<213> ORGANISM: Artificial Sequence
<220> FEATURE:
<223> OTHER INFORMATION: VL Domain of Humanized Anti-B7-H3 Antibody
      "hmAb-C"

<400> SEQUENCE: 20

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Ile Tyr Ser Tyr
            20                  25                  30

Leu Ala Trp Tyr Gln Gln Lys Pro Gly Lys Ala Pro Lys Leu Leu Val
            35                  40                  45

Tyr Asn Thr Lys Thr Leu Pro Glu Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Gly Thr Pro Pro
                 85                  90                  95

Trp Thr Phe Gly Gln Gly Thr Arg Leu Glu Ile Lys
                100                 105
```

<210> SEQ ID NO 21
<211> LENGTH: 117
<212> TYPE: PRT
<213> ORGANISM: Artificial Sequence
<220> FEATURE:
<223> OTHER INFORMATION: VH Domain of Humanized Anti-B7-H3 Antibody
      "hmAb-C"

<400> SEQUENCE: 21

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
            35                  40                  45

Ala Thr Ile Asn Ser Gly Gly Ser Asn Thr Tyr Tyr Pro Asp Ser Leu
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ala Arg His Asp Gly Gly Ala Met Asp Tyr Trp Gly Gln Gly Thr Thr
            100                 105                 110

Val Thr Val Ser Ser
        115

<210> SEQ ID NO 22
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of Murine Anti-B7-H3 Antibody "mAb-D"

<400> SEQUENCE: 22

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Gln Gly His Ser Pro Glu Ala Leu Ile
        35                  40                  45

Tyr Ser Ala Ser Tyr Arg Tyr Ser Gly Val Pro Ala Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Gly Gly Thr Lys Leu Glu Ile Lys
            100                 105

<210> SEQ ID NO 23
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Light Chain CDR1 of Antibody mAb-D

<400> SEQUENCE: 23

Lys Ala Ser Gln Asn Val Asp Thr Asn Val Ala
1               5                   10

<210> SEQ ID NO 24
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Light Chain CDR2 of Antibody mAb-D

<400> SEQUENCE: 24

Ser Ala Ser Tyr Arg Tyr Ser
1               5

<210> SEQ ID NO 25
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Light Chain CDR3 of Antibody mAb-D
```

```
<400> SEQUENCE: 25

Gln Gln Tyr Asn Asn Tyr Pro Phe Thr
1               5

<210> SEQ ID NO 26
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VL Domain of Murine Anti-B7-H3 Antibody "mAb-D"

<400> SEQUENCE: 26

Asp Val Gln Leu Ala Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Gly Thr Ile Tyr Tyr Ala Asp Thr Val
    50                  55                  60

Lys Gly Arg Phe Thr Ile Ser Arg Asp Asn Pro Lys Asn Ser Leu Phe
65                  70                  75                  80

Leu Gln Met Thr Ser Leu Arg Ser Glu Asp Thr Ala Met Tyr Tyr Cys
                85                  90                  95

Ala Arg His Gly Tyr Arg Tyr Glu Gly Phe Asp Tyr Trp Gly Gln Gly
            100                 105                 110

Thr Thr Leu Thr Val Ser Ser
        115

<210> SEQ ID NO 27
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: Heavy Chain CDR1 of Antibody mAb-D

<400> SEQUENCE: 27

Ser Phe Gly Met His
1               5

<210> SEQ ID NO 28
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Heavy Chain CDR2 of Antibody mAb-D

<400> SEQUENCE: 28

Tyr Ile Ser Ser Gly Ser Gly Thr Ile Tyr Tyr Ala Asp Thr Val Lys
1               5                   10                  15

Gly

<210> SEQ ID NO 29
<211> LENGTH: 10
<212> TYPE: PRT
<213> ORGANISM: Mus musculus
<220> FEATURE:
```

```
<221> NAME/KEY: MISC_FEATURE
<222> LOCATION: (1)..(10)
<223> OTHER INFORMATION: Heavy Chain CDR3 of Antibody mAb-D

<400> SEQUENCE: 29

His Gly Tyr Arg Tyr Glu Gly Phe Asp Tyr
1               5                   10

<210> SEQ ID NO 30
<211> LENGTH: 107
<212> TYPE: PRT
<213> ORGANISM: Artificial Sequence
<220> FEATURE:
<223> OTHER INFORMATION: VL Domain of Humanized Anti-B7-H3 Antibody
      "hmAb-D"

<400> SEQUENCE: 30

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Phe Cys Gln Gln Tyr Asn Asn Tyr Pro Phe
                85                  90                  95

Thr Phe Gly Gln Gly Thr Lys Leu Glu Ile Lys
            100                 105

<210> SEQ ID NO 31
<211> LENGTH: 119
<212> TYPE: PRT
<213> ORGANISM: Artificial Sequence
<220> FEATURE:
<223> OTHER INFORMATION: VH Domain of Humanized Anti-B7-H3 Antibody
      "hmAb-D"

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Gly Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Tyr Arg Tyr Glu Gly Phe Asp Tyr Trp Gly Gln Gly
            100                 105                 110

Thr Thr Val Thr Val Ser Ser
            115

<210> SEQ ID NO 32
<211> LENGTH: 8
```

```
<212> TYPE: PRT
<213> ORGANISM: Artificial Sequence
<220> FEATURE:
<223> OTHER INFORMATION: Polypeptide Linker (Linker 1)

<400> SEQUENCE: 32

Gly Gly Gly Ser Gly Gly Gly Gly
1               5

<210> SEQ ID NO 33
<211> LENGTH: 6
<212> TYPE: PRT
<213> ORGANISM: Artificial Sequence
<220> FEATURE:
<223> OTHER INFORMATION: Cysteine-Containing Spacer Peptide (Linker 2)

<400> SEQUENCE: 33

Gly Gly Cys Gly Gly Gly
1               5

<210> SEQ ID NO 34
<211> LENGTH: 4
<212> TYPE: PRT
<213> ORGANISM: Artificial Sequence
<220> FEATURE:
<223> OTHER INFORMATION: Polypeptide Spacer Linker (Alternative Linker
      2)

<400> SEQUENCE: 34

Gly Gly Gly Ser
1

<210> SEQ ID NO 35
<211> LENGTH: 6
<212> TYPE: PRT
<213> ORGANISM: Artificial Sequence
<220> FEATURE:
<223> OTHER INFORMATION: Polypeptide Spacer Linker (Alternative Linker
      2)

<400> SEQUENCE: 35

Leu Gly Gly Gly Ser Gly
1               5

<210> SEQ ID NO 36
<211> LENGTH: 11
<212> TYPE: PRT
<213> ORGANISM: Artificial Sequence
<220> FEATURE:
<223> OTHER INFORMATION: Polypeptide Spacer Linker (Alternative Linker
      2)

<400> SEQUENCE: 36

Gly Gly Gly Ser Gly Gly Gly Ser Gly Gly Gly
1               5                   10

<210> SEQ ID NO 37
<211> LENGTH: 5
<212> TYPE: PRT
<213> ORGANISM: Artificial Sequence
<220> FEATURE:
<223> OTHER INFORMATION: Polypeptide Spacer Linker (Alternative Linker
      2)

<400> SEQUENCE: 37

Ala Ser Thr Lys Gly
1               5
```

```
<210> SEQ ID NO 38
<211> LENGTH: 6
<212> TYPE: PRT
<213> ORGANISM: Artificial Sequence
<220> FEATURE:
<223> OTHER INFORMATION: Polypeptide Spacer Linker (Alternative Linker
      2)

<400> SEQUENCE: 38

Leu Glu Pro Lys Ser Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Polypeptide Spacer Linker (Alternative Linker
      2)

<400> SEQUENCE: 39

Ala Pro Ser Ser Ser
1               5

<210> SEQ ID NO 40
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Heterodimer-Promoting Domain

<400> SEQUENCE: 40

Gly Val Glu Pro Lys Ser Cys
1               5

<210> SEQ ID NO 41
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Heterodimer-Promoting Domain

<400> SEQUENCE: 41

Val Glu Pro Lys Ser Cys
1               5

<210> SEQ ID NO 42
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Heterodimer-Promoting Domain

<400> SEQUENCE: 42

Ala Glu Pro Lys Ser Cys
1               5

<210> SEQ ID NO 43
<211> LENGTH: 7
<212> TYPE: PRT
<213> ORGANISM: Homo sapiens
<220> FEATURE:
```

-continued

```
<221> NAME/KEY: MISC_FEATURE
<222> LOCATION: (1)..(7)
<223> OTHER INFORMATION: Heterodimer-Promoting Domain

<400> SEQUENCE: 43

Gly Phe Asn Arg Gly Glu Cys
1               5

<210> SEQ ID NO 44
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Heterodimer-Promoting Domain

<400> SEQUENCE: 44

Phe Asn Arg Gly Glu Cys
1               5

<210> SEQ ID NO 45
<211> LENGTH: 28
<212> TYPE: PRT
<213> ORGANISM: Artificial Sequence
<220> FEATURE:
<223> OTHER INFORMATION: Heterodimer-Promoting E-Coil Domain

<400> SEQUENCE: 45

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 46
<211> LENGTH: 28
<212> TYPE: PRT
<213> ORGANISM: Artificial Sequence
<220> FEATURE:
<223> OTHER INFORMATION: Heterodimer-Promoting K-Coil Domain

<400> SEQUENCE: 46

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 47
<211> LENGTH: 28
<212> TYPE: PRT
<213> ORGANISM: Artificial Sequence
<220> FEATURE:
<223> OTHER INFORMATION: Heterodimer-Promoting Cysteine-Containing
      E-Coil Domain

<400> SEQUENCE: 47

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 48
<211> LENGTH: 28
<212> TYPE: PRT
<213> ORGANISM: Artificial Sequence
<220> FEATURE:
```

-continued

<223> OTHER INFORMATION: Heterodimer-Promoting Cysteine-Containing
      K-Coil Domain

<400> SEQUENCE: 48

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 49
<211> LENGTH: 46
<212> TYPE: PRT
<213> ORGANISM: Streptococcus agalactiae
<220> FEATURE:
<221> NAME/KEY: MISC_FEATURE
<222> LOCATION: (1)..(46)
<223> OTHER INFORMATION: Albumin-Binding Domain 3 (ABD3) of Protein G of
      Streptococcus strain G148

<400> SEQUENCE: 49

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 50
<211> LENGTH: 46
<212> TYPE: PRT
<213> ORGANISM: Artificial Sequence
<220> FEATURE:
<223> OTHER INFORMATION: Deimmunized Variant of Albumin-Binding Domain 3
      (ABD3) of Protein G of Streptococcus strain G148

<400> SEQUENCE: 50

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 51
<211> LENGTH: 46
<212> TYPE: PRT
<213> ORGANISM: Artificial Sequence
<220> FEATURE:
<223> OTHER INFORMATION: Deimmunized Variant of Albumin-Binding Domain 3
      (ABD3) of Protein G of Streptococcus strain G148

<400> SEQUENCE: 51

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Val Glu
            20                  25                  30

Gly Val Lys Ala Leu Ile Ala Glu Ile Leu Ala Ala Leu Pro
        35                  40                  45

<210> SEQ ID NO 52
<211> LENGTH: 46
<212> TYPE: PRT
<213> ORGANISM: Artificial Sequence
<220> FEATURE:

<223> OTHER INFORMATION: Deimmunized Variant of Albumin-Binding Domain 3
      (ABD3) of Protein G of Streptococcus strain G148

<400> SEQUENCE: 52

Leu Ala Glu Ala Lys Val Leu Ala Asn Arg Glu Leu Asp Lys Tyr Gly
1               5                   10                  15

Val Ser Asp Tyr Tyr Lys Asn Leu Ile Ser Asn Ala Lys Ser Val Glu
            20                  25                  30

Gly Val Lys Ala Leu Ile Ala Glu Ile Leu Ala Ala Leu Pro
        35                  40                  45

<210> SEQ ID NO 53
<211> LENGTH: 8
<212> TYPE: PRT
<213> ORGANISM: Artificial Sequence
<220> FEATURE:
<223> OTHER INFORMATION: Polypeptide Linker

<400> SEQUENCE: 53

Ala Pro Ser Ser Ser Pro Met Glu
1               5

<210> SEQ ID NO 54
<211> LENGTH: 16
<212> TYPE: PRT
<213> ORGANISM: Artificial Sequence
<220> FEATURE:
<223> OTHER INFORMATION: Polypeptide Linker

<400> SEQUENCE: 54

Val Glu Pro Lys Ser Ala Asp Lys Thr His Thr Cys Pro Pro Cys Pro
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Polypeptide Linker

<400> SEQUENCE: 55

Leu Glu Pro Lys Ser Ala Asp Lys Thr His Thr Cys Pro Pro Cys
1               5                   10                  15

<210> SEQ ID NO 56
<211> LENGTH: 10
<212> TYPE: PRT
<213> ORGANISM: Artificial Sequence
<220> FEATURE:
<223> OTHER INFORMATION: Polypeptide Linker

<400> SEQUENCE: 56

Asp Lys Thr His Thr Cys Pro Pro Cys Pro
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Polypeptide Linker

<400> SEQUENCE: 57

Gly Gly Gly Asp Lys Thr His Thr Cys Pro Pro Cys Pro
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Polypeptide Linker

<400> SEQUENCE: 58

Leu Glu Pro Lys Ser Ser Asp Lys Thr His Thr Cys Pro Pro Cys Pro
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Polypeptide Linker

<400> SEQUENCE: 59

Gly Gly Gly Gly Ser Gly Gly Gly Gly Ser Gly Gly Gly Gly Ser
1               5                   10                  15

<210> SEQ ID NO 60
<211> LENGTH: 217
<212> TYPE: PRT
<213> ORGANISM: Artificial Sequence
<220> FEATURE:
<223> OTHER INFORMATION: L234A/L235A Human IgG1 CH2 and CH3 Domain
<220> FEATURE:
<221> NAME/KEY: MISC_FEATURE
<222> LOCATION: (217)..(217)
<223> OTHER INFORMATION: X is Lysine or Absent

<400> SEQUENCE: 60

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

```
Lys Ser Leu Ser Leu Ser Pro Gly Xaa
    210                 215

<210> SEQ ID NO 61
<211> LENGTH: 217
<212> TYPE: PRT
<213> ORGANISM: Artificial Sequence
<220> FEATURE:
<223> OTHER INFORMATION: "Knob-Bearing" Variant of Human IgG1 CH2 and
      CH3 Domain
<220> FEATURE:
<221> NAME/KEY: MISC_FEATURE
<222> LOCATION: (217)..(217)
<223> OTHER INFORMATION: X is Lysine or Absent

<400> SEQUENCE: 61

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 62
<211> LENGTH: 217
<212> TYPE: PRT
<213> ORGANISM: Artificial Sequence
<220> FEATURE:
<223> OTHER INFORMATION: "Hole-Bearing" Variant of Human IgG1 CH2 and
      CH3 Domain
<220> FEATURE:
<221> NAME/KEY: MISC_FEATURE
<222> LOCATION: (217)..(217)
<223> OTHER INFORMATION: X is Lysine or Absent

<400> SEQUENCE: 62

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
```

```
                    20                  25                  30
Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Ser Cys Ala Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
            195                 200                 205

Lys Ser Leu Ser Leu Ser Pro Gly Xaa
    210                 215

<210> SEQ ID NO 63
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of Lo-CD2a Murine Anti-Human CD2
      Antibody

<400> SEQUENCE: 63

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Ile Phe Thr Glu Tyr
            20                  25                  30

Tyr Met Tyr Trp Val Lys Gln Arg Pro Lys Gln Gly Leu Glu Leu Val
        35                  40                  45

Gly Arg Ile Asp Pro Glu Asp Gly Ser Ile Asp Tyr Val Glu Lys Phe
    50                  55                  60

Lys Lys Lys Ala Thr Leu Thr Ala Asp Thr Ser Ser Asn Thr Ala Tyr
65                  70                  75                  80

Met Gln Leu Ser Ser Leu Thr Ser Glu Asp Thr Ala Thr Tyr Phe Cys
                85                  90                  95

Ala Arg Gly Lys Phe Asn Tyr Arg Phe Ala Tyr Trp Gly Gln Gly Thr
            100                 105                 110

Leu Val Thr Val Ser Ser
            115

<210> SEQ ID NO 64
<211> LENGTH: 112
<212> TYPE: PRT
```

<213> ORGANISM: Mus musculus
<220> FEATURE:
<221> NAME/KEY: MISC_FEATURE
<222> LOCATION: (1)..(112)
<223> OTHER INFORMATION: VL Domain of Lo-CD2a Murine Anti-Human CD2
      Antibody

<400> SEQUENCE: 64

Asp Val Val Leu Thr Gln Thr Pro Pro Thr Leu Leu Ala Thr Ile Gly
1               5                   10                  15

Gln Ser Val Ser Ile Ser Cys Arg Ser Ser Gln Ser Leu Leu His Ser
            20                  25                  30

Ser Gly Asn Thr Tyr Leu Asn Trp Leu Leu Gln Arg Thr Gly Gln Ser
        35                  40                  45

Pro Gln Pro Leu Ile Tyr Leu Val Ser Lys Leu Glu Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Met Gln Phe
                85                  90                  95

Thr His Tyr Pro Tyr Thr Phe Gly Ala Gly Thr Lys Leu Glu Leu Lys
            100                 105                 110

<210> SEQ ID NO 65
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of CD3 mAb-1 VH(1) Murine Anti-Human
      CD3 Antibody

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 66
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of CD3 mAb-1 VH(2) Murine Anti-Human
      CD3 Antibody

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 67
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: VL Domain of CD3 mAb-1 Murine Anti-Human CD3
      Antibody

<400> SEQUENCE: 67

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 68
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of CD3 mAb-1 (D65G) Murine Anti-Human
      CD3 Antibody

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
```

```
                35                  40                  45

Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 69
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of CD3 mAb-1 Low Murine Anti-Human
      CD3 Antibody

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Thr Trp Phe
            100                 105                 110

Ala Tyr Trp Gly Gln Gly Thr Leu Val Thr Val Ser Ser
        115                 120                 125

<210> SEQ ID NO 70
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of CD3 mAb-1 Fast Murine Anti-Human
      CD3 Antibody

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
        50                  55                  60
```

```
Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Lys Asn Phe Gly Asn Ser Tyr Val Thr Trp Phe
            100                 105                 110

Ala Tyr Trp Gly Gln Gly Thr Leu Val Thr Val Ser Ser
            115                 120                 125
```

<210> SEQ ID NO 71
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VH Domain of OKT3 Murine Anti-Human CD3
      Antibody

<400> SEQUENCE: 71

```
Gln Val Gln Leu Gln Gln Ser Gly Ala Glu Leu Ala Arg Pro Gly Ala
  1               5                  10                  15

Ser Val Lys Met Ser Cys Lys Ala Ser Gly Tyr Thr Phe Thr Arg Tyr
                 20                  25                  30

Thr Met His Trp Val Lys Gln Arg Pro Gly Gln Gly Leu Glu Trp Ile
             35                  40                  45

Gly Tyr Ile Asn Pro Ser Arg Gly Tyr Thr Asn Tyr Asn Gln Lys Phe
 50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115
```

<210> SEQ ID NO 72
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of OKT3 Murine Anti-Human CD3
      Antibody

<400> SEQUENCE: 72

```
Gln Ile Val Leu Thr Gln Ser Pro Ala Ile Met Ser Ala Ser Pro Gly
  1               5                  10                  15

Glu Lys Val Thr Met Thr Cys Ser Ala Ser Ser Ser Val Ser Tyr Met
                 20                  25                  30

Asn Trp Tyr Gln Gln Lys Ser Gly Thr Ser Pro Lys Arg Trp Ile Tyr
             35                  40                  45

Asp Thr Ser Lys Leu Ala Ser Gly Val Pro Ala His Phe Arg Gly Ser
 50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95
```

Phe Gly Ser Gly Thr Lys Leu Glu Ile Asn Arg
            100                 105

<210> SEQ ID NO 73
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of OKT8 Murine Anti-Human CD8
      Antibody

<400> SEQUENCE: 73

Gln Val Gln Leu Leu Glu Ser Gly Pro Glu Leu Leu Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Thr Gly Gly Thr Gly Tyr Asn Gln Lys Phe
    50                  55                  60

Lys Asn Lys Ala Thr Leu Thr Val Asp Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asn Phe Arg Tyr Thr Tyr Trp Tyr Phe Asp Val Trp Gly Gln
            100                 105                 110

Gly Thr Thr Val Thr Val Ser Ser
            115                 120

<210> SEQ ID NO 74
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of OKT8 Murine Anti-Human CD8
      Antibody

<400> SEQUENCE: 74

Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Asp Asn Ser Leu Met His Trp Tyr Gln Gln Lys Pro Gly Gln Pro Pro
        35                  40                  45

Lys Val Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110

<210> SEQ ID NO 75
<211> LENGTH: 121
<212> TYPE: PRT

```
<213> ORGANISM: Mus musculus
<220> FEATURE:
<221> NAME/KEY: MISC_FEATURE
<222> LOCATION: (1)..(121)
<223> OTHER INFORMATION: VH Domain of TRX2 Murine Anti-Human CD8
      Antibody

<400> SEQUENCE: 75
```

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asp Phe
            20                  25                  30

Gly Met Asn Trp Val Arg Gln Ala Pro Gly Lys Gly Leu Glu Trp Val
            35                  40                  45

Ala Leu Ile Tyr Tyr Asp Gly Ser Asn Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Tyr Asp Gly Tyr Tyr His Phe Phe Asp Ser Trp Gly
            100                 105                 110

Gln Gly Thr Leu Val Thr Val Ser Ser
        115                 120

```
<210> SEQ ID NO 76
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of TRX2 Murine Anti-Human CD8
      Antibody

<400> SEQUENCE: 76
```

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asp Ile Asn Asn Tyr
            20                  25                  30

Leu Ala Trp Tyr Gln Gln Lys Pro Gly Lys Ala Pro Lys Leu Leu Ile
            35                  40                  45

Tyr Asn Thr Asp Ile Leu His Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Tyr Gln Tyr Asn Asn Gly Tyr Thr
                85                  90                  95

Phe Gly Gln Gly Thr Lys Val Glu Ile Lys
            100                 105

```
<210> SEQ ID NO 77
<211> LENGTH: 118
<212> TYPE: PRT
<213> ORGANISM: Mus musculus
<220> FEATURE:
<221> NAME/KEY: MISC_FEATURE
<223> OTHER INFORMATION: VH Domain of 3G8 Murine Anti-Human CD16
      Antibody

<400> SEQUENCE: 77
```

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Ser Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
                100                 105                 110

Leu Val Thr Val Ser Ala
            115
```

<210> SEQ ID NO 78
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of 3G8 Murine Anti-Human CD16
      Antibody

<400> SEQUENCE: 78

```
Asp Thr Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
                100                 105                 110
```

<210> SEQ ID NO 79
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: VH Domain of A9 Murine Anti-Human CD16 Antibody

<400> SEQUENCE: 79

```
Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45
```

```
Gly Asp Ile Tyr Pro Gly Gly Gly Tyr Thr Asn Tyr Asn Glu Lys Phe
            50                  55                  60

Lys Gly Lys Ala Thr Val Thr Ala Asp Thr Ser Ser Arg Thr Ala Tyr
 65                  70                  75                  80

Val Gln Val Arg Ser Leu Thr Ser Glu Asp Ser Ala Val Tyr Phe Cys
                 85                  90                  95

Ala Arg Ser Ala Ser Trp Tyr Phe Asp Val Trp Gly Ala Arg Thr Thr
            100                 105                 110

Val Thr Val Ser Ser
            115

<210> SEQ ID NO 80
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of A9 Murine Anti-Human CD16 Antibody

<400> SEQUENCE: 80

Asp Ile Gln Ala Val Val Thr Gln Glu Ser Ala Leu Thr Thr Ser Pro
1               5                   10                  15

Gly Glu Thr Val Thr Leu Thr Cys Arg Ser Asn Thr Gly Thr Val Thr
                 20                  25                  30

Thr Ser Asn Tyr Ala Asn Trp Val Gln Glu Lys Pro Asp His Leu Phe
             35                  40                  45

Thr Gly Leu Ile Gly His Thr Asn Asn Arg Ala Pro Gly Val Pro Ala
 50                  55                  60

Arg Phe Ser Gly Ser Leu Ile Gly Asp Lys Ala Ala Leu Thr Ile Thr
 65                  70                  75                  80

Gly Ala Gln Thr Glu Asp Glu Ala Ile Tyr Phe Cys Ala Leu Trp Tyr
                 85                  90                  95

Asn Asn His Trp Val Phe Gly Gly Gly Thr Lys Leu Thr Val Leu
            100                 105                 110

<210> SEQ ID NO 81
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of BMA 031 Murine Anti-Human T Cell
      Receptor Antibody

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
                 20                  25                  30

Val Met His Trp Val Arg Gln Ala Pro Gly Gln Gly Leu Glu Trp Ile
             35                  40                  45

Gly Tyr Ile Asn Pro Tyr Asn Asp Val Thr Lys Tyr Asn Glu Lys Phe
 50                  55                  60

Lys Gly Arg Val Thr Ile Thr Ala Asp Lys Ser Thr Ser Thr Ala Tyr
 65                  70                  75                  80

Leu Gln Met Asn Ser Leu Arg Ser Glu Asp Thr Ala Val His Tyr Cys
                 85                  90                  95
```

-continued

Ala Arg Gly Ser Tyr Tyr Asp Tyr Asp Gly Phe Val Tyr Trp Gly Gln
                100                 105                 110

Gly Thr Leu Val Thr Val Ser Ser
        115                 120

<210> SEQ ID NO 82
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of BMA 031 Murine Anti-Human T Cell
      Receptor Antibody

<400> SEQUENCE: 82

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Leu Glu Ile Lys
            100                 105

<210> SEQ ID NO 83
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of KYK-1.0 Murine Anti-Human NKG2D
      Receptor Antibody

<400> SEQUENCE: 83

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Lys Tyr
65                  70                  75                  80

Leu Gln Met Asn Ser Leu Arg Ala Glu Asp Thr Ala Val Tyr Tyr Cys
                85                  90                  95

Ala Lys Asp Arg Phe Gly Tyr Tyr Leu Asp Tyr Trp Gly Gln Gly Thr
            100                 105                 110

Leu Val Thr Val Ser Ser
        115

<210> SEQ ID NO 84

```
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: VL Domain of KYK-1.0 Murine Anti-Human NKG2D
      Receptor Antibody

<400> SEQUENCE: 84
```

Gln Pro Val Leu Thr Gln Pro Ser Ser Val Ser Val Ala Pro Gly Glu
1               5                   10                  15

Thr Ala Arg Ile Pro Cys Gly Gly Asp Asp Ile Glu Thr Lys Ser Val
            20                  25                  30

His Trp Tyr Gln Gln Lys Pro Gly Gln Ala Pro Val Leu Val Ile Tyr
        35                  40                  45

Asp Asp Asp Asp Arg Pro Ser Gly Ile Pro Glu Arg Phe Phe Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Asp Asn Asn Asp Glu
                85                  90                  95

Trp Val Phe Gly Gly Gly Thr Gln Leu Thr Val Leu
            100                 105

```
<210> SEQ ID NO 85
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: VH Domain of KYK-2.0 Murine Anti-Human NKG2D
      Receptor Antibody

<400> SEQUENCE: 85
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120

```
<210> SEQ ID NO 86
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: VL Domain of KYK-2.0 Murine Anti-Human NKG2D
      Receptor Antibody
```

<400> SEQUENCE: 86

```
Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110
```

<210> SEQ ID NO 87
<211> LENGTH: 275
<212> TYPE: PRT
<213> ORGANISM: Artificial Sequence
<220> FEATURE:
<223> OTHER INFORMATION: First Polypeptide Chain of DART-D1

<400> SEQUENCE: 87

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Thr Lys Thr Leu Pro Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Pro
                85                  90                  95

Trp Thr Phe Gly Gln Gly Thr Arg Leu Glu Ile Lys Gly Gly Gly Ser
            100                 105                 110

Gly Gly Gly Gly Glu Val Gln Leu Val Glu Ser Gly Gly Gly Leu Val
        115                 120                 125

Gln Pro Gly Gly Ser Leu Arg Leu Ser Cys Ala Ala Ser Gly Phe Thr
130                 135                 140

Phe Ser Thr Tyr Ala Met Asn Trp Val Arg Gln Ala Pro Gly Lys Gly
145                 150                 155                 160

Leu Glu Trp Val Gly Arg Ile Arg Ser Lys Tyr Asn Asn Tyr Ala Thr
                165                 170                 175

Tyr Tyr Ala Asp Ser Val Lys Gly Arg Phe Thr Ile Ser Arg Asp Asp
            180                 185                 190

Ser Lys Asn Ser Leu Tyr Leu Gln Met Asn Ser Leu Lys Thr Glu Asp
        195                 200                 205

Thr Ala Val Tyr Tyr Cys Val Arg His Gly Asn Phe Gly Asn Ser Tyr
210                 215                 220

Val Ser Trp Phe Ala Tyr Trp Gly Gln Gly Thr Leu Val Thr Val Ser
225                 230                 235                 240
```

Ser Gly Gly Cys Gly Gly Gly Glu Val Ala Ala Leu Glu Lys Glu Val
            245                 250                 255

Ala Ala Leu Glu Lys Glu Val Ala Ala Leu Glu Lys Glu Val Ala Ala
            260                 265                 270

Leu Glu Lys
        275

<210> SEQ ID NO 88
<211> LENGTH: 269
<212> TYPE: PRT
<213> ORGANISM: Artificial Sequence
<220> FEATURE:
<223> OTHER INFORMATION: Second Polypeptide Chain of DART-D1

<400> SEQUENCE: 88

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Glu Ser Gly Gly Gly
        115                 120                 125

Leu Val Lys Pro Gly Gly Ser Leu Arg Leu Ser Cys Ala Ala Ser Gly
    130                 135                 140

Phe Thr Phe Ser Ser Tyr Gly Met Ser Trp Val Arg Gln Ala Pro Gly
145                 150                 155                 160

Lys Gly Leu Glu Trp Val Ala Thr Ile Asn Ser Gly Gly Ser Asn Thr
                165                 170                 175

Tyr Tyr Pro Asp Ser Leu Lys Gly Arg Phe Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Arg His Asp Gly Gly Ala Met Asp Tyr
    210                 215                 220

Trp Gly Gln Gly Thr Thr Val Thr Val Ser Ser Gly Gly Cys Gly Gly
225                 230                 235                 240

Gly Lys Val Ala Ala Leu Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 89
<211> LENGTH: 273
<212> TYPE: PRT
<213> ORGANISM: Artificial Sequence
<220> FEATURE:
<223> OTHER INFORMATION: First Polypeptide Chain of DART-D2

<400> SEQUENCE: 89

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Phe Cys Gln Gln Tyr Asn Asn Tyr Pro Phe
                85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Gly Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
210                 215                 220

Ser Trp Phe Ala Tyr Trp Gly Gln Gly Thr Leu Val Thr Val Ser Ser
225                 230                 235                 240

Ala Ser Thr Lys Gly Glu Val Ala Ala Cys Glu Lys Glu Val Ala Ala
                245                 250                 255

Leu Glu Lys Glu Val Ala Ala Leu Glu Lys Glu Val Ala Ala Leu Glu
            260                 265                 270

Lys

<210> SEQ ID NO 90
<211> LENGTH: 270
<212> TYPE: PRT
<213> ORGANISM: Artificial Sequence
<220> FEATURE:
<223> OTHER INFORMATION: Second Polypeptide Chain of DART-D2

<400> SEQUENCE: 90

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
            85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Glu Ser Gly Gly Gly
            115                 120                 125

Leu Val Gln Pro Gly Gly Ser Leu Arg Leu Ser Cys Ala Ala Ser Gly
            130                 135                 140

Phe Thr Phe Ser Ser Phe Gly Met His Trp Val Arg Gln Ala Pro Gly
145                 150                 155                 160

Lys Gly Leu Glu Trp Val Ala Tyr Ile Ser Ser Gly Ser Gly Thr Ile
            165                 170                 175

Tyr Tyr Ala Asp Thr Val Lys Gly Arg Phe Thr Ile Ser Arg Asp Asn
            180                 185                 190

Ala Lys Asn Ser Leu Tyr Leu Gln Met Asn Ser Leu Arg Ala Glu Asp
            195                 200                 205

Thr Ala Val Tyr Tyr Cys Ala Arg His Gly Tyr Arg Tyr Glu Gly Phe
            210                 215                 220

Asp Tyr Trp Gly Gln Gly Thr Thr Val Thr Val Ser Ser Ala Ser Thr
225                 230                 235                 240

Lys Gly Lys Val Ala Ala Cys Lys Glu Lys Val Ala Ala Leu Lys Glu
            245                 250                 255

Lys Val Ala Ala Leu Lys Glu Lys Val Ala Ala Leu Lys Glu
            260                 265                 270

<210> SEQ ID NO 91
<211> LENGTH: 503
<212> TYPE: PRT
<213> ORGANISM: Artificial Sequence
<220> FEATURE:
<223> OTHER INFORMATION: First Polypeptide Chain of "DART-D3"
<220> FEATURE:
<221> NAME/KEY: MISC_FEATURE
<222> LOCATION: (503)..(503)
<223> OTHER INFORMATION: X is Lysine or Absent

<400> SEQUENCE: 91

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
            35                  40                  45

Tyr Ser Ala Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Glu Tyr Phe Cys Gln Gln Tyr Asn Asn Tyr Pro Phe
            85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
            115                 120                 125

Pro Gly Gly Ser Leu Arg Leu Ser Cys Ala Ala Ser Gly Phe Thr Phe
            130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
            165                 170                 175

Tyr Ala Asp Ser Val Lys Gly Arg Phe Thr Ile Ser Arg Asp Asp Ser
            180                 185                 190

Lys Asn Ser Leu Tyr Leu Gln Met Asn Ser Leu Lys Thr Glu Asp Thr
            195                 200                 205

Ala Val Tyr Tyr Cys Val Arg His Gly Asn Phe Gly Asn Ser Tyr Val
            210                 215                 220

Ser Trp Phe Ala Tyr Trp Gly Gln Gly Thr Leu Val Thr Val Ser Ser
225                 230                 235                 240

Ala Ser Thr Lys Gly Glu Val Ala Ala Cys Glu Lys Glu Val Ala Ala
            245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
            275                 280                 285

Glu Ala Ala Gly Gly Pro Ser Val Phe Leu Phe Pro Pro Lys Pro Lys
            290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
            325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
            355                 360                 365

Trp Leu Asn Gly Lys Glu Tyr Lys Cys Lys Val Ser Asn Lys Ala Leu
            370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
            405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
            435                 440                 445

Thr Thr Pro Pro Val Leu Asp Ser Asp Gly Ser Phe Phe Leu Tyr Ser
            450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
            485                 490                 495

Leu Ser Leu Ser Pro Gly Xaa
            500

<210> SEQ ID NO 92
<211> LENGTH: 270
<212> TYPE: PRT
<213> ORGANISM: Artificial Sequence
<220> FEATURE:
<223> OTHER INFORMATION: Second Polypeptide Chain of "DART-D3"

<400> SEQUENCE: 92

Gln Ala Val Val Thr Gln Glu Pro Ser Leu Thr Val Ser Pro Gly Gly
1               5                   10                  15

-continued

```
Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
             35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
                100                 105                 110

Gly Ser Gly Gly Gly Gly Glu Val Gln Leu Val Glu Ser Gly Gly Gly
                115                 120                 125

Leu Val Gln Pro Gly Gly Ser Leu Arg Leu Ser Cys Ala Ala Ser Gly
    130                 135                 140

Phe Thr Phe Ser Ser Phe Gly Met His Trp Val Arg Gln Ala Pro Gly
145                 150                 155                 160

Lys Gly Leu Glu Trp Val Ala Tyr Ile Ser Ser Gly Ser Gly Thr Ile
                165                 170                 175

Tyr Tyr Ala Asp Thr Val Lys Gly Arg Phe Thr Ile Ser Arg Asp Asn
                180                 185                 190

Ala Lys Asn Ser Leu Tyr Leu Gln Met Asn Ser Leu Arg Ala Glu Asp
            195                 200                 205

Thr Ala Val Tyr Tyr Cys Ala Arg His Gly Tyr Arg Tyr Glu Gly Phe
    210                 215                 220

Asp Tyr Trp Gly Gln Gly Thr Thr Val Thr Val Ser Ser Ala Ser Thr
225                 230                 235                 240

Lys Gly Lys Val Ala Ala Cys Lys Glu Lys Val Ala Ala Leu Lys Glu
                245                 250                 255

Lys Val Ala Ala Leu Lys Glu Lys Val Ala Ala Leu Lys Glu
                260                 265                 270
```

<210> SEQ ID NO 93
<211> LENGTH: 227
<212> TYPE: PRT
<213> ORGANISM: Artificial Sequence
<220> FEATURE:
<223> OTHER INFORMATION: Third Polypeptide Chain of "DART-D3"
<220> FEATURE:
<221> NAME/KEY: MISC_FEATURE
<222> LOCATION: (227)..(227)
<223> OTHER INFORMATION: X is Lysine or Absent

<400> SEQUENCE: 93

```
Asp Lys Thr His Thr Cys Pro Pro Cys Pro Ala Pro Glu Ala Ala Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
```

```
                            85                  90                  95
Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Xaa
225

<210> SEQ ID NO 94
<211> LENGTH: 4
<212> TYPE: PRT
<213> ORGANISM: Artificial Sequence
<220> FEATURE:
<223> OTHER INFORMATION: Tetrapeptide Substrate of Streptoverticillium
      mobaraense Transglutaminase

<400> SEQUENCE: 94

Leu Leu Gln Leu
1

<210> SEQ ID NO 95
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of Murine Anti-B7-H3 Antibody "mAb-A"

<400> SEQUENCE: 95

Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys
            100                 105

<210> SEQ ID NO 96
<211> LENGTH: 122
```

```
<212> TYPE: PRT
<213> ORGANISM: Mus musculus
<220> FEATURE:
<221> NAME/KEY: MISC_FEATURE
<222> LOCATION: (1)..(122)
<223> OTHER INFORMATION: VH Domain of Murine Anti-B7-H3 Antibody "mAb-A"

<400> SEQUENCE: 96

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser
        115                 120

<210> SEQ ID NO 97
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of Murine Anti-B7-H3 Antibody "mAb-B"

<400> SEQUENCE: 97

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asp Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 98
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of Murine Anti-B7-H3 Antibody "mAb-B"

<400> SEQUENCE: 98

Gln Val Gln Leu Gln Gln Ser Gly Ala Glu Leu Ala Arg Pro Gly Ala
```

```
                1               5                      10                      15
            Ser Val Lys Leu Ser Cys Lys Ala Ser Gly Tyr Thr Phe Thr Ser Tyr
                            20                      25                      30

Trp Met Gln Trp Val Lys Gln Arg Pro Gly Gln Gly Leu Glu Trp Ile
                            35                      40                      45

Gly Thr Ile Tyr Pro Gly Asp Gly Asp Thr Arg Tyr Thr Gln Lys Phe
                            50                      55                      60

Lys Gly Lys Ala Thr Leu Thr Ala Asp Lys Ser Ser Thr Ala Tyr
            65                      70                      75                      80

Met Gln Leu Ser Ser Leu Ala Ser Glu Asp Ser Ala Val Tyr Tyr Cys
                            85                      90                      95

Ala Arg Arg Gly Ile Pro Arg Leu Trp Tyr Phe Asp Val Trp Gly Ala
                            100                     105                     110

Gly Thr Thr Val Thr Val Ser Ser
                            115                     120
```

<210> SEQ ID NO 99
<211> LENGTH: 107
<212> TYPE: PRT
<213> ORGANISM: Artificial Sequence
<220> FEATURE:
<223> OTHER INFORMATION: VL Domain of Humanized Anti-B7-H3 Antibody
      "hmAb-B"

<400> SEQUENCE: 99

```
            Asp Ile Gln Met Thr Gln Ser Pro Ser Ser Leu Ser Ala Ser Val Gly
            1               5                      10                      15

Asp Arg Val Thr Ile Thr Cys Arg Ala Ser Gln Asp Ile Ser Asn Tyr
                            20                      25                      30

Leu Asn Trp Tyr Gln Gln Lys Pro Gly Lys Ala Pro Lys Leu Leu Ile
                            35                      40                      45

Tyr Tyr Thr Ser Arg Leu His Ser Gly Val Pro Ser Arg Phe Ser Gly
                            50                      55                      60

Ser Gly Ser Gly Thr Asp Phe Thr Leu Thr Ile Ser Ser Leu Gln Pro
            65                      70                      75                      80

Glu Asp Ile Ala Thr Tyr Tyr Cys Gln Gln Asn Thr Leu Pro Pro
                            85                      90                      95

Thr Phe Gly Gly Gly Thr Lys Leu Glu Ile Lys
                            100                     105
```

<210> SEQ ID NO 100
<211> LENGTH: 11
<212> TYPE: PRT
<213> ORGANISM: Artificial Sequence
<220> FEATURE:
<223> OTHER INFORMATION: Light Chain CDR1 of Humanized Anti-B7-H3
      Antibody "hmAb-B"

<400> SEQUENCE: 100

```
            Arg Ala Ser Gln Asp Ile Ser Asn Tyr Leu Asn
            1               5                      10
```

<210> SEQ ID NO 101
<211> LENGTH: 11
<212> TYPE: PRT
<213> ORGANISM: Artificial Sequence
<220> FEATURE:
<223> OTHER INFORMATION: Alternative Light Chain CDR1 of Humanized
      Anti-B7-H3 Antibody "hmAb-B"

<400> SEQUENCE: 101

Arg Ala Ser Gln Ser Ile Ser Ser Tyr Leu Asn
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Light Chain CDR2 of Humanized Anti-B7-H3
      Antibody "hmAb-B"

<400> SEQUENCE: 102

Tyr Thr Ser Arg Leu His Ser
1               5

<210> SEQ ID NO 103
<211> LENGTH: 7
<212> TYPE: PRT
<213> ORGANISM: Artificial Sequence
<220> FEATURE:
<223> OTHER INFORMATION: Alternative Light Chain CDR2 of Humanized
      Anti-B7-H3 Antibody "hmAb-B"

<400> SEQUENCE: 103

Tyr Thr Ser Arg Leu Gln Ser
1               5

<210> SEQ ID NO 104
<211> LENGTH: 120
<212> TYPE: PRT
<213> ORGANISM: Artificial Sequence
<220> FEATURE:
<223> OTHER INFORMATION: VH Domain of Humanized Anti-B7-H3 Antibody
      "hmAb-B"

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Gln Trp Val Arg Gln Ala Pro Gly Gln Gly Leu Glu Trp Met
            35                  40                  45

Gly Thr Ile Tyr Pro Gly Asp Gly Asp Thr Arg Tyr Thr Gln Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Pro Arg Leu Trp Tyr Phe Asp Val Trp Gly Gln
            100                 105                 110

Gly Thr Thr Val Thr Val Ser Ser
        115                 120

<210> SEQ ID NO 105
<211> LENGTH: 17
<212> TYPE: PRT
<213> ORGANISM: Artificial Sequence
<220> FEATURE:
<223> OTHER INFORMATION: Heavy Chain CDR2 of Humanized Anti-B7-H3
      Antibody "hmAb-B"

<400> SEQUENCE: 105

Thr Ile Tyr Pro Gly Asp Gly Asp Thr Arg Tyr Thr Gln Lys Phe Lys

```
1               5                  10                 15
Gly

<210> SEQ ID NO 106
<211> LENGTH: 17
<212> TYPE: PRT
<213> ORGANISM: Artificial Sequence
<220> FEATURE:
<223> OTHER INFORMATION: Alternative Heavy Chain CDR2 of Humanized
      Anti-B7-H3 Antibody "hmAb-B"

<400> SEQUENCE: 106

Thr Ile Tyr Pro Gly Gly Gly Asp Thr Arg Tyr Thr Gln Lys Phe Gln
1               5                   10                  15

Gly
```

B7-H3 DIRECTED ANTIBODY DRUG CONJUGATES

CROSS-REFERENCE TO RELATED APPLICATIONS

This patent application is a continuation of U.S. patent application Ser. No. 16/092,740, filed on Oct. 10, 2018, entitled NOVEL B7-H3 BINDING MOLECULES, ANTIBODY DRUG CONJUGATES THEREOF AND METHODS OF USE THEREOF, naming Deryk T. Loo, Ling Huang, Leslie S. Johnson, Thomas Son, Juniper A. Scribner and Ezio Bonvini as inventors, which is a 35 U.S.C. 371 national phase patent application of PCT/US2017/027317, filed on Apr. 13, 2017, entitled NOVEL B7-H3 BINDING MOLECULES, ANTIBODY DRUG CONJUGATES THEREOF AND METHODS OF USE THEREOF, naming Deryk T. Loo, Ling Huang, Leslie S. Johnson, Thomas Son, Juniper A. Scribner and Ezio Bonvini as inventors, which claims priority to U.S. Patent Applications Ser. Nos. 62/432,314 (filed Dec. 9, 2016), 62/323,249 (filed Apr. 15, 2016), and 62/323,228 (filed Apr. 15, 2016), each of which applications is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: 1301_0143-0144PCT_ST25.txt, created on Mar. 28, 2017, and having a size of 104,762 bytes), which file is herein incorporated by reference in its entirety.

FIELD OF THE INVENTION

The present invention is directed to novel B7-H3-binding molecules capable of binding to human and non-human B7-H3, and in particular to such molecules that are cross-reactive with B7-H3 of a non-human primate (e.g., a cynomolgus monkey). The invention additionally pertains to B7-H3-binding molecules that comprise Variable Light Chain and/or Variable Heavy Chain (VH) Domains that have been humanized and/or deimmunized so as to exhibit a reduced immunogenicity upon administration to recipient subjects. The invention particularly pertains to bispecific, trispecific or multispecific B7-H3-binding molecules, including bispecific diabodies, BiTEs, bispecific antibodies, trivalent binding molecules, etc. that comprise: (i) such B7-H3-binding Variable Domains and (ii) a domain capable of binding to an epitope of a molecule present on the surface of an effector cell. The invention is also directed to pharmaceutical compositions that contain any of such B7-H3-binding molecules, and to methods involving the use of any of such B7-H3-binding molecules in the treatment of cancer and other diseases and conditions. The invention also particularly pertains to a molecule that comprises the human B7-H3 binding domain of a humanized anti-human B7-H3 antibody conjugated to at least one drug moiety (a "B7-H3-ADC"). The invention is also directed to pharmaceutical compositions that contain such B7-H3-ADCs, and to methods involving the use of any of such B7-H3-ADCs in the treatment of cancer and other diseases and conditions.

BACKGROUND OF THE INVENTION

The growth and metastasis of tumors depends to a large extent on their capacity to evade host immune surveillance and overcome host defenses. Most tumors express antigens that can be recognized to a variable extent by the host immune system, but in many cases, an inadequate immune response is elicited because of the ineffective activation of effector T cells (Khawli, L. A. et al. (2008) "*Cytokine, Chemokine, and Co-Stimulatory Fusion Proteins for the Immunotherapy of Solid Tumors*," Exper. Pharmacol. 181: 291-328).

I. B7 Superfamily and B7-H3

B7-H3 is a member of the B7-CD28 Superfamily and is expressed on Antigen-Presenting Cells. It binds to T Cells, however, the B7-H3 counter-receptor on the surface of such T Cells has not yet been fully characterized.

B7-H3 is unique in that the major human form contains two extracellular tandem IgV-IgC domains (i.e., IgV-IgC-IgV-IgC) (Collins, M. et al. (2005) "*The B7 Family Of Immune-Regulatory Ligands*," Genome Biol. 6:223.1-223.7). Although initially thought to comprise only 2 Ig domains (IgV-IgC) a four immunoglobulin extracellular domain variant ("4Ig-B7-H3") has been identified and found to be the more common human form of the protein (Sharpe, A. H. et al. (2002) "*The B7-CD28 Superfamily*," Nature Rev. Immunol. 2:116-126). However, the natural murine form (2Ig) and the human 4Ig form exhibit similar function (Hofmeyer, K. et al. (2008) "*The Contrasting Role Of B7-H3*," Proc. Natl. Acad. Sci. (U.S.A.) 105(30):10277-10278). The 4Ig-B7-H3 molecule inhibits the NK-cell-mediated lysis of cancer cells (Castriconi, R. et al. "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34): 12640-12645). The human B7-H3 (2Ig form) has been reported to promote T-cell activation and IFN-γ production by binding to a putative receptor on activated T Cells (Chapoval, A. et al. (2001) "*B7-H3: A Costimulatory Molecule For T Cell Activation and IFN-γ Production*," Nature Immunol. 2:269-274) however, more recent studies point to an inhibitory role of murine and human B7-H3 (Prasad, D. V., et al. (2004) "*Murine B7-H3 Is A Negative Regulator Of T Cells*, J Immunol. 173:2500-2506; Leitner, J., et al. (2009) "B7-H3 *Is A Potent Inhibitor Of Human T-Cell Activation: No Evidence For B7-H3 And TREML2 Interaction*." Eur. J. Immunol. 39:1754-1764; Veenstra, R. G., et al. (2015) "*B7-H3 expression in Dnor T Cells and Host Cells Negatively Regulates Acute Graft-Versus-Host Disease Lethality*," Blood 125:3335-3346.). B7-H3 mRNA expression has been found in heart, kidney, testes, lung, liver, pancreas, prostate, colon, and osteoblast cells (Collins, M. et al. (2005) "*The B7Family Of Immune-Regulatory Ligands*," Genome Biol. 6:223.1-223.7). At the protein level, B7-H3 is found in human liver, lung, bladder, testis, prostate, breast, placenta, and lymphoid organs (Hofmeyer, K. et al. (2008) "*The Contrasting Role Of B7-H3*," Proc. Natl. Acad. Sci. (U.S.A.) 105(30):10277-10278).

Although B7-H3 is not expressed on resting B or T Cells, monocytes, or dendritic cells, it is induced on dendritic cells by IFN-γ and on monocytes by GM-CSF (Sharpe, A. H. et al. (2002) "*The B7-CD28 Superfamily*," Nature Rev. Immunol. 2:116-126). The mode of action of B7-H3 is complex, and the protein is reported to mediate both T Cell co-stimulation and co-inhibition (Hofmeyer, K. et al. (2008) "*The Contrasting Role Of B7- H3*," Proc. Natl. Acad. Sci. (U.S.A.) 105(30):10277-10278; Martin-Orozco, N. et al. (2007) "*Inhibitory Costimulation And Anti-Tumor Immunity*," Semin. Cancer Biol. 17(4):288-298; Subudhi, S. K. et al. (2005) "*The Balance Of Immune Responses: Costimulation Verse Coinhibition*," J. Mol. Med. 83:193-202). B7-H3 binds to an as yet unidentified receptor(s) to mediate co-inhibition of T Cells. In addition, B7-H3, through interactions with unknown receptor(s) is an inhibitor for NK-cells and osteoblastic cells (Hofmeyer, K. et al. (2008) "*The Contrasting Role Of B7-H3*," Proc. Natl. Acad. Sci. (U.S.A.) 105(30):10277-10278). The inhibition may operate through interactions with members of the major signaling pathways through which T Cell receptor (TCR) regulates gene transcription (e.g., NFTA, NF-κB, or AP-1 factors). B7-H3 is also believed to inhibit Th1, Th2, or Th17 in vivo (Prasad, D. V. et al. (2004) "*Murine B7-H3 Is A Negative Regulator Of T Cells*," J. Immunol. 173:2500-2506; Fukushima, A. et al. (2007) "*B7-H3 Regulates The Development Of Experimental Allergic Conjunctivitis In Mice*," Immunol. Lett. 113:52-57; Yi. K. H. et al. (2009) "Fine *Tuning The Immune Response Through B7-H3 And B7-H4*," Immunol. Rev. 229:145-151).

II. B7-H3 Expressing Tumors

B7-H3 is also known to be expressed on a variety of cancer cells (e.g., neuroblastoma, gastric, ovarian, non-small cell lung cancers, etc., see, e.g., Modak, S., et al. (2001) "*Monoclonal antibody 8H9 targets a novel cell surface antigen expressed by a wide spectrum of human solid tumors*," Cancer Res 61:4048-54) and cultured cancer stem-like cells. Several independent studies have shown that human malignant tumor cells exhibit a marked increase in expression of B7-H3 protein and that this increased expression was associated with increased disease severity (Zang, X. et al. (2007) "*The B7 Family And Cancer Therapy: Costimulation And Coinhibition*," Clin. Cancer Res. 13:5271-5279; Sun, Y., et al. (2006) "*B7-H3 and B7-H4 expression in non-small-cell lung cancer*," Lung Cancer 53:143-51; Tekle, C., et al. (2012) "*B7-H3 Contributes To The Metastatic Capacity Of Melanoma Cells By Modulation Of Known Metastasis-Associated Genes*," Int. J. Cancer 130:2282-90; Wang, L., et al. (2013) "*B7-H3 Mediated Tumor Immunology: Friend Or Foe?*," Int. J. Cancer 134 (12):2764-2771), suggesting that B7-H3 is exploited by tumors as an immune evasion pathway (Hofmeyer, K. et al. (2008) "*The Contrasting Role Of B7-H3*," Proc. Natl. Acad. Sci. (U.S.A.) 105(30):10277-10278).

B7-H3 protein expression has also been immunohistologically detected in tumor cell lines (Chapoval, A. et al. (2001) "*B7-H3: A Costimulatory Molecule For T Cell Activation and IFN-γ Production*," Nature Immunol. 2:269-274; Saatian, B. et al. (2004) "*Expression Of Genes For B7-H3 And Other T Cell Ligands By Nasal Epithelial Cells During Differentiation And Activation*," Amer. J. Physiol. Lung Cell. Mol. Physiol. 287:L217-L225; Mather, J. et al, WO 2004/001381; Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34):12640-12645); Sun, M. et al. (2002) "*Characterization of Mouse and Human B7-H3 Genes*," J. Immunol. 168:6294-6297).

The role of B7-H3 in inhibiting the immune system and the increased expression of B7-H3 on human tumors has suggested that this molecule might serve as a therapeutic target for the treatment of cancer. Thus, the use of anti-B7-H3 antibodies and other molecules that modulate B7-H3 expression to treat tumors and/or up-modulate an immune response has been proposed (see, Loo, D. et al. (2012) "*Development of an Fc- Enhanced Anti-B7-H3 Monoclonal Antibody with Potent Antitumor Activity*," Clin Cancer Res; 18: 3834-3845; Ahmed, M. et al. (2015) "*Humanized Affinity-Matured Monoclonal Antibody 8H9 Has Potent Anti-Tumor Activity and Binds to FG Loop of B7-H3*," J. Biol. Chem. 290: 30018-30029; Nagase-Zembutsu, A. et al. (2016) "*Development of DS-5573a: A novel afucosylated monoclonal antibody directed at B7-H3 with potent antitumor activity*," Cancer Sci. 2016, doi: 10.1111/cas.12915; Modak, S. et al. (March 1999) "*Disialoganglioside GD2 And Antigen 8H9: Potential Targets For Antibody-Based Immunotherapy Against Desmoplastic Small Round Cell Tumor (DSRCT) And Rhabdomyosarcoma (RMS)*," Proceedings Of The American Association For Cancer Research Annual Meeting, Vol. 40:474 (9$^{th}$ Annual Meeting Of The American Association For Cancer Research; Philadelphia, Pa., US; Apr. 10-14, 1999; Modak, S. et al. (March 2000) "*Radioimmunotargeting To Human Rhabdomyosarcoma Using Monoclonal Antibody 8H9*," Proc. Am. Assoc. Cancer Res. 41:724; Modak, S. et al. (2001) "*Monoclonal Antibody 8H9 Targets A Novel Cell Surface Antigen Expressed By A Wide Spectrum Of Human Solid Tumors*," Cancer Res. 61(10):4048-4054; Steinberger, P. et al. (2004) "*Molecular Characterization of Human 4Ig-B7-H3, a Member of the B7 Family with Four Ig-Like Domains*," J. Immunol. 172(4): 2352-2359; Xu, H. et al. (2009) "*MicroRNA miR-29Modulates Expression of Immunoinhibitory Molecule B7-H3: Potential Implications for Immune Based Therapy of Human Solid Tumors*," Cancer Res. 69(15):5275-6281; see also, U.S. Pat. Nos. 7,279,567, 7,358,354, 7,368,554, 7,527,969, 7,718,774, 8,216,570, 8,779,098, 8,802,091, 9,150,656, US Patent Publication Nos. 2002/0168762; 2005/0202536, 2008/0081346, 2008/0116219, 2009/0018315, 2009/0022747, 2009/0087416, 2013/0078234, 2015/0274838, PCT Publications Nos. WO 2008/066691; WO 2006/016276; WO 2008/116219; WO 04/001381, WO 2001/094413, WO 2002/10187, WO 2002/32375, WO 2004/093894, WO 2006/016276, WO 2008/116219, WO 2011/109400; and EP 1292619B.

Notwithstanding all such prior success, a need remains for additional therapeutic agents which target and kill tumor cells expressing B7-H3. The present invention is directed to this and other goals.

SUMMARY OF THE INVENTION

The present invention is directed to novel B7-H3-binding molecules capable of binding to human and non-human B7-H3, and in particular to such molecules that are cross-reactive with B7-H3 of a non-human primate (e.g., a cynomolgus monkey). The invention additionally pertains to B7-H3-binding molecules that comprise Variable Light Chain and/or Variable Heavy Chain (VH) Domains that have been humanized and/or deimmunized so as to exhibit a reduced immunogenicity upon administration to recipient subjects. The invention particularly pertains to bispecific, trispecific or multispecific B7-H3-binding molecules, including bispecific diabodies, BiTEs, bispecific antibodies, trivalent binding molecules, etc. that comprise: (i) such B7-H3-binding Variable Domains and (ii) a domain capable of binding to an epitope of a molecule present on the surface of an effector cell. The invention is also directed to pharmaceutical compositions that contain any of such B7-H3-binding molecules, and to methods involving the use of any of such B7-H3-binding molecules in the treatment of cancer and other diseases and conditions. The invention also particularly pertains to a molecule that comprises the human B7-H3 binding domain of a humanized anti-human B7-H3 antibody conjugated to at least one drug moiety (a "B7-H3-ADC"). The invention is also directed to pharmaceutical compositions that contain such B7-H3-ADCs, and to methods involving the use of any of such B7-H3-ADCs in the treatment of cancer and other diseases and conditions.

In detail, one aspect of the present invention provides a B7-H3-binding molecule that comprises a Variable Light Chain (VL) Domain and a Variable Heavy Chain (VH) Domain, wherein said Variable Heavy Chain Domain comprises a $CDR_H1$ Domain, a $CDR_H2$ Domain and a $CDR_H3$ Domain, and said Variable Light Chain Domain comprises a $CDR_L1$ Domain, a $CDR_L2$ Domain, and a $CDR_L3$ Domain, wherein at least three of said domains, at least four of said domains, at least five of said domains or all of said domains are selected from the group consisting of:
(1) a $CDR_H1$ Domain comprising the amino acid sequence of SEQ ID NO:27;
(2) a $CDR_H2$ Domain comprising the amino acid sequence of SEQ ID NO:28;
(3) a $CDR_H3$ Domain comprising the amino acid sequence of SEQ ID NO:29;
(4) a $CDR_L1$ Domain comprising the amino acid sequence of SEQ ID NO:23;
(5) a $CDR_L2$ Domain comprising the amino acid sequence of SEQ ID NO:24; and
(6) a $CDR_L3$ Domain comprising the amino acid sequence of SEQ ID NO:25.

The invention additionally concerns the embodiment of such B7-H3-binding molecule that comprises said Variable Light Chain (VL) Domain that comprises a $CDR_L1$ Domain, a $CDR_L2$ Domain, and a $CDR_L3$ Domain, and said Variable Heavy Chain (VH) Domain that comprises a $CDR_H1$ Domain, a $CDR_H2$ Domain and a $CDR_H3$ Domain, wherein:
(1) said $CDR_H1$ Domain comprises the amino acid sequence of SEQ ID NO:27;
(2) said $CDR_H2$ Domain comprises the amino acid sequence of SEQ ID NO:28;
(3) said $CDR_H3$ Domain comprises the amino acid sequence of SEQ ID NO:29.

The invention additionally concerns the embodiment of such B7-H3-binding molecule that comprises said Variable Light Chain (VL) Domain that comprises a $CDR_L1$ Domain, a $CDR_L2$ Domain, and a $CDR_L3$ Domain, and said Variable Heavy Chain (VH) Domain that comprises a $CDR_H1$ Domain, a $CDR_H2$ Domain and a $CDR_H3$ Domain, wherein:
(1) said $CDR_L1$ Domain comprises the amino acid sequence of SEQ ID NO:23;
(2) said $CDR_L2$ Domain comprises the amino acid sequence of SEQ ID NO:24; and
(3) said $CDR_L3$ Domain comprises the amino acid sequence of SEQ ID NO:25.

The invention additionally concerns the embodiment of such B7-H3-binding molecules wherein said Variable Heavy Chain (VH) Domain comprises the amino acid sequence of SEQ ID NO:26 or SEQ ID NO:31.

The invention additionally concerns the embodiment of such B7-H3-binding molecules wherein said Variable Light Chain (VL) Domain comprises the amino acid sequence of SEQ ID NO:22 or SEQ ID NO:30.

The invention additionally concerns B7-H3-binding molecules that comprise a VL Domain and a VH Domain, wherein said VL Domain comprises the amino acid sequence of SEQ ID NO:20.

The invention additionally concerns B7-H3-binding molecules that comprise a VL Domain and a VH Domain, wherein said VH Domain comprises the amino acid sequence of SEQ ID NO:21.

The invention additionally concerns B7-H3-binding molecules that comprise a VL Domain and a VH Domain, wherein said VL Domain comprises the amino acid of SEQ ID NO:20 and said VH Domain comprises the amino acid sequence of SEQ ID NO:21.

The invention further concerns the embodiment of such B7-H3-binding molecules, wherein the molecule is an antibody or an epitope-binding fragment thereof. The invention also concerns the embodiments of such a B7-H3-binding molecule, wherein the molecule is a bispecific antibody or a diabody, especially a diabody, or diabody complex, that comprises two, three, four or five polypeptide chains each having an N-terminus and a C-terminus in which such polypeptide chains are associated together via one or more covalent, and especially one or more covalent disulfide, bonds. The invention additionally concerns the embodiment of such B7-H3-binding molecules wherein the molecule is a trivalent binding molecule, and especially wherein the trivalent binding molecule is a covalently bonded complex that comprises three, four, five, or more polypeptide chains. The invention further concerns the embodiment of such a B7-H3-binding molecule, wherein the molecule comprises an Fc Domain. The invention additionally concerns the embodiment of such B7-H3-binding molecules wherein the molecule is a diabody and comprises an Albumin-Binding Domain, and especially a deimmunized Albumin-Binding Domain.

The invention further concerns the embodiments of all such B7-H3-binding molecules that additionally comprise an Fc Domain, and especially wherein the Fc Domain is a variant Fc Domain that comprises one or more amino acid modifications that reduces the affinity of the variant Fc Domain for an FcγR and/or enhances the serum half-life of the B7-H3-binding molecule, and more particularly, wherein the modifications comprise at least one substitution selected from the group consisting of
(a) L234A;
(b) L235A;
(c) L234A and L235A;
(d) M252Y; M252Y and S254T;
(e) M252Y and T256E;
(f) M252Y, S254T and T256E; and
(g) K288D and H435K;
wherein the numbering is that of the EU index as in Kabat.

The invention further concerns the embodiment of such B7-H3-binding molecules, wherein the molecule is bispecific, and particularly concerns the embodiment wherein the molecule comprises two epitope-binding sites capable of immunospecific binding to an epitope of B7-H3 and two epitope-binding sites capable of immunospecific binding to an epitope of a molecule present on the surface of an effector cell, or the embodiment wherein the molecule comprises one epitope-binding site capable of immunospecific binding to an epitope of B7-H3 and one epitope-binding site capable of immunospecific binding to an epitope of a molecule present on the surface of an effector cell.

The invention additionally concerns the embodiment of such B7-H3 binding molecules wherein the molecule is a trivalent binding molecule, and particularly concerns the embodiments wherein the molecule comprises, one epitope-binding site capable of immunospecific binding to an epitope of B7-H3, one epitope-binding site capable of immunospecific binding to an epitope of a first molecule present on the surface of an effector cell; and one epitope-binding site capable of immunospecific binding to an epitope of a second molecule present on the surface of an effector cell, wherein such first and second molecules are not B7-H3.

The invention further concerns the embodiment of such a B7-H3-binding molecule, wherein the molecule is capable of simultaneously binding to B7-H3 and to a second epitope, and particularly concerns the embodiment wherein the second epitope is an epitope of a second molecule present on the surface of an effector cell (especially wherein the second epitope is an epitope of CD2, CD3, CD8, CD16, TCR, or NKG2D, and most particularly wherein the second epitope is an epitope of CD3). The invention additionally concerns the embodiment of such B7-H3-binding molecules, wherein the effector cells is a cytotoxic T-cell or a Natural Killer (NK) cell. The invention additionally concerns the embodiment of such B7-H3-binding molecules, wherein the molecule is also capable of binding a third epitope, and particularly concerns the embodiment wherein the third epitope is an epitope of CD8. The invention further concerns the embodiments of such molecules wherein molecule mediates coordinated binding of a cell expressing B7-H3 and a cytotoxic T cell.

The invention further provides pharmaceutical compositions comprising an effective amount of any of the above-described B7-H3-binding molecules and a pharmaceutically acceptable carrier, excipient or diluent.

The invention is additionally directed to the use of any of the above-described B7-H3-binding molecules in the treatment of a disease or condition associated with or characterized by the expression of B7-H3, or in a method of treating a disease or condition characterized by the expression of B7-H3, particularly wherein the disease or condition associated with or characterized by the expression of B7-H3 is cancer, and more particularly, wherein the cancer is selected from the group consisting of: an adrenal gland tumor, an AIDS-associated cancer, an alveolar soft part sarcoma, an astrocytic tumor, an adrenal cancer, a bladder cancer, a bone cancer, a brain and spinal cord cancer, a metastatic brain tumor, a B-cell cancer, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gastric cancer, a gestational trophoblastic disease, a germ cell tumor, a head and neck cancer, a hepatocellular carcinoma, an islet cell tumor, a Kaposi's Sarcoma, a kidney cancer, a leukemia, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a renal metastatic cancer, a rhabdoid tumor, a rhabdomyosacoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

A second aspect of the present invention is directed to a molecule that comprises the human B7-H3 binding domain of a humanized anti-human B7-H3 antibody conjugated to at least one drug moiety (a "B7-H3-ADC"). The invention is also directed to pharmaceutical compositions that contain such B7-H3-ADCs, and to methods involving the use of any of such B7-H3-ADCs in the treatment of cancer and other diseases and conditions.

In detail, the invention provides an anti-B7-H3 antibody drug conjugate (B7-H3-ADC) comprising the formula:

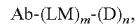

$$Ab\text{-}(LM)_m\text{-}(D)_n,$$

wherein:
Ab is an antibody that binds to B7-H3 that comprises a humanized Variable Heavy Chain (VH) Domain and a humanized Variable Light Chain (VL) Domain, or is a B7-H3-binding fragment thereof, and;
D is a cytotoxic drug moiety;
LM is a Linker Molecule that covalently links Ab and D;
m is an integer between 0 and n and denotes the number of Linker Molecules of the B7-H3-ADC;
and
n is an integer between 1 and 10 and denotes the number of cytotoxic drug moieties covalently linked to the ADC.

The invention further provides such B7-H3-ADCs, wherein the Linker Molecule LM is absent (i.e., m=0), and B7-H3-ADCs that possess more than one Linker Molecule LM (i.e., m is an integer from 2 through n), each of which Linker Molecule LM covalently links a cytotoxic drug moiety D to the Ab of such B7-H3-ADCs. The invention further provides such B7-H3-ADCs whose Ab are covalently linked to more than one Linker Molecule LM, wherein all such Linker Molecules are identical. The cytotoxic drug moieties D that are covalently linked to the Ab of such B7-H3-ADCs may all be identical or may include 2, 3, 4, or more non-identical cytotoxic drug moieties D. The invention further provides such B7-H3-ADCs whose Ab are covalently linked to more than one Linker Molecule LM, wherein all such Linker Molecules are not identical. The cytotoxic drug moieties D that are covalently linked to the Ab of such B7-H3-ADCs may all be identical or may include 2, 3, 4, or more non-identical cytotoxic drug moieties D.

The invention further provides such B7-H3-ADCs, wherein:
(A) (i) the humanized VL Domain comprises the amino acid sequence of SEQ ID NO:99, and
(ii) the humanized VH Domain comprises the amino acid sequence of SEQ ID NO:104;
or
(B) (i) the humanized VL Domain comprises the amino acid sequence of SEQ ID NO:20, and
(ii) the humanized VH Domain comprises the amino acid sequence of SEQ ID NO:21;
or
(C) (i) the humanized VL Domain comprises the amino acid sequence of SEQ ID NO:30, and
(ii) the humanized VH Domain comprises the amino acid sequence of SEQ ID NO:31.

The invention further provides such B7-H3-ADCs, wherein the humanized VL Domain comprises the amino acid sequence of SEQ ID NO:99 and the humanized VH Domain comprises the amino acid sequence of SEQ ID NO:104.

The invention further provides such B7-H3-ADCs, wherein the humanized VL Domain comprises the amino acid sequence of SEQ ID NO:20 and the humanized VH Domain comprises the amino acid sequence of SEQ ID NO:21.

The invention further provides such B7-H3-ADCs, wherein the humanized the humanized VL Domain comprises the amino acid sequence of SEQ ID NO:30 and the humanized VH Domain comprises the amino acid sequence of SEQ ID NO:31.

The invention further provides such B7-H3-ADCs, wherein the Ab is an antibody or an antigen binding fragment of an antibody.

The invention further provides such B7-H3-ADCs, wherein the B7-H3-ADC comprises an Fc Domain of a human IgG (especially a human IgG1, IgG2, IgG3, or IgG4).

The invention further provides such B7-H3-ADCs, wherein the B7-H3-ADC comprises a variant Fc Domain that comprises:
  (a) one or more amino acid modifications that reduces the affinity of the variant Fc Domain for an FcγR; and/or
  (b) one or more amino acid modifications that enhances the serum half-life of the variant Fc Domain.

The invention further provides such B7-H3-ADCs that comprise a variant Fc Domain, wherein the modifications that reduces the affinity of the variant Fc Domain for an FcγR comprise the substitution of L234A; L235A; or L234A and L235A, wherein the numbering is that of the EU index as in Kabat.

The invention further provides such B7-H3-ADCs that comprise a variant Fc Domain, wherein the modifications that that enhances the serum half-life of the variant Fc Domain comprise the substitution of M252Y; M252Y and S254T; M252Y and T256E; M252Y, S254T and T256E; or K288D and H435K, wherein the numbering is that of the EU index as in Kabat.

The invention further provides such B7-H3-ADCs wherein at least one of the LM is a Linker Molecule, and particularly wherein the LM Linker Molecule is a peptidic linker and/or a cleavable linker.

The invention further provides such B7-H3-ADCs wherein the molecule comprises the formula:

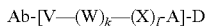

wherein:
V is the cleavable LM Linker Molecule,
$(W)_k$—$(X)_l$-A is an elongated, self-eliminating spacer system, that self-eliminates via a 1, (4+2n)-elimination,
W and X are each a 1, (4+2n) electronic cascade spacer, being the same or different,
A is either a spacer group of formula $(Y)_m$, wherein Y is a 1, (4+2n) electronic cascade spacer, or a group of formula U, being a cyclisation elimination spacer,
k, l and m are independently an integer of 0 (included) to 5 (included),
n is an integer of 0 (included) to 10 (included),
with the provisos that:
  when A is $(Y)_m$: then k+l+m≥1, and
  if k+l+m=1, then n>1;
  when A is U: then k+l≥1.
W, X, and Y are independently selected from compounds having the formula:

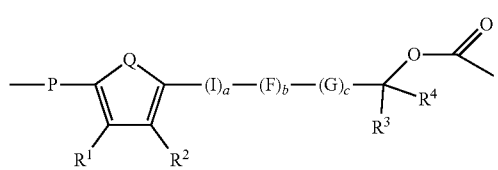

or the formula:

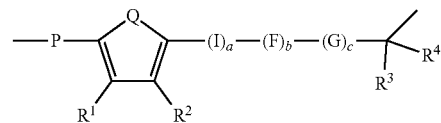

wherein: Q is —R$^5$C=CR$^6$—, S, O, NR$^5$, —R$^5$C=N—, or —N=CR$^5$—
P is NR$^7$, O or S
a, b, and c are independently an integer of 0 (included) to 5 (included);
I, F and G are independently selected from compounds having the formula:

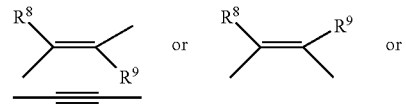

wherein R$^1$, R$^2$, R$^3$, R$^4$, R$^5$, R$^6$, R$^7$, R$^8$, and R$^9$ independently represent H, C$_{1-6}$ alkyl, C$_{3-20}$ heterocyclyl, C$_{5-20}$ aryl, C$_{1-6}$ alkoxy, hydroxy (OH), amino (NH$_2$), mono-substituted amino (NR$_x$H), di-substituted amino (NR$_x^1$R$_x^2$), nitro (NO$_2$), halogen, CF$_3$, CN, CONH$_2$, SO$_2$Me, CONHMe, cyclic C$_{1-5}$ alkylamino, imidazolyl, C$_{1-6}$ alkylpiperazinyl, morpholino, thiol (SH), thioether (SR$_x$), tetrazole, carboxy (COOH), carboxylate (COOR$_x$), sulphoxy (S(=O)$_2$OH), sulphonate (S(=O)$_2$OR$_x$), sulphonyl (S(=O)$_2$R$_x$), sulphixy (S(=O)OH), sulphinate (S(=O)OR$_x$), sulphinyl (S(=O)R$_x$), phosphonooxy (OP(=O)(OH)$_2$), and phosphate (OP(=O)(OR$_x$)$_2$), where R$_x$, R$_x^1$ and R$_x^2$ are independently selected from a C$_{1-6}$ alkyl group, a C$_{3-20}$ heterocyclyl group or a C$_{5-20}$ aryl group, two or more of the substituents R$^1$, R$^2$, R$^3$, R$^4$, R$^5$, R$^6$, R$^7$, R$^8$, or R$^9$ optionally being connected to one another to form one or more aliphatic or aromatic cyclic structures;
U is selected from compounds having the formula:

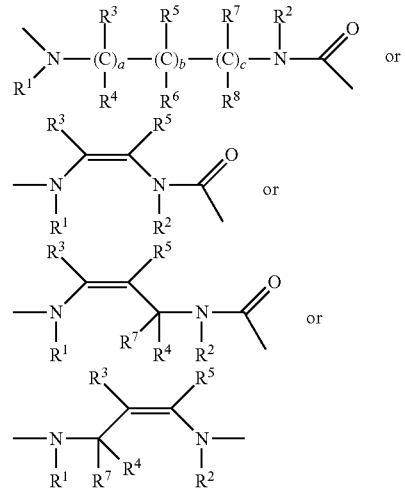

wherein:
a, b and c are independently selected to be an integer of 0 or 1; provided that a+b+c=2 or 3;

$R^1$ and/or $R^2$ independently represent H, $C_{1-6}$ alkyl, the alkyl being optionally substituted with one or more of the following groups: hydroxy (OH), ether ($OR_x$), amino ($NH_2$), mono-substituted amino ($NR_xH$), disubstituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are selected from a $C_{1-6}$ alkyl group, a $C_{3-20}$ heterocyclyl group or a $C_{5-20}$ aryl group; and $R^3$, $R^4$, $R^5$, $R^6$, $R^7$ and $R^8$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), disubstituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are selected from a $C_{1-6}$ alkyl group, a $C_{3-20}$ heterocyclyl group or a $C_{5-20}$ aryl group, and two or more of the substituents $R^1$, $R^2$, $R^3$, $R^4$, $R^5$, $R^6$, $R^7$, or $R^8$ are optionally connected to one another to form one or more aliphatic or aromatic cyclic structures.

The invention further provides such B7-H3-ADCs wherein the LM Linker Molecule comprises:
(1) p-aminobenzyloxycarbonyl-p-aminobenzyloxycarbonyl;
(2) p-aminobenzyloxycarbonyl-p-aminobenzyloxycarbonyl-p-aminobenzyloxycarbonyl;
(3) p-aminocinnamyloxycarbonyl;
(4) p-aminocinnamyloxycarbonyl-p-aminobenzyloxycarbonyl;
(5) p-amino-benzyloxycarbonyl-p-aminocinnamyloxycarbonyl;
(6) p-aminocinnamyloxycarbonyl-p-aminocinnamyloxycarbonyl;
(7) p-aminophenylpentadienyloxycarbonyl;
(8) p-aminophenylpentadienyloxycarbonyl-p-aminocinnamyloxycarbonyl;
(9) p-aminophenylpentadienyloxycarbonyl-p-aminobenzyloxycarbonyl;
(10) p-aminophenylpentadienyloxycarbonyl-p-aminophenylpentadienyloxycarbonyl;
(11) p-aminobenzyloxycarbonyl(methylamino)ethyl(methylamino) carbonyl;
(12) p-aminocinnamyloxycarbonyl(methylamino)ethyl (methylamino) carbonyl;
(13) p-aminobenzyloxycarbonyl-p-aminobenzyloxycarbonyl(methylamino) ethyl(methylamino)carbonyl;
(14) p-aminocinnamyloxycarbonyl-p-aminobenzyloxycarbonyl (methylamino)ethyl(methylamino)carbonyl;
(15) p-aminobenzyloxycarbonyl-p-aminocinnamyloxycarbonyl (methylamino)ethyl(methylamino)-carbonyl;
(16) p-aminocinnamyloxycarbonyl-p-aminocinnamyloxycarbonyl (methylamino)ethyl(methylamino)carbonyl;
(17) p-aminobenzyloxycarbonyl-p-aminobenzyl;
(18) p-aminobenzyloxycarbonyl-p-aminobenzyloxycarbonyl-p-aminobenzyl;
(19) p-aminocinnamyl;
(20) p-aminocinnamyloxycarbonyl-p-aminobenzyl;
(21) p-aminobenzyloxycarbonyl-p-aminocinnamyl;
(22) p-amino-cinnamyloxycarbonyl-p-aminocinnamyl;
(23) p-aminophenylpentadienyl;
(24) p-aminophenylpentadienyloxycarbonyl-p-aminocinnamyl;
(25) p-aminophenylpentadienyloxycarbonyl-p-aminobenzyl;
or
(26) p-aminophenylpentadienyloxycarbonyl-p-aminophenylpentadienyl.

The invention further provides such B7-H3-ADCs wherein the LM Linker Molecule is conjugated to the side chain of an amino acid of a polypeptide chain of Ab and binds the Ab to a molecule of the cytotoxic drug moiety D, and in particular, wherein the cytotoxic drug moiety D comprises a cytotoxin, a radioisotope, an immunomodulator, a cytokine, a lymphokine, a chemokine, a growth factor, a tumor necrosis factor, a hormone, a hormone antagonist, an enzyme, an oligonucleotide, a DNA, an RNA, an siRNA, an RNAi, a microRNA, a photoactive therapeutic agent, an anti-angiogenic agent, a pro-apoptotic agent, a peptide, a lipid, a carbohydrate, a chelating agent, or a combinations thereof.

The invention further provides such B7-H3-ADCs wherein the LM Linker Molecule is conjugated to the side chain of an amino acid of a polypeptide chain of Ab and binds the Ab to a molecule of the cytotoxic drug moiety D, and in particular, wherein the cytotoxic drug moiety D comprises a cytotoxin selected from the group consisting of a tubulysin (especially a tubulysin cytotoxin selected from the group consisting of tubulysin A, tubulysin B, tubulysin C, and tubulysin D), an auristatin (especially an auristatin cytotoxin selected from the group consisting of MMAE (N-methylvaline-valine-dolaisoleuine-dolaproine-norephedrine) and MMAF (N-methylvaline-valine-dolaisoleuine-dolaproine-phenylalanine), a maytansinoid (especially a maytansinoid cytotoxin selected from the group consisting of Mytansine, DM1 and DM4), a calicheamicin (especially a calichearmicin cytotoxin selected from the group consisting of calicheamicin γ1, calicheamicin β1Br, calicheamicin γ1Br, calicheamicin α2I, calicheamicin α3I, calicheamicin β1I, calicheamicin γ1I, and calicheamicin Δ1I), a pyrrolobenzodiazepine (especially a pyrrolobenzodiazepine cytotoxin selected from the group consisting of vadastuximab talirine, SJG-136, SG2000, SG2285 and SG2274), and a duocarmycin (especially a duocarmycin cytotoxin and is selected from the group consisting of duocarmycin A, duocarmycin B1, doucarmycin B2, duocarmycin C1, duocarmycin C2, duocarmycin D, duocarmycin SA, CC-1065, adozelesin, bizelesin, carzelesin (U-80244) and spiro-duocarmycin (DUBA)).

The invention further provides pharmaceutical compositions comprising an effective amount of any of the above-described B7-H3-ADCs and a pharmaceutically acceptable carrier, excipient or diluent.

The invention is additionally directed to the use of any of the above-described B7-H3-ADCs in the treatment of a disease or condition associated with or characterized by the expression of B7-H3, or in a method of treating a disease or condition characterized by the expression of B7-H3, particularly wherein the disease or condition associated with or characterized by the expression of B7-H3 is cancer, and more particularly, wherein the cancer is selected from the group consisting of an acute myeloid leukemia, an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, a glioblastoma, an islet cell tumor, a Kaposi's Sarcoma, a kidney cancer, a leukemia, a liposarcoma/malignant lipomatous tumor, a liver cancer, a lymphoma, a lung cancer, a medulloblastoma, a melanoma, a meningioma, a malignant mesothelioma, a multiple endocrine neoplasia, a multiple myeloma, a myelodysplastic syndrome, a neuroblastoma, a neuroendocrine tumors, a non-small cell lung cancer, an ovarian cancer, a pancreatic cancer, a pharyngeal cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a renal cell carcinoma, a renal metastatic cancer, a rhabdoid tumor, a rhabdomyosacoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

BRIEF DESCRIPTION OF THE DRAWINGS

FIG. 3A shows an Fc Domain-containing diabody which contains a peptide Heterodimer-Promoting Domain comprising a cysteine residue. FIG. 3B shows an Fc Domain-containing diabody, which contains E-coil and K-coil Heterodimer-Promoting Domains comprising a cysteine residue and a linker (with an optional cysteine residue). FIG. 3C, shows an Fc-Region-Containing diabody, which contains antibody CH1 and CL domains.

FIGS. 6A and 6B, respectively, illustrate schematically the domains of trivalent binding molecules comprising two diabody-type binding domains and a Fab-type binding domain having different domain orientations in which the diabody-type binding domains are N-terminal or C-terminal to an Fc Domain. The molecules in FIGS. 6A and 6B comprise four chains. FIGS. 6C and 6D, respectively, illustrate schematically the domains of trivalent binding molecules comprising two diabody-type binding domains N-terminal to an Fc Domain, and a Fab-type binding domain in which the light chain and heavy chain are linked via a polypeptide spacer, or an scFv-type binding domain. The trivalent binding molecules in FIGS. 6E and 6F, respectively, illustrate schematically the domains of trivalent binding molecules comprising two diabody-type binding domains C-terminal to an Fc Domain, and a Fab-type binding domain in which the light chain and heavy chain are linked via a polypeptide spacer, or an scFv-type binding domain. The trivalent binding molecules in FIGS. 6C-6F comprise three chains. VL and VH Domains that recognize the same epitope are shown using the same shading or fill pattern.

FIG. 15A, Calu-6 cells; FIG. 15B, NCI-H1703 cells; FIG. 15C, Hs700T cells. The control molecule binds CD20 and is conjugated to DUBA ("Ctrl-DUBA").

FIG. 20A shows results for vehicle, hmAb-C-DUBA or Ctrl-DUBA at 6 mg/kg (single dose). FIG. 20B shows results for vehicle, hmAb-C-DUBA or Ctrl-DUBA at 3 mg/kg (single dose). FIG. 20C shows results for vehicle, hmAb-C-DUBA or Ctrl-DUBA at 3 mg/kg (three doses). FIG. 20D shows all of the results on a single graph.

FIG. 21A shows results for vehicle, hmAb-C-DUBA or Ctrl-DUBA at 10 mg/kg (single or double dose). FIG. 21B shows results for vehicle, hmAb-C-DUBA or Ctrl-DUBA at 6 mg/kg (single or quadruple dose). FIG. 21C shows results for vehicle, hmAb-C-DUBA or Ctrl-DUBA at 3 mg/kg (single doses). FIG. 21D shows all of the results on a single graph.

DETAILED DESCRIPTION OF THE INVENTION

Figure 1:
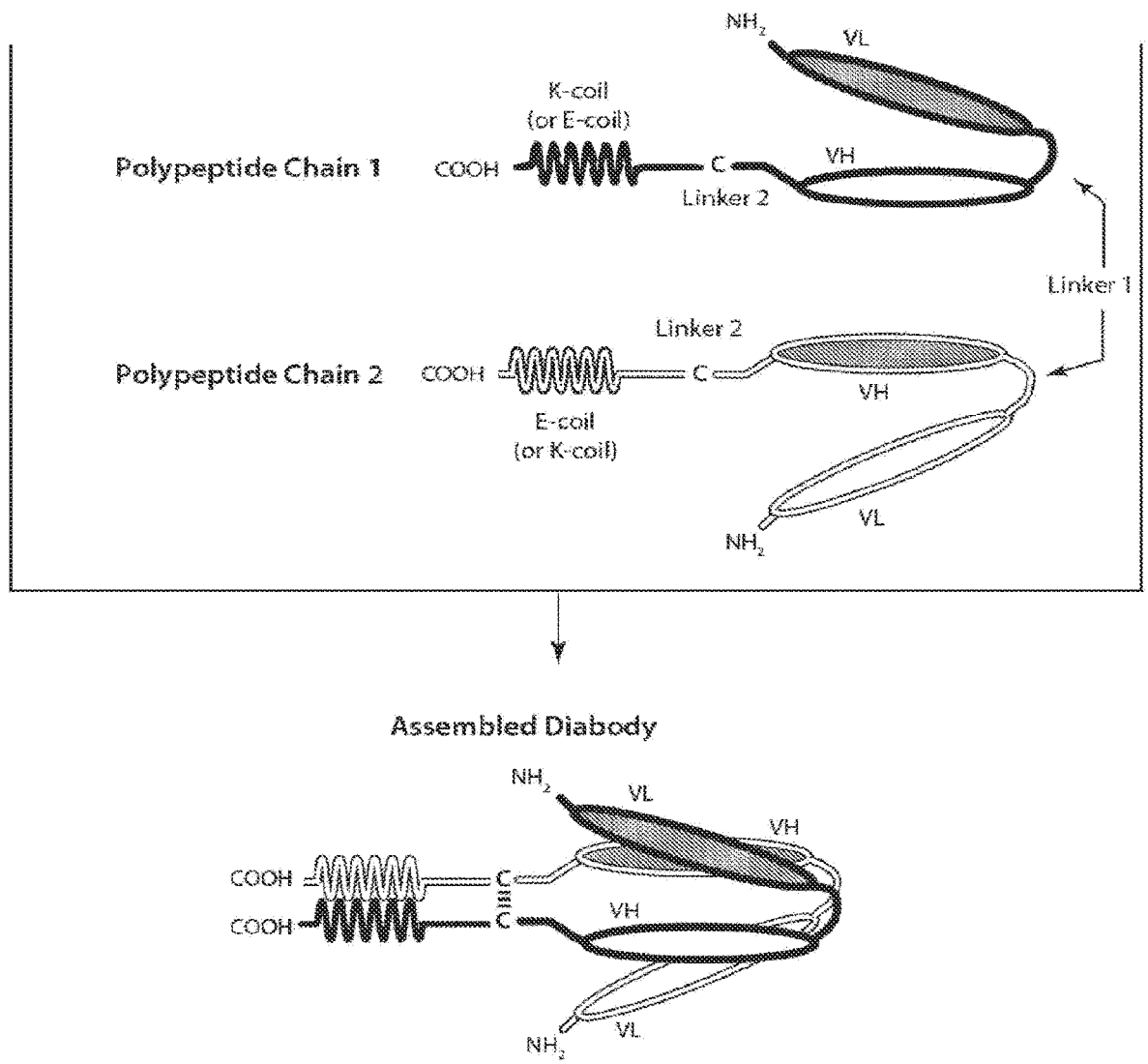
FIG. 1 provides a schematic of a representative covalently bonded diabody having two epitope-binding sites composed of two polypeptide chains, each having an E-coil or K-coil Heterodimer-Promoting Domain (alternative Heterodimer-Promoting Domains are provided below). A cysteine residue may be present in a linker and/or in the Heterodimer-Promoting Domain as shown in FIG. 3B. VL and VH Domains that recognize the same epitope are shown using the same shading or fill pattern.

The present invention is directed to novel B7-H3-binding molecules capable of binding to human and non-human B7-H3, and in particular to such molecules that are cross-reactive with B7-H3 of a non-human primate (e.g., a cynomolgus monkey). The invention additionally pertains to B7-H3-binding molecules that comprise Variable Light Chain and/or Variable Heavy Chain (VH) Domains that have been humanized and/or deimmunized so as to exhibit a reduced immunogenicity upon administration to recipient subjects. The invention particularly pertains to bispecific, trispecific or multispecific B7-H3-binding molecules, including bispecific diabodies, BiTEs, bispecific antibodies, trivalent binding molecules, etc. that comprise: (i) such B7-H3-binding Variable Domains and (ii) a domain capable of binding to an epitope of a molecule present on the surface of an effector cell. The invention is also directed to pharmaceutical compositions that contain any of such B7-H3-binding molecules, and to methods involving the use of any of such B7-H3-binding molecules in the treatment of cancer and other diseases and conditions. The invention also particularly pertains to a molecule that comprises the human B7-H3 binding domain of a humanized anti-human B7-H3 antibody conjugated to at least one drug moiety (a "B7-H3-ADC"). The invention is also directed to pharmaceutical compositions that contain such B7-H3-ADCs, and to methods involving the use of any of such B7-H3-ADCs in the treatment of cancer and other diseases and conditions.

The present invention is also directed to a molecule that comprises the human B7-H3 binding domain of a humanized anti-human B7-H3 antibody conjugated to at least one drug moiety (a "B7-H3-ADC"). The invention is also directed to pharmaceutical compositions that contain such B7-H3-ADCs, and to methods involving the use of any of such B7-H3-ADCs in the treatment of cancer and other diseases and conditions.

The B7-H3-ADC molecules of the present invention comprise the formula:

$$Ab\text{-}(LM)_m\text{-}(D)_n,$$

wherein:
Ab is an antibody that binds to B7-H3 that comprises a humanized Variable Heavy Chain (VH) Domain and a humanized Variable Light Chain (VL) Domain, or is a B7-H3-binding fragment thereof, and;
D is a cytotoxic drug moiety;
LM is a bond or a Linker Molecule that covalently links Ab and D;
m is an integer between 0 and n and denotes the number of Linker Molecules of the B7-H3-ADC; and
n is an integer between 1 and 10 and denotes the number of cytotoxic drug moieties covalently linked to the B7-H3-ADC molecule.

I. Antibodies and their Binding Domains

The antibodies of the present invention are immunoglobulin molecules capable of specific binding to a target, such as a carbohydrate, polynucleotide, lipid, polypeptide, etc., through at least one antigen recognition site, located in the Variable Domain of the immunoglobulin molecule. The B7-H3-ADC molecules of the present invention thus comprise an antibody that binds to B7-H3 or a B7-H3-binding fragment thereof. As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, Fab fragments, F(ab') fragments, disulfide-linked bispecific Fvs (sdFv), intrabodies, and epitope-binding fragments of any of the above. In particular, the term "antibody" includes immunoglobulin molecules and immunologically active fragments of immunoglobulin molecules, i.e., molecules that contain an epitope-binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. Antibodies are capable of "immunospecifically binding" to a polypeptide or protein or a non-protein molecule (or of binding to such molecule in an "immunospecific manner") due to the presence on such molecule of a particular domain or moiety or conformation (an "epitope"). An epitope-containing molecule may have immunogenic activity, such that it elicits an antibody production response in an animal; such molecules are termed "antigens". The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Over 200 antibody-based drugs have been approved for use or are under development.

As used herein, an antibody, diabody or other epitope-binding molecule is said to "immunospecifically" bind a region of another molecule (i.e., an epitope) if it reacts or associates more frequently, more rapidly, with greater duration and/or with greater affinity with that epitope relative to alternative epitopes. For example, an antibody that immunospecifically binds to a viral epitope is an antibody that binds this viral epitope with greater affinity, avidity, more readily, and/or with greater duration than it immunospecifically binds to other viral epitopes or non-viral epitopes. It is also understood by reading this definition that, for example, an antibody (or moiety or epitope) that immunospecifically binds to a first target may or may not specifically or preferentially bind to a second target. As such, "immuno-specific binding" does not necessarily require (although it can include) exclusive binding. Generally, but not necessarily, reference to binding means "immunospecific" binding. Two molecules are said to be capable of binding to one another in a "physiospecific" manner, if such binding exhibits the specificity with which receptors bind to their respective ligands.

The term "monoclonal antibody" refers to a homogeneous antibody population wherein the monoclonal antibody is comprised of amino acids (naturally occurring or non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', F(ab')$_2$, Fv, etc.), single-chain (scFv) binding molecules, mutants thereof, fusion proteins comprising an antibody

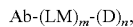

portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3):119-125). In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody. The general principle in humanizing an antibody involves retaining the basic sequence of the antigen-binding portion of the antibody, while swapping the non-human remainder of the antibody with human antibody sequences.

Natural antibodies (such as IgG antibodies) are composed of two "Light Chains" complexed with two "Heavy Chains." Each Light Chain contains a Variable Domain ("VL") and a Constant Domain ("CL"). Each Heavy Chain contains a Variable Domain ("VH"), three Constant Domains ("CH1," "CH2" and "CH3"), and a "Hinge" Region ("H") located between the CH1 and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal ("N-terminal") portion of each chain includes a Variable Domain of about 100 to 110 or more amino acids primarily responsible for antigen recognition. The carboxy-terminal ("C-terminal") portion of each chain defines a constant region, with light chains having a single Constant Domain and heavy chains usually having three Constant Domains and a Hinge Domain. Thus, the structure of the light chains of an IgG molecule is n-VL-CL-c and the structure of the IgG heavy chains is n-VH-CH1-H-CH2-CH3-c (where n and c represent, respectively, the N-terminus and the C-terminus of the polypeptide).

A. Characteristics of Antibody Variable Domains

The Variable Domains of an IgG molecule consist of the complementarity determining regions ("CDR"), which contain the residues in contact with epitope, and non-CDR segments, referred to as framework segments ("FR"), which in general maintain the structure and determine the positioning of the CDR loops so as to permit such contacting (although certain framework residues may also contact antigen). Thus, the VL and VH Domains have the structure n-FR1-CDR1-FR2-CDR2-FR3-CDR3-FR4-c. Polypeptides that are (or may serve as) the first, second and third CDR of the Light Chain of an antibody are herein respectively designated as: $CDR_L1$ Domain, $CDR_L2$ Domain, and $CDR_L3$ Domain. Similarly, polypeptides that are (or may serve as) the first, second and third CDR of the Heavy Chain of an antibody are herein respectively designated as: $CDR_H1$ Domain, $CDR_H2$ Domain, and $CDR_{11}3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or is a diabody or a single-chain binding molecule (e.g., an scFv, a BiTe, etc.), or is another type of protein. Accordingly, as used herein, the term "epitope-binding fragment" denotes a fragment of a molecule capable of immunospecifically binding to an epitope. An epitope-binding fragment may contain any 1, 2, 3, 4, or 5 the CDR Domains of an antibody, or may contain all 6 of the CDR Domains of an antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino terminus and a carboxy terminus (e.g., a diabody, a Fab fragment, an $Fab_2$ fragment, etc.). Unless specifically noted, the order of domains of the protein molecules described herein is in the "N-terminal to C-Terminal" direction.

The invention particularly encompasses single-chain Variable Domain fragments ("scFv") comprising a humanized anti-B7-H3-VL and/or VH Domain of this invention and multispecific binding molecules comprising the same. Single-chain Variable Domain fragments comprise VL and VH Domains that are linked together using a short "Linker" peptide. Such Linkers can be modified to provide additional functions, such as to permit the attachment of a drug or to permit attachment to a solid support. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention also particularly encompasses the $CDR_H1$, $CDR_H2$, $CDR_H3$, $CDR_L1$, $CDR_L2$, $CDR_L3$, or the VL Domain and/or the VH Domain of humanized variants of the B7-H3 antibodies of the invention, as well as multispecific-binding molecules comprising the same. The term "humanized" antibody refers to a chimeric molecule, generally prepared using recombinant techniques, having an epitope-binding site of an immunoglobulin from a non-human species and a remaining immunoglobulin structure of the molecule that is based upon the structure and/or sequence of a human immunoglobulin. The anti-B7-H3 antibodies of the present invention particularly include humanized, chimeric or caninized variants of antibodies mAb-A, mAb-B, mAb-C or mAb-D. The polynucleotide sequence of the variable domains of such antibodies may be used for genetic manipulation to generate such derivatives and to improve the affinity, or other characteristics of such antibodies. The general principle in humanizing an antibody involves retaining the basic sequence of the epitope-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

The epitope-binding site may comprise either a complete Variable Domain fused onto Constant Domains or only the complementarity determining regions (CDRs) of such Variable Domain grafted to appropriate framework regions. Epitope-binding domains may be wild-type or modified by one or more amino acid substitutions. This eliminates the constant region as an immunogen in human individuals, but the possibility of an immune response to the foreign variable domain remains (LoBuglio, A. F. et al. (1989) "*Mouse Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable domains as well so as to reshape them as closely as possible to human form. It is known that the variable domains of both heavy and light chains contain three complementarity determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable domains can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

A number of humanized antibody molecules comprising an epitope-binding site derived from a non-human immunoglobulin have been described, including chimeric antibodies having rodent or modified rodent Variable Domain and their associated complementarity determining regions (CDRs) fused to human constant domains (see, for example, Winter et al. (1991) "*Man-made Antibodies*," Nature 349: 293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody (17-4A) To A Colon Cancer Tumor-Associated Antigen*," J. Immunol. 138:4534-4538, and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody Constant Domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321: 522-525). Another reference describes rodent CDRs supported by recombinantly veneered rodent framework regions. See, for example, European Patent Publication No. 519,596. These "humanized" molecules are designed to minimize unwanted immunological response towards rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866,692.

B. Characteristics of Antibody Constant Domains

1. Constant Domains of the Light Chain

As indicated above, each Light Chain of an antibody contains a Variable Domain ("VL") and a Constant Domain ("CL").

A preferred CL Domain is a human IgG CL Kappa Domain. The amino acid sequence of an exemplary human CL Kappa Domain is (SEQ ID NO:1):

```
RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC
```

Alternatively, an exemplary CL Domain is a human IgG CL Lambda Domain. The amino acid sequence of an exemplary human CL Lambda Domain is (SEQ ID NO:2):

```
QPKAAPSVIL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS
```

2. Constant Domains of the Heavy Chain

As indicated above, the heavy chains of an antibody may comprise CH1, Hinge Domain, CH2 and CH3 constant domains. The CH1 Domains of the two heavy chains of an antibody complex with the antibody's Light Chain's "CL" constant region, and are attached to the heavy chains CH2 Domains via an intervening Hinge Domain.

An exemplary CH1 Domain is a human IgG1 CH1 Domain. The amino acid sequence of an exemplary human IgG1 CH1 Domain is (SEQ ID NO:3):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRV
```

An exemplary CH1 Domain is a human IgG2 CH1 Domain. The amino acid sequence of an exemplary human IgG2 CH1 Domain is (SEQ ID NO:4):

```
ASTKGPSVFP LAPCSRSTSE STAALGCLVK DYFPEPVTVS

WNSGALTSGV HTFPAVLQSS GLYSLSSVVT VPSSNFGTQT

YTCNVDHKPS NTKVDKTV
```

An exemplary CH1 Domain is a human IgG3 CH1 Domain. The amino acid sequence of an exemplary human IgG3 CH1 Domain is (SEQ ID NO:5):

```
ASTKGPSVFP LAPCSRSTSG GTAALGCLVK DYFPEPVTVS

WNSGALTSGV HTFPAVLQSS GLYSLSSVVT VPSSSLGTQT

YTCNVNHKPS NTKVDKRV
```

An exemplary CH1 Domain is a human IgG4 CH1 Domain. The amino acid sequence of an exemplary human IgG4 CH1 Domain is (SEQ ID NO:6):

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRV
```

An exemplary Hinge Domain is a human IgG1 Hinge Domain. The amino acid sequence of an exemplary human IgG1 Hinge Domain is (SEQ ID NO:7):

```
EPKSCDKTHTCPPCP
```

Another exemplary Hinge Domain is a human IgG2 Hinge Domain. The amino acid sequence of an exemplary human IgG2 Hinge Domain is (SEQ ID NO:8):

```
ERKCCVECPPCP
```

Another exemplary Hinge Domain is a human IgG3 Hinge Domain. The amino acid sequence of an exemplary human IgG3 Hinge Domain is (SEQ ID NO:9):

```
ELKTPLGDTT HTCPRCPEPK SCDTPPPCPR CPEPKSCDTP

PPCPRCPEPK SCDTPPPCPR CP
```

Another exemplary Hinge Domain is a human IgG4 Hinge Domain. The amino acid sequence of an exemplary human IgG4 Hinge Domain is (SEQ ID NO:10): ESKYGPPCPSCP. As described herein, an IgG4 Hinge Domain may comprise a stabilizing mutation such as the S228P substitution. The amino acid sequence of an exemplary S228P-stabilized human IgG4 Hinge Domain is (SEQ ID NO:11): ESKYGPPCPPCP.

The CH2 and CH3 Domains of the two heavy chains of an antibody interact to form an "Fc Domain," which is a domain that is recognized by cellular Fc Receptors, including but not limited to Fc gamma Receptors (FcγRs). As used herein, the term "Fc Domain" is used to define a C-terminal region of an IgG heavy chain. An Fc Domain is said to be of a particular IgG isotype, class or subclass if its amino acid sequence is most homologous to that isotype relative to other IgG isotypes. In addition to their known uses in diagnostics, antibodies have been shown to be useful as therapeutic agents.

Throughout the present specification, the numbering of the residues in the constant region of an IgG heavy chain is that of the EU index as in Kabat et al., *SEQUENCES OF PROTEINS OF IMMUNOLOGICAL INTEREST*, 5$^{th}$ Ed. Public Health Service, NH1, MD (1991) ("Kabat"), expressly incorporated herein by reference. The term "EU index as in Kabat" refers to the numbering of the constant domains of human IgG1 EU antibody. Amino acids from the Variable Domains of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid, and the CDRs are identified as defined by Kabat (it will be understood that CDR$_H$1 as defined by Chothia, C. & Lesk, A. M. ((1987) "*Canonical structures for the hypervariable regions of immunoglobulins*," J. Mol. Biol. 196:901-917) begins five residues earlier). Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

The amino acid sequence of the CH2-CH3 Domain of an exemplary human IgG1 is (SEQ ID NO:12):

```
         231        240        250        260        270        280
         APELLGGPSV FLFPPKPKDT LMISRTPEVT CVVVDVSHED PEVKFNWYVD 290        300        310        320        330
         GVEVHNAKTK PREEQYNSTY RVVSVLTVLH QDWLNGKEYK CKVSNKALPA 340        350        360        370        380
         PIEKTISKAK GQPREPQVYT LPPSREEMTK NQVSLTCLVK GFYPSDIAVE 390        400        410        420        430
         WESNGQPENN YKTTPPVLDS DGSFFLYSKL TVDKSRWQQG NVFSCSVMHE 440        447
         ALHNHYTQKS LSLSPGX
``` as numbered by the EU index as set forth in Kabat, wherein X is a lysine (K) or is absent.

The amino acid sequence of the CH2-CH3 Domain of an exemplary human IgG2 is (SEQ ID NO:13):

```
         231        240        250        260        270        280
         APPVA-GPSV FLFPPKPKDT LMISRTPEVT CVVVDVSHED PEVQFNWYVD 290        300        310        320        330
         GVEVHNAKTK PREEQFNSTF RVVSVLTVVH QDWLNGKEYK CKVSNKGLPA 340        350        360        370        380
         PIEKTISKTK GQPREPQVYT LPPSREEMTK NQVSLTCLVK GFYPSDISVE 390        400        410        420        430
         WESNGQPENN YKTTPPMLDS DGSFFLYSKL TVDKSRWQQG NVFSCSVMHE 440        447
         ALHNHYTQKS LSLSPGX
``` as numbered by the EU index as set forth in Kabat, wherein X is a lysine (K) or is absent.

The amino acid sequence of the CH2-CH3 Domain of an exemplary human IgG3 is (SEQ ID NO:14):

```
         231        240        250        260        270        280
         APELLGGPSV FLFPPKPKDT LMISRTPEVT CVVVDVSHED PEVQFKWYVD 290        300        310        320        330
         GVEVHNAKTK PREEQYNSTF RVVSVLTVLH QDWLNGKEYK CKVSNKALPA 340        350        360        370        380
         PIEKTISKTK GQPREPQVYT LPPSREEMTK NQVSLTCLVK GFYPSDIAVE 390        400        410        420        430
         WESSGQPENN YNTTPPMLDS DGSFFLYSKL TVDKSRWQQG NIFSCSVMHE 440        447
         ALHNRFTQKS LSLSPGX
``` as numbered by the EU index as set forth in Kabat, wherein X is a lysine (K) or is absent.

The amino acid sequence of the CH2-CH3 Domain of an exemplary human IgG4 is (SEQ ID NO:15):

```
         231        240        250        260        270        280
         APEFLGGPSV FLFPPKPKDT LMISRTPEVT CVVVDVSQED PEVQFNWYVD 290        300        310        320        330
         GVEVHNAKTK PREEQFNSTY RVVSVLTVLH QDWLNGKEYK CKVSNKGLPS
```

```
            340        350        360        370        380
SIEKTISKAK GQPREPQVYT LPPSQEEMTK NQVSLTCLVK GFYPSDIAVE 390        400        410        420        430
WESNGQPENN YKTTPPVLDS DGSFFLYSRL TVDKSRWQEG NVFSCSVMHE 440    447
ALHNHYTQKS LSLSLGX
``` as numbered by the EU index as set forth in Kabat, wherein X is a lysine (K) or is absent.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., "*The Human IgG Subclasses: Molecular Analysis Of Structure, Function And Regulation.*" Pergamon, Oxford, pp. 43-78 (1990); Lefranc, G. et al., 1979, Hum. Genet.: 50, 199-211). It is specifically contemplated that the antibodies of the present invention may incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the B7-H3-binding molecules (including B7-H3-ADC molecules) of the invention. Specifically encompassed by the instant invention are B7-H3-binding molecules (including B7-H3-ADC molecules) lacking the C-terminal residue of the CH3 Domain. Also specifically encompassed by the instant invention are such constructs comprising the C-terminal lysine residue of the CH3 Domain.

In traditional immune function, the interaction of antibody-antigen complexes with cells of the immune system results in a wide array of responses, ranging from effector functions such as antibody dependent cytotoxicity, mast cell degranulation, and phagocytosis to immunomodulatory signals such as regulating lymphocyte proliferation and antibody secretion. All of these interactions are initiated through the binding of the Fc Domain of antibodies or immune complexes to specialized cell surface receptors on hematopoietic cells, and particularly to receptors (singularly referred to as an "Fc gamma receptor" "FcγR," and collectively as "FcγRs") found on the surfaces of multiple types of immune system cells (e.g., B lymphocytes, follicular dendritic cells, natural killer cells, macrophages, neutrophils, eosinophils, basophils and mast cells). Such receptors have an "extracellular" portion (which is thus capable of ligating to an Fc Domain), a "transmembrane" portion (which extends through the cellular membrane, and a "cytoplasmic" portion (positioned inside the cell).

The diversity of cellular responses triggered by antibodies and immune complexes results from the structural heterogeneity of the three Fc receptors: FcγRI (CD64), CD32A (FcγRIIA), FcγRIIB (CD32B), CD16A (FcγRIIIA) and CD16B (FcγRIIIB). FcγRI (CD64), FcγRIIA (CD32A) and FcγRIII (CD16) are activating receptors such that their ligation to an Fc Domain activates the immune system or enhances the immune response. In contrast, FcγRIIB (CD32B) is an inhibiting receptor; ligation to an Fc Domain inhibits an immune response or dampens an existing immune response. In addition, interaction of an Fc Domain with with the neonatal Fc Receptor (FcRn) mediates the recycling of IgG molecules from the endosome to the cell surface and release into the blood. The amino acid sequence of exemplary wild-type Fc Domains of IgG1 (SEQ ID NO:12), IgG2 (SEQ ID NO:13), IgG3 (SEQ ID NO:14), and IgG4 (SEQ ID NO:15) are presented above.

CD16 is a generic name for the activating Fc receptors, FcγRIIIA (CD16A) and FcγRIIIB (CD16B). CD16 is expressed by neutrophils, eosinophils, natural killer (NK) cells, and tissue macrophages that bind aggregated but not monomeric human IgG (Peltz, G. A. et al. (1989) "*Human Fc Gamma RII: Cloning, Expression, And Identification Of The Chromosomal Locus Of Two Fc Receptors For IgG,*" Proc. Natl. Acad. Sci. (U.S.A.) 86(3):1013-1017; Bachanova, V. et al. (2014) "*NK Cells In Therapy Of Cancer,*" Crit. Rev. Oncog. 19(1-2):133-141; Miller, J. S. (2013) "*Therapeutic Applications: Natural Killer Cells In The Clinic,*" Hematology Am. Soc. Hematol. Educ. Program. 2013:247-253; Youinou, P. et al. (2002) "*Pathogenic Effects Of Anti-Fc Gamma Receptor IIIB (CD16) On Polymorphonuclear Neutrophils In Non-Organ-Specific Autoimmune Diseases,*" Autoimmun Rev. 1(1-2):13-19; Peipp, M. et al. (2002) "*Bispecific Antibodies Targeting Cancer Cells,*" Biochem. Soc. Trans. 30(4):507-511). These receptors bind to the Fc portion of IgG antibodies, thereby triggering the release of cytokines. If such antibodies are bound to the antigen of foreign cells (e.g., tumor cells), then such release mediates the killing of the tumor cell. Since such killing is antibody-dependent, it is termed antibody-dependent cell-mediated cytotoxicity (ADCC).

CD32A (FcγRIIA) (Brandsma, A. M. (2015) "Fc Receptor Inside-Out Signaling And Possible Impact On Antibody Therapy," Immunol Rev. 268(1):74-87; van Sorge, N. M. et al. (2003) "Fcgammar Polymorphisms: Implications For Function, Disease Susceptibility And Immunotherapy," Tissue Antigens 61(3):189-202; Selvaraj, P. et al. (2004) "Functional Regulation Of Human Neutrophil Fc Gamma Receptors," Immunol. Res. 29(1-3):219-230) and CD64 (FcγRI) (Lu, S. et al. (2015) "Structural Mechanism Of High Affinity FcγRI recognition Of Immunoglobulin G," Immunol. Rev. 268(1):192-200; Swisher, J. F. et al. (2015) "The Many Faces Of FeyRI: Implications For Therapeutic Antibody Function," Immunol. Rev. 268(1):160-174; Thepen, T. et al. (2009) "Fcgamma Receptor 1 (CD64), A Target Beyond Cancer," Curr. Pharm. Des. 15(23):2712-2718; Rouard, H. et al. (1997) "Fc Receptors As Targets For Immunotherapy," Int. Rev. Immunol. 16(1-2):147-185) are activating Fc receptors that are expressed on macrophages, neutrophils, eosinophils and dendritic cells (and for CD32A, also on platelets and Langerhan cells). In contrast, CD32B (FcγRIIB) is an inhibiting Fc receptor on B lymphocytes (macrophages, neutrophils, and eosinophils) (Stopforth, R. J. et al. (2016) "Regulation of Monoclonal Antibody Immunotherapy by FcγRIIB," J. Clin. Immunol. [2016 Feb. 27

Epub], pp. 1-7; Bruhns, P. et al. (2009) "*Specificity And Affinity Of Human Fcgamma Receptors And Their Polymorphic Variants For Human IgG Subclasses*," Blood. 113 (16):3716-3725; White, A. L. et al. (2014) "*FcγRIIB As A Key Determinant Of Agonistic Antibody Efficacy*," Curr. Top. Microbiol. Immunol. 382:355-372; Selvaraj, P. et al. (2004) "*Functional Regulation Of Human Neutrophil Fc Gamma Receptors*," Immunol. Res. 29(1-3):219-230).

The ability of the different FcγRs to mediate diametrically opposing functions reflects their structural differences, and in particular whether the FcγR possesses an immunoreceptor tyrosine-based activation motif ("ITAM") or an immunoreceptor tyrosine-based inhibitory motif ("ITIM"). The recruitment of different cytoplasmic enzymes to these structures dictates the outcome of the FcγR-mediated cellular responses. ITAM-containing FcγRs include FcγRI, FcγRIIA, FcγRIIIA, and activate the immune system when bound to Fc Domains (e.g., aggregated Fc Domains present in an immune complex). FcγRIIB is the only currently known natural ITIM-containing FcγR; it acts to dampen or inhibit the immune system when bound to aggregated Fc Domains. Human neutrophils express the FcγRIIA gene. FcγRIIA clustering via immune complexes or specific antibody cross-linking serves to aggregate ITAMs with receptor-associated kinases which facilitate ITAM phosphorylation. ITAM phosphorylation serves as a docking site for Syk kinase, the activation of which results in the activation of downstream substrates (e.g., PI$_3$K). Cellular activation leads to release of pro-inflammatory mediators. The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular Ca$^{++}$. Thus, cross-linking of FcγRIIB dampens the activating response to FcγR ligation and inhibits cellular responsiveness and aborts B-cell activation, B-cell proliferation and antibody secretion is thus aborted.

II. Bispecific Antibodies, Multispecific Diabodies and DART® Diabodies

The ability of an antibody to bind an epitope of an antigen depends upon the presence and amino acid sequence of the antibody's VL and VH Domains. Interaction of an antibody's Light Chain and Heavy Chain and, in particular, interaction of its VL and VH Domains forms one of the two epitope-binding sites of a natural antibody, such as an IgG. Natural antibodies are capable of binding to only one epitope species (i.e., they are monospecific), although they can bind multiple copies of that species (i.e., exhibiting bivalency or multivalency).

The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two binding sites) for the same epitope and/or antigen.

In order to provide molecules having greater capability than natural antibodies, a wide variety of recombinant bispecific antibody formats have been developed (see, e.g., PCT Publication Nos. WO 2008/003116, WO 2009/132876, WO 2008/003103, WO 2007/146968, WO 2009/018386, WO 2012/009544, WO 2013/070565), most of which use linker peptides either to fuse a further epitope-binding fragment (e.g., an scFv, VL, VH, etc.) to, or within the antibody core (IgA, IgD, IgE, IgG or IgM), or to fuse multiple epitope-binding fragments (e.g., two Fab fragments or scFvs). Alternative formats use linker peptides to fuse an epitope-binding fragment (e.g., an scFv, VL, VH, etc.) to a dimerization domain such as the CH2-CH3 Domain or alternative polypeptides (WO 2005/070966, WO 2006/107786A WO 2006/107617A, WO 2007/046893). PCT Publications Nos. WO 2013/174873, WO 2011/133886 and WO 2010/136172 disclose a trispecific antibody in which the CL and CH1 Domains are switched from their respective natural positions and the VL and VH Domains have been diversified (WO 2008/027236; WO 2010/108127) to allow them to bind to more than one antigen. PCT Publications Nos. WO 2013/163427 and WO 2013/119903 disclose modifying the CH2 Domain to contain a fusion protein adduct comprising a binding domain. PCT Publications Nos. WO 2010/028797, WO2010028796 and WO 2010/028795 disclose recombinant antibodies whose Fc Domains have been replaced with additional VL and VH Domains, so as to form trivalent binding molecules. PCT Publications Nos. WO 2003/025018 and WO2003012069 disclose recombinant diabodies whose individual chains contain scFv Domains. PCT Publication Nos. WO 2013/006544 discloses multivalent Fab molecules that are synthesized as a single polypeptide chain and then subjected to proteolysis to yield heterodimeric structures. PCT Publications Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional binding domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another).

The art has additionally noted the capability to produce diabodies that differ from such natural antibodies in being capable of binding two or more different epitope species (i.e., exhibiting bispecificity or multispecificity in addition to bivalency or multivalency) (see, e.g., Holliger et al. (1993) "'*Diabodies*': *Small Bivalent And Bispecific Antibody Fragments*," Proc. Natl. Acad. Sci. (U.S.A.) 90:6444-6448; US 2004/0058400 (Hollinger et al.); US 2004/0220388/WO 02/02781 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672; WO 02/02781 (Mertens et al.); Olafsen, T. et al. (2004) "*Covalent Disulfide-Linked Anti- CEA Diabody Allows Site-Specific Conjugation And Radiolabeling For Tumor Targeting Applications*," Protein Eng. Des. Sel. 17(1):21-27; Wu, A. et al. (2001) "*Multimerization Of A Chimeric Anti-CD20 Single Chain Fv-Fv Fusion Protein Is Mediated Through Variable Domain Exchange*," Protein Engineering 14(2): 1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P.

A. et al. (2009) "*Bispecific T-Cell Engaging Antibodies For Cancer Therapy,*" Cancer Res. 69(12):4941-4944).

The design of a diabody is based on the antibody derivative known as a single-chain Variable Domain fragment (scFv). Such molecules are made by linking Light and/or Heavy Chain Variable Domains by using a short linking peptide. Bird et al. (1988) ("*Single-Chain Antigen-Binding Proteins,*" Science 242:423-426) describes example of linking peptides which bridge approximately 3.5 nm between the carboxy terminus of one Variable Domain and the amino terminus of the other Variable Domain. Linkers of other sequences have been designed and used (Bird et al. (1988) "*Single-Chain Antigen-Binding Proteins,*" Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The provision of bispecific binding molecules (e.g., non-monospecific diabodies) provides a significant advantage over antibodies, including but not limited to, a "trans" binding capability sufficient to co-ligate and/or co-localize different cells that express different epitopes and/or a "cis" binding capability sufficient to co-ligate and/or co-localize different molecules expressed by the same cell. Bispecific binding molecules (e.g., non-monospecific diabodies) thus have wide-ranging applications including therapy and immunodiagnosis. Bispecificity allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris,*" Protein Eng. 10:1221-1225).

The ability to produce bispecific diabodies has led to their use (in "trans") to co-ligate two cells together, for example, by co-ligating receptors that are present on the surface of different cells (e.g., cross-linking cytotoxic T-cells to tumor cells) (Staerz et al. (1985) "*Hybrid Antibodies Can Target Sites For Attack By T Cells,*" Nature 314:628-631, and Holliger et al. (1996) "*Specific Killing Of Lymphoma Cells By Cytotoxic T-Cells Mediated By A Bispecific Diabody,*" Protein Eng. 9:299-305; Marvin et al. (2005) "*Recombinant Approaches To IgG-Like Bispecific Antibodies,*" Acta Pharmacol. Sin. 26:649-658). Alternatively (or additionally), bispecific (or tri- or multispecific) diabodies can be used (in "cis") to co-ligate molecules, such as receptors, etc., that are present on the surface of the same cell. Co-ligation of different cells and/or receptors is useful to modulate effector functions and/or immune cell signaling. Multispecific molecules (e.g., bispecific diabodies) comprising epitope-binding sites may be directed to a surface determinant of any immune cell such as CD2, CD3, CD8, CD16, T-Cell Receptor (TCR), NKG2D, etc., which are expressed on T lymphocytes, Natural Killer (NK) cells, Antigen-Presenting Cells or other mononuclear cells. In particular, epitope-binding sites directed to a cell surface receptor that is present on immune effector cells, are useful in the generation of multispecific binding molecules capable of mediating redirected cell killing.

However, the above advantages come at a salient cost. The formation of such non-monospecific diabodies requires the successful assembly of two or more distinct and different polypeptides (i.e., such formation requires that the diabodies be formed through the heterodimerization of different polypeptide chain species). This fact is in contrast to monospecific diabodies, which are formed through the homodimerization of identical polypeptide chains. Because at least two dissimilar polypeptides (i.e., two polypeptide species) must be provided in order to form a non-monospecific diabody, and because homodimerization of such polypeptides leads to inactive molecules (Takemura, S. et al. (2000) "*Construction Of A Diabody (Small Recombinant Bispecific Antibody) Using A Refolding System,*" Protein Eng. 13(8):583-588), the production of such polypeptides must be accomplished in such a way as to prevent covalent bonding between polypeptides of the same species (i.e., so as to prevent homodimerization) (Takemura, S. et al. (2000) "*Construction Of A Diabody (Small Recombinant Bispecific Antibody) Using A Refolding System,*" Protein Eng. 13(8):583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications,*" Prot. Engr. Des. Sel. 17:21-27; Asano et al. (2004) "*A Diabody For Cancer Immunotherapy And Its Functional Enhancement By Fusion Of Human Fc Domain,*" Abstract 3P-683, J. Biochem. 76(8):992; Takemura, S. et al. (2000) "*Construction Of A Diabody (Small Recombinant Bispecific Antibody) Using A Refolding System,*" Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity,*" J. Biol. Chem. 280(20):19665-19672).

However, the art has recognized that bispecific diabodies composed of non-covalently associated polypeptides are unstable and readily dissociate into non-functional monomers (see, e.g., Lu, D. et al. (2005) "*A Fully Human RecombinantIgG-Like Bispecific Antibody To Both The Epidermal Growth Factor Receptor And The Insulin-Like Growth Factor Receptor For Enhanced Antitumor Activity,*" J. Biol. Chem. 280(20):19665-19672).

In the face of this challenge, the art has succeeded in developing stable, covalently bonded heterodimeric non-monospecific diabodies, termed DART® diabodies; see, e.g., United States Patent Publication Nos. 2013-0295121; 2010-0174053 and 2009-0060910; European Patent Publication No. EP 2714079; EP 2601216; EP 2376109; EP 2158221 and PCT Publication Nos. WO 2012/162068; WO 2012/018687; WO 2010/080538; and Sloan, D. D. et al. (2015) "*Targeting HIV Reservoir in Infected CD4 T Cells byDual-Affinity Re-targetingMolecules (DARTs) that BindHIVEnvelope andRecruit Cytotoxic T Cells,*" PLoS Pathog. 11(11):e1005233. doi: 10.1371/journal.ppat.1005233; Al Hussaini, M. et al. (2015) "*Targeting CD123InIAML UsingA T-Cell Directed Dual-Affinity Re-Targeting (DART®) Platform,*" Blood pii: blood-2014-05-575704; Chichili, G. R. et al. (2015) "*A CD3xCD123 Bispecific DART For Redirecting Host T Cells To Myelogenous Leukemia: Preclinical Activity*

And Safety In Nonhuman Primates," Sci. Transl. Med. 7(289):289ra82; Moore, P. A. et al. (2011) "*Application Of Dual Affinity Retargeting Molecules To Achieve Optimal Redirected T-Cell Killing Of B-Cell Lymphoma,*" Blood 117(17):4542-4551; Veri, M. C. et al. (2010) "*Therapeutic Control Of B Cell Activation Via Recruitment Of Fcgamma Receptor IIb (CD32B) Inhibitory Function With A Novel Bispecific Antibody Scaffold,*" Arthritis Rheum. 62(7):1933-1943; Johnson, S. et al. (2010) "*Effector Cell Recruitment With Novel Fv-Based Dual-Affinity Re-Targeting Protein Leads To Potent Tumor Cytolysis And in vivo B-Cell Depletion,*" J. Mol. Biol. 399(3):436-449). Such diabodies comprise two or more covalently complexed polypeptides and involve engineering one or more cysteine residues into each of the employed polypeptide species that permit disulfide bonds to form and thereby covalently bond one or more pairs of such polypeptide chains to one another. For example, the addition of a cysteine residue to the C-terminus of such constructs has been shown to allow disulfide bonding between the involved polypeptide chains, stabilizing the resulting diabody without interfering with the diabody's binding characteristics.

Many variations of such molecules have been described (see, e.g., United States Patent Publication Nos. 2015/0175697; 2014/0255407; 2014/0099318; 2013/0295121; 2010/0174053; 2009/0060910; 2007-0004909; European Patent Publication Nos. EP 2714079; EP 2601216; EP 2376109; EP 2158221; EP 1868650; and PCT Publication Nos. WO 2012/162068; WO 2012/018687; WO 2010/080538; WO 2006/113665), and are provided herein.

Alternative constructs are known in the art for applications where a tetravalent molecule is desirable but an Fc is not required including, but not limited to, tetravalent tandem antibodies, also referred to as "TandAbs" (see, e.g. United States Patent Publications Nos. 2005-0079170, 2007-0031436, 2010-0099853, 2011-020667 2013-0189263; European Patent Publication Nos. EP 1078004, EP 2371866, EP 2361936 and EP 1293514; PCT Publications Nos. WO 1999/057150, WO 2003/025018, and WO 2013/013700) which are formed by the homo-dimerization of two identical polypeptide chains, each possessing a VH1, VL2, VH2, and VL2 Domain.

Recently, trivalent structures incorporating two diabody-type binding domains and one non-diabody-type domain and an Fc Domain have been described (see, e.g., PCT Publication Nos. WO 2015/184207 and WO 2015/184203). Such trivalent binding molecules may be utilized to generate monospecific, bispecific or trispecific molecules. The ability to bind three different epitopes provides enhanced capabilities.

III. Human B7-H3

Human B7-H3 exists as a "4Ig" form and as a "2Ig" form. The amino acid sequence of a representative "4Ig" form of human B7-H3 (including a 29 amino acid residue signal sequence, shown underlined) is provided by NCBI Sequence NP_001019907 (SEQ ID NO:16, the 29 amino acid residue signal sequence, shown underlined):

```
MLRRRGSPGM GVHVGAALGA LWFCLTGALE VQVPEDPVVA

LVGTDATLCC SFSPEPGFSL AQLNLIWQLT DTKQLVHSFA

EGQDQGSAYA NRTALFPDLL AQGNASLRLQ RVRVADEGSF
```

-continued
```
TCFVSIRDFG SAAVSLQVAA PYSKPSMTLE PNKDLRPGDT

VTITCSSYQG YPEAEVFWQD GQGVPLTGNV TTSQMANEQG

LFDVHSILRV VLGANGTYSC LVRNPVLQQD AHSSVTITPQ

RSPTGAVEVQ VPEDPVVALV GTDATLRCSF SPEPGFSLAQ

LNLIWQLTDT KQLVHSFTEG RDQGSAYANR TALFPDLLAQ

GNASLRLQRV RVADEGSFTC FVSIRDFGSA AVSLQVAAPY

SKPSMTLEPN KDLRPGDTVT ITCSSYRGYP EAEVFWQDGQ

GVPLTGNVTT SQMANEQGLF DVHSVLRVVL GANGTYSCLV

RNPVLQQDAH GSVTITGQPM TFPPEALWVT VGLSVCLIAL

LVALAFVCWR KIKQSCEEEN AGAEDQDGEG EGSKTALQPL

KHSDSKEDDG QEIA
```

The amino acid sequence of the "2Ig" form of human B7-H3 is completely embraced within the "4Ig" form of human B7-H3. The amino acid sequence of a representative "2Ig" form of human B7-H3 (including a 29 amino acid residue signal sequence, shown underlined) is provided by NCBI Sequence NP_079516 (SEQ ID NO:17):

```
MLRRRGSPGM GVHVGAALGA LWFCLTGALE VQVPEDPVVA

LVGTDATLCC SFSPEPGFSL AQLNLIWQLT DTKQLVHSFA

EGQDQGSAYA NRTALFPDLL AQGNASLRLQ RVRVADEGSF

TCFVSIRDFG SAAVSLQVAA PYSKPSMTLE PNKDLRPGDT

VTITCSSYRG YPEAEVFWQD GQGVPLTGNV TTSQMANEQG

LFDVHSVLRV VLGANGTYSC LVRNPVLQQD AHGSVTITGQ

PMTFPPEALW VTVGLSVCLI ALLVALAFVC WRKIKQSCEE

ENAGAEDQDG EGEGSKTALQ PLKHSDSKED DGQEIA
```

In certain embodiments, B7-H3-binding molecules (e.g., scFvs, antibodies, bispecific diabodies, etc.) of the invention are characterized by any one, two, three, four, five, six, seven, eight or nine of the following criteria:
 (1) the ability to immunospecifically bind human B7-H3 as endogenously expressed on the surface of a cancer cell;
 (2) specifically binds non-human primate B7-H3 (e.g., B7-H3 of cynomolgus monkey);
 (3) specifically binds human B7-H3 with an equilibrium binding constant ($K_D$) of 1 nM or less;
 (4) specifically binds non-human primate B7-H3 with an equilibrium binding constant ($K_D$) of 1 nM or less;
 (5) specifically binds human B7-H3 with an on rate (ka) of $1 \times 10^6$ $M^{-1}$ $min^{-1}$ or more;
 (6) specifically binds non-human primate B7-H3 with an on rate (ka) of $1 \times 10^6$ $M^{-1}$ $min^{-1}$ or more;
 (7) specifically binds human B7-H3 with an off rate (kd) of $15 \times 10^{-4}$ $min^{-1}$ or less;
 (8) specifically binds non-human primate B7-H3 with an off rate (kd) of $15 \times 10^{-4}$ $min^{-1}$ or less;
 (9) ability to mediate redirected cell killing (e.g., killing of cancer cells expressing B7-H3).

As described elsewhere herein, the binding constants of a B7-H3-binding molecule may be determined using surface plasmon resonance e.g., via a BIACORE® analysis. Surface plasmon resonance data may be fitted to a 1:1 Langmuir binding model (simultaneous ka kd) and an equilibrium binding constant $K_D$ calculated from the ratio of rate constants kd/ka. Such binding constants may be determined for a monovalent B7-H3-binding molecule (i.e., a molecule comprising a single B7-H3 epitope-binding site), a bivalent B7-H3-binding molecule (i.e., a molecule comprising two B7-H3 epitope-binding sites), or B7-H3-binding molecules having higher valency (e.g., a molecule comprising three, four, or more B7-H3 epitope-binding sites).

As used herein the term "redirected cell killing" refers to the ability of a molecule to mediate the killing of a target cell (e.g., cancer cell) by localizing an immune effector cell (e.g., T-cell, NK cell, etc.) to the location of the target cell by binding epitopes present on the surfaces of such effector and target cells, resulting in the killing of the target cell. The ability of a B7-H3-binding molecule (e.g., a bispecific B7-H3×CD3-binding molecule) to mediate redirected cell killing activity may be determined using a cytotoxic T lymphocyte (CTL) assay. Such assays are well known in the art and preferred assays are described below.

The present invention particularly encompasses B7-H3-binding molecules (e.g., antibodies, diabodies, trivalent binding molecules, etc.) comprising anti-B7-H3 Variable Domains (i.e., VL and/or VH Domains) that immunospecifically bind to an epitope of a human B7-H3 polypeptide. Unless otherwise stated, all such B7-H3-binding molecules are capable of immunospecifically binding to human B7-H3. As used herein such B7-H3 Variable Domains are referred to as "anti-B7-H3-VL" and "anti-B7-H3-VH," respectively.

IV. Murine Anti-Human B7-H3 Antibodies and their Humanized Derivatives

Four exemplary anti-B7-H3 antibodies, designated "mAb-A," "mAb-B," "mAb-C" and "mAb-D," were isolated from hybridoma cells that had been produced through immunization with cells expressing human B7-H3, with a B7-H3 polypeptide or a peptide epitope thereof. Antibodies "mAb-B," "mAb-C" and "mAb-D," were humanized.

Antibodies "mAb-C," and "mAb-D" were found to be cross-reactive with B7-H3 of cynomolgus monkeys. The amino acid sequences of the VL and VH Domains of mAb-C and mAb-D are provided below. In one embodiment, the preferred anti-human B7-H3-binding molecules of the present invention possess 1, 2 or all 3 of the CDRHs of the VH Domain and/or 1, 2 or all 3 of the CDRLs of the VL Domain the VH and/or VL Domains of the murine anti-B7-H3 monoclonal antibody mAb-D, of chimeric monoclonal antibody mAb-D ("chmAb-D") or of humanized monoclonal antibody mAb-C or mAb-D ("hmAb-C" or "hmAb-D"). Such preferred anti-human B7-H3-binding molecules include bispecific (or multispecific) antibodies, chimeric or humanized antibodies, BiTes, diabodies, etc, and such binding molecules having variant Fc Domains. The invention encompasses the use of any of mAb-A, mAb-B, mAb-C or mAb-D to form B7-H3 binding molecules, and in particular, B7-H3-ADCs.

A. Murine Anti-Human B7-H3 Antibody mAb-A

The amino acid sequence of the VL Domain of the murine anti-B7-H3 antibody designated "mAb-A" (SEQ ID NO:95) is shown below (CDR$_L$ residues are shown underlined):

```
DIAMTQSQKF MSTSVGDRVS VTCKASQNVD TNVAWYQQKP

GQSPKALIYS ASYRYSGVPD RFTGSGSGTD FTLTINNVQS

EDLAEYFCQQ YNNYPFTFGS GTKLEIK
```

The amino acid sequence of the VH Domain of mAb-A (SEQ ID NO:96) is shown below (CDR$_H$ residues are shown underlined):

```
DVQLVESGGG LVQPGGSRKL SCAASGFTFS SFGMHWVRQA

PEKGLEWVAY ISSDSSAIYY ADTVKGRFTI SRDNPKNTLF

LQMTSLRSED TAMYYCGRGR ENIYYGSRLD YWGQGTTLTV

SS
```

B. Murine Anti-Human B7-H3 Antibody mAb-B

The amino acid sequence of the VL Domain of the murine anti-B7-H3 antibody designated "mAb-B" (SEQ ID NO:97) is shown below (CDR$_L$ residues are shown underlined):

```
DIQMTQTTSS LSASLGDRVT ISCRASQDIS NYLNWYQQKP

DGTVKLLIYY TSRLHSGVPS RFSGSGSGTD YSLTIDNLEQ

EDIATYFCQQ GNTLPPTFGG GTKLEIK
```

The amino acid sequence of the VH Domain of mAb-B (SEQ ID NO:98) is shown below (CDR$_H$ residues are shown underlined).

```
QVQLQQSGAE LARPGASVKL SCKASGYTFT SYWMQWVKQR

PGQGLEWIGT IYPGDGDTRY TQKFKGKATL TADKSSSTAY

MQLSSLASED SAVYYCARRG IPRLWYFDVW GAGTTVTVSS
```

C. Humanized Anti-Human B7-H3 Antibody hmAb-B

The amino acid sequence of the VL Domain of hmAb-B (SEQ ID NO:99) is shown below (CDR$_L$ residues are shown underlined):

```
DIQMTQSPSS LSASVGDRVT ITCRASQDIS NYLNWYQQKP

GKAPKLLIYY TSRLHSGVPS RFSGSGSGTD FTLTISSLQP

EDIATYYCQQ GNTLPPTFGG GTKLEIK
```

In some embodiments, the amino acid sequence of CDR$_L$1 of hmAb-B (RASQDISNYLN) (SEQ ID NO:100) may be replaced with an alternative CDR$_L$1 having the amino acid sequence RASQSIS SYLN (SEQ ID NO:101). Likewise, the amino acid sequence of CDR$_L$2 of hmAb-B (YTSRLHS) (SEQ ID NO:102) may be replaced with an alternative CDR$_L$2 having the amino acid sequence YTSRL QS (SEQ ID NO:103).

The amino acid sequence of the VH Domain of hmAb-B (SEQ ID NO:104) is shown below (CDR$_H$ residues are shown underlined):

```
QVQLVQSGAE VKKPGASVKV SCKASGYTFT SYWMQWVRQA

PGQGLEWMGT IYPGDGDTRY TQKFKGRVTI TADKSTSTAY

MELSSLRSED TAVYYCARRG IPRLWYFDVW GQGTTVTVSS
```

In some embodiments, the amino acid sequence of CDR$_H$2 of hmAb-B (TIYPGDGDTRYTQKFKG) (SEQ ID NO:105) may be replaced with an alternative CDR$_H$2 having the amino acid sequence: TIYPGGGDTRYTQKFQG (SEQ ID NO:106)

D. Murine Anti-Human B7-H3 Antibody mAb-C

The amino acid sequence of the VL Domain of the murine anti-B7-H3 antibody designated "mAb-C" (SEQ ID NO:18) is shown below (CDR$_L$ residues are shown underlined):

```
DIQMTQSPAS LSVSVGETVT ITCRASESIY SYLANYQQKQ

GKSPQLLVYN TKTLPEGVPS RFSGSGSGTQ FSLKINSLQP

EDFGRYYCQH HYGTPPWTFG GGTNLEIK
```

The amino acid sequence of the VH Domain of mAb-C (SEQ ID NO:19) is shown below (CDR$_H$ residues are shown underlined).

```
EVQQVESGGD LVKPGGSLKL SCAASGFTFS SYGMSWVRQT

PDKRLEWVAT INSGGSNTYY PDSLKGRFTI SRDNAKNTLY

LQMRSLKSED TAMYYCARHD GGAMDYWGQG TSVTVSS
```

E. Humanized Anti-Human B7-H3 Antibody hmAb-C

The Variable Domains of the anti-B7-H3 antibody mAb-C were humanized. In in some instances alternative humanized Variable Domains were generated to optimize binding activity and/or to remove antigenic epitopes and/or to remove potentially labile amino acid residues.

The amino acid sequence of the VL Domain of hmAb-C (SEQ ID NO:20) is shown below (CDR$_L$ residues are shown underlined):

```
DIQMTQSPSS LSASVGDRVT ITCRASESIY SYLAWYQQKP

GKAPKLLVYN TKTLPEGVPS RFSGSGSGTD FTLTISSLQP

EDFATYYCQH HYGTPPWTFG QGTRLEIK
```

The amino acid sequence of the VH Domain of hmAb-C (SEQ ID NO:21) is shown below (CDR$_H$ residues are shown underlined).

```
EVQLVESGGG LVKPGGSLRL SCAASGFTFS SYGMSWVRQA

PGKGLEWVAT INSGGSNTYY PDSLKGRFTI SRDNAKNSLY

LQMNSLRAED TAVYYCARHD GGAMDYWGQG TTVTVSS
```

F. Murine Anti-Human B7-H3 Antibody mAb-D

The amino acid sequence of the VL Domain of the murine anti-B7-H3 antibody designated "mAb-D" (SEQ ID NO:22) is shown below (CDR$_L$ residues are shown underlined):

```
DIVMTQSQKF MSTSVGDRVS VTCKASQNVD TNVAWYQQKQ

GHSPEALIYS ASYRYSGVPA RFTGSGSGTD FTLTISNVQS

EDLAEYFCQQ YNNYPFTFGG GTKLEIK
```

The amino acid sequence of the CDR$_L$1 Domain of mAb-D is (SEQ ID NO:23): KASQNVDTNVA.

The amino acid sequence of the CDR$_L$2 Domain of mAb-D is (SEQ ID NO:24): SASYRYS.

The amino acid sequence of the CDR$_L$3 Domain of mAb-D is (SEQ ID NO:25): QQYNNYPFT.

The amino acid sequence of the VH Domain of mAb-D (SEQ ID NO:26) is shown below (CDR$_H$ residues are shown underlined):

```
DVQLAESGGG LVQPGGSRKL SCAASGFTFS SFGMHWVRQA

PEKGLEWVAY ISSGSGTIYY ADTVKGRFTI SRDNPKNSLF

LQMTSLRSED TAMYYCARHG YRYEGFDYWG QGTTLTVSS
```

The amino acid sequence of the CDR$_H$1 Domain of mAb-D is (SEQ ID NO:27): SFGMH.

The amino acid sequence of the CDR$_H$2 Domain of mAb-D is (SEQ ID NO:28): YISSGSGTIYYADTVKG.

The amino acid sequence of the CDR$_H$3 Domain of mAb-D is (SEQ ID NO:29): HGYRYEGFDY.

G. Humanized Anti-Human B7-H3 Antibody mAb-D

The Variable Domains of the anti-B7-H3 antibody mAb-D were humanized. In in some instances alternative humanized Variable Domains were generated to optimize binding activity and/or to remove antigenic epitopes and/or to remove potentially labile amino acid residues.

The amino acid sequence of the VL Domain of hmAb-D (SEQ ID NO:30) is shown below (CDR$_L$ residues are shown underlined).

```
DIQMTQSPSF LSASVGDRVT ITCKASQNVD TNVAWYQQKP

GKAPKALIYS ASYRYSGVPS RFSGSGSGTD FTLTISSLQP

EDFAEYFCQQ YNNYPFTFGQ GTKLEIK
```

The amino acid sequence of the VH Domain of hmAb-D (SEQ ID NO:31) is shown below (CDR$_H$ residues are shown underlined).

```
EVQLVESGGG LVQPGGSLRL SCAASGFTFS SFGMHWVRQA

PGKGLEWVAY ISSGSGTIYY ADTVKGRFTI SRDNAKNSLY

LQMNSLRAED TAVYYCARHG YRYEGFDYWG QGTTVTVSS
```

V. Chimeric Antigen Receptors

The B7-H3-binding molecules of the present invention may be monospecific single-chain molecules such as single-chain variable fragments ("anti-B7-H3-scFvs") or Chimeric Antigen Receptors ("anti-B7-H3-CARs"). As discussed above, scFvs are made by linking Light and Heavy Chain Variable Domains together via a short linking peptide. First-generation CARs typically had the intracellular domain from the CD3 ζ-chain, which is the primary transmitter of signals from endogenous TCRs. Second-generation CARs possessed additional intracellular signaling domains from various costimulatory protein receptors (e.g., CD28, 41BB, ICOS, etc.) to the cytoplasmic tail of the CAR in order to provide additional signals to the T-cell. Third-generation CARs combine multiple signaling domains, such as CD3z-CD28-41BB or CD3z-CD28-OX40, in order to further augment potency (Tettamanti, S. et al. (2013) "*Targeting Of Acute Myeloid Leukaemia By Cytokine- Induced Killer Cells Redirected With A Novel CD123-Specific Chimeric Antigen Receptor*," Br. J. Haematol. 161:389-401; Gill, S. et al. (2014) "*Efficacy Against Human Acute Myeloid Leukemia And Myeloablation Of Normal Hematopoiesis In A Mouse Model Using Chimeric Antigen Receptor-Modified T Cells*," Blood 123(15): 2343-2354; Mardiros, A. et al. (2013) "*T Cells Expressing CD123-Specific Chimeric Antigen Receptors Exhibit Specific Cytolytic Effector Functions And Antitumor Effects Against Human Acute Myeloid Leukemia*," Blood 122:3138-3148; Pizzitola, I. et al. (2014)

"Chimeric Antigen Receptors Against CD33 CD123 Antigens Efficiently Target Primary Acute Myeloid Leukemia Cells in vivo," Leukemia doi: 10.1038/leu.2014.62).

The anti-B7-H3-CARs of the present invention comprise an anti-B7-H3-scFv fused to an intracellular domain of a receptor. The Variable Light Chain and Variable Heavy Chain Domains of the anti-B7-H3-scFv are preferably hmAb-C VL (SEQ ID NO:20) and hmAb-C VH (SEQ ID NO:21) or are preferably hmAb-D VL (SEQ ID NO:30) and hmAb-D VH (SEQ ID NO:31).

The intracellular domain of the anti-B7-H3-CARs of the present invention is preferably selected from the intracellular domain of any of: 41BB-CD3ζ, b2c-CD3ζ, CD28, CD28-4-1BB-CD3ζ, CD28-CD3ζ, CD28-FcεRIγ, CD28mut-CD3ζ, CD28-OX40-CD3ζ, CD28-OX40-CD3ζ, CD3ζ, CD4-CD3ζ, CD4-FcεRIγ, CD8-CD3ζ, FcεRIγ, FcεRIγCAIX, Heregulin-CD3ζ, IL-13-CD3ζ, or Ly49H-CD3ζ (Tettamanti, S. et al. (2013) "*Targeting Of Acute Myeloid Leukaemia By Cytokine-Induced Killer Cells Redirected With A Novel CD123-Specific Chimeric Antigen Receptor,*" Br. J. Haematol. 161:389-401; Gill, S. et al. (2014) "*Efficacy Against Human Acute Myeloid Leukemia And Myeloablation Of Normal Hematopoiesis In A Mouse Model Using Chimeric Antigen Receptor-Modified T Cells,*" Blood 123(15): 2343-2354; Mardiros, A. et al. (2013) "*T Cells Expressing CD123-Specific Chimeric Antigen Receptors Exhibit Specific Cytolytic Effector Functions And Antitumor Effects Against Human Acute Myeloid Leukemia,*" Blood 122:3138-3148; Pizzitola, I. et al. (2014) "*Chimeric Antigen Receptors Against CD33 CD123 Antigens Efficiently Target Primary Acute Myeloid Leukemia Cells in vivo,*" Leukemia doi:10.1038/leu.2014.62).

VI. Multispecific B7-H3-Binding Molecules

The present invention is also directed to multispecific (e.g., bispecific, trispecific, etc.) B7-H3-binding molecules comprising an epitope-binding site (preferably comprising 1, 2 or all 3 of the CDRHs of an anti-B7-H3-VH Domain of the invention and/or 1, 2 or all 3 of the CDRLS of an anti-B7-H3-VL Domain of the invention, or such anti-B7-H3-VH Domain and/or such anti-B7-H3-VL Domain) and further comprising a second epitope-binding site that immunospecifically binds to a second epitope, where such second epitope is (i) a different epitope of B7-H3, or (ii) an epitope of a molecule that is not B7-H3. Such multispecific B7-H3-binding molecules preferably comprise a combination of epitope-binding sites that recognize a set of antigens unique to target cells or tissue type. In particular, the present invention relates to multispecific B7-H3-binding molecules that are capable of binding to an epitope of B7-H3 and an epitope of a molecule present on the surface of an effector cell, especially a T lymphocyte, a natural killer (NK) cell or other mononuclear cell. For example, such B7-H3-binding molecules of the present invention may be constructed to comprise an epitope-binding site that immunospecifically binds CD2, CD3, CD8, CD16, T-Cell Receptor (TCR), or NKG2D.

One embodiment of the present invention relates to bispecific B7-H3-binding molecules that are capable of binding to a "first epitope" and a "second epitope," such epitopes not being identical to one another. Such bispecific molecules comprise "VL1"/"VH1" domains that are capable of binding to the first epitope, and "VL2"/"VH2" domains that are capable of binding to the second epitope. The notation "VL1" and "VH1" denote respectively, the Variable Light Chain Domain and Variable Heavy Chain Domain that bind the "first" epitope of such bispecific molecules. Similarly, the notation "VL2" and "VH2" denote respectively, the Light Chain Variable Domain and Heavy Chain Variable Domain that bind the "second" epitope of such bispecific molecules. It is irrelevant whether a particular epitope is designated as the first vs. the second epitope; such notation having relevance only with respect to the presence and orientation of domains of the polypeptide chains of the binding molecules of the present invention. In one embodiment, one of such epitopes is an epitope of human B7-H3 and the other is a different epitope of B7-H3, or is an epitope of a molecule that is not B7-H3. In particular embodiments, one of such epitopes is an epitope of human B7-H3 and the other is an epitope of a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. In certain embodiments, a bispecific molecule comprises more than two epitope-binding sites. Such bispecific molecules will bind at least one epitope of B7-H3 and at least one epitope of a molecule that is not B7-H3, and may further bind additional epitopes of B7-H3 and/or additional epitopes of a molecule that is not B7-H3.

The present invention particularly relates to bispecific, trispecific and multispecific B7-H3-binding molecules (e.g., bispecific antibodies, bispecific diabodies, trivalent binding molecules, etc.) that possess epitope-binding fragments of antibodies (e.g., VL and VH Domains) that enable them to be able to coordinately bind to at least one epitope of B7-H3 and at least one epitope of a second molecule that is not B7-H3. Selection of the VL and VH Domains of the polypeptide domains of such molecules is coordinated so that the polypeptides chains that make up such multispecific B7-H3-binding molecules assemble to form at least one functional epitope-binding site that is specific for at least one epitope of B7-H3 and at least one functional epitope-binding site that is specific for at least one epitope of a molecule that is not B7-H3. Preferably, the multispecific B7-H3-binding molecules comprise 1, 2 or all 3 of the CDRHs of an anti-B7-H3-VH Domain of the invention and/or 1, 2 or all 3 of the CDRLs of an anti-B7-H3-VL Domain of the invention, or such anti-B7-H3-VH Domain and/or such anti-B7-H3-VL Domain, as provided herein.

A. Bispecinc Antibodies

The instant invention encompasses bispecific antibodies capable of simultaneously binding to an epitope of B7-H3 and an epitope of a molecule that is not B7-H3. In some embodiments, the bispecific antibody capable of simultaneously binding to B7-H3 and a second molecule that is not B7-H3 is produced using any of the methods described in PCT Publication Nos. WO 1998/002463, WO 2005/070966, WO 2006/107786 WO 2007/024715, WO 2007/075270, WO 2006/107617, WO 2007/046893, WO 2007/146968, WO 2008/003103, WO 2008/003116, WO 2008/027236, WO 2008/024188, WO 2009/132876, WO 2009/018386, WO 2010/028797, WO2010028796, WO 2010/028795, WO 2010/108127, WO 2010/136172, WO 2011/086091, WO 2011/133886, WO 2012/009544, WO 2013/003652, WO 2013/070565, WO 2012/162583, WO 2012/156430, WO 2013/174873, and WO 2014/022540, each of which is hereby incorporated herein by reference in its entirety.

B. Bispecinc Diabodies Lacking Fc Domains

One embodiment of the present invention relates to bispecific diabodies that are capable of binding to a first epitope and a second epitope, wherein the first epitope is an epitope of human B7-H3 and the second is an epitope of a molecule that is not B7-H3, preferably a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. Such diabodies comprise, and most preferably are composed of, a first polypeptide chain and a second polypeptide chain, whose sequences permit the polypeptide chains to covalently bind to each other to form a covalently associated diabody that is capable of simultaneously binding to an epitope of B7-H3 and the second epitope.

The first polypeptide chain of such an embodiment of bispecific diabodies comprises, in the N-terminal to C-terminal direction: an N-terminus, the VL Domain of a monoclonal antibody capable of binding to either the first or second epitope (i.e., either $VL_{anti-B7-H3-VL}$ or $VL_{Epitope\ 2}$), a first intervening spacer peptide (Linker 1), a VH Domain of a monoclonal antibody capable of binding to either the second epitope (if such first polypeptide chain contains $VL_{anti-B7-H3-VL}$) or B7-H3 (if such first polypeptide chain contains $VL_{Epitope\ 2}$), a second intervening spacer peptide (Linker 2) optionally containing a cysteine residue, a Heterodimer-Promoting Domain and a C-terminus (FIG. 1).

The second polypeptide chain of this embodiment of bispecific diabodies comprises, in the N-terminal to C-terminal direction: an N-terminus, a VL Domain of a monoclonal antibody capable of binding to either the first or second epitope (i.e., either $VL_{anti-B7-H3-VL}$ or $VL_{Epitope\ 2}$, and being the VL Domain not selected for inclusion in the first polypeptide chain of the diabody), an intervening spacer peptide (Linker 1), a VH Domain of a monoclonal antibody capable of binding to either the second epitope (if such second polypeptide chain contains $VL_{anti-B7-H3-VL}$) or to B7-H3 (if such second polypeptide chain contains $VL_{Epitope\ 2}$), a second intervening spacer peptide (Linker 2) optionally containing a cysteine residue, a Heterodimer-Promoting Domain, and a C-terminus (FIG. 1).

The VL Domain of the first polypeptide chain interacts with the VH Domain of the second polypeptide chain to form a first functional epitope-binding site that is specific for a first antigen (i.e., either B7-H3 or a molecule that contains the second epitope). Likewise, the VL Domain of the second polypeptide chain interacts with the VH Domain of the first polypeptide chain in order to form a second functional epitope-binding site that is specific for a second antigen (i.e., either the molecule that comprises the second epitope or B7-H3). Thus, the selection of the VL and VH Domains of the first and second polypeptide chains is coordinated, such that the two polypeptide chains of the diabody collectively comprise VL and VH Domains capable of binding to both an epitope of B7-H3 and to the second epitope (i.e., they collectively comprise $VL_{anti-B7-H3-VL}/VH_{anti-B7-H3-VH}$ and $VL_{Epitope\ 2}/VH_{Epitope\ 2}$).

Most preferably, the length of the intervening spacer peptide (i.e., "Linker 1," which separates such VL and VH Domains) is selected to substantially or completely prevent the VL and VH Domains of the polypeptide chain from binding to one another (for example consisting of from 0, 1, 2, 3, 4, 5, 6, 7, 8 or 9 intervening linker amino acid residues). Thus, the VL and VH Domains of the first polypeptide chain are substantially or completely incapable of binding to one another. Likewise, the VL and VH Domains of the second polypeptide chain are substantially or completely incapable of binding to one another. A preferred intervening spacer peptide (Linker 1) has the sequence (SEQ ID NO:32): GGGSGGGG.

The length and composition of the second intervening spacer peptide ("Linker 2") is selected based on the choice of one or more polypeptide domains that promote such dimerization (i.e., a "Heterodimer-Promoting Domain"). Typically, the second intervening spacer peptide (Linker 2) will comprise 3-20 amino acid residues. In particular, where the employed Heterodimer-Promoting Domain(s) do/does not comprise a cysteine residue a cysteine-containing second intervening spacer peptide (Linker 2) is utilized. A cysteine-containing second intervening spacer peptide (Linker 2) will contain 1, 2, 3 or more cysteines. A preferred cysteine-containing spacer peptide (Linker 2) has the sequence GGCGGG (SEQ ID NO:33). Alternatively, Linker 2 does not comprise a cysteine (e.g., GGG, GGGS (SEQ ID NO:34), LGGGSG (SEQ ID NO:35), GGGSGGGSGGG (SEQ ID NO:36), ASTKG (SEQ ID NO:37), LEPKS S (SEQ ID NO:38), APSSS (SEQ ID NO:39), etc.) and a Cysteine-Containing Heterodimer-Promoting Domain, as described below is used. Optionally, both a cysteine-containing Linker 2 and a cysteine-containing Heterodimer-Promoting Domain are used.

The Heterodimer-Promoting Domains may be GVEPKSC (SEQ ID NO:40) or VE PKSC (SEQ ID NO:41) or AE PKSC (SEQ ID NO:42) on one polypeptide chain and GFNRGEC (SEQ ID NO:43) or FNRGEC (SEQ ID NO:44) on the other polypeptide chain (US2007/0004909).

In a preferred embodiment, the Heterodimer-Promoting Domains will comprise tandemly repeated coil domains of opposing charge for example, "E-coil" helical domains (SEQ ID NO:45: EVAALEK-E̅VAALE̅K-E̅VAALE̅K-E̅VAALE̅K), whose glutamate residues will form a negative charge at pH 7, and "K-coil" domains (SEQ ID NO:46: K̅VAALK̅E-K̅VAALK̅E-K̅VAALK̅E-K̅VAALK̅E), whose lysine residues will form a positive charge at pH 7. The presence of such charged domains promotes association between the first and second polypeptides, and thus fosters heterodimer formation. Heterodimer-Promoting Domains that comprise modifications of the above-described E-coil and K-coil sequences so as to include one or more cysteine residues may be utilized. The presence of such cysteine residues permits the coil present on one polypeptide chain to become covalently bonded to a complementary coil present on another polypeptide chain, thereby covalently bonding the polypeptide chains to one another and increasing the stability of the diabody. Examples of such particularly preferred are Heterodimer-Promoting Domains include a Modified E-Coil having the amino acid sequence E̅VAAC E̅K-E̅VAALE̅K-E̅VAALE̅K-E̅VAALE̅K (SEQ ID NO:47), and a modified K-coil having the amino acid sequence K̅VAACK̅E-K̅VAALK̅E-K̅VAALK̅E-K̅VAAL K̅E (SEQ ID NO:48).

As disclosed in WO 2012/018687, in order to improve the in vivo pharmacokinetic properties of diabodies, a diabody may be modified to contain a polypeptide portion of a serum-binding protein at one or more of the termini of the diabody. Most preferably, such polypeptide portion of a serum-binding protein will be installed at the C-terminus of a polypeptide chain of the diabody. Albumin is the most abundant protein in plasma and has a half-life of 19 days in humans. Albumin possesses several small molecule binding sites that permit it to non-covalently bind to other proteins and thereby extend their serum half-lives. The Albumin-Binding Domain 3 (ABD3) of protein G of *Streptococcus* strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-*

Binding Modules," J. Biol. Chem. 277(10):8114-8120. Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of *Streptococcus* strain G148 (SEQ ID NO:49):

```
LAEAKVLANR ELDKYGVSDY YKNLIDNAKS AEGVKALIDE ILAALP.
```

As disclosed in WO 2012/162068 (herein incorporated by reference), "deimmunized" variants of SEQ ID NO:49 have the ability to attenuate or eliminate MHC class II binding. Based on combinational mutation results, the following combinations of substitutions are considered to be preferred substitutions for forming such a deimmunized ABD: 66D/70S+71A; 66S/70S+71A; 66S/70S+79A; 64A/65A/71A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence:

```
                                        (SEQ ID NO: 50)
LAEAKVLANR ELDKYGVSDY YKNLID₆₆NAKS₇₀ A₇₁EGVKALIDE

ILAALP,
``` or the amino acid sequence:

```
                                        (SEQ ID NO: 51)
LAEAKVLANR ELDKYGVSDY YKNA₆₄A₆₅NNAKT VEGVKALIA₇₉E

ILAALP,
``` or the amino acid sequence:

```
                                        (SEQ ID NO: 52)
LAEAKVLANR ELDKYGVSDY YKNLIS₆₆NAKS₇₀ VEGVKALIA₇₉E

ILAALP,
``` are particularly preferred as such deimmunized ABD exhibit substantially wild-type binding while providing attenuated MHC class II binding. Thus, the first polypeptide chain of such a diabody having an ABD contains a third linker (Linker 3) preferably positioned C-terminally to the E-coil (or K-coil) Domain of such polypeptide chain so as to intervene between the E-coil (or K-coil) Domain and the ABD (which is preferably a deimmunized ABD). A preferred sequence for such Linker 3 is SEQ ID NO:34: GGGS.

C. Multispecific Diabodies Containing Fc Domains

Figure 2:
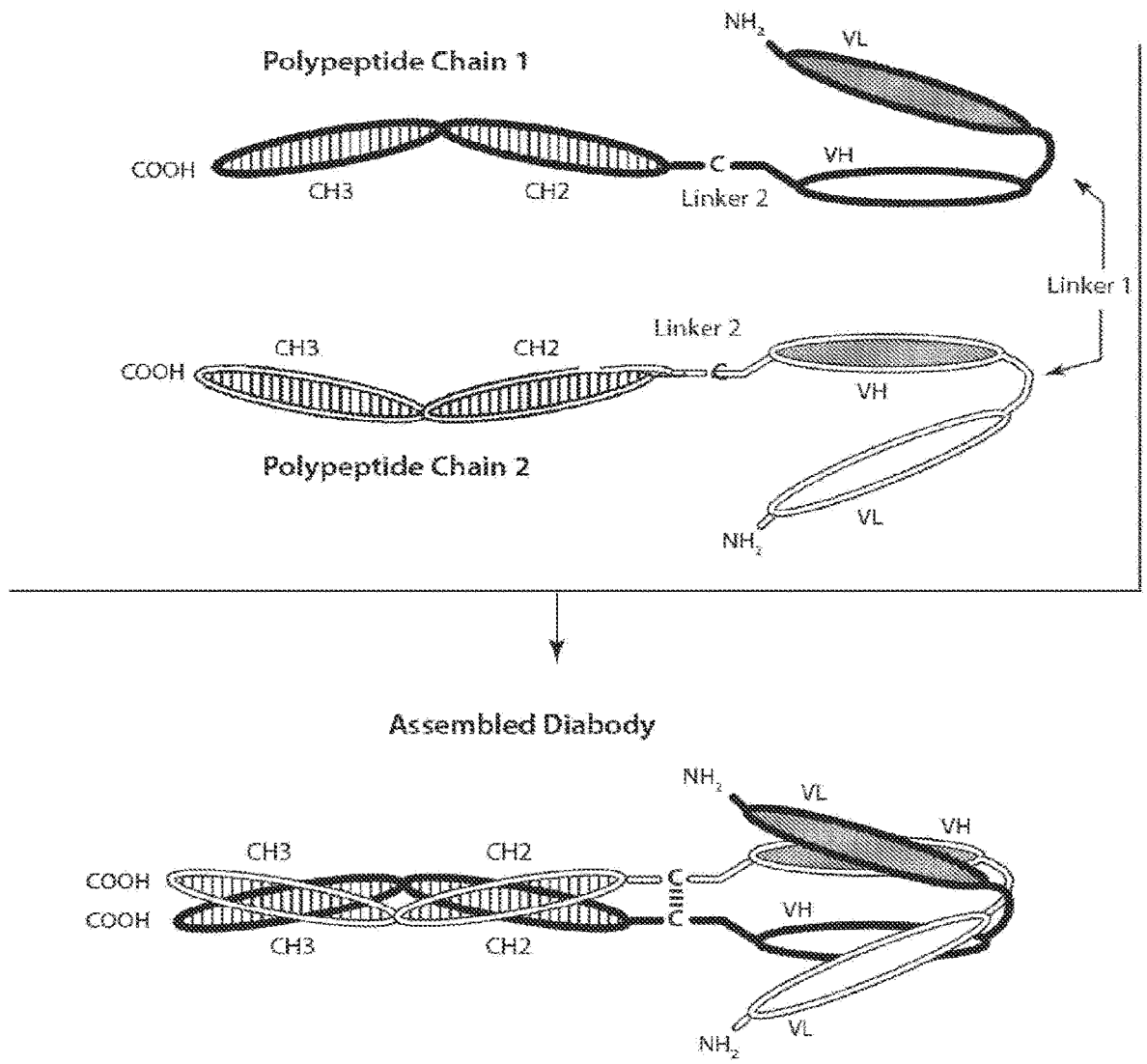
FIG. 2 provides a schematic of a representative covalently bonded diabody molecule having two epitope-binding sites composed of two polypeptide chains, each having a CH2 and CH3 Domain, such that the associated chains form all or part of an Fc Domain. VL and VH Domains that recognize the same epitope are shown using the same shading or fill pattern.

One embodiment of the present invention relates to multispecific diabodies capable of simultaneously binding to an epitope of B7-H3 and a second epitope (i.e., a different epitope of B7-H3 or an epitope of a molecule that is not B7-H3) that comprise an Fc Domain. The addition of an IgG CH2-CH3 Domain to one or both of the diabody polypeptide chains, such that the complexing of the diabody chains results in the formation of an Fc Domain, increases the biological half-life and/or alters the valency of the diabody. Such diabodies comprise, two or more polypeptide chains whose sequences permit the polypeptide chains to covalently bind to each other to form a covalently associated diabody that is capable of simultaneously binding to an epitope of B7-H3 and the second epitope. Incorporating an IgG CH2-CH3 Domains onto both of the diabody polypeptides will permit a two-chain bispecific Fc-Region-containing diabody to form (FIG. 2).

Figure 3A:
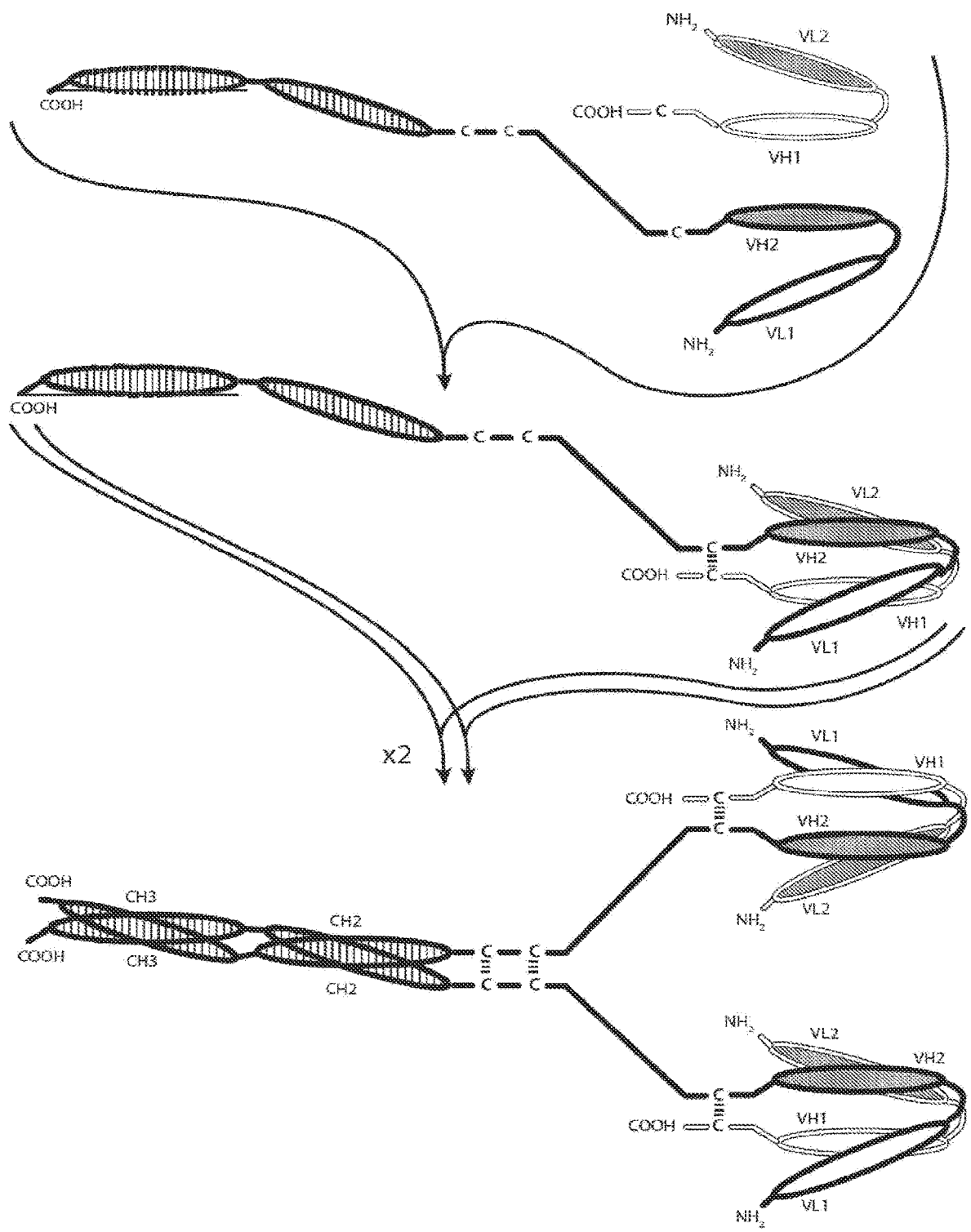
FIGS. 3A-3C provide schematics showing representative covalently bonded tetravalent diabodies having four epitope-binding sites composed of two pairs of polypeptide chains (i.e., four polypeptide chains in all). One polypeptide of each pair possesses a CH2 and CH3 Domain, such that the associated chains form all or part of an Fc Domain. VL and VH Domains that recognize the same epitope are shown using the same shading or fill pattern. The two pairs of polypeptide chains may be same. In such embodiments wherein the two pairs of polypeptide chains are the same and the VL and VH Domains recognize different epitopes (as shown in FIGS. 3A-3B), the resulting molecule possesses four epitope-binding sites and is bispecific and bivalent with respect to each bound epitope. In such embodiments wherein the VL and VH Domains recognize the same epitope (e.g., the same VL Domain CDRs and the same VH Domain CDRs are used on both chains) the resulting molecule possesses four epitope-binding sites and is monospecific and tetravalent with respect to a single epitope. Alternatively, the two pairs of polypeptides may be different. In such embodiments wherein the two pairs of polypeptide chains are different and the VL and VH Domains of each pair of polypeptides recognize different epitopes (as shown by the different shading and patterns in FIG. 3C), the resulting molecule possesses four epitope-binding sites and is tetraspecific and monovalent with respect to each bound epitope.
Figure 3B:
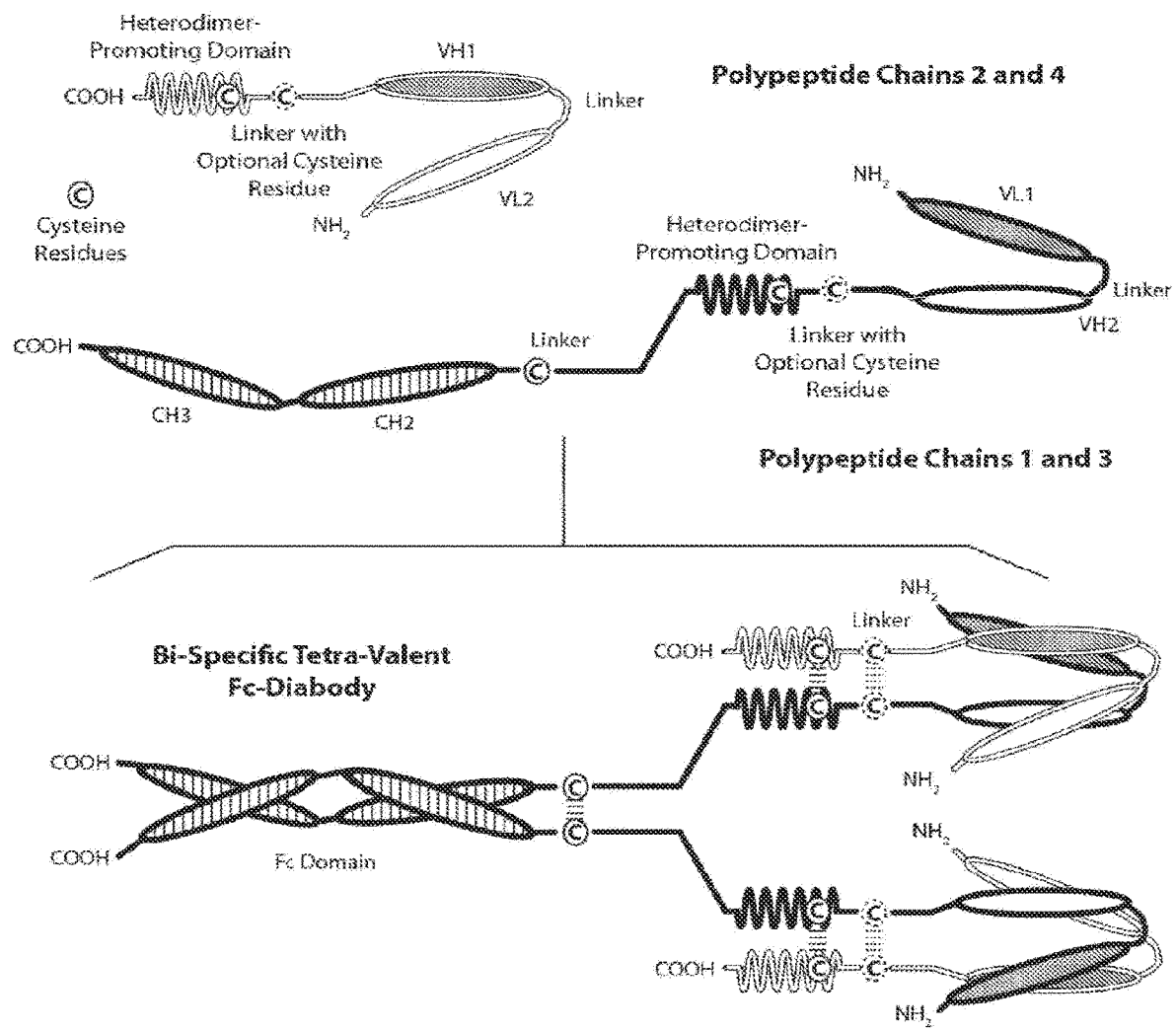
Figure 3C:
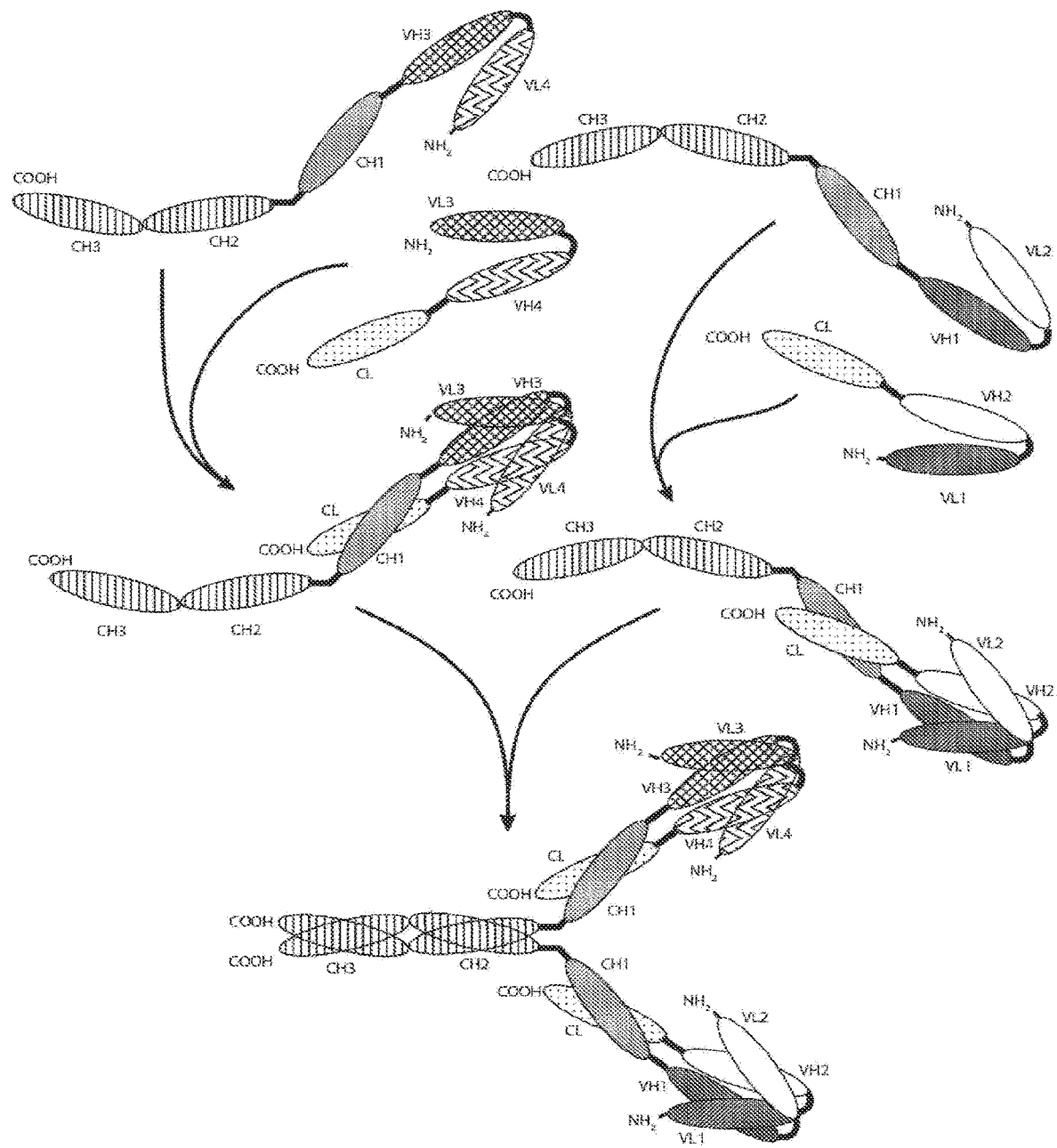

Alternatively, incorporating an IgG CH2-CH3 Domains onto only one of the diabody polypeptides will permit a more complex four-chain bispecific Fc Domain-containing diabody to form (FIGS. 3A-3C). FIG. 3C shows a representative four-chain diabody possessing the Constant Light (CL) Domain and the Constant Heavy CH1 Domain, however fragments of such domains as well as other polypeptides may alternatively be employed (see, e.g., FIGS. 3A and 3B, United States Patent Publication Nos. 2013-0295121; 2010-0174053 and 2009-0060910; European Patent Publication No. EP 2714079; EP 2601216; EP 2376109; EP 2158221 and PCT Publication Nos. WO 2012/162068; WO 2012/018687; WO 2010/080538). Thus, for example, in lieu of the CH1 Domain, one may employ a peptide having the amino acid sequence GVEPKSC (SEQ ID NO:40), VEPKSC (SEQ ID NO:41), or AEPKSC (SEQ ID NO:42), derived from the Hinge Domain of a human IgG, and in lieu of the CL Domain, one may employ the C-terminal 6 amino acids of the human kappa light chain, GFNRGEC (SEQ ID NO:43) or FNRGEC (SEQ ID NO:44). A representative peptide containing four-chain diabody is shown in FIG. 3A. Alternatively, or in addition, one may employ a peptide comprising tandem coil domains of opposing charge such as the "E-coil" helical domains (SEQ ID NO:45: EVAALEK-EVAALEK-EVAALEK-EVAALEKor SEQID NO:47: EVAACEK-EVAALEK-EVAALEK-EVAALEK); and the "K-coil" domains (SEQ ID NO:46: KVAALKE-KVAALKE-KVAALKE-KVAALKE or SEQ ID NO:48: KVAACKE-KVAALKE-KVAALKE-KVAALKE). A representative coil domain containing four-chain diabody is shown in FIG. 3B.

The Fc Domain-containing molecules of the present invention may include additional intervening spacer peptides (Linkers), generally such Linkers will be incorporated between a Heterodimer-Promoting Domain (e.g., an E-coil or K-coil) and a CH2-CH3 Domain and/or between a CH2-CH3 Domain and a Variable Domain (i.e., VH or VL). Typically, the additional Linkers will comprise 3-20 amino acid residues and may optionally contain all or a portion of an IgG Hinge Domain (preferably a cysteine-containing portion of an IgG Hinge Domain). Linkers that may be employed in the bispecific Fc Domain-containing diabody molecules of the present invention include: GGGS (SEQ ID NO:34), LGGGSG (SEQ ID NO:35), GGGSGGGSGGG (SEQ ID NO:36), ASTKG (SEQ ID NO:37), LEPKSS (SEQ ID NO:38), APSSS (SEQ ID NO:39), APSSS PME (SEQ ID NO:53), VEPKSADKTHTCPPCP (SEQ ID NO:54), LEPKSADKTHTCPPC (SEQ ID NO:55), DKTHTCPPCP (SEQ ID NO:56), GGC, and GGG. LEPKSS (SEQ ID NO:38) may be used in lieu of GGG or GGC for ease of cloning. Additionally, the amino acids GGG, or LEPKSS (SEQ ID NO:38) may be immediately followed by DKTHTCPPCP (SEQ ID NO:56) to form the alternate linkers: GGGDKTHTCPPCP (SEQ ID NO:57); and LEPKSSDKTHTCPPCP (SEQ ID NO:58). Bispecific Fc Domain-containing molecules of the present invention may incorporate an IgG Hinge Domain in addition to or in place of a linker. Exemplary Hinge Domains include: EPKSCDKTHTCPPCP (SEQ ID NO:7) from IgG1, ERKCCVECPPCP (SEQ ID NO:8) fromIgG2, ESKYGPPCPSCP (SEQ ID NO:10) from IgG4, and ESKYGPPCPPCP (SEQ ID NO:11) an IgG4 hinge variant comprising a stabilizing S228P substitution (as numbered by the EU index as set forth in Kabat) to reduce strand exchange.

As provided in FIG. 3A-3C, Fc Domain-containing diabodies of the invention may comprise four chains. The first and third polypeptide chains of such a diabody contain three domains: (i) a VL1-containing Domain, (ii) a VH2-containing Domain, (iii) a Heterodimer-Promoting Domain, and (iv) a Domain containing a CH2-CH3 sequence. The second and fourth polypeptide chains contain: (i) a VL2-containing Domain, (ii) a VH1-containing Domain, and (iii) a Heterodimer-Promoting Domain, where the Heterodimer-Promoting Domains promote the dimerization of the first/third polypeptide chains with the second/fourth polypeptide chains. The VL and/or VH Domains of the third and fourth polypeptide chains, and VL and/or VH Domains of the first and second polypeptide chains may be the same or different so as to permit tetravalent binding that is either monospecific, bispecific or tetraspecific. The notation "VL3" and "VH3" denote respectively, the Light Chain Variable Domain and Variable Heavy Chain Domain that bind a "third" epitope of such diabody. Similarly, the notation "VL4" and "VH4" denote respectively, the Light Chain Variable Domain and Variable Heavy Chain Domain that bind a "fourth" epitope of such diabody. The general structure of the polypeptide chains of a representative four-chain bispecific Fc Domain-containing diabodies of invention is provided in Table 1:

TABLE 1

| Bispecific | $2^{nd}$ Chain | NH$_2$-VL2-VH1-HPD-COOH |
|---|---|---|
| | $1^{st}$ Chain | NH$_2$-VL1-VH2-HPD-CH2—CH3—COOH |
| | $1^{st}$ Chain | NH$_2$-VL1-VH2-HPD-CH2—CH3—COOH |
| | $2^{nd}$ Chain | NH$_2$-VL2-VH1-HPD-COOH |
| Tetraspe- | $2^{nd}$ Chain | NH$_2$-VL2-VH1-HPD-COOH |
| cific | $1^{st}$ Chain | NH$_2$-VL1-VH2-HPD-CH2—CH3—COOH |
| | $3^{rd}$ Chain | NH$_2$-VL3-VH4-HPD-CH2—CH3—COOH |
| | $4^{th}$ Chain | NH$_2$-VL4-VH3-HPD-COOH |

HPD = Heterodimer-Promoting Domain

In a specific embodiment, diabodies of the present invention are bispecific, tetravalent (i.e., possess four epitope-binding sites), Fc-containing diabodies that are composed of four total polypeptide chains (FIGS. 3A-3C). The bispecific, tetravalent, Fc-containing diabodies of the invention comprise two epitope-binding sites immunospecific for B7-H3 (which may be capable of binding to the same epitope of B7-H3 or to different epitopes of B7-H3), and two epitope-binding sites immunospecific for a second molecule (which may be capable of binding to the same epitope of the second molecule or to different epitopes of the second molecule). Preferably, the second molecule is a molecule (e.g, CD2, CD3, CD8, CD16, T-Cell Receptor (TCR), NKG2D, etc.) present on the surface of an effector cell, such as a T lymphocyte, a natural killer (NK) cell or other mononuclear cell.

Figure 4A:
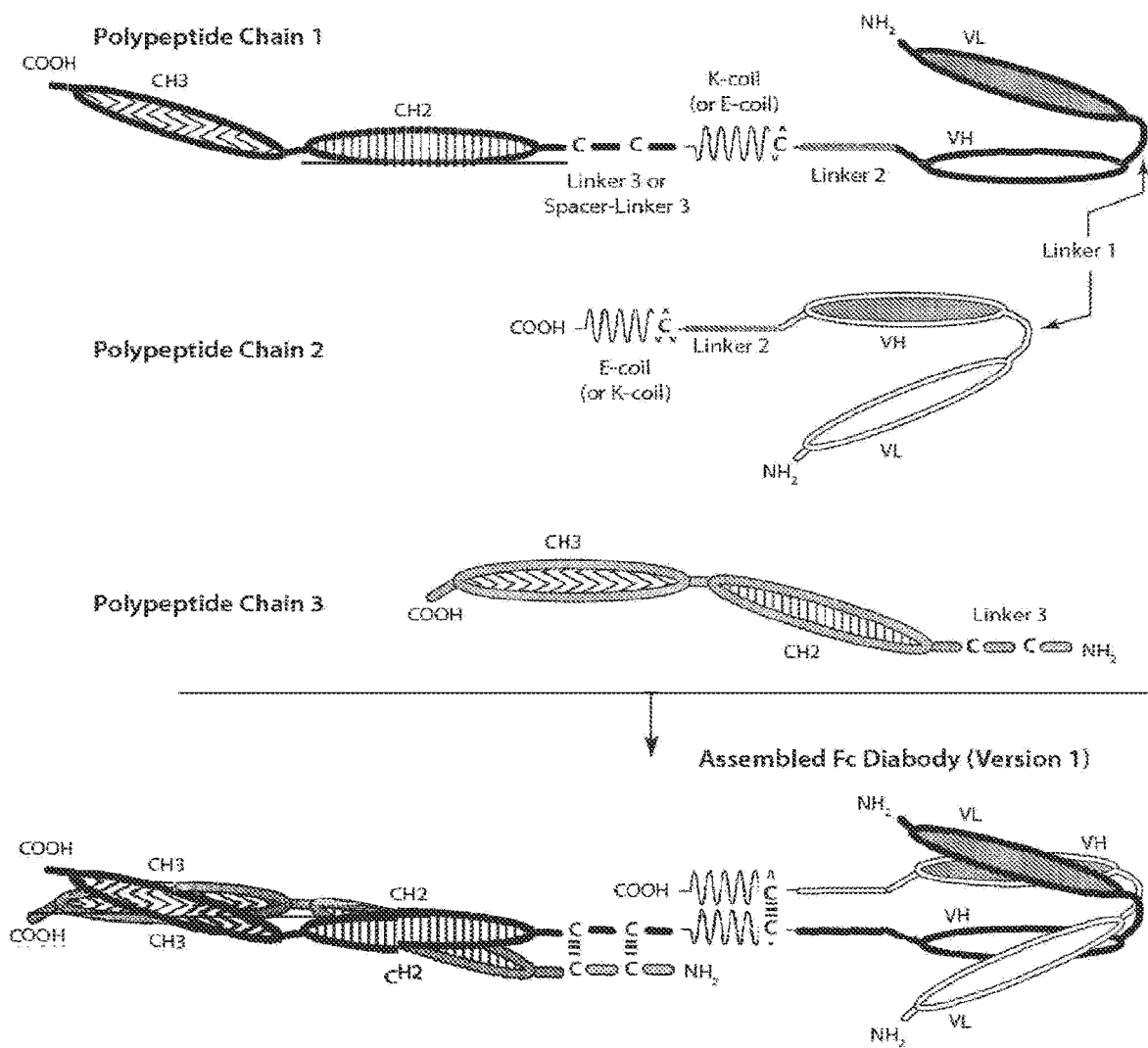
FIGS. 4A and 4B provide schematics of a representative covalently bonded diabody molecule having two epitope-binding sites composed of three polypeptide chains. Two of the polypeptide chains possess a CH2 and CH3 Domain, such that the associated chains form all or part of an Fc Domain. The polypeptide chains comprising the VL and VH Domain further comprise a Heterodimer-Promoting Domain. VL and VH Domains that recognize the same epitope are shown using the same shading or fill pattern.
Figure 4B:
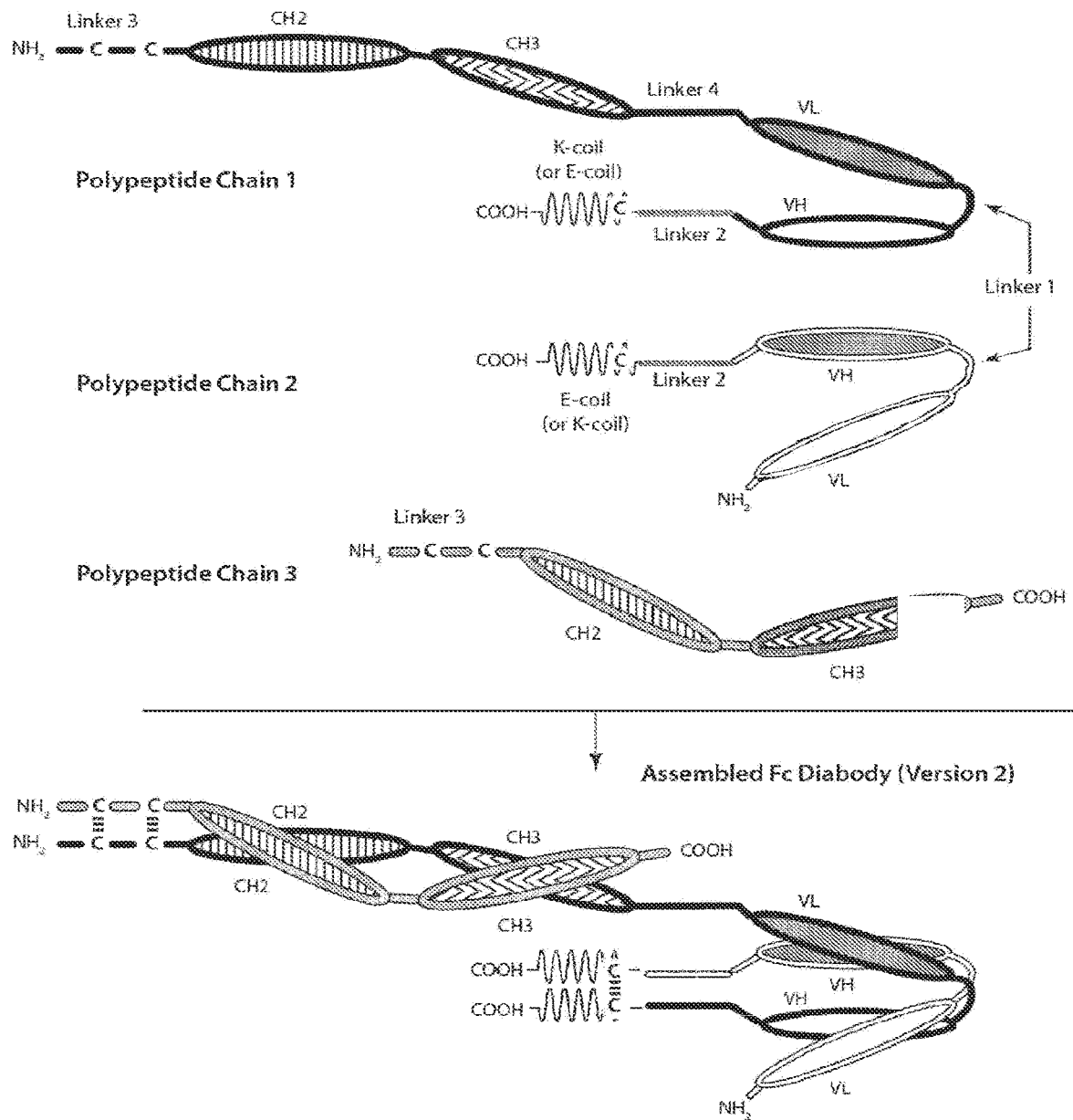

In a further embodiment, the Fc Domain-containing diabodies of the present invention may comprise three polypeptide chains. The first polypeptide of such a diabody contains three domains: (i) a VL1-containing Domain, (ii) a VH2-containing Domain and (iii) a Domain containing a CH2-CH3 sequence. The second polypeptide of such a diabody contains: (i) a VL2-containing Domain, (ii) a VH1-containing Domain and (iii) a Domain that promotes heterodimerization and covalent bonding with the diabody's first polypeptide chain. The third polypeptide of such a diabody comprises a CH2-CH3 sequence. Thus, the first and second polypeptide chains of such a diabody associate together to form a VLT/VHT epitope-binding site that is capable of binding to a first antigen (i.e., either B7-H3 or a molecule that comprises a second epitope), as well as a VL2/VH2 epitope-binding site that is capable of binding to a second antigen (i.e., either the molecule that contains the second epitope or B7-H3). The first and second polypeptides are bonded to one another through a disulfide bond involving cysteine residues in their respective Third Domains. Notably, the first and third polypeptide chains complex with one another to form an Fc Domain that is stabilized via a disulfide bond. Such bispecific diabodies have enhanced potency. FIGS. 4A and 4B illustrate the structures of such diabodies. Such Fc-Region-containing diabodies may have either of two orientations (Table 2):

TABLE 2

| First | $3^{rd}$ Chain | NH$_2$—CH2—CH3—COOH |
|---|---|---|
| Orien- | $1^{st}$ Chain | NH$_2$-VL1-VH2-HPD-CH2—CH3—COOH |
| tation | $2^{nd}$ Chain | NH$_2$-VL2-VH1-HPD-COOH |
| Second | $3^{rd}$ Chain | NH$_2$—CH2—CH3—COOH |
| Orien- | $1^{st}$ Chain | NH$_2$—CH2—CH3-VL1-VH2-HPD-COOH |
| tation | $2^{nd}$ Chain | NH$_2$-VL2-VH1-HPD-COOH |

HPD = Heterodimer-Promoting Domain

In a specific embodiment, diabodies of the present invention are bispecific, bivalent (i.e., possess two epitope-binding sites), Fc-containing diabodies that are composed of three total polypeptide chains (FIGS. 4A-4B). The bispecific, bivalent Fc-containing diabodies of the invention comprise one epitope-binding site immunospecific for B7-H3, and one epitope-binding site immunospecific for a second molecule. Preferably, the second molecule is a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell.

In a further embodiment, the Fc Domain-containing diabodies may comprise a total of five polypeptide chains. In a particular embodiment, two of said five polypeptide chains have the same amino acid sequence. The first polypeptide chain of such a diabody contains: (i) a VH1-containing domain, (ii) a CH1-containing domain, and (iii) a Domain containing a CH2-CH3 sequence. The first polypeptide chain may be the heavy chain of an antibody that contains a VH1 and a heavy chain constant region. The second and fifth polypeptide chains of such a diabody contain: (i) a VL1-containing domain, and (ii) a CL-containing domain. The second and/or fifth polypeptide chains of such a diabody may be light chains of an antibody that contains a VL1 complementary to the VH1 of the first/third polypeptide chain. The first, second and/or fifth polypeptide chains may be isolated from a naturally occurring antibody. Alternatively, they may be constructed recombinantly. The third polypeptide chain of such a diabody contains: (i) a VH1-containing domain, (ii) a CH1-containing domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies contains: (i) a VL3-containing Domain, (ii) a VH2-containing Domain and (iii) a Domain that promotes heterodimerization and covalent bonding with the diabody's third polypeptide chain.

Figure 5:
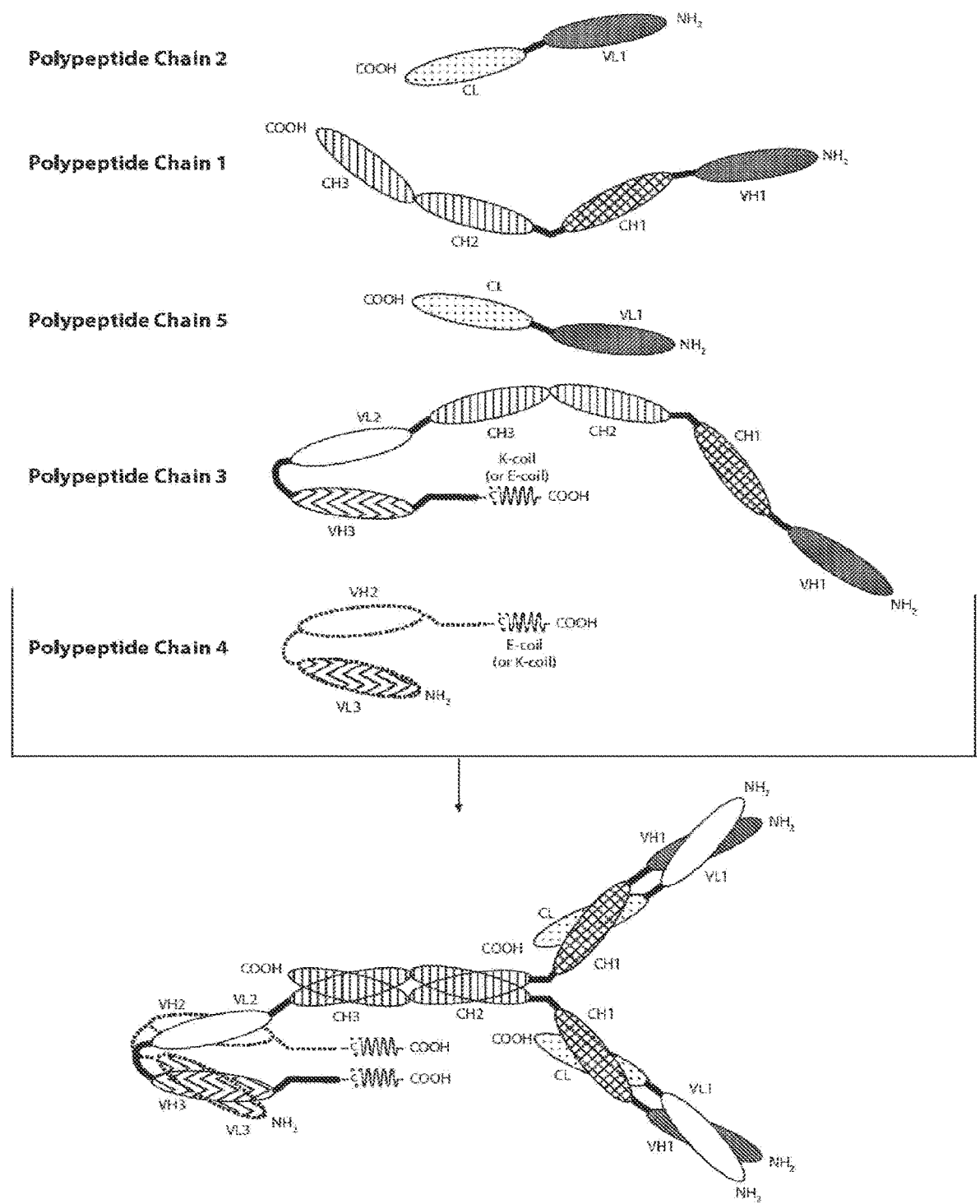
FIG. 5 provides the schematics of a representative covalently bonded diabody molecule having four epitope-binding sites composed of five polypeptide chains. Two of the polypeptide chains possess a CH2 and CH3 Domain, such that the associated chains form an Fc Domain that comprises all or part of an Fc Domain. The polypeptide chains comprising the linked VL and VH Domains further comprise a Heterodimer-Promoting Domain. VL and VH Domains that recognize the same epitope are shown using the same shading or fill pattern.
Figure 6A:
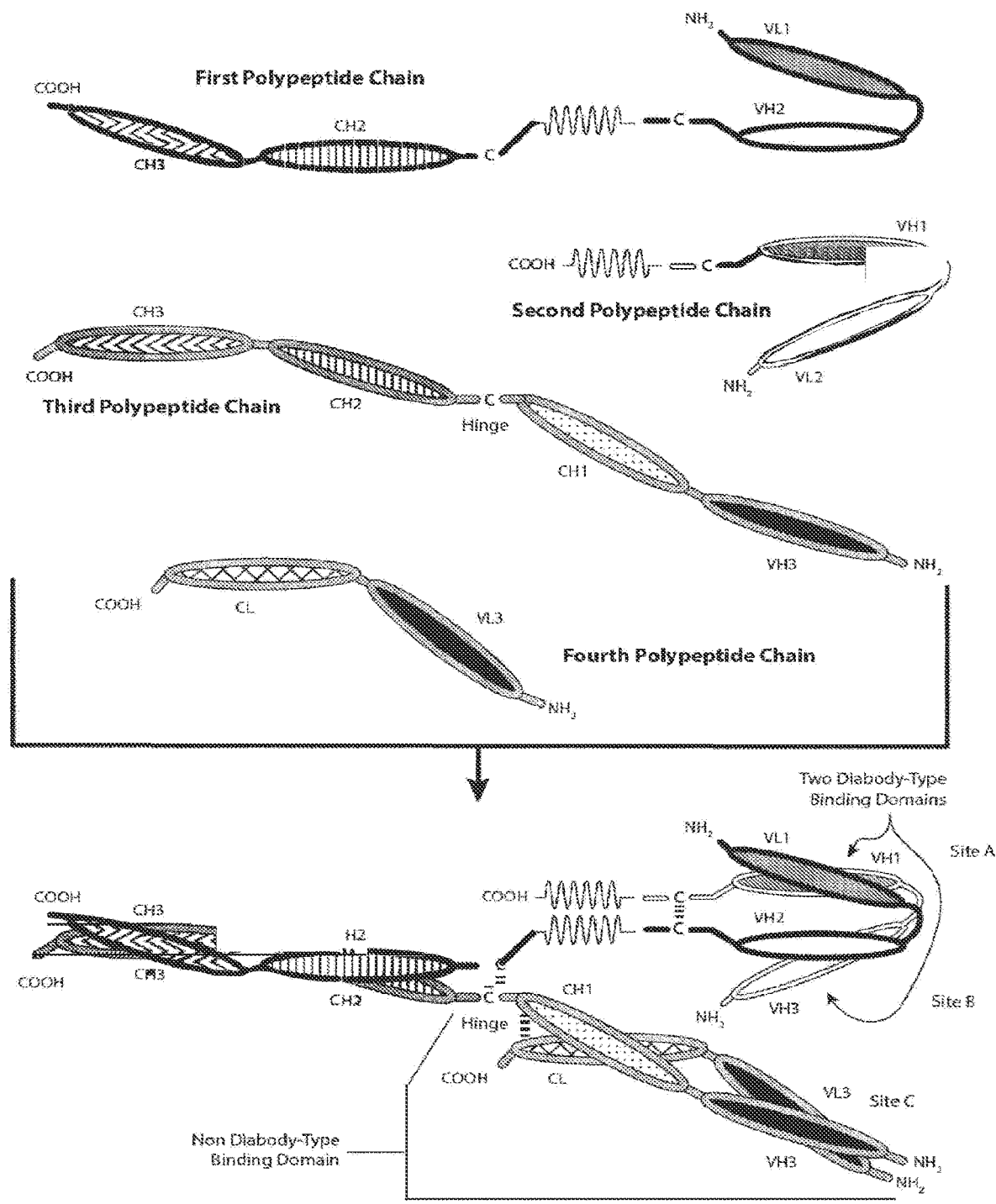
FIGS. 6A-6F provide schematics of representative Fc Domain-containing trivalent binding molecules having three epitope-binding sites.
Figure 6B:
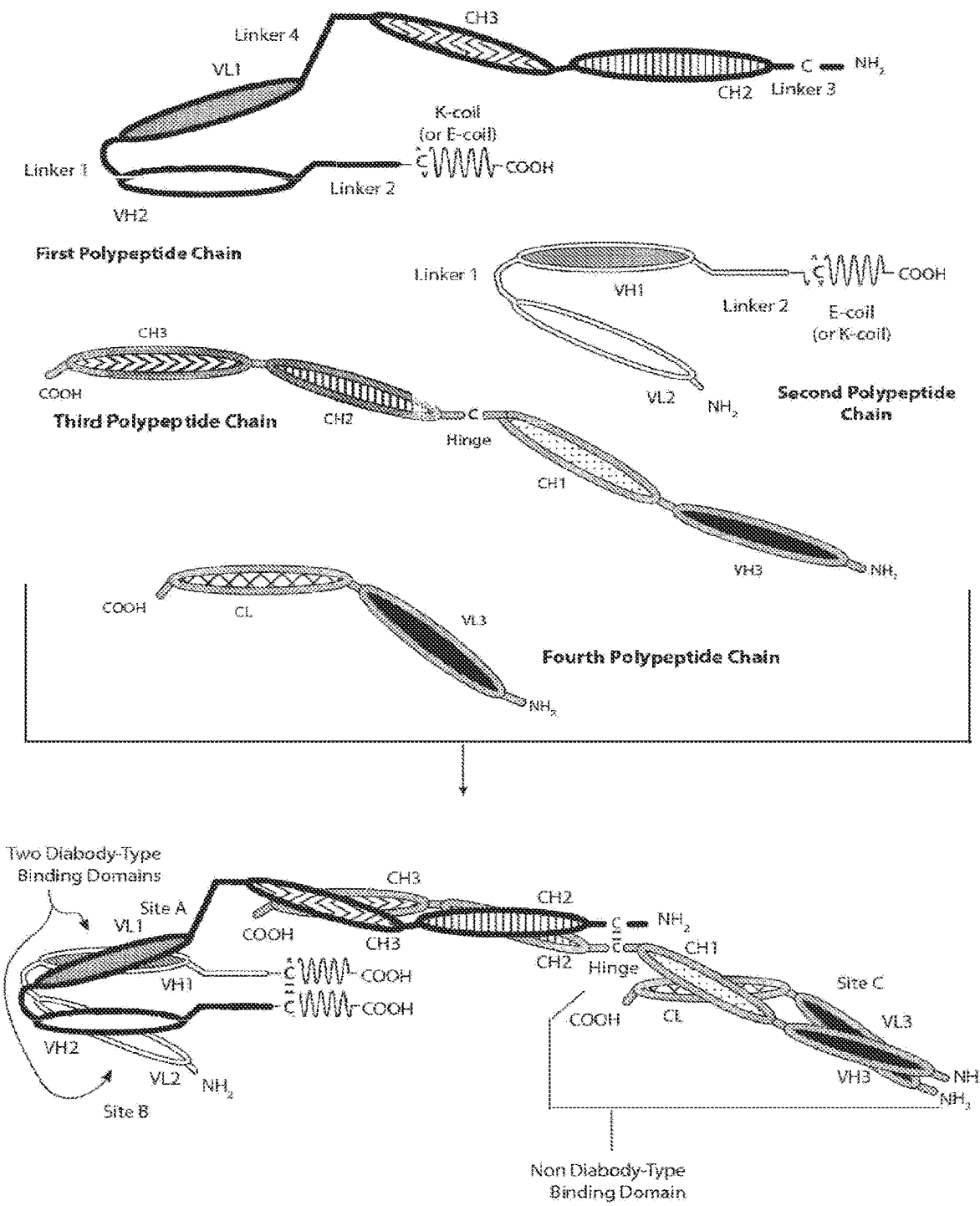
Figure 6C:
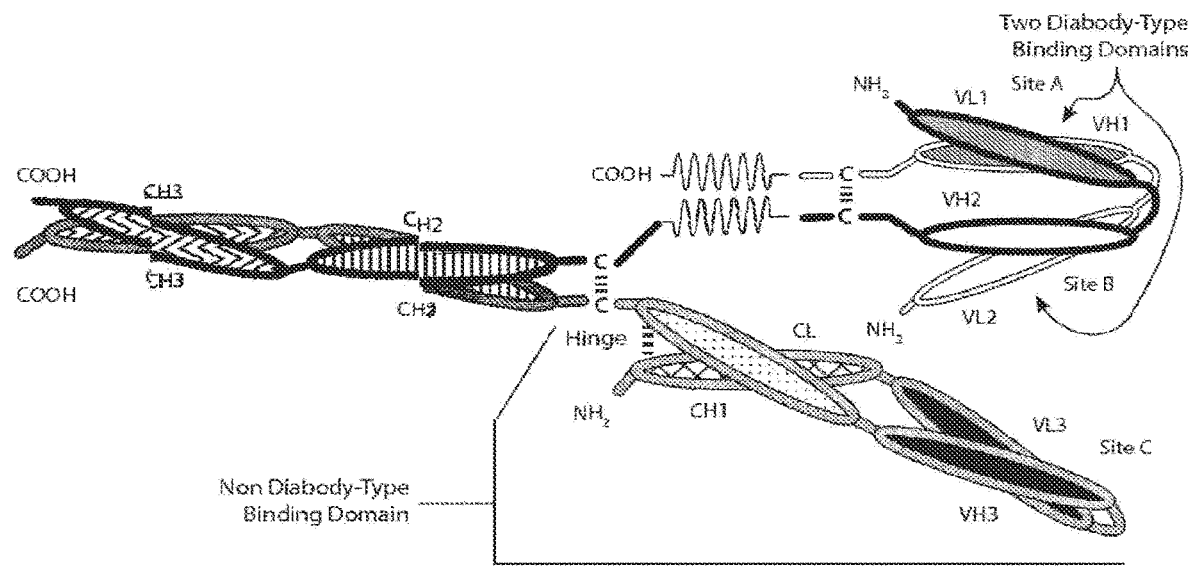
Figure 6D:
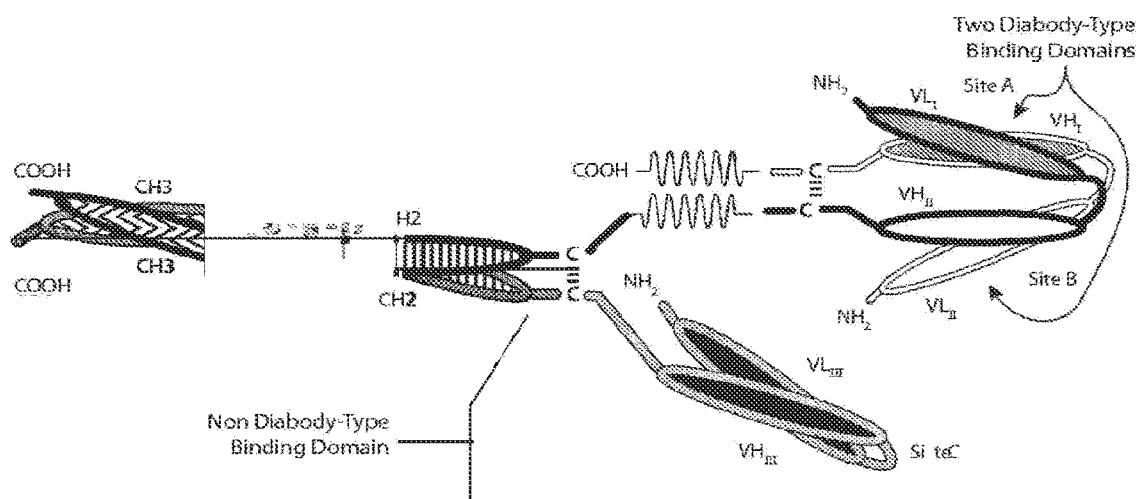
Figure 6E:
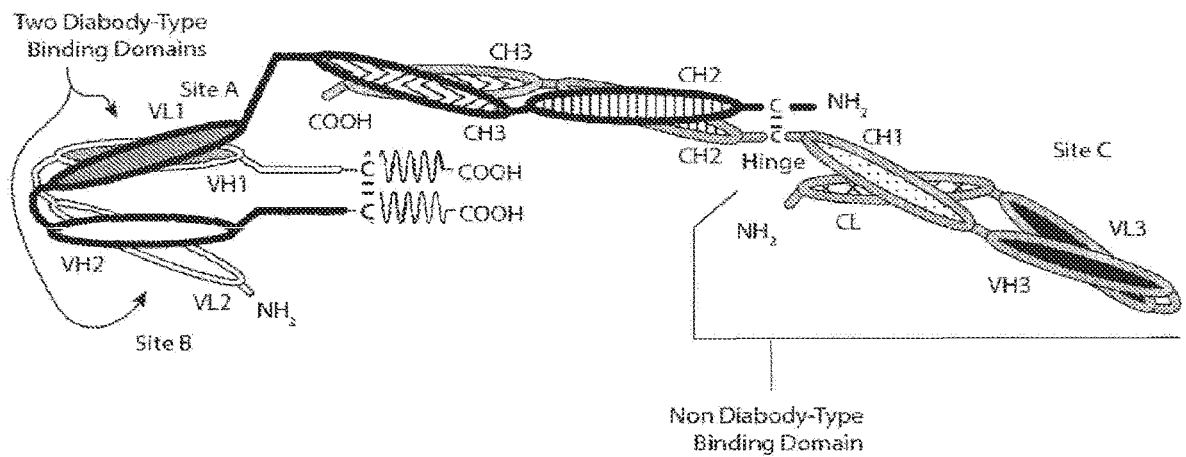
Figure 6F:
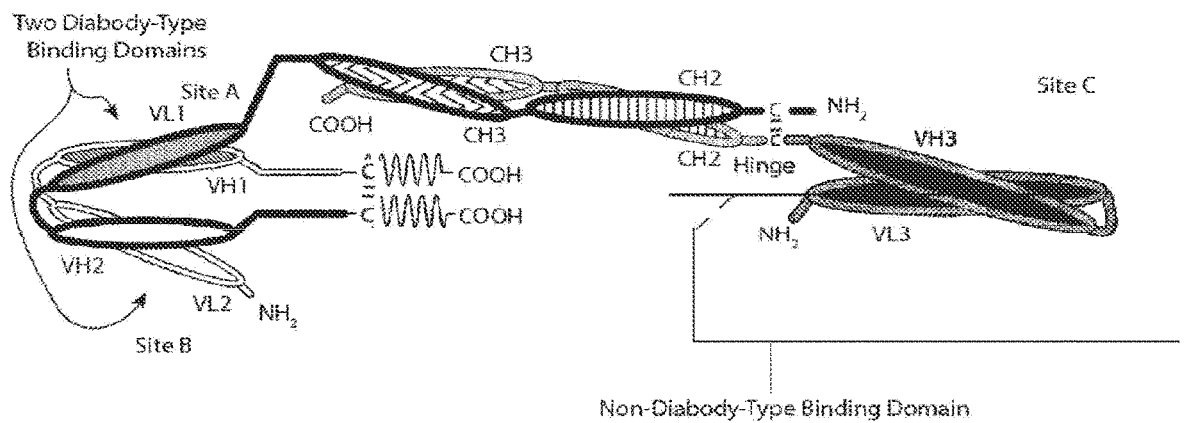

Thus, the first and second, and the third and fifth, polypeptide chains of such diabodies associate together to form two VL1/VH1 epitope-binding sites capable of binding a first epitope. The third and fourth polypeptide chains of such diabodies associate together to form a VL2/VH2 epitope-binding site that is capable of binding to a second epitope, as well as a VL3/VH3 binding site that is capable of binding to a third epitope. The first and third polypeptides are bonded to one another through a disulfide bond involving cysteine residues in their respective constant regions. Notably, the first and third polypeptide chains complex with one another to form an Fc Domain. Such multispecific diabodies have enhanced potency. FIG. 5 illustrates the structure of such diabodies. It will be understood that the VL1/VH1, VL2/VH2, and VL3/VH3 Domains may be the same or different so as to permit binding that is monospecific, bispecific or trispecific. As provided herein, these domains are preferably selected so as to bind an epitope of 7-H3, an epitope of second molecule and optionally an epitope ofiafthird molecule.

The VL and VH Domains ofthe polypeptide chains are selected so as to form VL2H binding sites specific for a desired epitope. The VL H binding sites formed by the association of the polypeptide chains may be the same or different so as to permit tetravalent binding that is monospecific, bispecific, trispecific ortetraspecific. In particular, the VL and VH Domains may be selected such that a multivalent diabody may comprise two binding sites for a first epitope and two binding sites for a second epitope, or three binding sites for a first epitope and one binding site for a second epitope, or two binding sites for a first epitope, one binding site for a second epitope and one binding site for a third epitope (as depicted in FIG. 5). The general structure of the polypeptide chains of representative five-chain Fc Domain-containing diabodies of invention is provided in Table 3:

TABLE 3

| | | |
|---|---|---|
| Bispecific (2 × 2) | $2^{nd}$ Chain | NH$_2$-VL1-CL-COOH |
| | $1^{st}$ Chain | NH$_2$—VH1—CH1—CH2—CH3—COOH |
| | $3^{rd}$ Chain | NH$_2$—VH1—CH1—CH2—CH3-VL2-VH2-HPD-COOH |
| | $5^{nd}$ Chain | NH$_2$-VL1-CL-COOH |
| | $4^{th}$ Chain | NH$_2$-VL2-VH2-HPD-COOH |
| Bispecific (3 × 1) | $2^{nd}$ Chain | NH$_2$-VL1-CL-COOH |
| | $1^{st}$ Chain | NH$_2$—VH1—CH1—CH2—CH3—COOH |
| | $3^{rd}$ Chain | NH$_2$—VH1—CH1—CH2—CH3-VL1-VH2-HPD-COOH |
| | $5^{nd}$ Chain | NH$_2$-VL1-CL-COOH |
| | $4^{th}$ Chain | NH$_2$-VL2-VH1-HPD-COOH |
| Trispecific (2 × 1 × 1) | $2^{nd}$ Chain | NH$_2$-VL1-CL-COOH |
| | $1^{st}$ Chain | NH$_2$—VH1—CH1—CH2—CH3—COOH |
| | $3^{rd}$ Chain | NH$_2$—VH1—CH1—CH2—CH3-VL2-VH3-HPD-COOH |
| | $5^{nd}$ Chain | NH$_2$-VL1-CL-COOH |
| | $4^{th}$ Chain | NH$_2$-VL3-VH2-HPD-COOH |

HPD = Heterodimer-Promoting Domain

In a specific embodiment, diabodies of the present invention are bispecific, tetravalent (i.e., possess four epitope-binding sites), Fc-containing diabodies that are composed of five total polypeptide chains having two epitope-binding sites immunospecific for B7-H3 (which may be capable of binding to the same epitope of B7-H3 or to different epitopes of B7-H3), and two epitope-binding sites specific for a second molecule (which may be capable of binding to the same epitope of the second molecule or to different epitopes of the second molecule). In another embodiment, the bispecific, tetravalent, Fc-containing diabodies of the invention comprise three epitope-binding sites immunospecific for B7-H3 (which may be capable of binding to the same epitope of B7-H3 or to two or three different epitopes of B7-H3), and one epitope-binding site specific for a second molecule. In another embodiment, the bispecific, tetravalent, Fc-containing diabodies of the invention comprise one epitope-binding site immunospecific for B7-H3, and three epitope-binding sites specific for a second molecule (which may be capable of binding to the same epitope of the second molecule or to two or three different epitopes of the second molecule). As provided above, the VL and VH domains may be selected to permit trispecific binding. Accordingly, the invention also encompasses trispecific, tetravalent, Fc-containing diabodies. The trispecific, tetravalent, Fc-containing diabodies of the invention comprise two epitope-binding sites immunospecific for B7-H3, one epitope-binding site immunospecific for a second molecule, and one epitope-binding site immunospecific for a third molecule. In certain embodiments, the second molecule is a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. In certain embodiments, the second molecule is CD3 and the third molecule is CD8.

D. Trivalent Binding Molecules Containing Fc Domains

A further embodiment of the present invention relates to trivalent binding molecules comprising an Fc Domain capable of simultaneously binding a first epitope, a second epitope and a third epitope, wherein at least one of such epitopes is not identical to another. Such trivalent binding molecules comprise three epitope-binding sites, two of which are Diabody-Type Binding Domains, which provide binding Site A and binding Site B, and one of which is a Fab-Type Binding Domain, or an scFv-Type Binding Domain, which provides binding Site C (see, e.g., FIGS. 6A-6F, and PCT Application No: PCT/US15/33081; and PCT/US15/33076). Such trivalent binding molecules thus comprise "VL1"/"VH1" domains that are capable of binding to the first epitope and "VL2"/"VH2" domains that are capable of binding to the second epitope and "VL3" and "VH3" domains that are capable of binding to the "third" epitope of such trivalent binding molecule. A "Diabody-Type Binding Domain" is the type of epitope-binding site present in a diabody, and especially, a DART® diabody, as described above. Each of a "Fab-Type Binding Domain" and an "scFv-Type Binding Domain" are epitope-binding sites that are formed by the interaction of the VL Domain of an immunoglobulin light chain and a complementing VH Domain of an immunoglobulin heavy chain. Fab-Type Binding Domains differ from Diabody-Type Binding Domains in that the two polypeptide chains that form a Fab-Type Binding Domain comprise only a single epitope-binding site, whereas the two polypeptide chains that form a Diabody-Type Binding Domain comprise at least two epitope-binding sites. Similarly, scFv-Type Binding Domains also differ from Diabody-Type Binding Domains in that they comprise only a single epitope-binding site. Thus, as used herein Fab-Type, and scFv-Type Binding Domains are distinct from Diabody-Type Binding Domains.

Typically, the trivalent binding molecules of the present invention will comprise four different polypeptide chains (see FIGS. 6A-6B), however, the molecules may comprise fewer or greater numbers of polypeptide chains, for example by fusing such polypeptide chains to one another (e.g., via a peptide bond) or by dividing such polypeptide chains to form additional polypeptide chains, or by associating fewer or additional polypeptide chains via disulfide bonds. FIGS. 6C-6F illustrate this aspect of the present invention by schematically depicting such molecules having three polypeptide chains. As provided in FIGS. 6A-6F, the trivalent binding molecules of the present invention may have alternative orientations in which the Diabody-Type Binding Domains are N-terminal (FIGS. 6A, 6C and 6D) or C-terminal (FIGS. 6B, 6E and 6F) to an Fc Domain.

In certain embodiments, the first polypeptide chain of such trivalent binding molecules of the present invention contains: (i) a VL1-containing Domain, (ii) a VH2-containing Domain, (iii) a Heterodimer-Promoting Domain, and (iv) a Domain containing a CH2-CH3 sequence. The VL1 and VL2 Domains are located N-terminal or C-terminal to the CH2-CH3-containing domain as presented in Table 3 (also see, FIGS. 6A and 6B). The second polypeptide chain of such embodiments contains: (i) a VL2-containing Domain, (ii) a VH1-containing Domain, and (iii) a Heterodimer-Promoting Domain. The third polypeptide chain of such embodiments contains: (i) a VH3-containing Domain, (ii) a CH1-containing Domain and (iii) a Domain containing a CH2-CH3 sequence. The third polypeptide chain may be the heavy chain of an antibody that contains a VH3 and a heavy chain constant region, or a polypeptide that contains such domains. The fourth polypeptide of such embodiments contains: (i) a VL3-containing Domain and (ii) a CL-containing Domain. The fourth polypeptide chains may be a light chain of an antibody that contains a VL3 complementary to the VH3 of the third polypeptide chain, or a polypeptide that contains such domains. The third or fourth polypeptide chains may be isolated from naturally occurring antibodies. Alternatively, they may be constructed recombinantly, synthetically or by other means.

The Light Chain Variable Domain of the first and second polypeptide chains are separated from the Heavy Chain Variable Domains of such polypeptide chains by an intervening spacer peptide having a length that is too short to permit their VL1/VH2 (or their VL2/VH1) domains to associate together to form epitope-binding site capable of binding to either the first or second epitope. A preferred intervening spacer peptide (Linker 1) for this purpose has the sequence (SEQ ID NO:32): GGGSGGGG. Other Domains of the trivalent binding molecules may be separated by one or more intervening spacer peptides (Linkers), optionally comprising a cysteine residue. In particular, as provided above, such Linkers will typically be incorporated between Variable Domains (i.e., VH or VL) and peptide Heterodimer-Promoting Domains (e.g., an E-coil or K-coil) and between such peptide Heterodimer-Promoting Domains (e.g., an E-coil or K-coil) and CH2-CH3 Domains. Exemplary linkers useful for the generation of trivalent binding molecules are provided above and are also provided in PCT Application Nos: PCT/US15/33081; and PCT/US15/33076. Thus, the first and second polypeptide chains of such trivalent binding molecules associate together to form a VL1/VH1 binding site capable of binding a first epitope, as well as a VL2/VH2 binding site that is capable of binding to a second epitope. The third and fourth polypeptide chains of such trivalent binding molecules associate together to form a VL3/VH3 binding site that is capable of binding to a third epitope.

As described above, the trivalent binding molecules of the present invention may comprise three polypeptides. Trivalent binding molecules comprising three polypeptide chains may be obtained by linking the domains of the fourth polypeptide N-terminal to the VH3-containing Domain of the third polypeptide (e.g., using an intervening spacer peptide (Linker 4)). Alternatively, a third polypeptide chain of a trivalent binding molecule of the invention containing the following domains is utilized: (i) a VL3-containing Domain, (ii) a VH3-containing Domain, and (iii) a Domain containing a CH2-CH3 sequence, wherein the VL3 and VH3 are spaced apart from one another by an intervening spacer peptide that is sufficiently long (at least 9 or more amino acid residues) so as to allow the association of these domains to form an epitope-binding site. One preferred intervening spacer peptide for this purpose has the sequence: GGGGSGGGGSGGGGS (SEQ ID NO:59).

It will be understood that the VLT/VH1, VL2/VH2, and VL3/VH3 Domains of such trivalent binding molecules may be different so as to permit binding that is monospecific, bispecific or trispecific. In particular, the VL and VH Domains may be selected such that a trivalent binding molecule comprises two binding sites for a first epitope and one binding sites for a second epitope, or one binding site for a first epitope and two binding sites for a second epitope, or one binding site for a first epitope, one binding site for a second epitope and one binding site for a third epitope.

However, as provided herein, these domains are preferably selected so as to bind an epitope of B7-H3, an epitope of second molecule, and an epitope of a third molecule. In certain embodiments, the second molecule is a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. In certain embodiments, the third molecule is CD8.

The general structure of the polypeptide chains of representative trivalent binding molecules of invention is provided in FIGS. 6A-6F and in Table 4:

TABLE 4

| | | |
|---|---|---|
| Four Chain 1st Orientation | 2nd Chain 1st Chain 3rd Chain 2nd Chain | NH₂-VL2-VH1-HPD-COOH NH₂-VL1-VH2-HPD-CH2—CH3—COOH NH₂-VH3-CH1—CH2—CH3—COOH NH₂-VL3-CL-COOH |
| Four Chain 2nd Orientation | 2nd Chain 1st Chain 3rd Chain 2nd Chain | NH₂-VL2-VH1-HPD-COOH NH₂—CH2—CH3-VL1-VH2-HPD-COOH NH₂—VH3—CH1—CH2—CH3—COOH NH₂-VL3-CL-COOH |
| Three Chain 1st Orientation | 2nd Chain 1st Chain 3rd Chain | NH₂-VL2-VH1-HPD-COOH NH₂-VL1-VH2-HPD-CH2—CH3—COOH NH₂-VL3-VH3-HPD-CH2—CH3—COOH |
| Three Chain 2nd Orientation | 2nd Chain 1st Chain 3rd Chain | NH₂-VL2-VH1-HPD-COOH NH₂—CH2—CH3-VL1-VH2-HPD-COOH NH₂-VL3-VH3-HPD-CH2—CH3—COOH |

HPD = Heterodimer-Promoting Domain

One embodiment of the present invention relates to trivalent binding molecules that comprise two epitope-binding sites for B7-H3 and one epitope-binding site for a second molecule. The two epitope-binding sites for B7-H3 may bind the same epitope or different epitopes. Another embodiment of the present invention relates to trivalent binding molecules that comprise, one epitope-binding site for B7-H3 and two epitope-binding sites for a second molecule. The two epitope-binding sites for the second molecule may bind the same epitope or different epitopes of the second molecule. A further embodiment of the present invention relates to trispecific trivalent binding molecules that comprise, one epitope-binding site for B7-H3, one epitope-binding site for a second molecule, and one epitope-binding site for a third molecule. In certain embodiments, the second molecule is a molecule (e.g., CD2, CD3, CD8, CD16, T-Cell Receptor (TCR), NKG2D, etc.) present on the surface of an effector cell, such as a T lymphocyte, a natural killer (NK) cell or other mononuclear cell. In certain embodiments, the second molecule is CD3 and the third molecule is CD8. As provided

VII. Modification of the Fc Domain

The Fc Domain of the Fc Domain-containing molecules (e.g., antibodies, diabodies, trivalent binding molecules, etc.) of the present invention may be either a complete Fc Domain (e.g., a complete IgG Fc Domain) or only a fragment of an Fc Domain. Optionally, the Fc Domain of the Fc Domain-containing molecules of the present invention lacks the C-terminal lysine amino acid residue.

In traditional immune function, the interaction of antibody-antigen complexes with cells of the immune system results in a wide array of responses, ranging from effector functions such as antibody dependent cytotoxicity, mast cell degranulation, and phagocytosis to immunomodulatory signals such as regulating lymphocyte proliferation and antibody secretion. All of these interactions are initiated through the binding of the Fc Domain of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. In addition, interaction with the neonatal Fc Receptor (FcRn) mediates the recycling of IgG molecules from the endosome to the cell surface and release into the blood. The amino acid sequence of exemplary wild-type IgG1 (SEQ ID NO:12), IgG2 (SEQ ID NO:13), IgG3 (SEQ ID NO:14), and IgG4 (SEQ ID NO:15) are presented above.

Modification of the Fc Domain may lead to an altered phenotype, for example altered serum half-life, altered stability, altered susceptibility to cellular enzymes or altered effector function. It may therefore be desirable to modify an Fc Domain-containing B7-H3-binding molecule of the present invention with respect to effector function, for example, so as to enhance the effectiveness of such molecule in treating cancer. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkin's lymphoma, CLL, and Burkitt's lymphoma). Molecules of the invention possessing such conferred or altered effector function activity are useful for the treatment and/or prevention of a disease, disorder or infection in which an enhanced efficacy of effector function activity is desired.

Accordingly, in certain embodiments, the Fc Domain of the Fc Domain-containing molecules of the present invention may be an engineered variant Fc Domain. Although the Fc Domain of the bispecific Fc Domain-containing molecules of the present invention may possess the ability to bind to one or more Fc receptors (e.g., FcγR(s)), more preferably such variant Fc Domain have altered binding to FcγRIA (CD64), FcγRIIA (CD32A), FcγRIIB (CD32B), FcγRIIIA (CD16a) or FcγRIIIB (CD16b) (relative to the binding exhibited by a wild-type Fc Domain), e.g., will have enhanced binding to an activating receptor and/or will have substantially reduced or no ability to bind to inhibitory receptor(s). Thus, the Fc Domain of the Fc Domain-containing molecules of the present invention may include some or all of the CH2 Domain and/or some or all of the CH3 Domain of a complete Fc Domain, or may comprise a variant CH2 and/or a variant CH3 sequence (that may include, for example, one or more insertions and/or one or more deletions with respect to the CH2 or CH3 domains of a complete Fc Domain). Such Fc Domains may comprise non-Fc polypeptide portions, or may comprise portions of non-naturally complete Fc Domains, or may comprise non-naturally occurring orientations of CH2 and/or CH3 Domains (such as, for example, two CH2 domains or two CH3 domains, or in the N-terminal to C-terminal direction, a CH3 Domain linked to a CH2 Domain, etc.).

Fc Domain modifications identified as altering effector function are known in the art, including modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) "*Fc Optimization Of Therapeutic Antibodies Enhances Their Ability To Kill Tumor Cells In Vitro And Controls Tumor Expansion In Vivo Via Low- Affinity Activating Fcgamma Receptors,*" Cancer Res. 57(18):8882-8890). Table 5 lists exemplary single, double, triple, quadruple and quintuple substitutions (numbering and substitutions are relative to the amino acid sequence of SEQ ID NO:12) of exemplary modification that increase binding to activating receptors and/or reduce binding to inhibitory receptors.

TABLE 5

Variations of Preferred Activating Fc Domains

Single-Site Variations

| | | | |
|---|---|---|---|
| F243L | R292G | D270E | R292P |
| Y300L | P396L | | |

Double-Site Variations

| | | | |
|---|---|---|---|
| F243L and R292P | F243L and Y300L | F243L and P396L | R292P and Y300L |
| D270E and P396L | R292P and V305I | P396L and Q419H | P247L and N421K |
| R292P and P396L | Y300L and P396L | R255L and P396L | R292P and P305I |
| K392T and P396L | | | |

Triple-Site Variations

| | |
|---|---|
| F243L, P247L and N421K | P247L, D270E and N421K |
| F243L, R292P and Y300L | R255L, D270E and P396L |
| F243L, R292P and V305I | D270E, G316D and R416G |

TABLE 5-continued

| Variations of Preferred Activating Fc Domains | |
|---|---|
| F243L, R292P and P396L | D270E, K392T and P396L |
| F243L, Y300L and P396L | D270E, P396L and Q419H |
| V284M, R292L and K370N | R292P, Y300L and P396L |
| Quadruple-Site Variations | |
| L234F, F243L, R292P and Y300L | F243L, P247L, D270E and N421K |
| L234F, F243L, R292P and Y300L | F243L, R255L, D270E and P396L |
| L235I, F243L, R292P and Y300L | F243L, D270E, G316D andR416G |
| L235Q, F243L, R292P and Y300L | F243L, D270E, K392T and P396L |
| P247L, D270E, Y300L and N421K | F243L, R292P, Y300L, and P396L |
| R255L, D270E, R292G and P396L | F243L, R292P, V305I and P396L |
| R255L, D270E, Y300L and P396L | F243L, D270E, P396L and Q419H |
| D270E, G316D, P396L and R416G | |
| Quintuple-Site Variations | |
| L235V, F243L, R292P, Y300L and P396L | F243L, R292P, V305I, Y300L and P396L |
| L235P, F243L, R292P, Y300L and P396L | |

Exemplary variants of human IgG1 Fc Domains with reduced binding to CD32B and/or increased binding to CD16A contain F243L, R292P, Y300L, V305I or P296L substitutions. These amino acid substitutions may be present in a human IgG1 Fc Domain in any combination. In one embodiment, the variant human IgG1 Fc Domain contains a F243L, R292P and Y300L substitution. In another embodiment, the variant human IgG1 Fc Domain contains a F243L, R292P, Y300L, V305I and P296L substitution.

In certain embodiments, it is preferred for the Fc Domains of B7-H3-binding molecules of the present invention to exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Domain (SEQ ID NO:12). In a specific embodiment, the B7-H3-binding molecules of the present invention comprise an IgG Fc Domain that exhibits reduced ADCC effector function. In a preferred embodiment, the CH2-CH3 Domains of such B7-H3-binding molecules include any 1, 2, 3, or 4 of the substitutions: L234A, L235A, D265A, N297Q, and N297G. In another embodiment, the CH2-CH3 Domains contain an N297Q substitution, an N297G substitution, L234A and L235A substitutions or a D265A substitution, as these mutations abolish FcR binding. Alternatively, a CH2-CH3 Domain of a naturally occurring Fc Domain that inherently exhibits decreased (or substantially no) binding to FcγRIIIA (CD16a) and/or reduced effector function (relative to the binding and effector function exhibited by the wild-type IgG1 Fc Domain (SEQ ID NO:12)) is utilized. In a specific embodiment, the B7-H3-binding molecules of the present invention comprise an IgG2 Fc Domain (SEQ ID NO:13) or an IgG4 Fc Domain (SEQ ID:NO:4). When an IgG4 Fc Domain is utilized, the instant invention also encompasses the introduction of a stabilizing mutation, such as the Hinge Domain S228P substitution described above (see, e.g., SEQ ID NO:11). Since the N297G, N297Q, L234A, L235A and D265A substitutions abolish effector function, in circumstances in which effector function is desired, these substitutions would preferably not be employed.

A preferred IgG1 sequence for the CH2 and CH3 Domains of the Fc Domain-containing molecules of the present invention having reduced or abolished effector function will comprise the substitutions L234A/L235A (SEQ ID NO:60):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein, X is a lysine (K) or is absent.

The serum half-life of proteins comprising Fc Domains may be increased by increasing the binding affinity of the Fc Domain for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from a subject's body (e.g., a human patient or other mammal) or a specific compartment thereof, for example, as measured in serum, i.e., circulating half-life, or in other tissues. In general, an increase in half-life results in an increase in mean residence time (MRT) in circulation for the molecule administered.

In some embodiments, the B7-H3-binding molecules of the present invention comprise a variant Fc Domain, wherein said variant Fc Domain comprises at least one amino acid modification relative to a wild-type Fc Domain, such that said molecule has an increased half-life (relative to a molecule comprising a wild-type Fc Domain). In some embodiments, the B7-H3-binding molecules of the present invention comprise a variant IgG Fc Domain, wherein said variant Fc Domain comprises a half-live extending amino acid substitution at one or more positions selected from the group consisting of 238, 250, 252, 254, 256, 257, 256, 265, 272, 286, 288, 303, 305, 307, 308, 309, 311, 312, 317, 340, 356, 360, 362, 376, 378, 380, 382, 413, 424, 428, 433, 434, 435, and 436. Numerous mutations capable of increasing the half-life of an Fc Domain-containing molecule are known in the art and include, for example M252Y, S254T, T256E, and combinations thereof. For example, see the mutations described in U.S. Pat. Nos. 6,277,375; 7,083,784; 7,217,797; 8,088,376; U.S. Publication Nos. 2002/0147311; 2007/0148164; and PCT Publication Nos. WO 98/23289; WO 2009/058492; and WO 2010/033279, which are herein incorporated by reference in their entireties. B7-H3-binding molecules with enhanced half-life also include those possessing variant Fc Domains comprising substitutions at two or more of Fc Domain residues 250, 252, 254, 256, 257, 288, 307, 308, 309, 311, 378, 428, 433, 434, 435 and 436. In particular, two or more substitutions selected from: T250Q, M252Y, S254T, T256E, K288D, T307Q, V308P, A378V, M428L, N434A, H435K, and Y436I.

In a specific embodiment, a B7-H3-binding molecule of the present invention possesses a variant IgG Fc Domain comprising the substitutions:

(A) M252Y, S254T and T256E;
(B) M252Y and S254T;
(C) M252Y and T256E;
(D) T250Q and M428L;
(E) T307Q and N434A;
(F) A378V and N434A;
(G) N434A and Y436I;
(H) V308P and N434A; or
(I) K288D and H435K.

In a preferred embodiment, a B7-H3-binding molecule of the present invention possesses a variant IgG Fc Domain comprising any 1, 2, or 3 of the substitutions: M252Y, S254T and T256E. The invention further encompasses B7-H3-binding molecules possessing variant Fc Domains comprising:

(A) one or more mutations which alter effector function and/or FcγR; and
(B) one or more mutations which extend serum half-life.

For certain antibodies, diabodies and trivalent binding molecules whose Fc Domain-containing first and third polypeptide chains are not identical, it is desirable to reduce or prevent homodimerization from occurring between the CH2-CH3 Domains of two first polypeptide chains or between the CH2-CH3 Domains of two third polypeptide chains. The CH2 and/or CH3 Domains of such polypeptide chains need not be identical in sequence, and advantageously are modified to foster complexing between the two polypeptide chains. For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any pair of polypeptides comprising CH2-CH3 Domains that forms an Fc Domain to foster heterodimerization. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*, "Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety).

A preferred knob is created by modifying an IgG Fc Domain to contain the modification T366W. A preferred hole is created by modifying an IgG Fc Domain to contain the modification T366S, L368A and Y407V. To aid in purifying the hole-bearing third polypeptide chain homodimer from the final bispecific heterodimeric Fc Domain-containing molecule, the protein A binding site of the hole-bearing CH2 and CH3 Domains of the third polypeptide chain is preferably mutated by amino acid substitution at position 435 (H435R). Thus, the hole-bearing third polypeptide chain homodimer will not bind to protein A, whereas the bispecific heterodimer will retain its ability to bind protein A via the protein A binding site on the first polypeptide chain. In an alternative embodiment, the hole-bearing third polypeptide chain may incorporate amino acid substitutions at positions 434 and 435 (N434A/N435K).

A preferred IgG amino acid sequence for the CH2 and CH3 Domains of the first polypeptide chain of an Fc Domain-containing molecule of the present invention will have the "knob-bearing" sequence (SEQ ID NO:61):

```
APEAAGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLWCLVK GFYPSDIAVE WESNGQPENN
YKTTPPVLDS DGSFFLYSKL TVDKSRWQQG NVFSCSVMHE
ALHNHYTQKS LSLSPGX
``` wherein X is a lysine (K) or is absent.

A preferred IgG amino acid sequence for the CH2 and CH3 Domains of the second polypeptide chain of an Fc Domain-containing molecule of the present invention having two polypeptide chains (or the third polypeptide chain of an Fc Domain-containing molecule having three, four, or five polypeptide chains) will have the "hole-bearing" sequence (SEQ ID NO:62):

```
APEAAGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLSCAVK GFYPSDIAVE WESNGQPENN
YKTTPPVLDS DGSFFLVSKL TVDKSRWQQG NVFSCSVMHE
ALHNRYTQKS LSLSPGX
``` wherein X is a lysine (K) or is absent.

As will be noted, the CH2-CH3 Domains of SEQ ID NO:61, and SEQ ID NO:62 include a substitution at position 234 with alanine and 235 with alanine, and thus form an Fc Domain exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc Domain (SEQ ID NO:12). The invention also encompasses such CH2-CH3 Domains, which comprise the wild-type alanine residues, alternative and/or additional substitutions which modify effector function and/or FγR binding activity of the Fc Domain. The invention also encompasses such CH2-CH3 Domains, which further comprise one or more half-live extending amino acid substitutions. In particular, the invention encompasses such hole-bearing and such knob-bearing CH2-CH3 Domains which further comprise the M252Y/S254T/T256E.

It is preferred that the first polypeptide chain will have a "knob-bearing" CH2-CH3 sequence, such as that of SEQ ID NO:61. However, as will be recognized, a "hole-bearing" CH2-CH3 Domain (e.g., SEQ ID NO:62 could be employed in the first polypeptide chain, in which case, a "knob-bearing" CH2-CH3 Domain (e.g., SEQ ID NO:61) would be employed in the second polypeptide chain of an Fc Domain-containing molecule of the present invention having two polypeptide chains (or in the third polypeptide chain of an Fc Domain-containing molecule having three, four, or five polypeptide chains).

In other embodiments, the invention encompasses B7-H3-binding molecules comprising CH2 and/or CH3 Domains that have been engineered to favor heterodimerization over homodimerization using mutations known in the art, such as those disclosed in PCT Publication No. WO 2007/110205; WO 2011/143545; WO 2012/058768; WO 2013/06867, all of which are incorporated herein by reference in their entirety.

VII. Effector Cell Binding Capabilities

As provided herein, the B7-H3-binding molecules of the invention, including B7-H3-ADC molecules, can be engineered to comprise a combination of epitope-binding sites that recognize a set of antigens unique to a target cell or tissue type. In particular, the present invention relates to multispecific B7-H3-binding molecules that are capable of binding to an epitope of B7-H3 and an epitope of a molecule present on the surface of an effector cell, such as a T lymphocyte, a natural killer (NK) cell or other mononuclear cell. For example, the B7-H3-binding molecules of the present invention may be construction to comprise an epitope-binding site that immunospecifically binds CD2, CD3, CD8, CD16, T-Cell Receptor (TCR), or NKG2D. The invention also relates to trispecific B7-H3-binding molecules that are capable of binding to an epitope of CD3 and an epitope of CD8 (see, e.g., PCT Publication No. WO 2015/026894).

A. CD2 Binding Capabilities

In one embodiment, the bispecific, trispecific or multi-specific B7-H3-binding molecules of the invention are capable of binding to an epitope of B7-H3 and an epitope of CD2. CD2 is a cell adhesion molecule found on the surface of T-cells and natural killer (NK) cells. CD2 enhances NK cell cytotoxicity, possibly as a promoter of NK cell nanotube formation (Mace, E. M. et al. (2014) "*Cell Biological Steps and Checkpoints in Accessing NK Cell Cytotoxicity*," Immunol. Cell. Biol. 92(3):245-255; Comerci, C. J. et al. (2012) "*CD2 Promotes Human Natural Killer Cell Membrane Nanotube Formation*," PLoS One 7(10):e47664:1-12). Molecules that specifically bind CD2 include the anti-CD2 antibody "Lo-CD2a."

The amino acid sequence of the VH Domain of Lo-CD2a (ATCC Accession No: 11423); SEQ ID NO:63) is shown below (CDR$_H$ residues are shown underlined):

```
EVQLQQSGPE LQRPGASVKL SCKASGYIFT EYYMYWVKQR

PKQGLELVGR IDPEDGSIDY VEKFKKKATL TADTSSNTAY

MQLSSLTSED TATYFCARGK FNYRFAYWGQ GTLVTVSS
```

The amino acid sequence of the VL Domain of Lo-CD2a (ATCC Accession No: 11423; SEQ ID NO:64) is shown below (CDR$_L$ residues are shown underlined):

```
DVVLTQTPPT LLATIGQSVS ISCRSSQSLL HSSGNTYLNW

LLQRTGQSPQ PLIYLVSKLE SGVPNRFSGS GSGTDFTLKI

SGVEAEDLGV YYCMQFTHYP YTFGAGTKLE LK
```

B. CD3 Binding Capabilities

In one embodiment, the bispecific, trispecific or multi-specific B7-H3-binding molecules of the invention are capable of binding to an epitope of B7-H3 and an epitope of CD3. CD3 is a T-cell co-receptor composed of four distinct chains (Wucherpfennig, K. W. et al. (2010) "*Structural Biology Of The T-Cell Receptor: Insights Into Receptor Assembly, Ligand Recognition, And Initiation Of Signaling*," Cold Spring Harb. Perspect. Biol. 2(4):a005140; pages 1-14). In mammals, the complex contains a CD3γ chain, a CD3δ chain, and two CD3ε chains. These chains associate with a molecule known as the T-Cell Receptor (TCR) in order to generate an activation signal in T lymphocytes. In the absence of CD3, TCRs do not assemble properly and are degraded (Thomas, S. et al. (2010) "*Molecular Immunology Lessons From Therapeutic T-Cell Receptor Gene Transfer*," Immunology 129(2):170-177). CD3 is found bound to the membranes of all mature T-cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer*," Cell 105(7):913-923; Kuhns, M. S. et al. (2006) "*Deconstructing The Form And Function Of The TCR/CD3 Complex*," Immunity. 2006 February; 24(2):133-139). Molecules that specifically binds CD3 include the anti-CD3 antibodies "CD3 mAb-1" and "OKT3." The anti-CD3 antibody CD3 mAb-1 is capable of binding non-human primates (e.g., cynomolgus monkey).

The amino acid sequence of the VH Domain of CD3 mAb-1 VH(1) (SEQ ID NO:65) is shown below (CDR$_H$ residues are shown underlined):

```
EVQLVESGGG LVQPGGSLRL SCAASGFTFS TYAMNWVRQA

PKGGLEWVGR IRSKYNNYAT YYADSVKDRF TISRDDSKNS

LYLQMNSLKT EDTAVYYCVR HGNFGNSYVS WFAYWGQGTL VTVSS
```

The amino acid sequence of an alternative VH Domain of CD3 mAb-1 VH(2) (SEQ ID NO:66) is shown below (CDR$_H$ residues are shown in single underline; differences relative to the VH Domain of CD3 mAb-1 VH(1) (SEQ ID NO:65) are shown in double underline).

```
EVQLVESGGG LVQPGGSLRL SCAASGFTFN TYAMNWVRQA

PKGGLEWVAR IRSKYNNYAT YYADSVKDRF TISRDDSKNS

LYLQMNSLKT EDTAVYYCVR HGNFGNSYVS WFAYWGQGTL VTVSS
```

The amino acid sequence of the VL Domain of CD3 mAb-1 (SEQ ID NO:67) is shown below (CDR$_L$ residues are shown underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG
```

The VH Domain of CD3 mAb-1 VH(1) (SEQ ID NO:65) may be used with the VL Domain of CD3 mAb-1 (SEQ ID NO:67) to form a functional CD3-binding molecule in accordance with the present invention. Likewise, the VH Domain of CD3 mAb-1 VH(2) (SEQ ID NO:66) may be used with the VL Domain of CD3 mAb-1 (SEQ ID NO:67) to form a functional CD3-binding molecule in accordance with the present invention.

As discussed below, in order to better illustrate the present invention, bispecific B7-H3×CD3-binding molecules were produced. In some of the B7-H3×CD3 constructs, a variant of CD3 mAb-1 was employed. The variant "CD3 mAb-1 (D65G)," comprises the VL Domain of CD3 mAb-1 (SEQ ID NO:67) and a VH CD3 mAb-1 Domain having a D65G substitution (Kabat position 65, corresponding to residue 68 of SEQ ID NO:65). The amino acid sequence of the VH Domain of CD3 mAb-1 (D65G) (SEQ ID NO:68) is shown below (CDR$_H$ residues are shown underlined, the substituted position (D65G) is shown in double underline):

EVQLVESGGG LVQPGGSLRL SCAASGFTFS TYAMNWVRQA PGKGLEWVGR

IRSKYNNYAT YYADSVKGRF TISRDDSKNS LYLQMNSLKT EDTAVYYCVR

HGNFGNSYVS WFAYWGQGTL VTVSS

Alternatively, an affinity variant of CD3 mAb-1 may be incorporated. Variants include a low affinity variant designated "CD3 mAb-1 Low" and a variant having a faster off rate designated "CD3 mAb-1 Fast." The VL Domain of CD3 mAb-1 (SEQ ID NO:67) is common to CD3 mAb-1 Low and CD3 mAb1 Fast and is provided above. The amino acid sequences of the VH Domains of each of CD3 mAb-1 Low and CD3 mAb-1 Fast are provided below.

The amino acid sequence of the VH Domain of anti-human CD3 mAb-1 Low (SEQ ID NO:69) is shown below (CDR$_H$ residues are shown underlined; differences relative to the VH Domain of CD3 mAb-1 VH(1) (SEQ ID NO:65) are shown in double underline):

EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVT WFAYWGQGTL VTVSS

The amino acid sequence of the VH Chain Domain of anti-human CD3 mAb-1 Fast (SEQ ID NO:70) is shown below (CDR$_H$ residues are shown underlined; differences relative to the VH Domain of CD3 mAb-1 VH(1) (SEQ ID NO:65) are shown in double underline):

EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HKNFGNSYVT WFAYWGQGTL VTVSS

Another anti-CD3 antibody, which may be utilized is antibody Muromonab-CD3 "OKT3" (Xu et al. (2000) "*In Vitro Characterization Of Five Humanized OKT3 Effector Function Variant Antibodies*," Cell. Immunol. 200:16-26); Norman, D. J. (1995) "*Mechanisms Of Action And Overview Of OKT3*," Ther. Drug Monit. 17(6):615-620; Canafax, D. M. et al. (1987) "*Monoclonal Antilymphocyte Antibody (OKT3) Treatment Of Acute Renal Allograft Rejection*," Pharmacotherapy 7(4):121-124; Swinnen, L. J. et al. (1993) "*OKT3 Monoclonal Antibodies Induce Interleukin-6 And Interleukin-10: A Possible Cause Of Lymphoproliferative Disorders Associated With Transplantation*," Curr. Opin. Nephrol. Hypertens. 2(4):670-678).

The amino acid sequence of the VH Domain of OKT3 (SEQ ID NO:71) is shown below (CDR$_H$ residues are shown underlined):

QVQLQQSGAE LARPGASVKM SCKASGYTFT RYTMHWVKQR

PGQGLEWIGY INPSRGYTNY NQKFKDKATL TTDKSSSTAY

MQLSSLTSED SAVYYCARYYDDHYCLDYWG QGTTLTVSS

The amino acid sequence of the VL Domain of OKT3 (SEQ ID NO:72) is shown below (CDR$_L$ residues are shown underlined):

QIVLTQSPAI MSASPGEKVT MTCSASSSVS YMNWYQQKSG

TSPKRWIYDT SKLASGVPAH FRGSGSGTSY SLTISGMEAE

DAATYYCQQW SSNPFTFGSG TKLEINR

Additional anti-CD3 antibodies that may be utilized include but are not limited to those described in PCT Publication Nos. WO 2008/119566; and WO 2005/118635.

C. CD8 Binding Capabilities

In one embodiment, the bispecific, trispecific or multispecific B7-H3-binding molecules of the invention are capable of binding to an epitope of B7-H3 and an epitope of CD8. CD8 is a T-cell co-receptor composed of two distinct chains (Leahy, D. J., (1995) "*A Structural View of CD4 and CD8*," FASEB J., 9:17-25) that is expressed on Cytotoxic T-cells. The activation of CD8$^+$ T-cells has been found to be mediated through co-stimulatory interactions between an antigen:major histocompability class I (MHC I) molecule complex that is arrayed on the surface of a target cell and a complex of CD8 and the T-cell Receptor, that are arrayed on surface of the CD8$^+$ T-cell (Gao, G., and Jakobsen, B., (2000). "*Molecular interactions of coreceptor CD8 and MHC class I: the molecular basis for functional coordination with the T-Cell Receptor*". Immunol Today 21: 630-636). Unlike MHC II molecules, which are expressed by only certain immune system cells, MHC I molecules are very widely expressed. Thus, cytotoxic T-cells are capable of binding to a wide variety of cell types. Activated cytotoxic T-cells mediate cell killing through their release of the cytotoxins perforin, granzymes, and granulysin. Antibodies that specifically bind CD8 include the anti-CD8 antibodies "OKT8" and "TRX2."

The amino acid sequence of the VH Domain of OKT8 (SEQ ID NO:73) is shown below (CDR$_H$ residues are shown underlined):

```
QVQLLESGPE LLKPGASVKM SCKASGYTFT DYNMHWVKQS

HGKSLEWIGY IYPYTGGTGY NQKFKNKATL TVDSSSTAY

MELRSLTSED SAVYYCARNF RYTYWYFDVW GQGTTVTVSS
```

The amino acid sequence of the VL Domain of OKT8 (SEQ ID NO:74) is shown below (CDR$_L$ residues are shown underlined):

```
DIVMTQSPAS LAVSLGQRAT ISCRASESVD SYDNSLMHWY

QQKPGQPPKV LIYLASNLES GVPARFSGSG SRTDFTLTID

PVEADDAATY YCQQNNEDPY TFGGGTKLEI KR
```

The amino acid sequence of the VH Domain of TRX2 (SEQ ID NO:75) is shown below (CDR$_H$ residues are shown underlined):

```
QVQLVESGGG VVQPGRSLRL SCAASGFTFS DFGMNWVRQA

PGKGLEWVAL IYYDGSNKFY ADSVKGRFTI SRDNSKNTLY

LQMNSLRAED TAVYYCAKPH YDGYYHFFDS WGQGTLVTVS S
```

The amino acid sequence of the VL Domain of TRX2 (SEQ ID NO:76) is shown below (CDR$_L$ residues are shown underlined):

```
DIQMTQSPSS LSASVGDRVT ITCKGSQDIN NYLANYQQKP

GKAPKLLIYN TDILHTGVPS RFSGSGSGTD FTFTISSLQP E

DIATYYCYQ YNNGYTFGQG TKVEIK
```

D. CD16 Binding Capabilities

In one embodiment, multispecific B7-H3-binding molecules of the invention are capable of binding to an epitope of B7-H3 and an epitope of CD16. CD16 is the FcγRIIIA receptor. CD16 is expressed by neutrophils, eosinophils, natural killer (NK) cells, and tissue macrophages that bind aggregated but not monomeric human IgG (Peltz, G. A. et al. (1989) *"Human Fc Gamma RIII: Cloning, Expression, And Identification Of The Chromosomal Locus Of Two Fc Receptors For IgG,"* Proc. Natl. Acad. Sci. (U.S.A.) 86(3):1013-1017; Bachanova, V. et al. (2014) *"NK Cells In Therapy Of Cancer,"* Crit. Rev. Oncog. 19(1-2):133-141; Miller, J. S. (2013) *"Therapeutic Applications: Natural Killer Cells In The Clinic,"* Hematology Am. Soc. Hematol. Educ. Program. 2013:247-253; Youinou, P. et al. (2002) *"Pathogenic Effects OfAnti-Fc Gamma Receptor IIIB (CD16) On Polymorphonuclear Neutrophils In Non-Organ-Specific Autoimmune Diseases,"* Autoimmun Rev. 1(1-2):13-19; Peipp, M. et al. (2002) *"Bispecific Antibodies Targeting Cancer Cells,"* Biochem. Soc. Trans. 30(4):507-511). Molecules that specifically bind CD16 include the anti-CD16 antibodies "3G8" and "A9." Humanized A9 antibodies are described in PCT Publication WO 03/101485.

The amino acid sequence of the VH Domain of 3G8 (SEQ ID NO:77) is shown below (CDR$_H$ residues are shown underlined):

```
QVTLKESGPG ILQPSQTLSL TCSFSGFSLR TSGMGVGWIR

QPSGKGLEWL AHIWWDDDKR YNPALKSRLT ISKDTSSNQV

FLKIASVDTA DTATYYCAQI NPAWFAYWGQ GT LVTVS A
```

The amino acid sequence of the VL Domain of 3G8 (SEQ ID NO:78) is shown below (CDR$_L$ residues are shown underlined):

```
DTVLTQSPAS LAVSLGQRAT ISCKASQSVD FDGDSFMNWY

QQKPGQPPKL LIYTTSNLES GIPARFSASG SGTDFTLNIH

PVEEEDTATY YCQQSNEDPY TFGGGTKLEI K
```

The amino acid sequence of the VH Domain of A9 (SEQ ID NO:79) is shown below (CDR$_H$ residues are shown underlined):

```
QVQLQQSGAE LVRPGTSVKI SCKASGYTFT NYWLGWVKQR

PGHGLEWIGD IYPGGGYTNY NEKFKGKATV TADTSSRTAY

VQVRSLTSED SAVYFCARSA SWYFDVWGAR TTVTVSS
```

The amino acid sequence of the VL Domain of A9 (SEQ ID NO:80) is shown below (CDR$_L$ residues are shown underlined):

```
DIQAVVTQES ALTTSPGETV TLTCRSNTGT VTTSNYANWV

QEKPDHLFTG LIGHTNNRAP GVPARFSGSL IGDKAALTIT

GAQTEDEAIY FCALWYNNHW VFGGGTKLTV L
```

Additional anti-CD19 antibodies that may be utilized include but are not limited to those described in PCT Publication Nos. WO 03/101485; and WO 2006/125668.

E. TCR Binding Capabilities

In one embodiment, the bispecific, trispecific or multispecific B7-H3-binding molecules of the invention are capable of binding to an epitope of B7-H3 and an epitope of the T Cell Receptor (TCR). The T Cell Receptor is natively expressed by CD4+ or CD8+ T cells, and permits such cells to recognize antigenic peptides that are bound and presented by class I or class II MHC proteins of antigen-presenting cells. Recognition of a pMHC (peptide-MHC) complex by a TCR initiates the propagation of a cellular immune response that leads to the production of cytokines and the lysis of the antigen-presenting cell (see, e.g., Armstrong, K. M. et al. (2008) *"Conformational Changes And Flexibility In T-Cell Receptor Recognition Of Peptide MHC Complexes,"* Biochem. J. 415(Pt 2):183-196; Willemsen, R. (2008) *"Selection Of Human Antibody Fragments Directed Against Tumor T-Cell Epitopes For Adoptive T-Cell Therapy,"* Cytometry A. 73(11):1093-1099; Beier, K. C. et al. (2007) *"Master Switches Of T-Cell Activation And Differentiation,"* Eur. Respir. J. 29:804-812; Mallone, R. et al. (2005) *"Targeting T Lymphocytes For Immune Monitoring And Intervention In Autoimmune Diabetes,"* Am. J. Ther. 12(6):534-550). CD3 is the receptor that binds to the TCR (Thomas, S. et al. (2010) *"Molecular Immunology Lessons From Therapeutic T-Cell Receptor Gene Transfer,"* Immunology 129(2):170-177; Guy, C. S. et al. (2009) *"Organization OfProximal Signal Initiation At The TCR: CD3 Complex,"* Immunol. Rev. 232(1):7-21; St. Clair, E. W. (Epub 2009 Oct. 12) *"Novel Targeted Therapies For Autoimmunity,"* Curr. Opin. Immunol. 21(6):648-657; Baeuerle, P. A. et al. (Epub 2009 Jun. 9) *"Bispecific T-Cell Engaging Antibodies For Cancer Therapy,"* Cancer Res. 69(12):4941-

4944; Smith-Garvin, J. E. et al. (2009) "*T Cell Activation,*" Annu. Rev. Immunol. 27:591-619; Renders, L. et al. (2003) "*Engineered CD3 Antibodies For Immunosuppression,*" Clin. Exp. Immunol. 133(3):307-309).

Molecules that specifically bind to the T Cell Receptor include the anti-TCR antibody "BMA 031" (EP 0403156; Kurrle, R. et al. (1989) "*BMA 031-A TCR-Specific Monoclonal Antibody For Clinical Application,*" Transplant Proc. 21(1 Pt 1):1017-1019; Nashan, B. et al. (1987) "Fine Specificity Of A Panel Of Antibodies Against The TCR/CD3 Complex," Transplant Proc. 19(5):4270-4272; Shearman, C. W. et al. (1991) "Construction, Expression, And Biologic Activity Of Murine/Human Chimeric Antibodies With Specificity For The Human α/β T Cell," J. Immunol. 146(3):928-935; Shearman, C. W. et al. (1991) "*Construction, Expression And Characterization of Humanized Antibodies Directed Against The Human α/β T Cell Receptor,*" J. Immunol. 147(12):4366-4373).

The amino acid sequence of a VH Domain of BMA 031 (SEQ ID NO:81) is shown below (CDR$_H$ residues are shown underlined):

```
QVQLVQSGAE VKKPGASVKV SCKASGYKFT SYVMHWVRQA

PGQGLEWIGY INPYNDVTKY NEKFKGRVTI TADKSTSTAY

LQMNSLRSED TAVHYCARGS YYDYDGFVYW GQGTLVTVSS
```

The amino acid sequence of the VL Domain of BMA 031 (SEQ ID NO:82) is shown below (CDR$_L$ residues are shown underlined):

```
EIVLTQSPAT LSLSPGERAT LSCSATSSVS YMHWYQQKPG

KAPKRWIYDT SKLASGVPSR FSGSGSGTEF TLTISSLQPE

DFATYYCQQW SSNPLTFGQG TKLEIK
```

F. NKG2D Binding Capabilities

In one embodiment, multispecific B7-H3-binding molecules of the invention are capable of binding to an epitope of B7-H3 and an epitope of the NKG2D receptor. The NKG2D receptor is expressed on all human (and other mammalian) Natural Killer cells (Bauer, S. et al. (1999) "*Activation Of NK Cells And T Cells By NKG2D, A Receptor For Stress-Inducible MICA,*" Science 285(5428):727-729; Jamieson, A. M. et al. (2002) "*The Role Of The NKG2D Immunoreceptor In Immune Cell Activation And Natural Killing,*" Immunity 17(1):19-29) as well as on all CD8$^+$ T cells (Groh, V. et al. (2001) "*Costimulation Of CD8αβ T Cells By NKG2D Via Engagement By MIC Induced On Virus-Infected Cells,*" Nat. Immunol. 2(3):255-260; Jamieson, A. M. et al. (2002) "*The Role Of The NKG2D Immunoreceptor In Immune Cell Activation And Natural Killing,*" Immunity 17(1):19-29). Such binding ligands, and particularly those which are not expressed on normal cells, include the histocompatibility 60 (H60) molecule, the product of the retinoic acid early inducible gene-1 (RAE-1), and the murine UL16-binding proteinlike transcript 1 (MULTi) (Raulet D. H. (2003) "*Roles Of The NKG2D Immunoreceptor And Its Ligands,*" Nature Rev. Immunol. 3:781-790; Coudert, J. D. et al. (2005) "*Altered NKG2D Function In NK Cells Induced By Chronic Exposure To Altered NKG2D Ligand-Expressing Tumor Cells,*" Blood 106:1711-1717). Molecules that specifically bind to the NKG2D Receptor include the anti-NKG2D antibodies "KYK-1.0" and "KYK-2.0" (Kwong, K Y et al. (2008) "*Generation, Affinity Maturation, And Characterization Of A Human Anti-Human NKG2D Monoclonal Antibody With Dual Antagonistic And Agonistic Activity,*" J. Mol. Biol. 384:1143-1156; and PCT/US09/54911).

The amino acid sequence of the VH Domain of KYK-1.0 (SEQ ID NO:83) is shown below (CDR$_H$ residues are shown underlined):

```
EVQLVESGGG VVQPGGSLRL SCAASGFTFS SYGMHWVRQA

PGKGLEWVAF IRYDGSNKYY ADSVKGRFTI SRDNSKNTKY

LQMNSLRAED TAVYYCAKDR FGYYLDYWGQ GTLVTVSS
```

The amino acid sequence of the VL Domain of KYK-1.0 (SEQ ID NO:84) is shown below (CDR$_L$ residues are shown underlined):

```
QPVLTQPSSV SVAPGETARI PCGGDDIETK SVHWYQQKPG

QAPVLVIYDD DDRPSGIPER FFGSNSGNTA TLSISRVEAG

DEADYYCQVW DDNNDEWVFG GGTQLTVL
```

The amino acid sequence of a VH Domain of KYK-2.0 (SEQ ID NO:85) is shown below (CDR$_H$ residues are shown underlined):

```
QVQLVESGGG LVKPGGSLRL SCAASGFTFS SYGMHWVRQA

PGKGLEWVAF IRYDGSNKYY ADSVKGRFTI SRDNSKNTLY

LQMNSLRAED TAVYYCAKDR GLGDGTYFDY WGQGTTVTVS S
```

The amino acid sequence of a VL Domain of KYK-2.0 (SEQ ID NO:86) is shown below (CDR$_L$ residues are shown underlined):

```
QSALTQPASV SGSPGQSITI SCSGSSSNIG NNAVNWYQQL

PGKAPKLLIY YDDLLPSGVS DRFSGSKSGT SAFLAISGLQ

SEDEADYYCA AWDDSLNGPV FGGGTKLTVL
```

IX. Multispecific B7-H3-Binding Molecules

A. B7-H3×CD3 Bispecific Two Chain Diabodies

The VL and VH Domains of the above-described B7-H3 binding molecules may be used to construct B7-H3×CD3 bispecific diabodies composed of two covalently linked polypeptide chains. To illustrate this aspect of the present invention, the VL and VH Domains of the above-described anti-B7-H3 mAb-D antibody is used to construct B7-H3× CD3 bispecific diabodies composed of two covalently linked polypeptide chains and comprising the above-discussed murine or humanized VL and VH Domains of mAb-D. The general structure and amino acid sequences of such B7-H3× CD3 bispecific diabodies is provided below.

The first polypeptide chain of one exemplary B7-H3× CD3 bispecific two chain diabody comprises, in the N-terminal to C-terminal direction: an N-terminus; the VL Domain of an anti-B7-H3 antibody (e.g., mAb-D VL (SEQ ID NO:22), or hmAb-D VL (SEQ ID NO:30)); an intervening spacer peptide (Linker 1: GGGSGGGG (SEQ ID NO:32)); the VH Domain of an anti-CD3 antibody (e.g., CD3 mAb 1 (D65G) (SEQ ID NO:68)); a cysteine-containing intervening spacer peptide (Linker 2: GGCGGG (SEQ ID NO:33));

a Heterodimer-Promoting (e.g., an E-coil) Domain (EVAALEK-EVAALEK-EVAALEK-EVAALEK (SEQ ID NO:45)); and a C-terminus.

The second polypeptide chain of such an exemplary B7-H3×CD3 bispecific two chain diabody comprises, in the N-terminal to C-terminal direction: an N-terminus; the VL Domain of a corresponding anti-CD3 antibody (e.g., a VL domain that in association with the VH Domain of the first polypeptide chain forms a CD3-binding site, e.g., the VL Domain of CD3 mAb-1 (SEQ ID NO:67); an intervening spacer peptide (Linker 1: GGGSGGGG (SEQ ID NO:32)); the VH Domain of a corresponding anti-B7-H3 antibody (e.g., a VH domain that in association with the VL Domain of the first polypeptide chain forms an B7-H3-binding site, e.g., mAb-D VH (SEQ ID NO:26) or hmAb-D VH (SEQ ID NO:31); a cysteine-containing intervening spacer peptide (Linker 2: GGCGGG (SEQ ID NO:33)); a Heterodimer-Promoting (e.g., K-coil) Domain (KVAALKE-KVAALKE-KVAALKE-KVAALKE (SEQ ID NO:46)); and a C-terminus.

As provided herein, alternative linkers and/or alternative Heterodimer-Promoting Domains may be utilized in the generation of such diabodies. For example, the first polypeptide chain of an alternative exemplary B7-H3×CD3 bispecific two chain diabody may comprise, in the N-terminal to C-terminal direction: an N-terminus; the VL Domain of an anti-B7-H3 antibody; the intervening spacer peptide (Linker 1: GGGSGGGG (SEQ ID NO:32)); the VH Domain of the anti-CD3 antibody or of a corresponding anti-CD3 antibody; an intervening spacer peptide (Linker 2: ASTKG (SEQ ID NO:37)); a cysteine-containing Heterodimer-Promoting (e.g., K-coil) Domain (KVAACKE-KVAALKE-KVAALKE-KVAALKE (SEQ ID NO:46)); and a C-terminus. The second polypeptide chain of such alternative exemplary diabody may comprise, in the N-terminal to C-terminal direction: an N-terminus; the VL Domain of a corresponding anti-CD3 antibody; an intervening spacer peptide (Linker 1: GGGSGGGG (SEQ ID NO:32)); the VH Domain of a corresponding anti-B7-H3 antibody (e.g., mAb-D VH (SEQ ID NO:26) or hmAb-D VH (SEQ ID NO:31)); an intervening spacer peptide (Linker 2: AST KG (SEQ ID NO:37)); a cysteine-containing Heterodimer-Promoting (e.g., E-coil) Domain (EVAACEK-EVAALEK-EVAALEK-EVAALEK (SEQ ID NO:47)); and a C-terminus.

1. DART-D1

A representative B7-H3×CD3 bispecific two chain diabody comprising the VH and VL Domains of hmAb-C ("DART-D1") is constructed.

The amino acid sequence of the first polypeptide chain of DART-D1 (SEQ ID NO:87) is shown below (the sequence of the hmAb-C VL Domain (SEQ ID NO:20) is underlined):

```
DIQMTQSPSS LSASVGDRVT ITCRASESIY SYLAWYQQKP

GKAPKLLVYN TKTLPEGVPS RFSGSGSGTD FTLTISSLQP

EDFATYYCQH HYGTPPWTFG QGTRLEIKGG GSGGGGEVQL

VESGGGLVQP GGSLRLSCAA SGFTFSTYAM NWVRQAPGKG

LEWVGRIRSK YNNYATYYAD SVKGRFTISR DDSKNSLYLQ

MNSLKTEDTA VYYCVRHGNF GNSYVSWFAY WGQGTLVTVS

SGGCGGGEVA ALEKEVAALE KEVAALEKEV AALEK
```

The amino acid sequence of the second polypeptide chain of DART-D1 (SEQ ID NO:88) is shown below (the sequence of the hmAb-C VH Domain (SEQ ID NO:21) is underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

QLVESGGGLV KPGGSLRLSC AASGFTFSSY GMSWVRQAPG

KGLEWVATIN SGGSNTYYPD SLKGRFTISR DNAKNSLYLQ

MNSLRAEDTA VYYCARHDGG AMDYWGQGTT VTVSSGGCGG

GKVAALKEKV AALKEKVAAL KEKVAALKE
```

2. DART-D2

A representative B7-H3×CD3 bispecific two chain diabody comprising the VH and VL Domains of hmAb-D ("DART-D2") is constructed.

The amino acid sequence of the first polypeptide chain of DART-D2 (SEQ ID NO:89) is shown below (the sequence of the hmAb-D VL Domain (SEQ ID NO:30) is underlined):

```
DIQMTQSPSF LSASVGDRVT ITCKASQNVD TNVAWYQQKP

GKAPKALIYS ASYRYSGVPS RFSGSGSGTD FTLTISSLQP

EDFAEYFCQQ YNNYPFTFGQ GTKLEIKGGG SGGGGEVQLV

ESGGGLVQPG GSLRLSCAAS GFTFSTYAMN WVRQAPGKGL

EWVGRIRSKY NNYATYYADS VKGRFTISRD DSKNSLYLQM

NSLKTEDTAV YYCVRHGNFG NSYVSWFAYW GQGTLVTVSS

ASTKGEVAAC EKEVAALEKE VAALEKEVAA LEK
```

The amino acid sequence of the second polypeptide chain of DART-D2 (SEQ ID NO:90) is shown below (the sequence of the hmAb-D VH Domain (SEQ ID NO:31) is underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

QLVESGGGLV QPGGSLRLSC AASGFTFSSF GMHWVRQAPG

KGLEWVAYIS SGSGTIYYAD TVKGRFTISR DNAKNSLYLQ

MNSLRAEDTA VYYCARHGYR YEGFDYWGQG TTVTVSSAST

KGKVAACKEK VAALKEKVAA LKEKVAALKE
```

It will be appreciated in view of the teachings provided herein that different domain orientations, VH Domains, VL Domains, linkers, and/or heterodimer promoting domains, could be utilized to generate alternative B7-H3×CD3 bispecific two chain diabodies.

B. B7-H3×CD3 Bispecific Three Chain Diabodies

A B7-H3×CD3 diabody having three chains and possessing an Fc Domain is generated having one binding site specific for B7-H3 (comprising humanized VH and VL Domains of hmAb-D) and one binding site specific for CD3 (comprising the VL and VH Domains of CD3 mAb 1 (D65G)). The diabody is designated "DART-D3."

The first polypeptide chain of the exemplary B7-H3×CD3 bispecific three chain DART-D3 diabody comprises, in the N-terminal to C-terminal direction: an N-terminus; the VL Domain of an anti-B7-H3 antibody (hmAb-D VL (SEQ ID NO:30); an intervening spacer peptide (Linker 1: GGGSGGGG (SEQ ID NO:32)); the VH Domain of CD3 mAb 1 (D65G) (SEQ ID NO:68); an intervening spacer peptide (Linker 2: ASTKG (SEQ ID NO:37)); a cysteine-containing Heterodimer-Promoting (E-coil) Domain (EVAACEK-EVAALEK-EVAALEK-EVAALEK (SEQ ID NO:47)); an intervening spacer peptide (Linker 3: GGGDKTHTCPPCP (SEQ ID NO:57)); a knob-bearing IgG1 CH2-CH3 Domain (SEQ ID NO:61); and a C-terminus. Polynucleotides encoding this polypeptide chain may encode the C-terminal lysine residue of SEQ ID NO:61 (i.e., x of SEQ ID NO:61), however, as discussed above, this lysine residue may be post-translationally removed in some expression systems. Accordingly, the invention encompasses such a first polypeptide chain that contains such lysine residue (i.e., SEQ ID NO:61, wherein x is lysine), as well as a first polypeptide chain that lacks such lysine residue (i.e., SEQ ID NO:61, wherein x is absent). The amino acid sequences of such first polypeptide chain (SEQ ID NO:91) is provided below (the sequence of the hmAb-D VL Domain (SEQ ID NO:30) is underlined):

```
DIQMTQSPSF LSASVGDRVT ITCKASQNVD TNVAWYQQKP

GKAPKALIYS ASYRYSGVPS RFSGSGSGTD FTLTISSLQP

EDFAEYFCQQ YNNYPFTFGQ GTKLEIKGGG SGGGGEVQLV

ESGGGLVQPG GSLRLSCAAS GFTFSTYAMN WVRQAPGKGL

EWVGRIRSKY NNYATYYADS VKGRFTISRD DSKNSLYLQM

NSLKTEDTAV YYCVRHGNFG NSYVSWFAYW GQGTLVTVSS

ASTKGEVAAC EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGX
``` wherein X is Lysine (K) or is absent.

The second polypeptide chain of the exemplary B7-H3×CD3 bispecific three chain DART-D3 diabody comprises, in the N-terminal to C-terminal direction: an N-terminus; the VL Domain of CD3 mAb-1 (SEQ ID NO:67); an intervening spacer peptide (Linker 1: GGGSGGGG (SEQ ID NO:32)); the VH Domain of an anti-B7-H3 antibody (hmAb-D VH (SEQ ID NO:31); an intervening spacer peptide (Linker 2: ASTKG (SEQ ID NO:37)); a cysteine-containing Heterodimer-Promoting (K-coil) Domain (KVAACKE-KVAALKE-KVAALKE-KVAALKE (SEQ ID NO:48)); and a C-terminus. The amino acid sequence of such second polypeptide chain (SEQ ID NO:92) is provided below (the sequence of the hmAb-D VH Domain (SEQ ID NO:31) is underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

QLVESGGGLV QPGGSLRLSC AASGFTFSSF GMHWVRQAPG

KGLEWVAYIS SGSGTIYYAD TVKGRFTISR DNAKNSLYLQ

MNSLRAEDTA VYYCARHGYR YEGFDYWGQG TTVTVSSAST

KGKVAACKEK VAALKEKVAA LKEKVAALKE
```

The third polypeptide chain of the exemplary B7-H3×CD3 bispecific three chain DART-D3 diabody comprises, in the N-terminal to C-terminal direction: an N-terminus; a spacer peptide (DKTHTCPPCP (SEQ ID NO:56)); a hole-bearing IgG1 CH2-CH3 Domain (SEQ ID NO:62); and a C-terminus. Polynucleotides encoding this polypeptide chain may encode the C-terminal lysine residue of SEQ ID NO:62 (i.e., X of SEQ ID NO:62), however, as discussed above, this lysine residue may be post-translationally removed in some expression systems. Accordingly, the invention encompasses such a third polypeptide chain that contains such lysine residue (i.e., SEQ ID NO:62, wherein X is lysine), as well as a third polypeptide chain that lacks such lysine residue (i.e., SEQ ID NO:62, wherein X is absent). The amino acid sequence of such third polypeptide chain (SEQ ID NO:93) is provided below:

```
DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK

GQPREPQVYT LPPSREEMTK NQVSLSCAVK GFYPSDIAVE

WESNGQPENN YKTTPPVLDS DGSFFLVSKL TVDKSRWQQG

NVFSCSVMHE ALHNRYTQKS LSLSPGX
``` wherein X is Lysine (K) or is absent.

It will be appreciated in view of the teachings provided herein that different domain orientations, VH Domains, VL Domains, linkers, and/or heterodimer promoting domains, could be utilized to generate alternative B7-H3×CD3 bispecific three chain diabodies. In particular, the VH Domain and VL Domain of hmAb-C(SEQ ID NOs:20-21) may be utilized.

C. B7-H3×CD3×CD8 Trivalent Binding Molecules

Exemplary trivalent "B7-H3×CD3×CD8" binding molecules having one binding site specific for B7-H3 (comprising a parental and/or humanized anti-B7-H3-VL Domain and a corresponding anti-B7-H3-VH Domain, as described above), one binding site specific for CD3 (comprising, for example, the VL Domain of CD3 mAb-1 (SEQ ID NO:67) and the VH Domain of anti-CD3 antibody (e.g., CD3 mAb 1 (D65G) (SEQ ID NO:68)), and one binding site specific for CD8 (comprising, for example, the VH and VL Domains of TRX2 (SEQ ID NOs:75 and 76, respectively). Such trivalent binding molecules may have two polypeptide chains (see, e.g., FIG. 6E, and FIG. 6F), three polypeptide chains (see, e.g., FIG. 6C and FIG. 6D), four polypeptide chains (see, e.g., FIG. 6A and FIG. 6B), or five polypeptide chains (see, e.g., FIG. 5).

X. Methods of Production

The B7-H3-binding molecules of the present invention are most preferably produced through the recombinant expression of nucleic acid molecules that encode such polypeptides, as is well-known in the art.

Polypeptides of the invention may be conveniently prepared using solid phase peptide synthesis (Merrifield, B. (1986) "*Solid Phase Synthesis*," Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids*," Proc. Natl. Acad. Sci. (U.S.A.) 82(15):5131-5135; Ganesan, A. (2006) "*Solid-Phase Synthesis In The Twenty-First Century*," Mini Rev. Med. Chem. 6(1):3-10).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants {e.g., tobacco) or transgenic milk. Suitable methods for expressing antibodies recombinantly in plants or milk have been disclosed (see, for example, Peeters et al. (2001) "*Production Of Antibodies And Antibody Fragments In Plants*," Vaccine 19:2756; Lonberg, N. et al. (1995) "*Human Antibodies From Transgenic Mice*," Int. Rev. Immunol 13:65-93; and Pollock et al. (1999) "*Transgenic Milk As A Method For The Production Of Recombinant Antibodies*," J. Immunol Methods 231:147-157). Suitable methods for making derivatives of antibodies, e.g., humanized, single-chain, etc. are known in the art, and have been described above. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology*," Annu. Rev. Immunol. 12.433-455).

Vectors containing polynucleotides of interest (e.g., polynucleotides encoding the polypeptide chains of the B7-H3-binding molecules of the present invention) can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cell capable of overexpressing heterologous DNAs can be used for the purpose of expressing a polypeptide or protein of interest. Non-limiting examples of suitable mammalian host cells include but are not limited to COS, HeLa, and CHO cells.

The invention includes polypeptides comprising an amino acid sequence of an B7-H3-binding molecule of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available.

The invention includes variants of B7-H3-binding molecules, including functionally equivalent polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues that can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the Variable Domain. Changes in the Variable Domain can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention encompasses fusion proteins comprising one or more of the anti-B7-H3-VL and/or VH of this invention. In one embodiment, a fusion polypeptide is provided that comprises a light chain, a heavy chain or both a light and heavy chain. In another embodiment, the fusion polypeptide contains a heterologous immunoglobulin constant region. In another embodiment, the fusion polypeptide contains a Light Chain Variable Domain and a Heavy Chain Variable Domain of an antibody produced from a publicly-deposited hybridoma. For purposes of this invention, an antibody fusion protein contains one or more polypeptide domains that specifically bind to B7-H3 and another amino acid sequence to which it is not attached in the native molecule, for example, a heterologous sequence or a homologous sequence from another region.

The present invention particularly encompasses B7-H3-binding molecules (e.g., antibodies, diabodies, trivalent binding molecules, etc.) conjugated to a diagnostic or therapeutic moiety. For diagnostic purposes, B7-H3-binding molecules of the invention may be coupled to a detectable substance. Such B7-H3-binding molecules are useful for monitoring and/or prognosing the development or progression of a disease as part of a clinical testing procedure, such as determining the efficacy of a particular therapy. Examples of detectable substances include various enzymes (e.g., horseradish peroxidase, beta-galactosidase, etc.), prosthetic groups (e.g., avidin/biotin), fluorescent materials (e.g., umbelliferone, fluorescein, or phycoerythrin), luminescent materials (e.g., luminol), bioluminescent materials (e.g., luciferase or aequorin), radioactive materials (e.g., carbon-14, manganese-54, strontium-85 or zinc-65), positron emitting metals, and nonradioactive paramagnetic metal ions. The detectable substance may be coupled or conjugated either directly to the B7-H3-binding molecule or indirectly, through an intermediate (e.g., a linker) using techniques known in the art.

For therapeutic purposes, B7-H3-binding molecules of the invention may be conjugated to atherapeutic moiety such as a cytotoxin, (e.g., a cytostatic or cytocidal agent), a therapeutic agent or a radioactive metal ion, e.g., alpha-emitters. A cytotoxin or cytotoxic agent includes any agent that is detrimental to cells such as, for example, *Pseudomonas* exotoxin, Diptheria toxin, a botulinum toxin A through F, ricin abrin, saporin, and cytotoxic fragments of such agents. A therapeutic agent includes any agent having a therapeutic effect to prophylactically or therapeutically treat a disorder. Such therapeutic agents may be may be chemical therapeutic agents, protein or polypeptide therapeutic agents, and include therapeutic agents that possess a desired biological activity and/or modify a given biological response. Examples of therapeutic agents include alkylating agents, angiogenesis inhibitors, anti-mitotic agents, hormone therapy agents, and antibodies useful for the treatment of cell proliferative disorders. The therapeutic moiety may be coupled or conjugated either directly to the B7-H3-binding molecule or indirectly, through an intermediate (e.g., a linker) using techniques known in the art.

XI. Antibody Drug Conjugates

The present invention relates to therapeutic anti-human B7-H3 antibodies (or the B7-H3 binding domains thereof), and particularly to any of the above-described anti-human B7-H3 antibodies or B7-H3 binding domains thereof, that are conjugated to a drug (a "B7-H3-ADC" molecule). Such B7-H3-ADCs enhance the cytotoxicity of anti-human B7-H3 therapy, particularly in the treatment of cancer. As indicated above, the B7-H3-ADC molecules of the present invention comprise the formula:

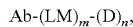

wherein:
Ab is an antibody that binds to B7-H3 that comprises a humanized Variable Heavy Chain (VH) Domain and a humanized Variable Light Chain (VL) Domain, or is a B7-H3-binding fragment thereof, and;
D is a cytotoxic drug moiety;
LM is a bond or a Linker Molecule that covalently links Ab and D;
m is an integer between 0 and n and denotes the number of Linker Molecules of the B7-H3-ADC; and
n is an integer between 1 and 10 and denotes the number of cytotoxic drug moieties covalently linked to the B7-H3-ADC molecule.

In preferred embodiments, the B7-H3-ADC will bind to a tumor cell expressing B7-H3, and will then be internalized into such cell through receptor-mediated endocytosis. Once inside a lysosome, the B7-H3-ADC will preferably be degraded so as to thereby cause the release of the cytotoxic drug moiety inside the cell, resulting in cell death. As will be appreciated, the mechanism of action of cell death can vary based on the class of cytotoxic drug used (e.g., disruption of cytokinesis by tubulin polymerization inhibitors such as maytansines and auristatins, DNA damage by DNA interacting agents such as calcheamicins and duocarmycins), etc. Neighboring cancer cells may also be killed when free drug is released into the tumor environment by the dying cell in a process known as the bystander effect (Panowski, S. et al. (2014) "*Site-Specific Antibody Drug Conjugates For Cancer Therapy*," mAbs 6(1):34-45; Kovtun, Y. V. et al. (2006) "*Antibody-Drug Conjugates Designed To Eradicate Tumors With Homogeneous And Heterogeneous Expression Of The Target Antigen*," Cancer Res. 66:3214-3221).

The B7-H3-ADCs of the present invention may comprise an Fc Domain, which may be a naturally occurring Fc Domain, or may have a sequence that possesses one or more differences from a naturally occurring Fc Domain, and which may be a complete Fc Domain (e.g., a complete IgG Fc Domain) or only a portion of a complete Fc Domain. Such Fc Domains may be of any isotype (e.g., IgG1, IgG2, IgG3, or IgG4). Such Fc Domain may comprise, or may lack, the C-terminal lysine residue of a CH3 Domain. The B7-H3-ADCs of the invention may further comprise a CH1 Domain and/or a Hinge Domain. When present, the CH1 Domain and/or Hinge Domain may be of any isotype (e.g., IgG1, IgG2, IgG3, or IgG4), and will preferably of the same isotype as the desired Fc Domain.

A. Exemplary Linker Molecules of the Invention

The invention thus particularly contemplates such B7-H3-ADCs wherein the Linker Molecule LM is absent (i.e., m=0), and B7-H3-ADCs that possess more than one Linker Molecule LM (i.e., m is an integer from 2 through n, wherein n is an integer from 2 through 10), each of which Linker Molecule LM covalently links a cytotoxic drug moiety D to the Ab of such B7-H3-ADCs.

The invention further provides B7-H3-ADCs whose Ab are covalently linked to more than one Linker Molecule LM, wherein all such Linker Molecules are identical. The cytotoxic drug moieties D that are covalently linked to the Ab of such B7-H3-ADCs may all be identical or may include 2, 3, 4, or more independently different cytotoxic drug moieties D.

The invention further provides such B7-H3-ADCs whose Ab are covalently linked to more than one Linker Molecule LM, wherein all such Linker Molecules are not identical and may independently differ. The cytotoxic drug moieties D that are covalently linked to the Ab of such B7-H3-ADCs may all be identical or may include 2, 3, 4, or more independently different cytotoxic drug moieties D.

Exemplary humanized VH and VL Domains of antibodies that bind to human B7-H3, and exemplary human antibody Constant Domains that may be included in a B7-H3-ADC of the invention are provided above. As stated above, the B7-H3-ADC of the invention additionally comprise at least one cytotoxic drug moiety, which is preferably covalently linked to an atom of a side chain of an amino acid residue of such VH Domain or VL Domain and/or Constant Domain, either directly, or via a Linker Molecule intercalated between the side chain atom and the drug moiety. The Linker Molecule may be a non-peptide molecule, or a molecule that comprises a non-peptide portion and a peptide portion, or it may be a molecule that is composed solely of amino acid residues. The amino acid residues of any such Linker Molecules may contain naturally occurring or non-naturally occurring amino acid residues, including D-versions of naturally occurring amino acid residues, p-acetylphenylalanine, selenocysteine, etc. Optionally, or additionally, particular residues having a desired side chain (e.g., a —CH$_2$—SH side chain, a-CH$_2$—OH side chain, a —CH(CH$_2$)—SH side chain, a —CH$_2$—CH$_2$—S—CH$_3$ side chain; a —CH$_2$—C(O)—NH$_2$ side chain, a —CH$_2$—CH$_2$—C(O)—NH$_2$ side chain, a —CH$_2$—C(O)OH— side chain, a CH$_2$—CH$_2$—C(O)OH— side chain, a —CH$_2$—CH$_2$—CH$_2$—NH$_2$ side chain, a —CH$_2$—CH$_2$—CH$_2$—NH—C(NH$_2$)$_2$ side chain, an imidazole side chain, a benzyl side chain, a phenol side chain, an indole side chain, etc.) may be engineered into a B7-H3-ADC of the invention.

The Linker Molecule may be non-cleavable under physiologic conditions, for example composed of a hydrolytically stable moiety, for example, a thioether linker or a hindered disulfide linker. Hydrolytically stable linkers are substantially stable in water and do not react with water at useful pH values, including but not limited to, under physiological conditions for an extended period of time. In contrast, hydrolytically unstable or degradable linkers are degradable in water or in aqueous solutions, including for example, blood.

Alternatively, the Linker Molecule may be cleavable, or may contain a cleavable portion. Examples of such a cleavable portion includes an acid labile linker (e.g., a 4-(4'-acetylpheonxy)butanoic acid linker which forms a hydrazine bond), a cleavable disulfide linker (that is cleaved in the reducing intracellular environment), and a protease cleavable linker. Acid-labile linkers are designed to be stable at pH levels encountered in the blood, but become unstable and degrade when the low pH environment in lysosomes is encountered. Protease-cleavable linkers are also designed to be stable in blood/plasma, but rapidly release free drug inside lysosomes in cancer cells upon cleavage by lysosomal enzymes (Panowski, S. et al. (2014) "*Site-Specific Antibody Drug Conjugates For Cancer Therapy*," mAbs 6(1):34-45). Alternatively, the Linker Molecule may be an enzyme-cleavable-substrate or contain an enzyme-cleavable-substrate, such as a cleavable peptide, (e.g., a cleavable dipeptide such as a valine-citrulline dipeptide para-aminobenzylalcohol linker (cAC10-mc-vc-PABA) which is selectively cleaved by lysosomal enzymes). Suitable cleavable linkers are known in the art, see, e.g., de Groot, Franciscus M. H., et al. (2002) "*Design, Synthesis, and Biological Evaluation of a Dual Tumor-Specific Motive Containing Integrin-Targeted Plasmin-Cleavable Doxorubicin Prodrug*," Molecular Cancer Therapeutics, 1: 901-911; Dubowchik et al., (2002) "Doxorubicin Immunoconjugates Containing Bivalent, Lysosomally-Cleavable Dipeptide Linkages." Bioorganic & Medicinal Chemistry Letters 12: 1529-1532; U.S. Pat. Nos. 5,547,667; 6,214,345; 7,585,491; 7,754,681; 8,080,250; 8,461,117; and WO 02/083180.

Enzymatically unstable or degradable linkers can be employed. Such linkers are degraded by one or more enzymes. By way of example only, PEG and related polymers can include a degradable Linker Molecule(s) in the polymer backbone or in the linker group between the polymer backbone and one or more of the terminal functional groups of the polymer molecule. Such degradable Linker Molecule(s) include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable Linker Molecules include but are not limited to carbonate linkages; imine linkages resulting from reaction of an amine and an aldehyde; phosphate ester linkages formed by reacting an alcohol with a phosphate group; hydrazone linkages that are a reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

In one embodiment, the Linker Molecule of the present invention may be, or may comprise, a cleavable Linker Molecule, V—(W)$_k$—(X)$_l$-A, as disclosed in PCT Publication WO 02/083180, having the formula:

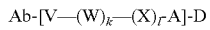

wherein:
V is an optional cleavable moiety,
(W)$_k$—(X)$_l$-A is an elongated, self-eliminating spacer system, that self-eliminates via a 1, (4+2n)-elimination,
W and X are each a 1, (4+2n) electronic cascade spacer, being the same or different,
A is either a spacer group of formula (Y)$_m$, wherein Y is a 1, (4+2n) electronic cascade spacer, or a group of formula U, being a cyclisation elimination spacer,
k, l and m are independently an integer of 0 (included) to 5 (included),
n is an integer of 0 (included) to 10 (included),
with the provisos that:
when A is (Y)$_m$: then k+l+m≥1, and
if k+l+m=1, then n≥1;
when A is U: then k+l≥1.
W, X, and Y are independently selected from compounds having the formula:

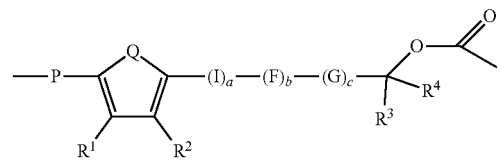

or the formula:

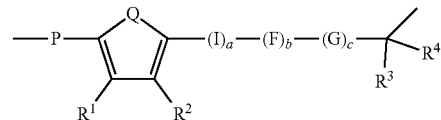

wherein: Q is —R$^5$C═CR$^6$—, S, O, NR$^5$, —R$^5$C═N—, or —N═CR$^5$—
P is NR$^7$, O or S
a, b, and c are independently an integer of 0 (included) to 5 (included);
I, F and G are independently selected from compounds having the formula:

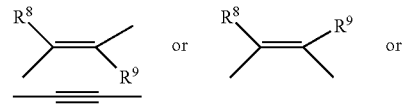

wherein R$^1$, R$^2$, R$^3$, R$^4$, R$^5$, R$^6$, R$^7$, R$^8$, and R$^9$ independently represent H, C$_{1-6}$ alkyl, C$_{3-20}$ heterocyclyl, C$_{5-20}$ aryl, C$_{1-6}$ alkoxy, hydroxy (OH), amino (NH$_2$), mono-substituted amino (NR$_x$H), di-substituted amino (NR$_x^1$R$_x^2$), nitro (NO$_2$), halogen, CF$_3$, CN, CONH$_2$, SO$_2$Me, CONHMe, cyclic C$_{1-5}$ alkylamino, imidazolyl, C$_{1-6}$ alkylpiperazinyl, morpholino, thiol (SH), thioether (SR$_x$), tetrazole, carboxy (COOH), carboxylate (CO- $OR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are independently selected from a $C_{1-6}$ alkyl group, a $C_{3-20}$ heterocyclyl group or a $C_{5-20}$ aryl group, two or more of the substituents $R^1$, $R^2$, $R^3$, $R^4$, $R^5$, $R^6$, $R^7$, $R^8$, or $R^9$ optionally being connected to one another to form one or more aliphatic or aromatic cyclic structures;

U is selected from compounds having the formula:

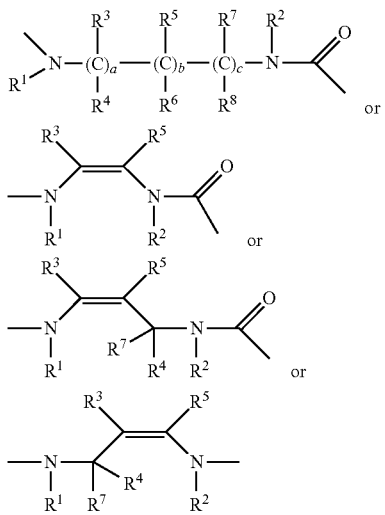

wherein:
a, b and c are independently selected to be an integer of 0 or 1; provided that a+b+c=2 or 3;

$R^1$ and/or $R^2$ independently represent H, C1-6 alkyl, said alkyl being optionally substituted with one or more of the following groups: hydroxy (OH), ether ($OR_x$), amino ($NH_2$), mono-substituted amino ($NR_xH$), disubstituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are selected from a $C_{1-6}$ alkyl group, a $C_{3-20}$ heterocyclyl group or a $C_{5-20}$ aryl group; and $R^3$, $R^4$, $R^5$, $R^6$, $R^7$ and $R^8$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), disubstituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are selected from a $C_{1-6}$ alkyl group, a $C_{3-20}$ heterocyclyl group or a $C_{5-20}$ aryl group, and two or more of the substituents $R^1$, $R^2$, $R^3$, $R^4$, $R^5$, $R^6$, $R^7$, or $R^8$ are optionally connected to one another to form one or more aliphatic or aromatic cyclic structures.

Exemplary molecules include:
p-aminobenzyloxy carbonyl-p-aminobenzyloxy carbonyl;
p-aminobenzyloxy carbonyl-p-aminobenzyloxy carbonyl-p-aminobenzyloxycarbonyl;
p-aminocinnamyloxy carbonyl;
p-aminocinnamyloxycarbonyl-p-aminobenzyloxycarbonyl;
p-amino-benzyloxycarbonyl-p-aminocinnamyloxycarbonyl;
p-aminocinnamyloxycarbonyl-p-aminocinnamyloxycarbonyl;
p-aminophenylpentadienyloxycarbonyl;
p-aminophenylpentadienyloxycarbonyl-p-aminocinnamyloxycarbonyl;
p-aminophenylpentadienyloxycarbonyl-p-aminobenzyloxycarbonyl;
p-aminophenylpentadienyloxycarbonyl-p-aminophenylpentadienyloxycarbonyl;
p-aminobenzyloxycarbonyl(methylamino)ethyl(methylamino)carbonyl;
p-aminocinnamyloxycarbonyl(methylamino)ethyl(methylamino)carbonyl;
p-aminobenzyloxycarbonyl-p-aminobenzyloxycarbonyl (methylamino)ethyl(methylamino)carbonyl;
p-aminocinnamyloxycarbonyl-p-aminobenzyloxycarbonyl (methylamino)ethyl(methylamino)carbonyl;
p-aminobenzyloxycarbonyl-p-aminocinnamyloxycarbonyl (methylamino)ethyl(methylamino)-carbonyl;
p-aminocinnamyloxycarbonyl-p-aminocinnamyloxycarbonyl(methylamino)ethyl(methylamino)carbonyl;
p-aminobenzyloxycarbonyl-p-aminobenzyl;
p-aminobenzyloxycarbonyl-p-aminobenzyloxycarbonyl-p-aminobenzyl;
p-aminocinnamyl;
p-aminocinnamyloxycarbonyl-p-aminobenzyl;
p-aminobenzyloxycarbonyl-p-aminocinnamyl;
p-amino-cinnamyloxy carbonyl-p-aminocinnamyl;
p-aminophenylpentadienyl;
p-aminophenylpentadienyloxycarbonyl-p-aminocinnamyl;
p-aminophenylpentadienyloxycarbonyl-p-aminobenzyl; and
p-aminophenylpentadienyloxycarbonyl-p-aminophenylpentadienyl.

In some embodiments, a B7-H3-ADC of the invention comprises two, three, four, five, six, seven, eight, nine or ten cytotoxic drug moieties, which may be the same, or may independently be the same or different from another cytotoxic drug moiety of the B7-H3-ADC. In one embodiment, each such cytotoxic drug moiety is conjugated to the Ab of the B7-H3-ADC of the invention via a separate Linker Molecule. Alternatively, more than one cytotoxic drug moiety may be attached to the Ab of the B7-H3-ADC of the invention via the same Linker Molecule.

Cytotoxic drug moieties may be conjugated to the Ab of the B7-H3-ADC of the invention by means known in the art (see, e.g., Yao, H. et al. (2016) "*Methods to Design and Synthesize Antibody-Drug Conjugates (ADC),*" Intl. J. Molec. Sci. 17(194):1-16); Behrens, C. R. et al. (2014) "*Methods For Site-Specific Drug Conjugation To Antibodies,*" mAbs 6(1):46-53; Bouchard, H. et al. (2014) "*Antibody-Drug Conjugates-A New Wave Of Cancer Drugs,*" Bioorganic & Medicinal Chem. Lett 24:5357-5363). The thiol group of a cysteine, the amino side group of lysine, glutamine or arginine, or the carboxyl group of glutamate or aspartate can be employed to conjugate the Linker Molecule-cytotoxic drug moiety (LM-D) to the Ab of the B7-H3-ADC of the invention. Native antibodies contain numerous lysine conjugation sites, and thus are capable of linking multiple conjugated molecules per antibody. Indeed, peptide mapping has determined that conjugation occurs on both the heavy and light chain at approximately 20 different lysine residues (40 lysines per mAb). Therefore, greater than one million different ADC species can be generated. Cysteine conjugation occurs after reduction of one to four inter-chain disulfide bonds, and the conjugation is thus limited in native VL and VH Domains to the eight exposed sulfhydryl groups. However, if desired, additional reactive (e.g., lysine, cysteine, selenocysteine, etc.) residues may be engineered into an antibody (e.g., within a VL Domain and/or a VH Domain and/or a Constant Domain). For example, one or more native amino acid residues may be substituted with a cysteine residue. An unnatural amino acid (e.g. p-acetylphenylalanine) may be genetically incorporated into an antibody using an amber stop codon suppressor tRNA/aaRS pair. (See, e.g., Behrens CR, and Liu B. (2014) "Methods For Site-Specific Drug Conjugation To Antibodies," mAbs 6(1):46-53. doi:10.4161/mabs.26632; Panowksi, S., et al. (2014) "Site-Specific Antibody Drug Conjugates For Cancer Therapy," mAbs, 6(1), 34-45, doi:10.4161/mabs.27022; and WO 2008/070593). Alternatively, or additionally, enzymes (e.g., a glycotransferase) may be used to conjugate the Linker Molecule-cytotoxic drug moiety (LM-D) to the Ab of the B7-H3-ADC of the invention. The glycotransferase platform attaches a sugar moiety to a glycosylation site on an antibody (for example, position N297 of the Fc Domain of a human IgG antibody), which can then serve as the Linker Molecule of the present invention and conjugate the cytotoxic drug moiety (D) to the Ab of the B7-H3-ADC of the invention. Alternatively, a transglutaminase may be used to catalyze the formation of a covalent bond between a free amine group and a glutamine side chain.

Preferred for such purpose is the commercially available transglutaminase from Streptoverticillium mobaraense (mTG) (Pastemack, R. et al. (1998) "Bacterial Pro-Transglutaminase From Streptoverticillium mobaraense—Purification, Characterisation And Sequence Of The Zymogen," Eur. J. Biochem. 257(3):570-576; Yokoyama, K. et al. (2004) "Properties And Applications Of Microbial Transglutaminase," Appl. Microbiol. Biotechnol. 64:447-454). This enzyme does not recognize any of the natural occurring glutamine residues in the Fc Domain of glycosylated antibodies, but does recognize the tetrapeptide LLQL (SEQ ID NO:94) (Jeger, S. et al. (2010) "Site-Specific And Stoichiometric Modification Of Antibodies By Bacterial Transglutaminase," Angew Chem. Int. Ed. Engl. 49:9995-9997) that may be engineered into a VL Domain and/or a VH Domain and/or a Constant Domain. Such considerations are reviewed by Panowski, S. et al. (2014) "Site-Specific Antibody Drug Conjugates For Cancer Therapy," mAbs 6(1): 34-45.

B. Exemplary Cytotoxic Drug Moieties of the Invention

In some embodiments, the cytotoxic drug moiety of the B7-H3-ADC of the invention comprises a cytotoxin, a radioisotope, an immunomodulator, a cytokine, a lymphokine, a chemokine, a growth factor, a tumor necrosis factor, a hormone, a hormone antagonist, an enzyme, an oligonucleotide, a DNA molecule, an RNA molecule, an siRNA molecule, an RNAi molecule, a microRNA molecule, a photoactive therapeutic agent, an anti-angiogenic agent, a pro-apoptotic agent, a peptide, a lipid, a carbohy drate, a chelating agent, or a combination thereof.

1. Tubulysin Cytotoxic Drug Moieties

The B7-H3-ADC of the invention may comprise a tubulysin cytotoxic drug moiety:

| Tubulysin Derivative | R1 | R2 |
| --- | --- | --- |
| Tubulysin A | $CH_2CH(CH_3)_2$ | OH |
| Tubulysin B | $CH(CH_3)_2$ | OH |
| Tubulysin C | $CH_2CH_3$ | OH |
| Tubulysin D | $CH_2CH(CH_3)_2$ | H |

Tubulysins are members of a class of natural products isolated from myxobacterial species (Sasse et al. (2000) "Tubulysins, New Cytostatic Peptides From Myxobacteria Acting On Microtubuli. Production, Isolation, Physico-Chemical And Biological Properties," J. Antibiot. 53:879-885). As cytoskeleton interacting agents, tubulysins are mitotic poisons that inhibit tubulin polymerization and lead to cell cycle arrest and apoptosis (Steinmetz et al. (2004) "Isolation, Crystal And Solution Structure Determination, And Biosynthesis Of Tubulysins—Powerful Inhibitors Of Tubulin Polymerization From Myxobacteria," Chem. Int. Ed. 43:4888-4892; Khalil et al. (2006) "Mechanism Of Action Of Tubulysin, An Antimitotic Peptide From Myxobacteria," ChemBioChem. 7:678-683; Kaur et al. (2006) "Biological Evaluation Of Tubulysin A: A Potential Anticancer And Antiangiogenic Natural Product," Biochem. J. 396: 235-242). Tubulysins are extremely potent cytotoxic molecules, exceeding the cell growth inhibition of any clinically relevant traditional chemotherapeutic, e.g., epothilones, paclitaxel, and vinblastine. Furthermore, they are potent against multidrug resistant cell lines (Domling, A. et al. (2005) "Myxobacterial Epothilones And Tubulysins As Promising Anticancer Agents," Mol. Diversity 9:141-147). These compounds show high cytotoxicity tested against a panel of cancer cell lines with $IC_{50}$ values in the low picomolar range; thus, they are of interest as anticancer therapeutics. See, e.g., WO 2012/019123, WO 2015/157594. Tubulysin conjugates are disclosed, e.g., in U.S. Pat. No. 7,776,814. In some embodiments, the tubulysin molecule or derivative thereof is a prodrug.

2. Auristatin Cytotoxic Drug Moieties

The B7-H3-ADC of the invention may alternatively or additionally comprise an auristatin cytotoxic drug moiety (e.g., MMAE (N-methylvaline-valine-dolaisoleuine-dolaproine-norephedrine) and MMAF (N-methylvaline-valine-dolaisoleuine-dolaproine-phenylalanine). Dolastatins were originally discovered as constituents of the sea hare Dolabella auricularia and have been modified to generate derivatives also known as auristatins (e.g., monomethyl auristatin E and F). Dolastatins and auristatins interact with the Vinca alkaloid binding site on α-tubulin and block its polymerization. They have been shown to interfere with microtubule dynamics, GTP hydrolysis, and nuclear and cellular division (Woyke et al., Antimicrob. Agents and Chemother. 45:3580-3584 (2001)) and have anticancer activity (U.S. Pat. Nos. 5,663,149, 6,884,869, 7,964,566). The auristatin drug moiety can be attached to the antibody through the N (amino) terminus or the C (carboxyl) terminus of the peptidic drug moiety (See, e.g., WO 2002/088172). In some embodiments, the auristatine or dolastatine molecule, variant, or derivative thereof is a prodrug. MMAE may be conjugated to a protein via modification of native cysteine side chain thiols (Senter, P. D. et al. (2012) "*The Discovery And Development Of Brentuximab Vedotin For Use In Relapsed Hodgkin Lymphoma And Systemic Anaplastic Large Cell Lymphoma*," Nat. Biotechnol. 30:631-637; van de Donk, N. W. et al. (2012) "*Brentuximab vedotin*," MAbs 4:458-465). This method involves reduction of one or more solvent-exposed disulfide bonds of cysteine residues with a reducing agent (e.g., dithiothreitol (DTT) or tris(2-carboxyethyl)phosphine (TCEP)) followed by modification of the resulting thiols with a maleimide-containing drug (see, Behrens, C. R. et al. (2014) "*Methods For Site-Specific Drug Conjugation To Antibodies*," mAbs 6(1):46-53).

Scheme 1

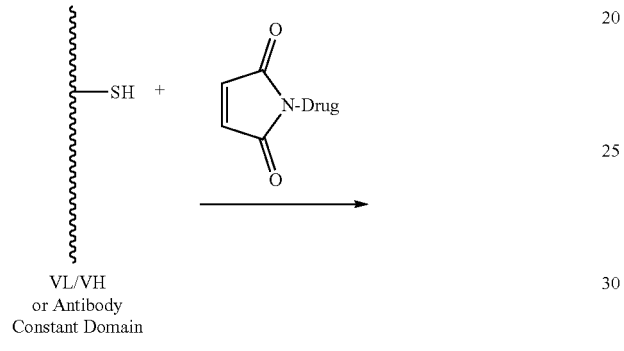

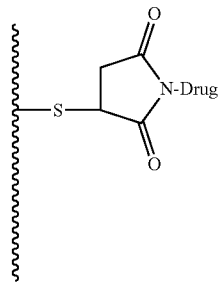

An exemplary cytotoxic drug that may be conjugated in this manner incorporates a cathepsin B protease cleavage site25 (VC: valine, citrulline) and a self-immolative linker (PAB: para-aminobenzyloxycarbonyl) between the maleimide group (MC: maleimidocaproyl) and the cytotoxic drug (MMAE) (Doronina, S. O. et al. (2003) "*Development Of Potent Monoclonal Antibody Auristatin Conjugates For Cancer Therapy*," Nat. Biotechnol. 21:778-784).

Scheme 2: Synthesis of MC-VC-PAB-MMAE

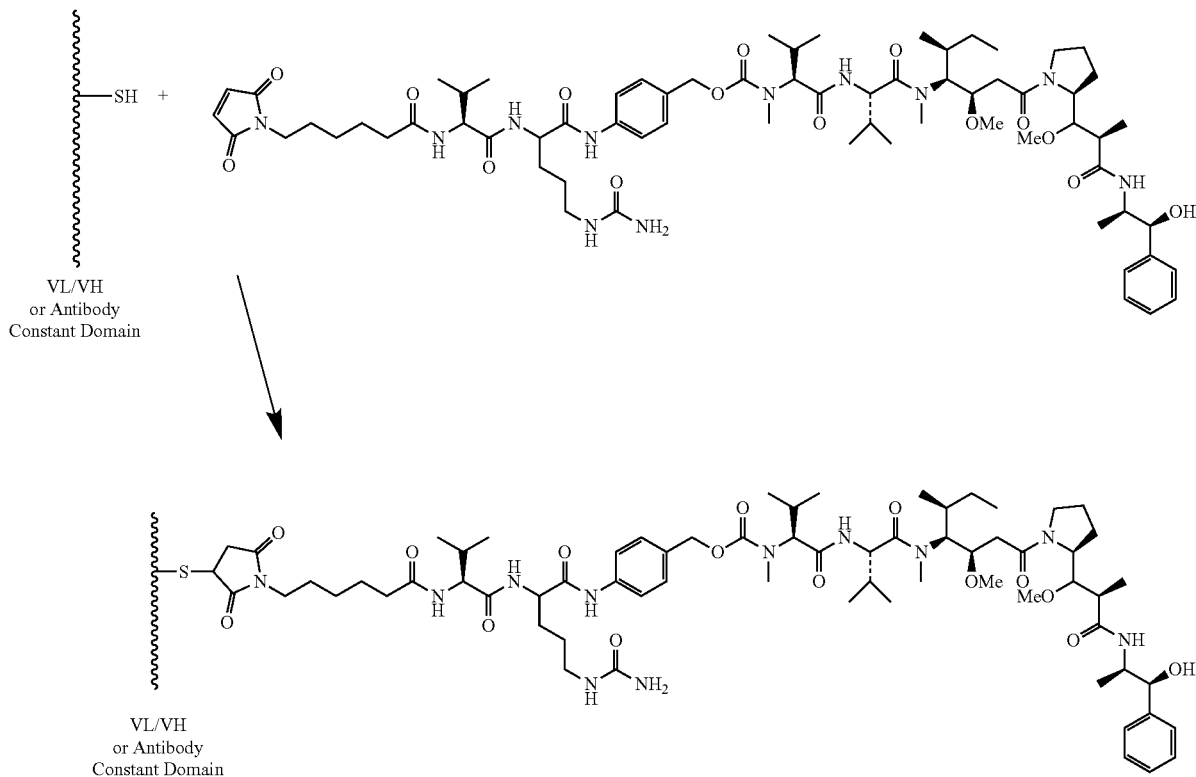

Alternatively, an auristatin cytotoxic drug moiety may be AcLys-VC-PAB-MMAD (acetyllysinevalinecitrulline-p-aminobenzyloxycarbonyl-monomethyldolastatin), which may be conjugated to an NH₂ side chain group of a glutamine residue of a VL Domain and/or a VH Domain and/or a Constant Domain of the Ab portion of the B7-H3-ADC of the invention using the enzyme microbial transglutaminase to catalyze the site-specific reaction between the side chain of the acetylated lysine residue and the glutamine side chains:

Scheme 3

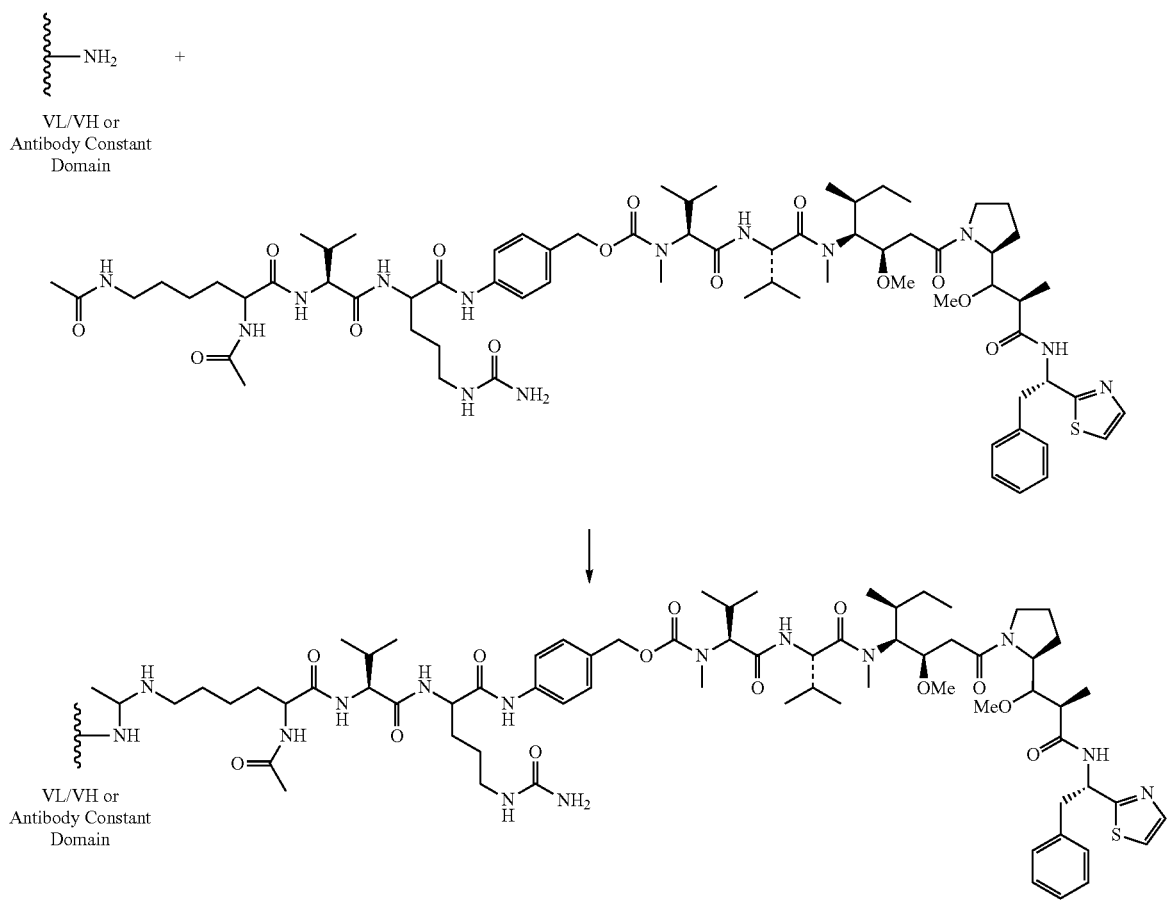

Alternatively, p-acetylphenylalanine may be incorporated into a VL Domain and/or a VH Domain and/or a Constant Domain of the Ab portion of the B7-H3-ADC of the invention and then employed to conjugate auristatin F-oxyamine to such Domain via oxime ligation.

Scheme 4

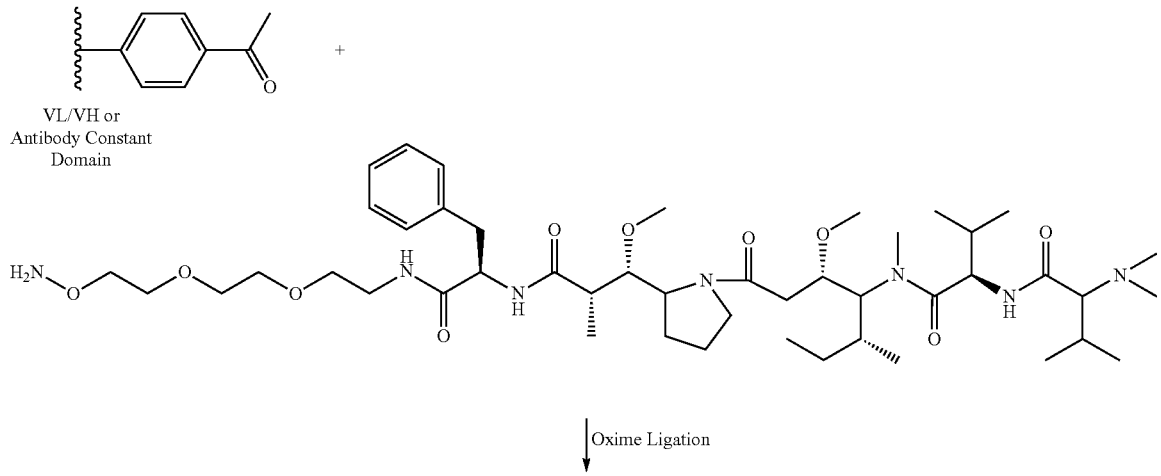

Oxime Ligation

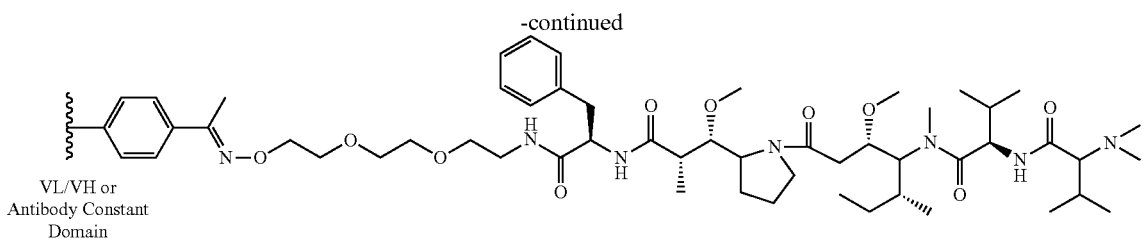

3. Maytansinoid Cytotoxic Drug Moieties

The B7-H3-ADC of the invention may alternatively or additionally comprise a maytansinoid cytotoxic drug moiety e.g., an ansamycin antibiotic characterized by a 19-member ansamacrolide structure attached to a chlorinated benzene ring chromophore. Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230 and 4,248,870. Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines. Immunoconjugates containing maytansinoids, methods of making same, and their therapeutic use are disclosed, for example, in U.S. Pat. Nos. 5,208,020 and 5,416,064 and European Patent EP 0425235B1; Liu, C. et al. (1996) "*Eradication Of Large Colon Tumor Xenografts By Targeted Delivery Of Maytansinoids*," Proc. Natl. Acad. Sci. (U.S.A.) 93:8618-8623 (described immunoconjugates comprising a maytansinoid designated DM1) and Chari, R. V. et al. (1992) "*Immunoconjugates Containing Novel Maytansinoids: Promising Anticancer Drugs*," Cancer Research 52:127-131.

Maytansine, DM1 and DM4 are exemplary maytansinoid cytotoxic drug moieties:

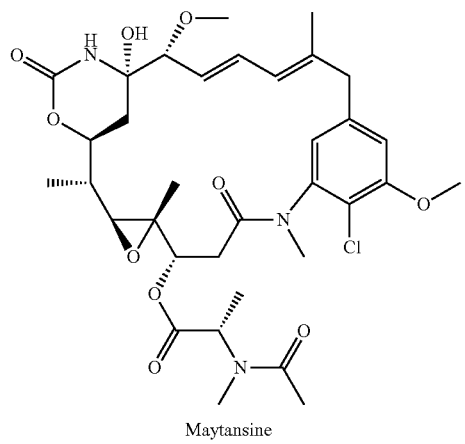

Maytansine

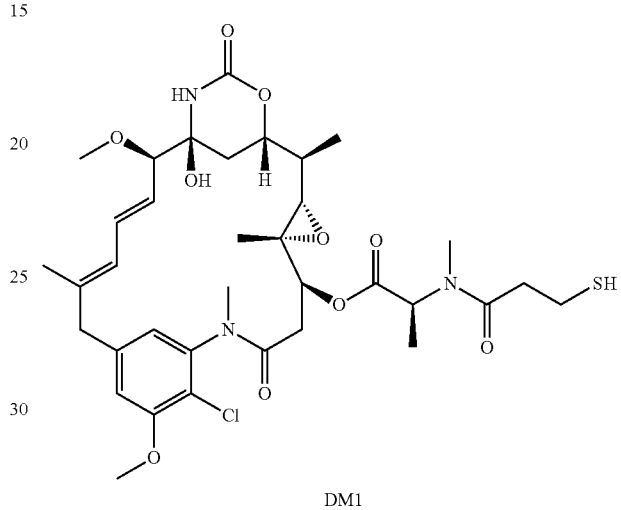

DM1

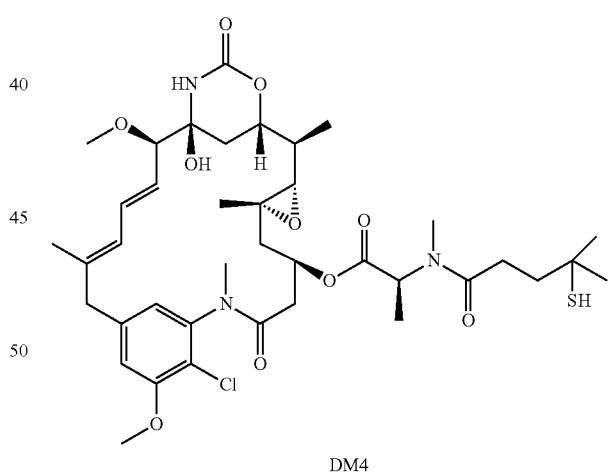

DM4

Maytansine may be conjugated to the Ab portion of the B7-H3-ADC of the invention by reaction with a lysine or glutamine side chain. DM1 and DM4 may be conjugated to a COOH side chain of a glutamate or aspartate residue of a VL Domain and/or a VH Domain and/or a Constant Domain of the Ab portion of the B7-H3-ADC of the invention (see, Behrens, C. R. et al. (2014) "*Methods For Site-Specific Drug Conjugation To Antibodies*," mAbs 6(1):46-53; Bouchard, H. et al. (2014) "*Antibody-Drug Conjugates—A New Wave Of Cancer Drugs*," Bioorganic & Medicinal Chem. Lett 24:5357-5363):

Scheme 5

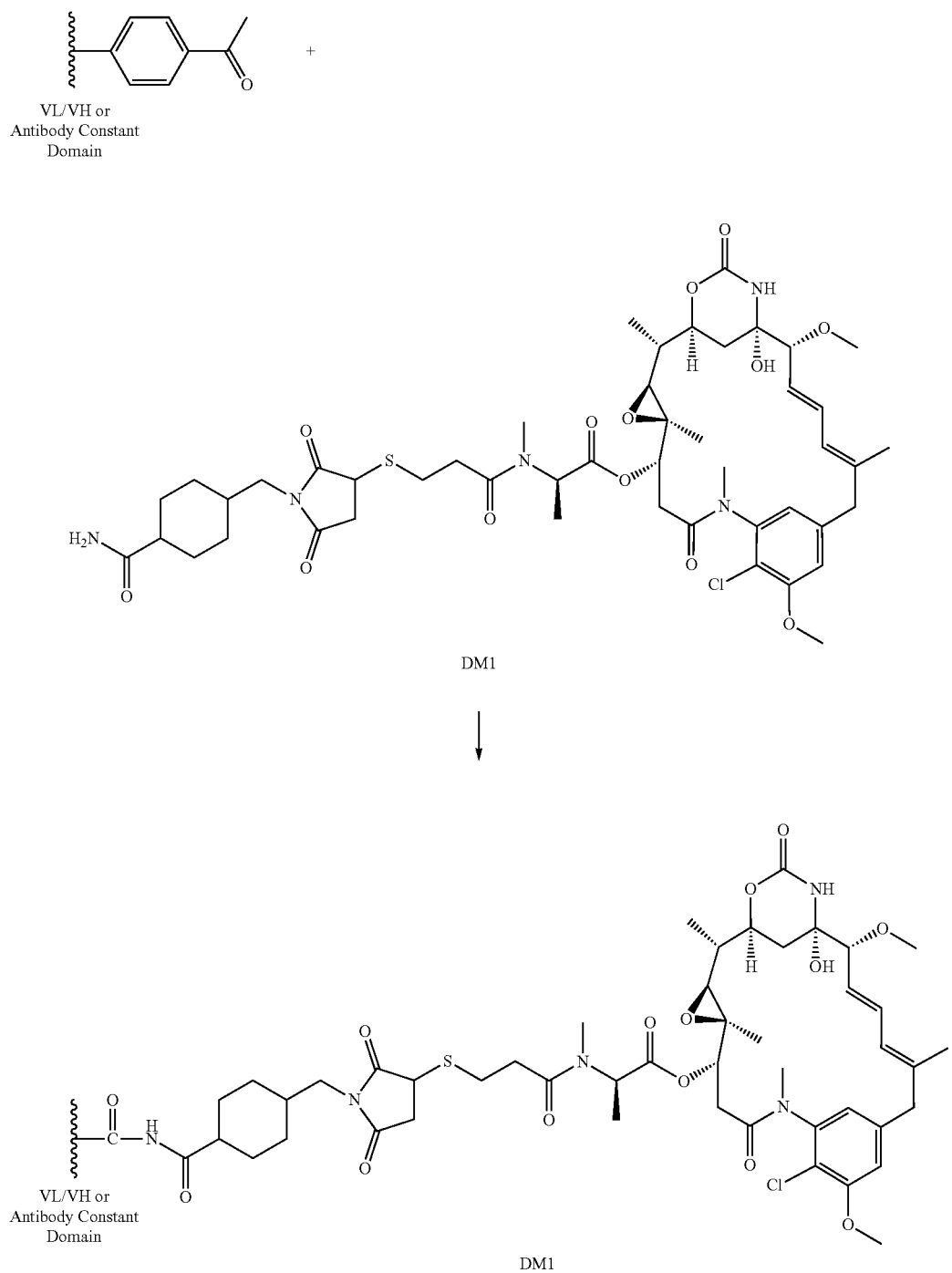

Trastuzumab emtansine (ado-trastuzumab emtansine, T-DM1, trade name KADCYLA®) is an antibody-drug conjugate consisting of the monoclonal antibody trastuzumab (HERCEPTIN®) conjugated to the maytansinoid mertansine (DM1). See, e.g., LoRusso et al. (2011) "*Trastuzumab Emtansine: A Unique Antibody-Drug Conjugate In Development For Human Epidermal Growth Factor Receptor 2-Positive Cancer*," Clin. Cancer Res. 20:6437-6447. An engineered thio-Trastuzumab-DM1 ADC has also been described in Junutual et al. (2010) "*Engineered Thio-Trastuzumab-DM1 Conjugate With An Improved Therapeutic Index To Target Human Epidermal Growth Factor Receptor 2- Positive Breast Cancer*," Clin, Cancer Res. 16:4769-4778. In some embodiments, the maytansinoid molecule, variant, or derivative thereof is a prodrug.

4. Calicheamicin Cytotoxic Drug Moieties

The B7-H3-ADC of the invention may alternatively or additionally comprise a calicheanicin cytotoxic drug moiety:

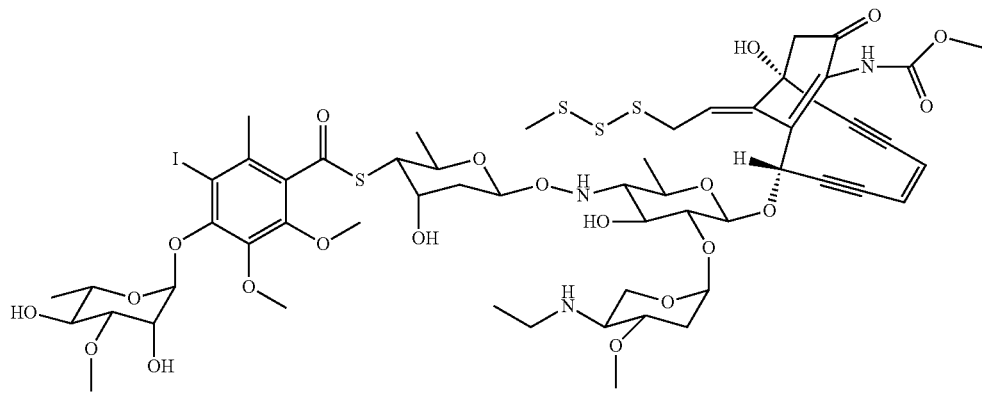 [SMILES: CCNC1COC(OC2C(O[C@H]3C#C/C=C\C#CC[C@]4(O)CC(=O)C(NC(=O)OC)=C3/C4=C\CSSSC)OC(C)C(NOC3CC(O)C(SC(=O)c4c(C)c(I)c(OC5OC(C)C(O)C(OC)C5O)c(OC)c4OC)C(C)O3)C2O)CC1OC]

The described calicheamicin-based antibody conjugates are disulfide versions of the trisulfide parent compound. Two coupling strategies with N-acetyl-c-calicheamicin dimethyl hydrazide (CalichDMH) have been reported to-date: (i) hydrazide; and (ii) amide coupling (Bouchard, H. et al. (2014) "*Antibody-Drug Conjugates-A New Wave Of Cancer Drugs,*" Bioorganic & Medicinal Chem. Lett 24:5357-5363).

The calicheamicin family of enediyne antitumor antibiotics are capable of producing double-stranded DNA breaks at sub-picomolar concentrations. The calicheamicins are a class of enediyne antibiotics derived from the bacterium *Micromonospora echinospora*, with calicheamicin γ1 being the most notable. Other calicheamicins are β1Br, γ1Br, α2I, α3I, β1I, γ1I, and Δ1I (see Lee, M. D. et al. (1989) "*Calicheamicins, A Novel Family Of Antitumor Antibiotics. 3. Isolation, Purification And Characterization Of Calicheamicins Beta 1Br, Gamma 1Br, Alpha 2I, Alpha 3I, Beta 1I, Gamma 1I And Delta 1I,*" J. Antibiotics 42(7):1070-1087). For the preparation of conjugates of the calicheamicin family, see U.S. Pat. Nos. 5,712,374, 5,714,586, 5,739,116, 5,767,285, 5,770,701, 5,770,710, 5,773,001 and 5,877,296. Structural analogues of calicheamicin which can be used include, but are not limited to, γ1I, α2I, α3I, N-acetyl-γ1I, PSAG and θ11 (Hinman et al. (1993) "*Preparation And Characterization Of Monoclonal Antibody Conjugates Of The Calicheamicins: A Novel And Potent Family Of Antitumor Antibiotics,*" Cancer Research 53:3336-3342 (1993), Lode et al. (1998) "*Targeted Therapy With A Novel Enediyene Antibiotic Calicheamicin Theta(I)I Effectively Suppresses Growth And Dissemination Of Liver Metastases In A Syngeneic Model Of Murine Neuroblastoma,*" Cancer Research 58:2925-2928 (1998). In some embodiments, the calicheamicin molecule, variant, or derivative thereof is a prodrug.

5. Pyrrolobenzodiazepine Cytotoxic Drug Moieties

The B7-H3-ADC of the invention may comprise alternatively or additionally a pyrrolobenzodiazepine drug moiety (e.g., natural pyrrolobenzodiazepine and SJG-136, a derivative thereof):

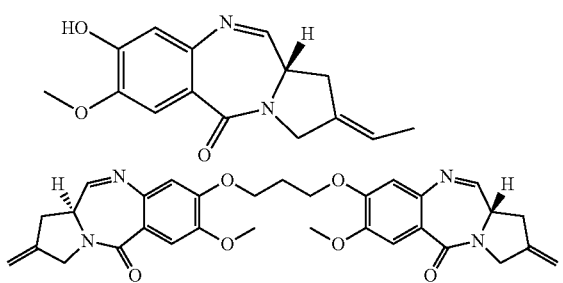

A preferred pyrrolobenzodiazepine drug moiety is vadastuximab talirine (SGN-CD33A; Seattle Genetics):

Scheme 6

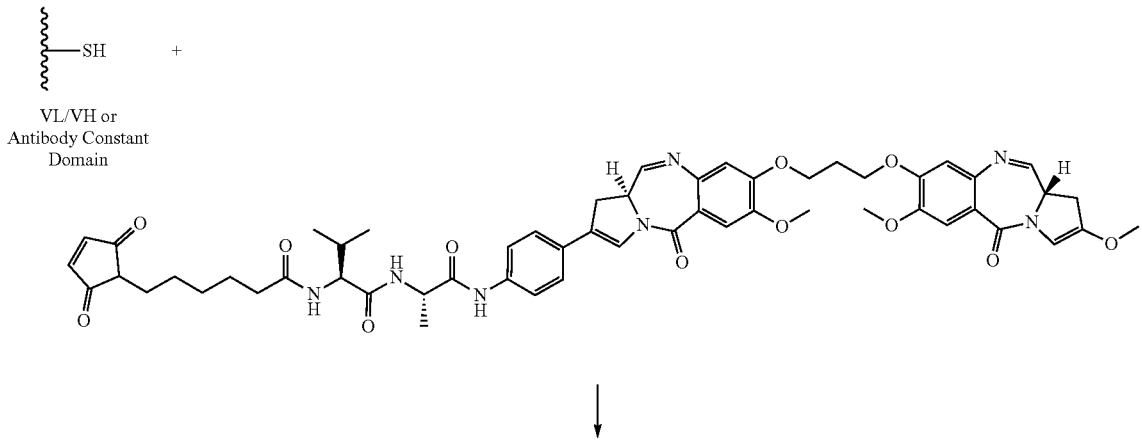

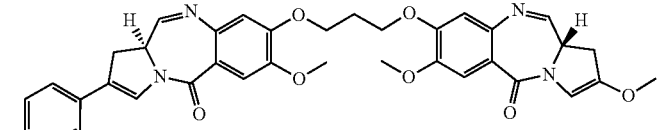
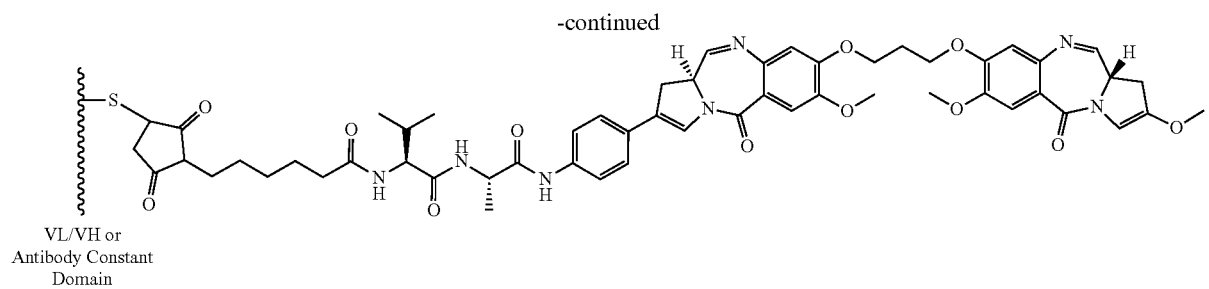

VL/VH or
Antibody Constant
Domain

Pyrrolobenzodiazepines (PBD) are a class of natural products with antibiotic or anti-tumor activity. They are naturally produced by actinomycetes. They are DNA alkylating compound and some are sequence-selective. A number of PBDs and derivatives thereof are known in the art, for example, PBD dimers (e.g., SJG-136 or SG2000), C2-unsaturated PBD dimers, pyrrolobenzodiazepine dimers bearing C2 aryl substitutions (e.g., SG2285), PBD dimer prodrug that is activated by hydrolysis (e.g., SG2285), and polypyrrole-PBD (e.g., SG2274). PBDs are further described WO 2000/012507, WO 2007/039752, WO 2005/110423, WO 2005/085251, and WO 2005/040170, and WO 2014/057119. In some embodiments, the PBD molecule, variant, or derivative thereof is a prodrug.

6. Duocarmycin Cytotoxic Drug Moieties

The B7-H3-ADC of the invention may alternatively or additionally comprise a duocarmycin drug moiety. Duocarmycins are members of a series of related natural products first isolated from *Streptomyces* bacteria and they are potent antitumor antibiotics (see Dokter, W. et al. (2014) "*Preclinical Profile of the HER2-Targeting ADC SYD983/SYD985: Introduction of a New Duocarmycin-Based Linker-Drug Platform*," Mol. Cancer Ther. 13(11):2618-2629; Boger, D. L. et al. (1991). "*Duocarmycins—A New Class Of Sequence Selective DNA Minor Groove Alkylating Agents*," Chemtracts: Organic Chemistry 4 (5): 329-349 (1991); Tercel et al. (2013) "*The Cytotoxicity Of Duocarmycin Analogues Is Mediated Through Alkylation Of DNA, Not Aldehyde Dehydrogenase 1: A Comment*," Chem. Int. Ed. Engl. 52(21):5442-5446; Boger, D. L. et al. (1995) "*CC-1065 And The Duocarmycins: Unraveling The Keys To A New Class OfNaturally Derived DNA Alkylating Agents*," Proc. Natl. Acad. Sci. (U.S.A.) 92(9):3642-3649; Cacciari, B. et al. (2000) "*CC-1065 And The Duocarmycins: Recent Developments*," Expert Opinion on Therapeutic Patents 10(12):1853-1871).

Natural duocarmycins include duocarmycin A, duocarmycin B1, duocarmycin B2, duocarmycin C1, duocarmycin C2, duocarmycin D, duocarmycin SA, and CC-1065 (PCT Publication No. WO 2010/062171; Martin, D. G. et al. (1980) "*Structure Of CC-1065 (NSC 298223), A New Antitumor Antibiotic*," J. Antibiotics 33:902-903; Boger, D. L. et al. (1995) "*CC-1065 And The Duocarmycins: Unraveling The Keys To A New Class Of Naturally Derived DNA Alkylating Agents*," Proc. Natl. Acad. Sci. (U.S.A.) 92:3642-3649).

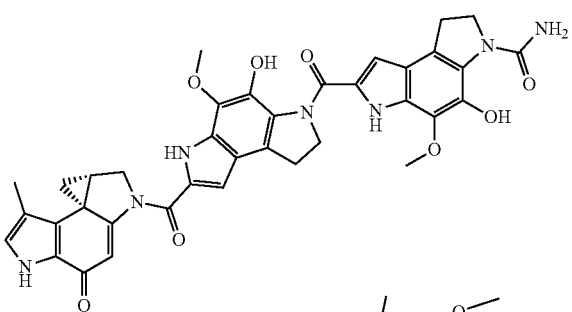

CC-1065

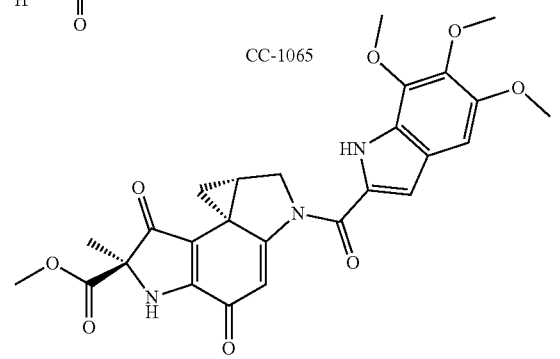

Duocarmycin A

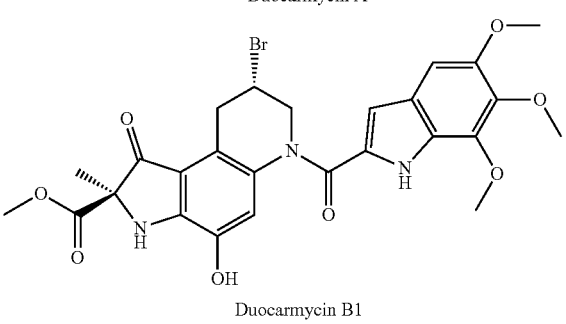

Duocarmycin B1

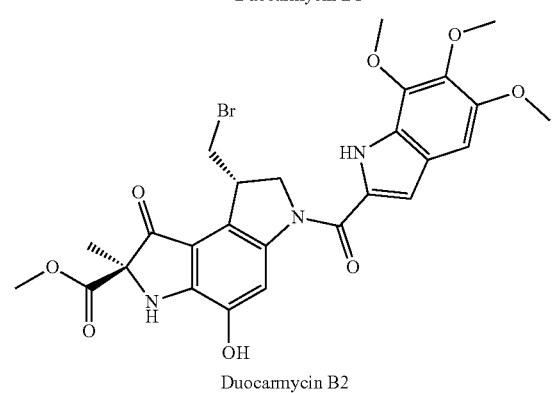

Duocarmycin B2

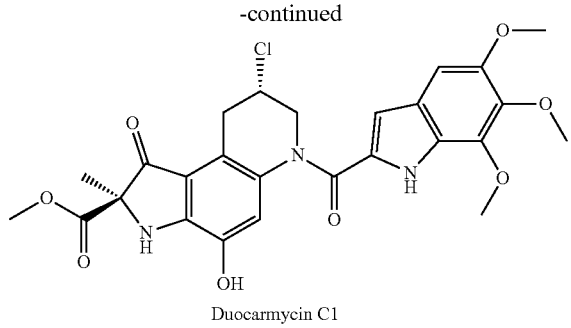

Duocarmycin C1

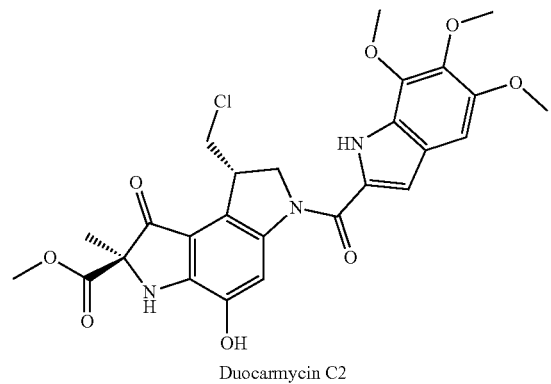

Duocarmycin C2

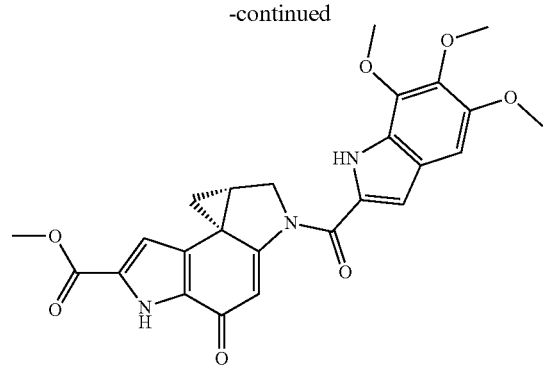

Duocarmycin SA

Suitable synthetic duocarmycin analogs include adozelesin, bizelesin, carzelesin (U-80244) and spiro-duocarmycin (DUBA) (Dokter, W. et al. (2014) "*Preclinical Profile of the HER2-Targeting ADC SYD983 SYD985: Introduction of a New Duocarmycin-Based Linker-Drug Platform,*" Mol. Cancer Ther. 13(11):2618-2629; Elgersma, R. C. et al. (2014) "*Design, Synthesis, and Evaluation of Linker-Duocarmycin Payloads: Toward Selection of HER2-Targeting Antibody-Drug Conjugate SYD985,*" Mol. Pharmaceut. 12:1813-1835):

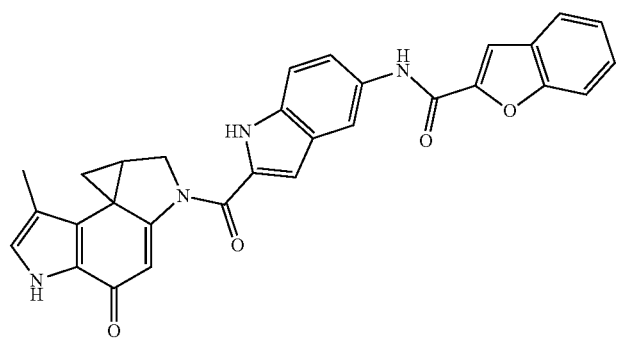

Adozelesin

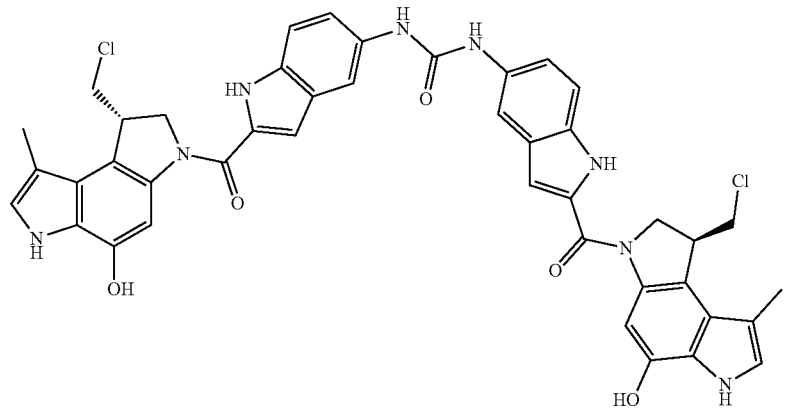

Bizelesin

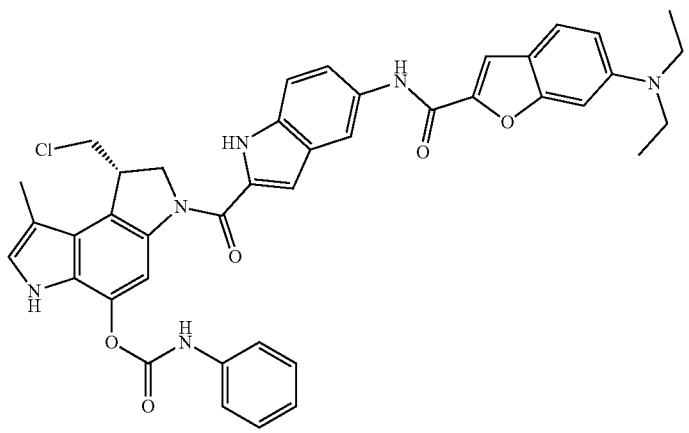
Carzelesin
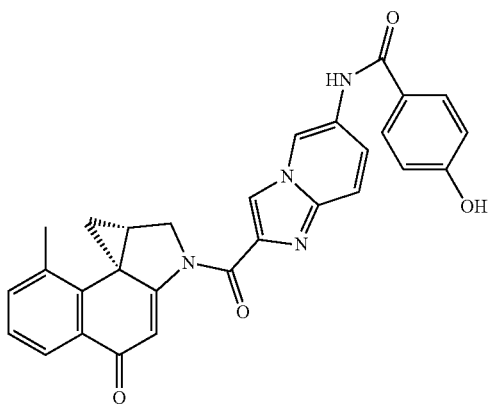
DUBA (spiro-duocarmycin)
Additional synthetic duocarmycin analogs include those disclosed in PCT Publication No. WO 2010/062171, and particularly such analogs that have the formula:
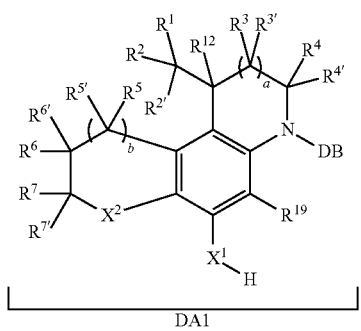
(I)
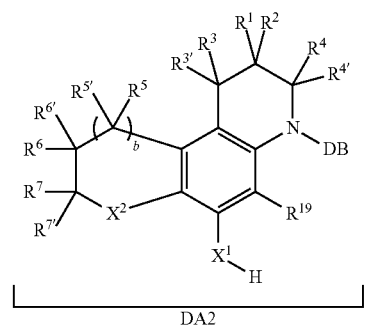
(II)
or a pharmaceutically acceptable salt, hydrate, or solvate thereof, wherein DB is a DNA-binding moiety and is selected from the group consisting of:

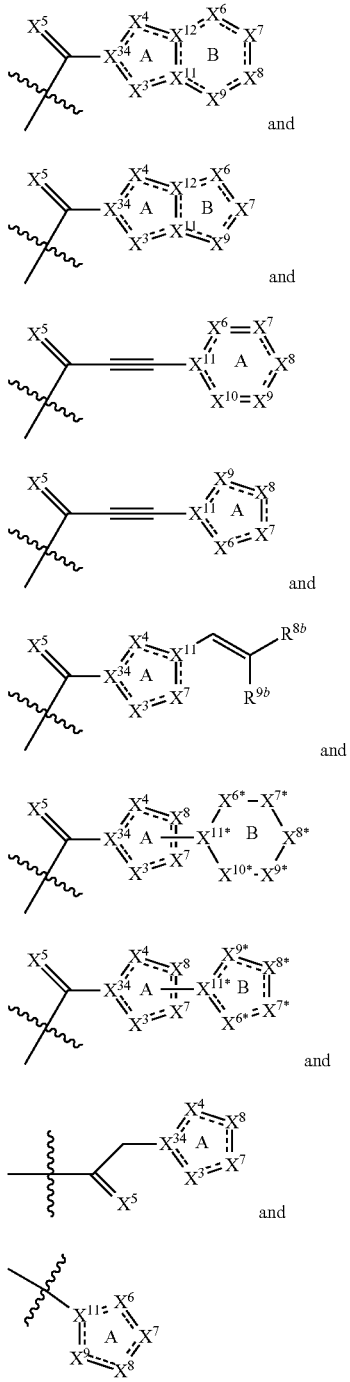

wherein:
R is a leaving group;
$R^2$, $R^{2'}$, $R^3$, $R^{3'}$, $R^4$, $R^{4'}$, $R^{12}$, and $R^{19}$ are independently selected from H, OH, SH, $NH_2$, $N_3$, $NO_2$, NO, $CF_3$, CN, $C(O)NH_2$, C(O)H, C(O)OH, halogen, $R^a$, $SR^a$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^a$, $NHR^a$, $N(R^a)R^b$, $^+N(R^a)(R^b)R^c$, $P(O)(OR^a)(OR^b)$, $OP(O)(OR^a)(OR^b)$, $SiR^aR^bR^c$, $C(O)R^a$, $C(O)OR^a$, $C(O)N(R^a)R^b$, $OC(O)R^a$, $OC(O)OR^a$, $OC(O)N(R^a)R^b$, $N(R^a)C(O)R^b$, $N(R^a)C(O)OR^b$, and $N(R^a)C(O)N(R^b)R^c$, wherein $R^a$, $R^b$, and $R^c$ are independently selected from H and optionally substituted $C_{1-3}$ alkyl or $C_{1-3}$ heteroalkyl, or $R^3+R^{3'}$ and/or $R^4+R^{4'}$ are independently selected from =O, =S, =$NOR^{18}$, =$C(R^{18})R^{18'}$, and =$NR^{18}$, $R^{18}$ and $R^{18'}$ being independently selected from H and optionally substituted $C_{1-3}$ alkyl, two or more of $R^2$, $R^{2'}$, $R^3$, $R^{3'}$, $R^4$, $R^{4'}$ and $R^{12}$ optionally being joined by one or more bonds to form one or more optionally substituted carbocycles and/or heterocycles;

$X^2$ is selected from O, $C(R^{14})(R^{14'})$, and $NR^{14}$, wherein $R^{14}$ and $R^{14'}$ have the same meaning as defined for $R^7$ and are independently selected, or $R^{14'}$ and $R^7$ are absent resulting in a double bond between the atoms designated to bear $R^7$ and $R^{14}$;

$R^5$, $R^{5'}$, $R^6$, $R^{6'}$, $R^7$, and $R^{7'}$ are independently selected from H, OH, SH, $NH_2$, $N_3$, $NO_2$, NO, $CF_3$, CN, $C(O)NH_2$, C(O)H, C(O)OH, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, $N(R^e)C(O)N(R^f)R^g$, and a water-soluble group, wherein
$R^e$, $R^f$, and $R^g$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, one or more of the optional substituents in $R^e$, $R^f$, and/or $R^g$ optionally being a water-soluble group, two or more of $R^e$, $R^f$, and $R^g$ optionally being joined by one or more bonds to form one or more optionally substituted carbocycles and/or heterocycles, or $R^5+R^{5'}$ and/or $R^6+R^{6'}$ and/or $R^7+R^{7'}$ are independently selected from O, =S, =$NOR^{e3}$, =$C(R^{e3})R^{e4}$, and =$NR^{e3}$, $R^{e3}$ and $R^{e4}$ being independently selected from H and optionally substituted $C_{1-3}$ alkyl, or $R^{5'}+R^6$ and/or $R^{6'}+R^{7'}$ and/or $R^{7'}+R^{14'}$ are absent, resulting in a double bond between the atoms designated to bear $R^{5'}+R^{6'}$ and/or $R^{6'}+R^{7'}$ and/or $R^{7'}+R^{14'}$ respectively, two or more of $R^5$, $R^{5'}$, $R^6$, $R^{6'}$, $R^7$, $R^{7'}$, $R^{14}$ and $R^{14'}$ optionally being joined by one or more bonds to form one or more optionally substituted carbocycles and/or heterocycles;

$X^1$ is selected from O, S, and NR, wherein R is selected from H and optionally substituted $C_{1-8}$ alkyl or $C_{1-8}$ heteroalkyl and not joined with any other substituent;

$X^3$ is selected from O, S, $C(R^{15})R^{15}$, —$C(R^{15})(R^{15'})$—C$(R^{5''})(R^{15'''})$—, —$N(R^{15})$—$N(R^{15'})$—, —$C(R^{15})(R^{15'})$—N$(R^{15''})$—, —$N(R^{15'})$—$C(R^{15})(R^{15'})$—, —$C(R^{15})(R^{15'})$—O—, —O—$C(R^{15})(R^{15'})$—, —$C(R^{15})(R^{15'})$—S—, —S—C$(R^{15})(R^{15'})$—, —$C(R^{15})$=$C(R^{15'})$—, =$C(R^{15})$—$C(R^{15'})$=, —N=$C(R^{15'})$—, =N—C$(R^{15'})$=, —$C(R^{15})$=N—, =$C(R^{15})$—N=, —N=N—, =N—N=, $CR^{15}$, N, $NR^{15}$, or in DB1 and DB2-X3- represents —$X^{3a}$ and $X^{3b}$—, wherein $X^{3a}$ is connected to $X^{34}$, a double bond is present between $X^{34}$ and $X^4$, and $X^{3b}$ is connected to $X^{11}$, wherein $X^{3a}$ is independently selected from H and optionally substituted $(CH_2CH_2O)_{ee}CH_2CH_2X^{13}R^{e1}$, $C_{1-8}$ alkyl, or $C_{1-8}$ heteroalkyl and not joined with any other substituent;

$X^4$ is selected from O, S, $C(R^{16})R^{16'}$, $NR^{16}$, N, and $CR^{16}$;
$X^5$ is selected from O, S, $C(R^{17})R^{17'}$, $NOR^{17}$, and $NR^{17}$, wherein $R^{17}$ and $R^{17'}$ are independently selected from H and optionally substituted $C_{1-8}$ alkyl or $C_{1-8}$ heteroalkyl and not joined with any other substituent;
$X^6$ is selected from $CR^{11}$, $CR^{11}(R^{11'})$, N, $NR^{11}$, O, and S;
$X^7$ is selected from $CR^8$, $CR^8(R^{8'})$, N, $NR^8$, O, and S;
$X^8$ is selected from $CR^9$, $CR^9(R^{9'})$, N, $NR^9$, O, and S;
$X^9$ is selected from $CR^{10}$, $CR^{10}(R^{10'})$, N, $NR^{10}$, O, and S;
$X^{10}$ is selected from $CR^{20}$, $CR^{20}(R^{20'})$, N, $NR^{20}$, O, and S;
$X^{11}$ is selected from C, $CR^{21}$, and N, or $X^{11}$—$X^{3b}$ is selected from $CR^{21}$, $CR^{21}(R^{21'})$, N, $NR^{21}$, O, and S;
$X^{12}$ is selected from C, $CR^{22}$, and N;

$X^{6*}, X^{7*}, X^{8*}, X^{9*}, X^{10*}$, and $X^{11*}$ have the same meaning as defined for $X^6, X^7, X^8, X^9, X^{10}$, and $X^{11}$, respectively, and are independently selected;

$X^{34}$ is selected from C, $CR^{23}$, and N;

the ring B atom of $X^{11*}$ in DB6 and DB7 is connected to a ring atom of ring A such that ring A and ring B in DB6 and DB7 are directly connected via a single bond;

a dashed double bond means that the indicated bond may be a single bond or a non-cumulated, optionally delocalized, double bond;

$R^8, R^{8'}, R^9, R^{9'}, R^{10}, R^{10'}, R^{11}, R^{11'}, R^{15}, R^{15'}, R^{15''}, R^{15'''}, R^{16}, R^{16'}, R^{20}, R^{20'}, R^{21}, R^{21'}, R^{22}$, and $R^{23}$ are each independently selected from H, OH, SH, $NH_2$, $N_3$, $NO_2$, NO, $CF_3$, CN, $C(O)NH_2$, C(O)H, C(O)OH, halogen, $R^h$, $SR^h$, $S(O)R^h$, $S(O)_2R^h$, $S(O)OR^h$, $S(O)_2OR^h$, $OS(O)R^h$, $OS(O)_2R^h$, $OS(O)OR^h$, $OS(O)_2OR^h$, $OR^h$, $NHR^h$, $N(R^h)R^i$, $\pm N(R^h)(R^i)R^j$, $P(O)(OR^h)(OR^i)$, $OP(O)(OR^h)(OR^i)$, $SiR^hR^iR^j$, $C(O)R^h$, $C(O)OR^h$, $C(O)N(R^h)R^i$, $OC(O)R^h$, $OC(O)OR^h$, $OC(O)N(R^h)R^i$, $N(R^h)C(O)R^i$, $N(R^h)C(O)OR^i$, $N(R^h)C(O)N(R^i)R^j$, and a water-soluble group, wherein $R^h$, $R^i$, and $R^j$ are independently selected from H and optionally substituted $(CH_2CH_2O)_{ee}CH_2CH_2X^3R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, one or more of the optional substituents in $R^h$, $R^i$, and/or $R^j$ optionally being a water-soluble group, two or more of $R^h$, $R^i$, and $R^j$ optionally being joined by one or more bonds to form one or more optionally substituted carbocycles and/or heterocycles, or $R^8+R^{8'}$ and/or $R^9+R^{9'}$ and/or $R^{10}+R^{10'}$ and/or $R^{11}+R^{11'}$ and/or $R^{15}+R^{15'}$ and/or $R^{15''}+R^{15'''}$ and/or $R^{16}+R^{16'}$ and/or $R^{20}+R^{20'}$ and/or $R^{21}+R^{21'}$ are independently selected from =O, =S, =$NOR^{h1}$, =$C(R^{h1})R^{h2}$, and =$NR^{h1}$, $R^{h1}$ and $R^{h2}$ being independently selected from H and optionally substituted $C_{1-3}$ alkyl, two or more of $R^8, R^{8'}, R^9, R^{9'}, R^{10}, R^{10'}, R^{11}, R^{11'}, R^{15}, R^{15'}, R^{15''}, R^{15'''}, R^{16}, R^{20}, R^{20'}, R^{21}, R^{21'}, R^{22}$, and $R^{23}$ optionally being joined by one or more bonds to form one or more optionally substituted carbocycles and/or heterocycles;

$R^{8b}$ and $R^{9b}$ are independently selected and have the same meaning as $R^8$, except that they may not be joined with any other substituent;

one of $R^4$ and $R^{4'}$ and one of $R^{16}$ and $R^{16'}$ may optionally be joined by one or more bonds to form one or more optionally substituted carbocycles and/or heterocycles;

one of $R^4$ and $R^{4'}$ and one of $R^{16}$ and $R^{16'}$ may optionally be joined by one of $R^2$, $R^{2'}$, $R^3$, and $R^{3'}$ and one of $R^5$ and $R^{5'}$ may optionally be joined by one or more bonds to form one or more optionally substituted carbocycles and/or heterocycles;

a and b are independently selected from 0 and 1;

the DB moiety does not comprise a DAI, DA2, DAI', or DA2' moiety;

ring B in DB1 is a heterocycle;

if $X^3$ in DB1 represents —$X^{3a}$ and $X^{3b}$— and ring B is aromatic, then two vicinal substituents on said ring B are joined to form an optionally substituted carbocycle or heterocycle fused to said ring B;

if $X^3$ in DB2 represents —$X^{3a}$ and $X^{3b}$— and ring B is aromatic, then two vicinal substituents on said ring B are joined to form an optionally substituted heterocycle fused to said ring B, an optionally substituted non-aromatic carbocycle fused to said ring B, or a substituted aromatic carbocycle which is fused to said ring B and to which at least one substituent is attached that contains a hydroxy group, a primary amino group, or a secondary amino group, the primary or secondary amine not being a ring atom in an aromatic ring system nor being part of an amide;

if ring A in DB2 is a 6-membered aromatic ring, then substituents on ring B are not joined to form a ring fused to ring B;

two vicinal substituents on ring A in DB8 are joined to form an optionally substituted carbocycle or heterocycle fused to said ring A to form a bicyclic moiety to which no further rings are fused; and ring A in DB9 together with any rings fused to said ring A contains at least two ring heteroatoms.

The above-described Linker Molecules can be conjugated to a cysteine thiol group using thiol-maleimide chemistry, as shown above. In some embodiments, the cytotoxic duocarmycin drug moiety is a prodrug. For example, the prodrug, vc-seco-DUBA can be conjugated to a self-elimination moiety linked to maleimide linker moiety via a cleavable peptide moiety:

Scheme 7

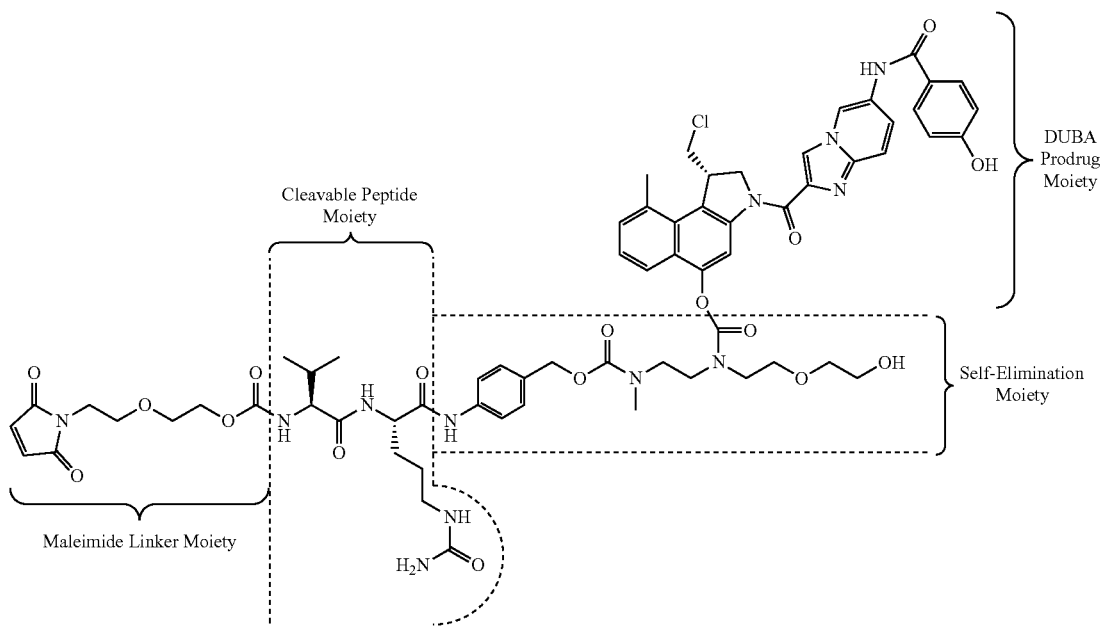

The maleimide linker moiety of the molecule can be conjugated to a thiol group of a cysteine residue of a VL Domain and/or a VH Domain and/or a Constant Domain of the Ab portion of the B7-H3-ADC of the invention. Subsequent proteolytic cleavage of the cleavable peptide moiety is followed by the spontaneous elimination of the self-elimination moiety, leading to the release of seco-DUBA, which spontaneously rearranges to form the active drug, DUBA:

Scheme 8

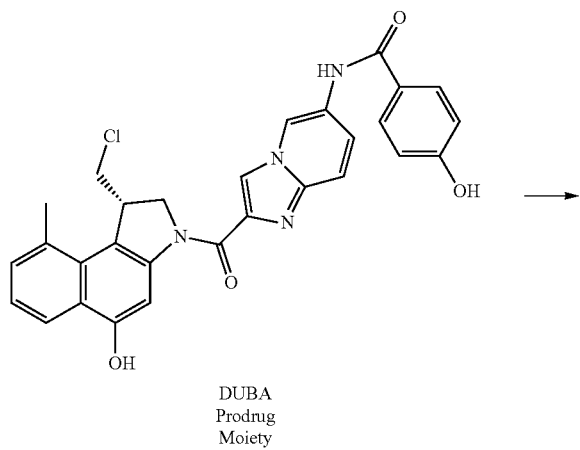

DUBA
Prodrug
Moiety

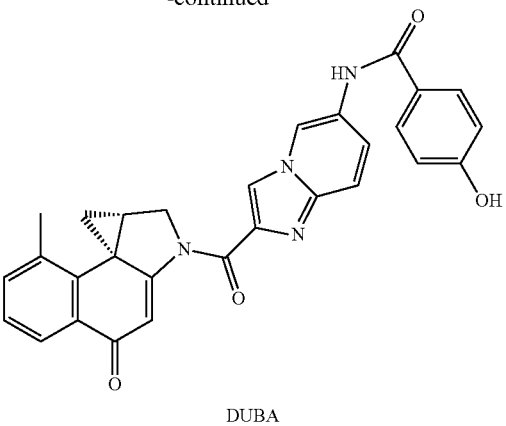

DUBA (see, Dokter, W. et al. (2014) "*Preclinical Profile of the HER2-Targeting ADC SYD983 SYD985: Introduction of a New Duocarmycin-Based Linker-Drug Platform*," Mol. Cancer Ther. 13(11):2618-2629).

In a preferred method for the production of B7-H3-duocarmycin drug moiety conjugates, the method of by Elgersma, R. C. et al. (2014) "*Design, Synthesis, and Evaluation of Linker-Duocarmycin Payloads: Toward Selection of HER2-Targeting Antibody-Drug Conjugate SYD985*," Mol. Pharmaceut. 12:1813-1835 or that of WO 2011/133039 will be employed. Thus, a thiol-containing group of the VL or VH chain of an anti-B7-H3 antibody or antibody fragment is conjugated to a seco-DUBA or other prodrug through a Maleimide Linker Moiety-Cleavable Peptide Moiety-Self-Elimination Moiety (Scheme 9A):

Scheme 9A

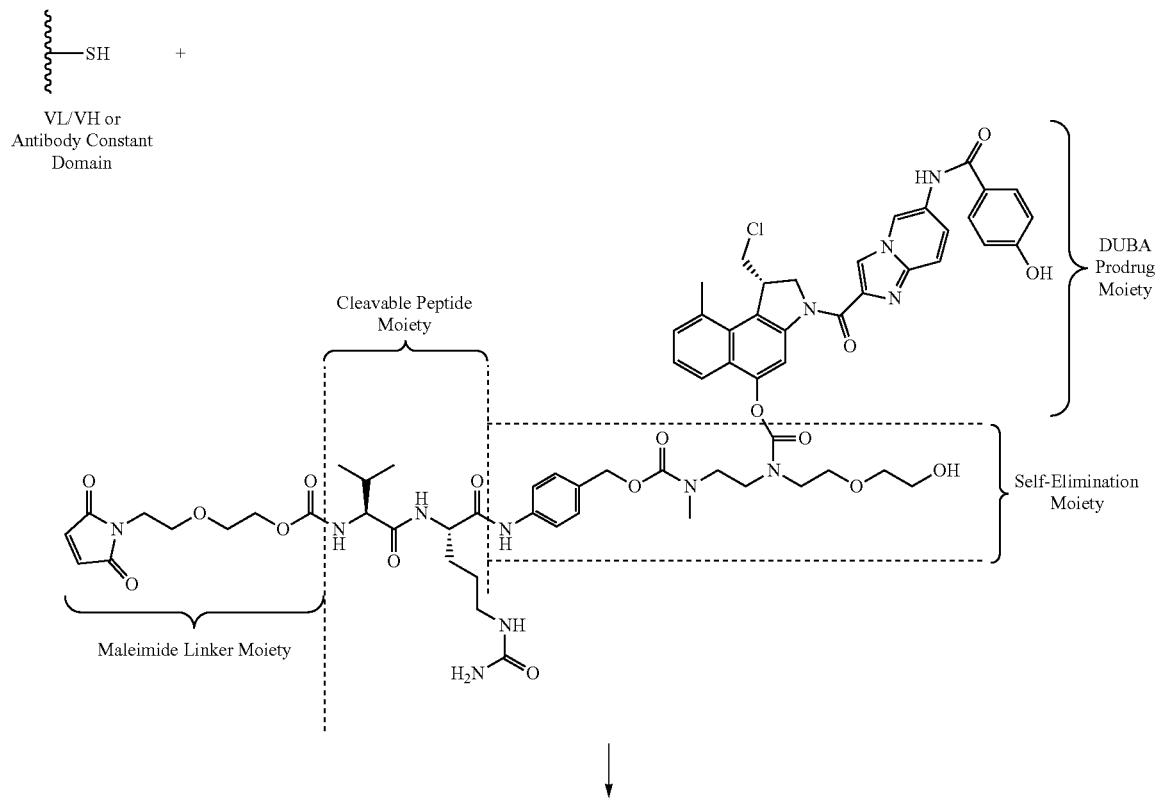

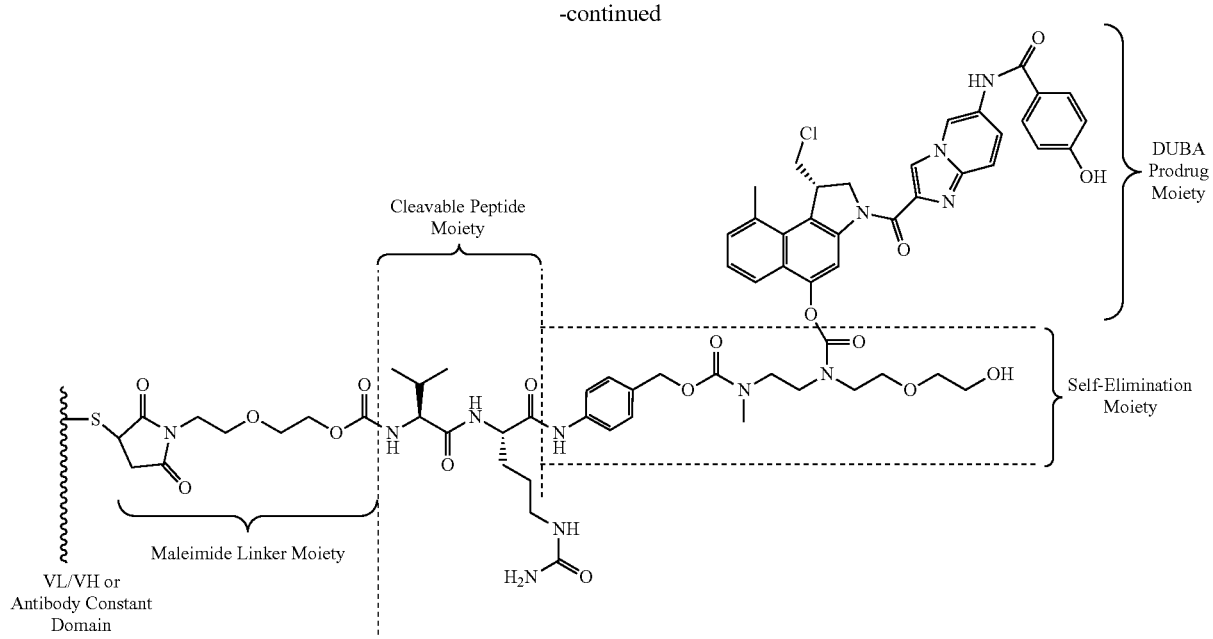
Although the invention is illustrated with regard to a DUBA prodrug, other prodrugs, e.g., CC-1065, may be alternatively employed, as shown in Scheme 9B:
Scheme 9B
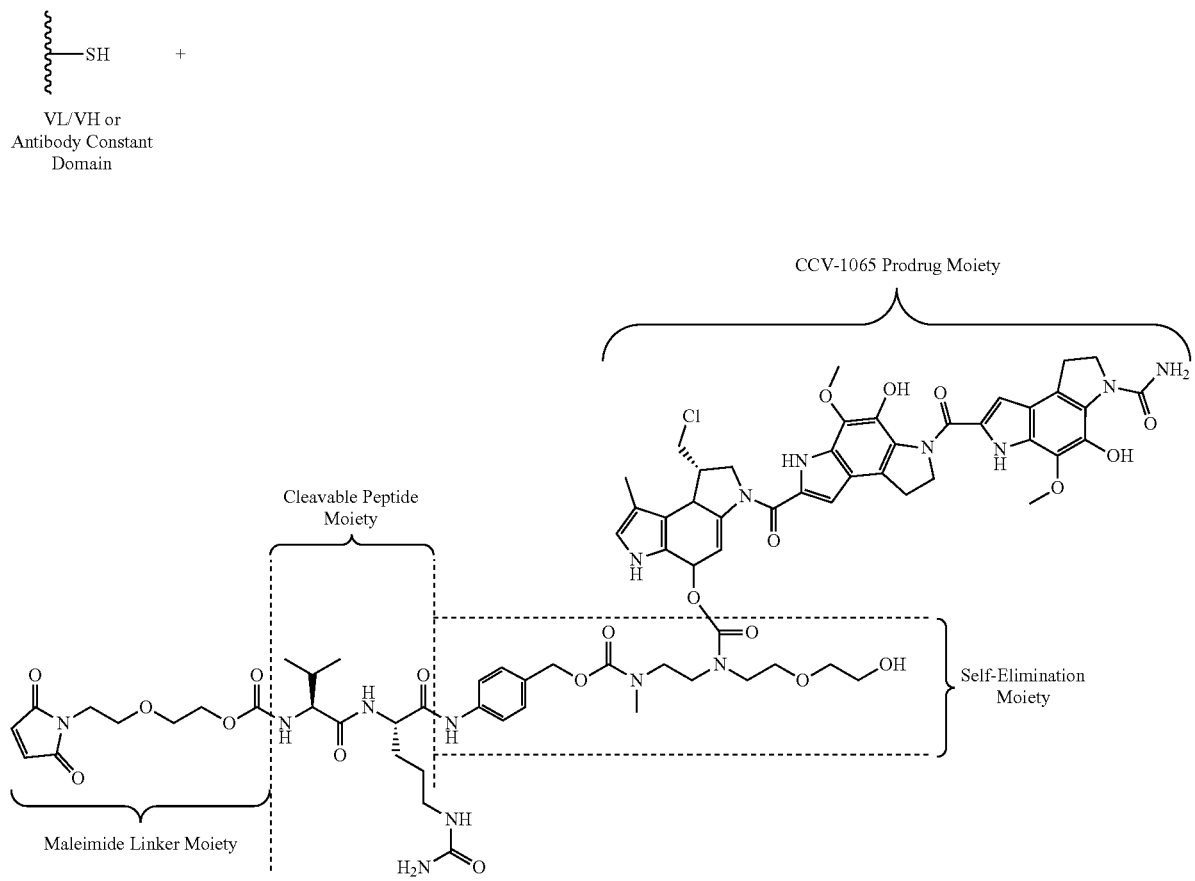

-continued

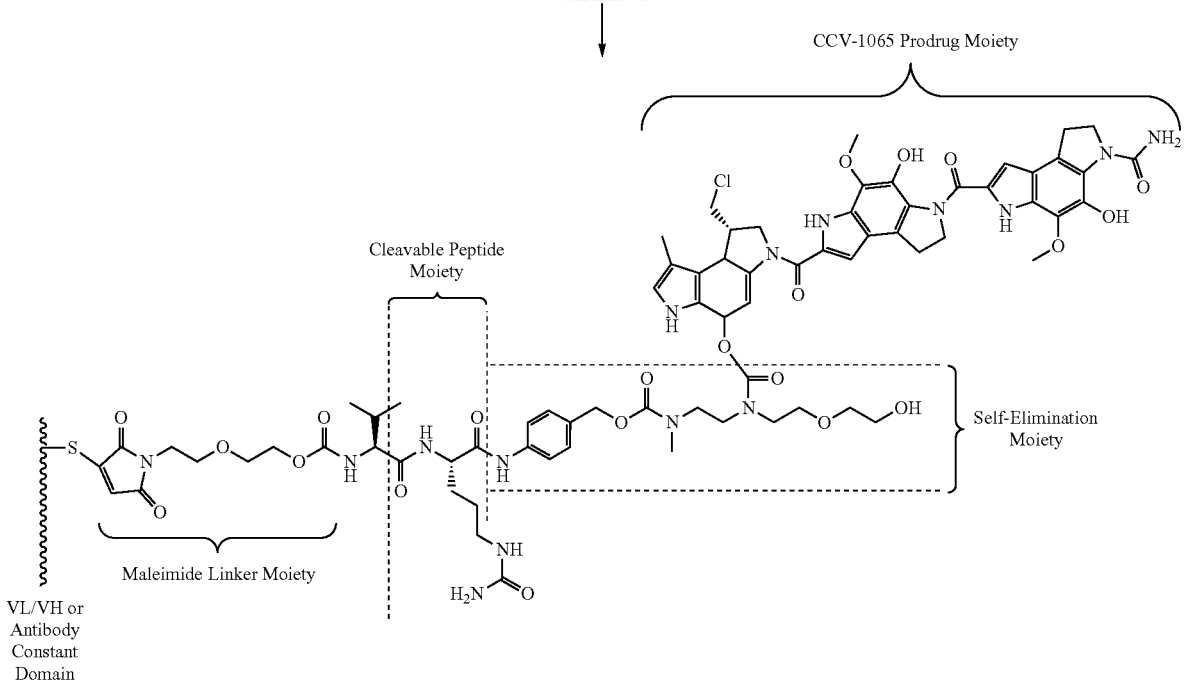

Upon cleavage of the Cleavable Peptide Moiety and elimination of the Self-Elimination Moiety, the Prodrug Moiety is believed to undergo a Winstein spirocyclization to yield the active drug (e.g., DUBA from seco-DUBA as shown in Scheme 9C).

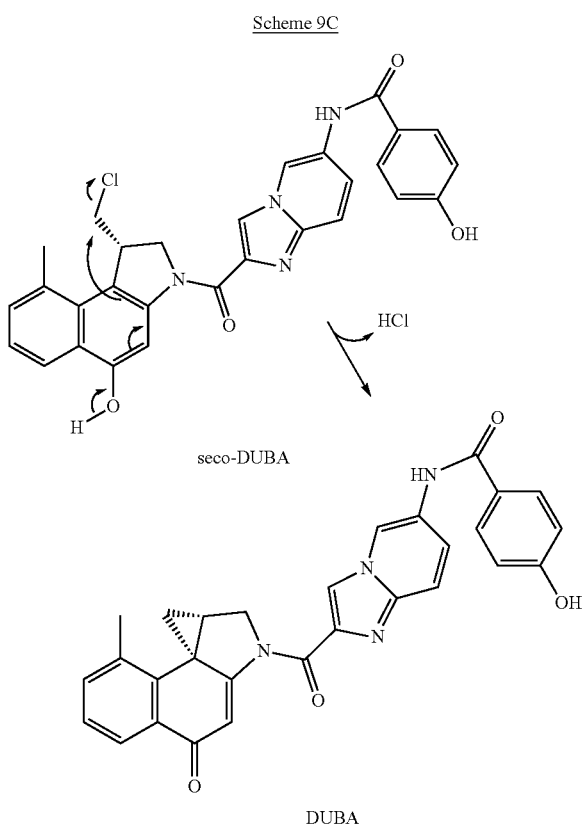

seco-DUBA is prepared from the corresponding DNA-alkylating and DNA-binding moieties (e.g., a 1,2,9,9a-tetrahydrocyclopropa-[c]benzo[e]indole-4-one framework as described by Elgersma, R. C. et al. (2014) "Design, Synthesis, and Evaluation of Linker- Duocarmycin Payloads: Toward Selection of HER2-Targeting Antibody-Drug Conjugate SYD985," Mol. Pharmaceut. 12:1813-1835 (see, Boger, D. L. et al. (1989) "Total Synthesis and Evaluation of (±)-N-(tert-Butoxycarbonyl)-CBI, (±)-CBI-CDPI1, and (±)-CBI-CDPI2: CC-1065 Functional Agents Incorporating the Equivalent 1,2,9,9a- Tetrahydrocyclopropa[1,2-c]benz[1,2-e]indol-4-one (CBI) Left-Hand Subunit," J. Am. Chem. Soc. 111:6461-6463; Boger, D. L. et al. (1992) "DNA Alkylation Properties of Enhanced Functional Analogs of CC-1065 Incorporating the 1,2,9,9a- Tetrahydrocyclopropa[1,2-c]benz[1,2-e]indol-4-one (CBI) Alkylation Subunit," J. Am. Chem. Soc. 114:5487-5496).

Scheme 9D illustrates the invention by showing the synthesis of the DNA-alkylating moiety for DUBA. Thus, o-tolualdehyde (1) and dimethyl succinate (2) are reacted to produce a mixture of acids (3a/3b) through a Stobbe condensation. Ring closure of the mixture of acids may be accomplished with trifluoroacetic anhydride and gave alcohol (4), which is then protected with benzyl chloride to afford benzyl ether (5). The ensuing hydrolysis of the methyl ester group yields the carboxylic acid (6) which is followed by a Curtius rearrangement in a mixture of toluene and tert-butyl alcohol to provide the carbamate (7). Bromination with N-bromosuccinimide give the bromide (8). The bromide (8) is alkylated with (S)-glycidyl nosylate in the presence of potassium tert-butoxide to give epoxide (9). Reaction with n-butyllithium provides a mixture of desired compound (10) and debrominated, rearranged derivative (11). Yields for desired compound (10) are higher when tetrahydrofuran is used as the solvent and the reaction temperature is kept between −25 and −20° C. Under these conditions, desired compound (10) and debrominated, rearranged derivative (11) are obtainable in an approximate 1:1 ratio. Workup with p-toluenesulfonic acid results in conversion of debrominated, rearranged derivative (11) to (7), thereby aiding recovery of desired compound (10). Mesylation of the hydroxyl group in (10) followed by chloride substitution using lithium chloride gives key intermediate (12).

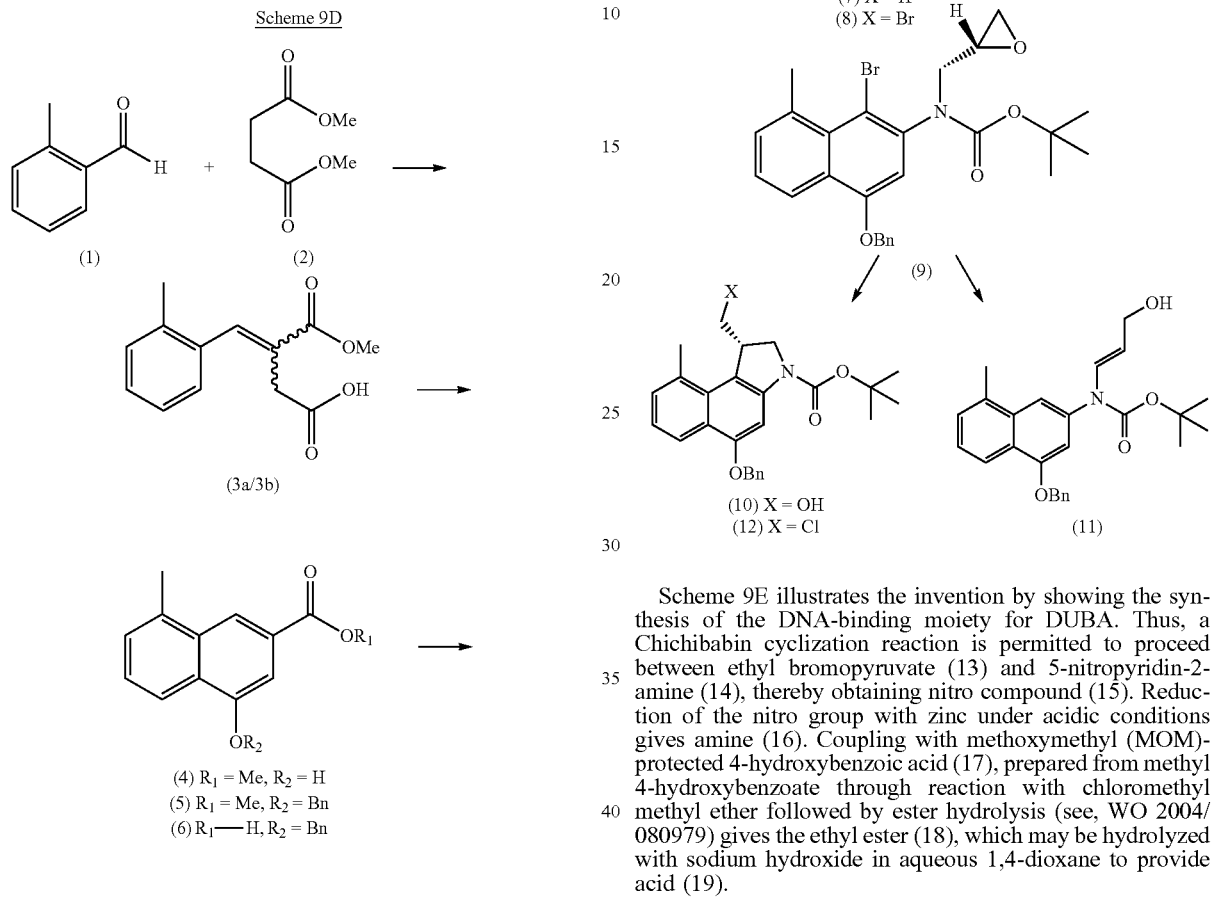

Scheme 9E illustrates the invention by showing the synthesis of the DNA-binding moiety for DUBA. Thus, a Chichibabin cyclization reaction is permitted to proceed between ethyl bromopyruvate (13) and 5-nitropyridin-2-amine (14), thereby obtaining nitro compound (15). Reduction of the nitro group with zinc under acidic conditions gives amine (16). Coupling with methoxymethyl (MOM)-protected 4-hydroxybenzoic acid (17), prepared from methyl 4-hydroxybenzoate through reaction with chloromethyl methyl ether followed by ester hydrolysis (see, WO 2004/080979) gives the ethyl ester (18), which may be hydrolyzed with sodium hydroxide in aqueous 1,4-dioxane to provide acid (19).

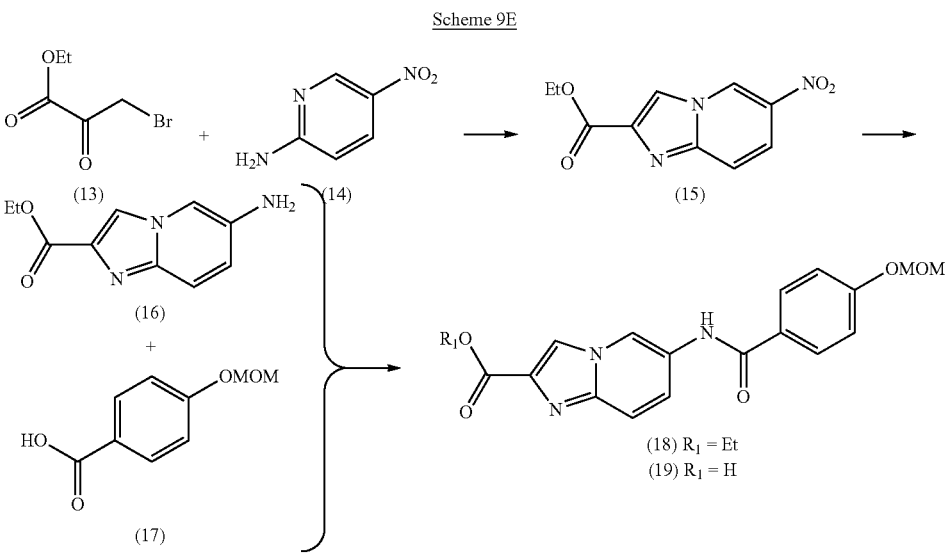

seco-DUBA is then synthesized from DNA-alkylating unit (12) and DNA-binding moiety (19). The tert-butoxycarbonyl (Boc) protective group is removed from (12) under acidic conditions to form the amine (20). EDC-mediated coupling of amine (20) and compound (19) yields protected compound (21), which is then fully deprotected in two consecutive steps (with Pd/C, $NH_4HCO_2$, MeOH/THF, 3 hours, 90%, to yield (22) and then with HCl, 1,4-dioxane/water, 1 h, 95% to provide seco-DUBA (23) as its HCl salt (Scheme 9F).

Scheme 9F

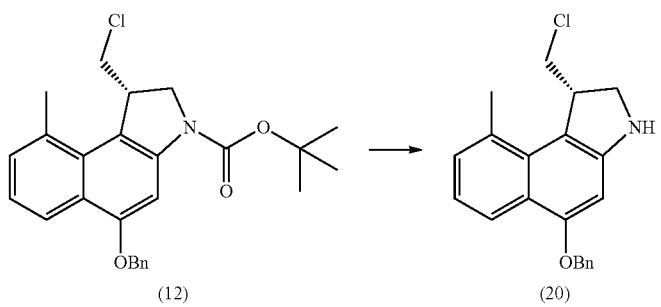

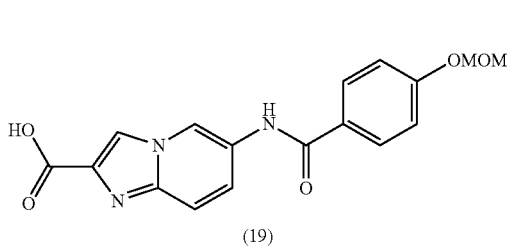

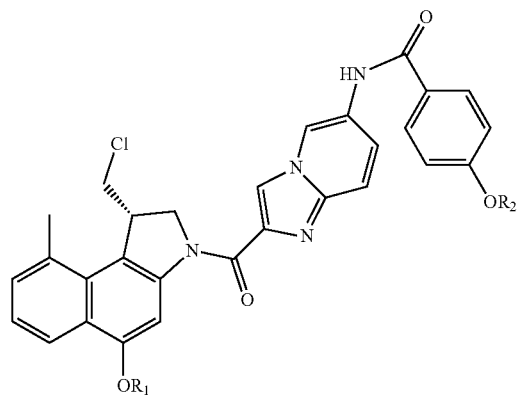

(21) $R_1$ = Bn, $R_2$ = MOM
(22) $R_1$ = H, $R_2$ = MOM
(23) seco-DUBA; $R_1$ = H, $R_2$ = H Prodrugs of other drugs, e.g., CC-1065, may be synthesized as described for example in WO 2010/062171.

The Prodrug Moiety is preferably linked to the other moieties of the ADC according to Scheme 9G. The Maleimide Linker building block was synthesized by starting with a condensation reaction between (24) and 2-(2-aminoethoxy)ethanol (25) to give alcohol (26), which was then converted to reactive carbonate (27) through reaction with 4-nitrophenyl chloroformate. Coupling of (27) to H-Valine-Citrulline-PABA (28), prepared according to Dubowchik, G. M. et al. (2002) "*Cathepsin B-Labile Dipeptide Linkers For Lysosomal Release Of Doxorubicin From Internalizing Immunoconjugates: Model Studies Of Enzymatic Drug Release And Antigen-Specific In Vitro Anticancer Activity*," Bioconjugate Chem. 13:855-869) results in the formation of linker (29), which was treated with bis(4-nitrophenyl) carbonate to give activated linker (30).

Scheme 9G

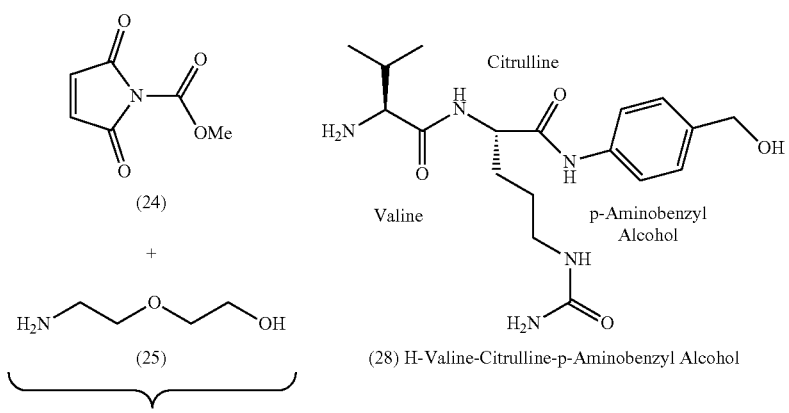

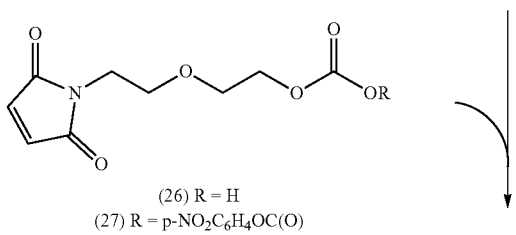

(26) R = H
(27) R = p-NO$_2$C$_6$H$_4$OC(O)

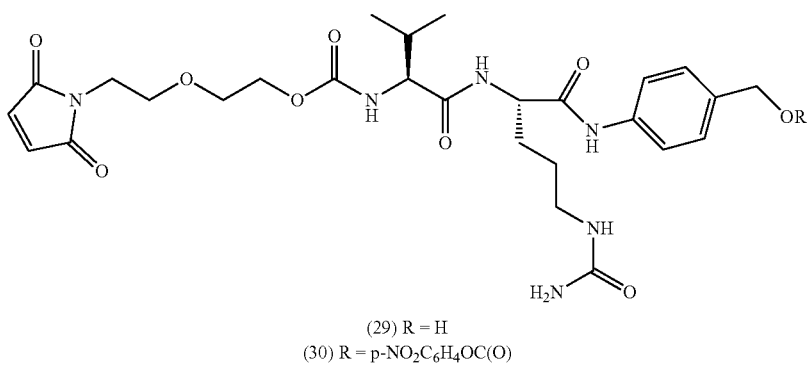

(29) R = H
(30) R = p-NO$_2$C$_6$H$_4$OC(O)

As shown in Scheme 9H, seco-DUBA-MOM (22) is modified for conjugation in two steps. Consecutive treatment of (22) with 4-nitrophenyl chloroformate and tert-butyl methyl (2-(methylamino)ethyl)carbamate (31) gives compound (32). Removal of the Boc and MOM protective groups in (32) with trifluoroacetic acid (TFA) provided (33) as its TFA salt.
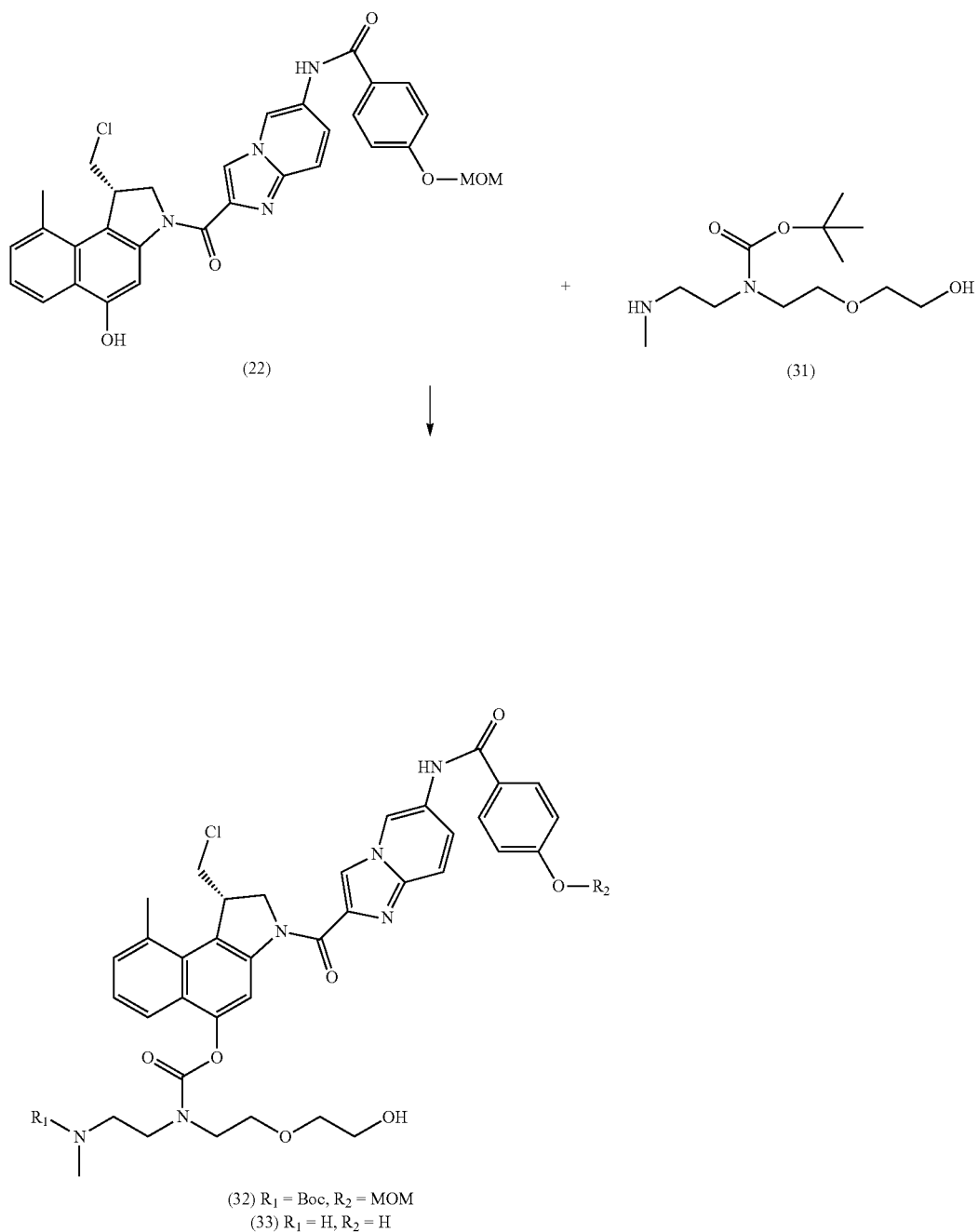

The ADC was synthesized through reaction of activated linker (30) with cyclization spacer-duocarmycin construct (33) under slightly basic conditions. Under these conditions, self-elimination of the cyclization spacer and resulting formation of 3a was suppressed (Scheme 9I).
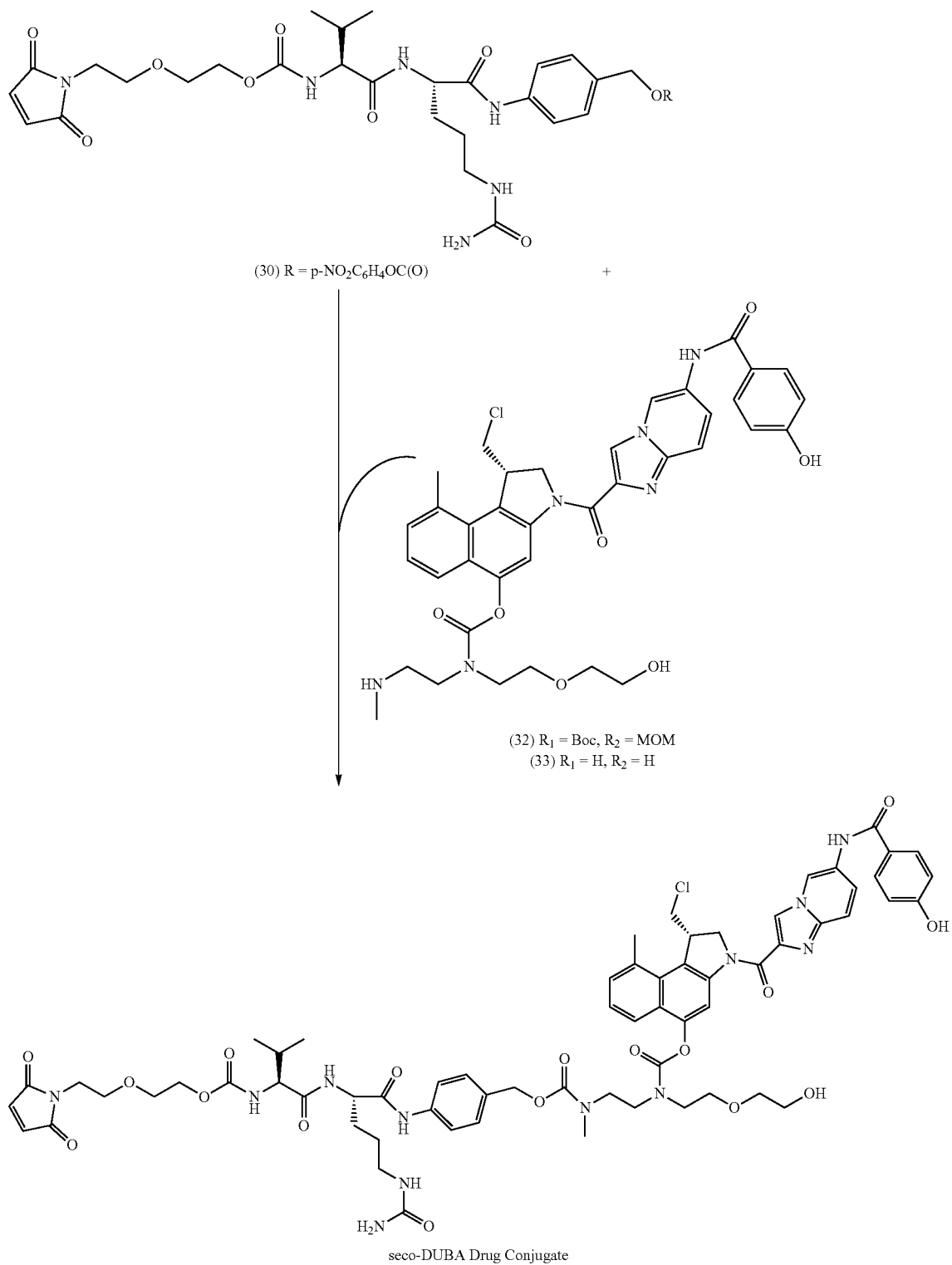
Scheme 9I
(30) R = p-NO$_2$C$_6$H$_4$OC(O)
(32) R$_1$ = Boc, R$_2$ = MOM
(33) R$_1$ = H, R$_2$ = H
seco-DUBA Drug Conjugate The process generates on average two free thiol groups per mAb leading to a statistical distribution of B7-H3-ADC with an average drug-to-antibody-ratio (DAR) of about two, and low amounts of high-molecular weight species and residual unconjugated duocarmycin moiety.

The order of the steps of the synthesis may be varied as desired. Preferably, the method used will be that of Schemes 9A-9I, as described above.

XII. Uses of the B7-H3-Binding Molecules of the Present Invention

The present invention encompasses compositions, including pharmaceutical compositions, comprising the B7-H3-binding molecules of the present invention (e.g., antibodies, bispecific antibodies, bispecific diabodies, trivalent binding molecules, B7-H3-ADC, etc.), polypeptides derived from such molecules, polynucleotides comprising sequences encoding such molecules or polypeptides, and other agents as described herein.

As provided herein, the B7-H3-binding molecules of the present invention, comprising the anti-B7-H3-VL and/or VH Domains provided herein, have the ability to bind B7-H3 present on the surface of a cell and induce antibody-dependent cell-mediated cytotoxicity (ADCC) and/or complement dependent cytotoxicity (CDC) and/or mediate redirected cell killing (e.g., redirected T-cell cytotoxicity). Without meaning to be bound by any mechanism of action, the B7-H3-ADC molecules of the present invention are internalized upon binding to B7-H3 expressed by a tumor cell and mediate the killing of the tumor cell via the action of the conjugated cytotoxin.

Thus, B7-H3-binding molecules of the present invention, comprising the anti-B7-H3-VL and/or VH Domains provided herein, have the ability to treat any disease or condition associated with or characterized by the expression of B7-H3. As discussed above, B7-H3 is an onco-embryonic antigen expressed in numerous blood and solid malignancies that is associated with high-grade tumors exhibiting a less-differentiated morphology, and is correlated with poor clinical outcomes. Thus, without limitation, the B7-H3-binding molecules of the present invention may be employed in the diagnosis or treatment of cancer, particularly a cancer characterized by the expression of B7-H3.

The cancers that may be treated by the B7-H3-binding molecules of the present invention include cancers characterized by the presence of a cancer cell selected from the group consisting of a cell of: an adrenal gland tumor, an AIDS-associated cancer, an alveolar soft part sarcoma, an astrocytic tumor, an adrenal cancer, a bladder cancer, a bone cancer, a brain and spinal cord cancer, a metastatic brain tumor, a B-cell cancer, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gastric cancer, a gestational trophoblastic disease, a germ cell tumor, a head and neck cancer, a glioblastoma, a hematological malignancy, a hepatocellular carcinoma, an islet cell tumor, a Kaposi's Sarcoma, a kidney cancer, a leukemia (e.g., an acute myeloid leukemia), a liposarcoma/malignant lipomatous tumor, a liver cancer, a lymphoma, a lung cancer (e.g., a non-small-cell lung cancer (NSCLC)), a medulloblastoma, a melanoma, a meningioma, a mesothelioma pharyngeal cancer, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a renal metastatic cancer, a rhabdoid tumor, a rhabdomyosacoma, a sarcoma, a skin cancer, a small round blue cell tumor of childhood (including neuroblastoma and rhabdomyosarcoma), a soft-tissue sarcoma, a squamous cell cancer (e.g., a squamous cell cancer of the head and neck (SCCHN), a stomach cancer, a synovial sarcoma, a testicular cancer, a thymic carcinoma, a thymoma, a thyroid cancer (e.g., a thyroid metastatic cancer), and a uterine cancer.

In particular, B7-H3-binding molecules of the present invention may be used in the treatment of adrenal cancer, bladder cancer, breast cancer, colorectal cancer, gastric cancer, glioblastoma, kidney cancer, non-small-cell lung cancer (NSCLC), acute lymphocytic leukemia, acute myeloid leukemia, chronic lymphocytic leukemia, chronic myeloid leukemia, hairy cell leukemia, Burkett's lymphoma, diffuse large B cell lymphoma, follicular lymphoma, mantle cell lymphoma, marginal zone lymphoma, mesothelioma pharyngeal cancer, non-Hodgkin's lymphoma, small lymphocytic lymphoma, multiple myeloma, melanoma, ovarian cancer, pancreatic cancer, prostate cancer, skin cancer, renal cell carcinoma, small round blue cell tumors of childhood (including neuroblastoma and rhabdomyosarcoma), squamous cell cancer (e.g., squamous cell cancer of the head and neck (SCCHN), testicular cancer, thyroid cancer (e.g., thyroid metastatic cancer), and uterine cancer.

The bispecific B7-H3-binding molecules of the present invention augment the cancer therapy provided by B7-H3 by promoting the redirected killing of tumor cells that express the second specificity of such molecules (e.g., CD2, CD3, CD8, CD16, the T Cell Receptor (TCR), NKG2D, etc.). Such B7-H3-binding molecules are particularly useful for the treatment of cancer.

In addition to their utility in therapy, the B7-H3-binding molecules of the present invention may be detectably labeled and used in the diagnosis of cancer or in the imaging of tumors and tumor cells.

XIII. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) that can be used in the preparation of unit dosage forms. Such compositions comprise a prophylactically or therapeutically effective amount of the B7-H3-binding molecules of the present invention, or a combination of such agents and a pharmaceutically acceptable carrier. Preferably, compositions of the invention comprise a prophylactically or therapeutically effective amount of the B7-H3-binding molecules of the present invention and a pharmaceutically acceptable carrier. The invention also encompasses such pharmaceutical compositions that additionally include a second therapeutic antibody (e.g., tumor-specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with a B7-H3-binding molecule of the present invention, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise any of the B7-H3-binding molecules of the present invention, including B7-H3-ADC. The kit can further comprise one or more other prophylactic and/or therapeutic agents useful for the treatment of cancer, in one or more containers.

XIV. Methods of Administration

The compositions of the present invention may be provided for the treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System,*" J. Biol. Chem. 262: 4429-4432), construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the B7-H3-binding molecules of the present invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that preparations of the B7-H3-binding molecules of the present invention are packaged in a hermetically sealed container such as an ampoule or sachette indicating the quantity of the molecule. In one embodiment, such molecules are supplied as a dry sterilized lyophilized powder or water free concentrate in a hermetically sealed container and can be reconstituted, e.g., with water or saline to the appropriate concentration for administration to a subject. Preferably, the B7-H3-binding molecules of the present invention are supplied as a dry sterile lyophilized powder in a hermetically sealed container.

The lyophilized preparations of the B7-H3-binding molecules of the present invention should be stored at between 2° C. and 8° C. in their original container and the molecules should be administered within 12 hours, preferably within 6 hours, within 5 hours, within 3 hours, or within 1 hour after being reconstituted. In an alternative embodiment, such molecules are supplied in liquid form in a hermetically sealed container indicating the quantity and concentration of the molecule, fusion protein, or conjugated molecule. Preferably, such B7-H3-binding molecules when provided in liquid form are supplied in a hermetically sealed container.

The amount of such preparations of the invention that will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

As used herein, an "effective amount" of a pharmaceutical composition is an amount sufficient to effect beneficial or desired results including, without limitation, clinical results such as decreasing symptoms resulting from the disease, attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals.

An effective amount can be administered in one or more administrations. For purposes of this invention, an effective amount of drug, compound, or pharmaceutical composition is an amount sufficient to reduce the proliferation of (or the effect of) viral presence and to reduce and/or delay the development of the viral disease, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art.

For the B7-H3-binding molecules encompassed by the invention, the dosage administered to a patient is preferably determined based upon the body weight (kg) of the recipient subject. For the B7-H3-binding molecules encompassed by the invention, the dosage administered to a patient is typically from about 0.01 μg/kg to about 30 mg/kg or more of the subject's body weight.

The dosage and frequency of administration of a B7-H3-binding molecule of the present invention may be reduced or altered by enhancing uptake and tissue penetration of the molecule by modifications such as, for example, lipidation.

The dosage of a B7-H3-binding molecule of the invention administered to a patient may be calculated for use as a single agent therapy. Alternatively, the molecule may be used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery*, "Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 3 17-327).

Treatment of a subject with a therapeutically or prophylactically effective amount of a B7-H3-binding molecule of the present invention can include a single treatment or, preferably, can include a series of treatments. In a preferred example, a subject is treated with such a diabody one time per week for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day with such administration occurring once a week, twice a week, once every two weeks, once a month, once every six weeks, once every two months, twice a year or once per year, etc. Alternatively, the pharmaceutical compositions of the invention can be administered twice a day with such administration occurring once a week, twice a week, once every two weeks, once a month, once every six weeks, once every two months, twice a year or once per year, etc. Alternatively, the pharmaceutical compositions of the invention can be administered three times a day with such administration occurring once a week, twice a week, once every two weeks, once a month, once every six weeks, once every two months, twice a year or once per year, etc. It will also be appreciated that the effective dosage of the molecules used for treatment may increase or decrease over the course of a particular treatment.

XV. Embodiments of the Invention

The invention particularly concerns the following embodiments ($E_A$ and $E_B$):

$E_A1$. An anti-B7-H3 antibody drug conjugate (B7-H3-ADC) that comprises the formula:

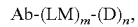

wherein:
Ab is an antibody that binds to B7-H3 that comprises a humanized Variable Heavy Chain (VH) Domain and a humanized Variable Light Chain (VL) Domain, or is a B7-H3-binding fragment thereof, and;
D is a cytotoxic drug moiety;
LM is a bond or a Linker Molecule that covalently links Ab and D;
m is an integer between 0 and n and denotes the number of Linker Molecules of the B7-H3-ADC; and
n is an integer between 1 and 10 and denotes the number of cytotoxic drug moieties covalently linked to the B7-H3-ADC molecule.

$E_A2$. The B7-H3-ADC of $E_A1$, wherein:
(A) (i) said humanized VL Domain comprises the amino acid sequence of SEQ ID NO:99, and
    (ii) said humanized VH Domain comprises the amino acid sequence of SEQ ID NO:104;
or
(B) (i) said humanized VL Domain comprises the amino acid sequence of SEQ ID NO:20, and
    (ii) said humanized VH Domain comprises the amino acid sequence of SEQ ID NO:21;
or
(C) (i) said humanized VL Domain comprises the amino acid sequence of SEQ ID NO:30, and
    (ii) said humanized VH Domain comprises the amino acid sequence of SEQ ID NO:31.

$E_A3$. The B7-H3-ADC of $E_A1$, wherein said humanized VL Domain comprises the amino acid sequence of SEQ ID NO:99 and said humanized VH Domain comprises the amino acid sequence of SEQ ID NO:104.

$E_A4$. The B7-H3-ADC of $E_A1$, wherein said humanized VL Domain comprises the amino acid sequence of SEQ ID NO:20 and said humanized VH Domain comprises the amino acid sequence of SEQ ID NO:21.

$E_A5$. The B7-H3-ADC of $E_A1$, wherein said humanized VL Domain comprises the amino acid sequence of SEQ ID NO:30 and said humanized VH Domain comprises the amino acid sequence of SEQ ID NO:31.

$E_A6$. The B7-H3-ADC of any one of $E_A1$-$E_A5$, wherein said Ab is an antibody.

$E_A7$. The B7-H3-ADC of any one of E1- $E_A5$, wherein said Ab is an antigen binding fragment of an antibody.

$E_A8$. The B7-H3-ADC of any one of $E_A1$-$E_A7$, wherein said B7-H3-ADC comprises an Fc Domain of a human IgG.

$E_A9$. The B7-H3-ADC of $E_A8$, wherein said human IgG is a human IgG1, IgG2, IgG3, or IgG4.

$E_A10$. The B7-H3-ADC of $E_A8$ or $E_A9$, wherein said Fc Domain is a variant Fc Domain that comprises:
(a) one or more amino acid modifications that reduces the affinity of the variant Fc Domain for an FcγR; and/or (b) one or more amino acid modifications that enhances the serum half-life of the variant Fc Domain.

$E_A11$. The B7-H3-ADC of $E_A10$, wherein said modifications that reduces the affinity of the variant Fc Domain for an FcγR comprise the substitution of L234A; L235A; or L234A and L235A, wherein said numbering is that of the EU index as in Kabat.

$E_A12$. The B7-H3-ADC of $E_A10$ or $E_A11$, wherein said modifications that that enhances the serum half-life of the variant Fc Domain comprise the substitution of M252Y; M252Y and S254T; M252Y and T256E; M252Y, S254T and T256E; or K288D and H435K, wherein said numbering is that of the EU index as in Kabat.

$E_A13$. The B7-H3-ADC of any one of $E_A1$-$E_A12$, wherein at least one of said LM is a Linker Molecule.

$E_A14$. The B7-H3-ADC of $E_A13$, wherein said LM Linker Molecule is a peptidic linker.

$E_A15$. The B7-H3-ADC of $E_A13$, wherein said LM Linker Molecule is a cleavable linker.

$E_A16$. The B7-H3-ADC of $E_A15$, wherein said molecule comprises the formula:

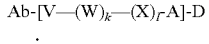

wherein:
V is said cleavable LM Linker Molecule,
$(W)_k$—$(X)_l$-A is an elongated, self-eliminating spacer system, that self-eliminates via a 1, (4+2n)-elimination,
W and X are each a 1, (4+2n) electronic cascade spacer, being the same or different,
A is either a spacer group of formula $(Y)_m$, wherein Y is a 1, (4+2n) electronic cascade spacer, or a group of formula U, being a cyclisation elimination spacer,
k, l and m are independently an integer of 0 (included) to 5 (included),
n is an integer of 0 (included) to 10 (included),
with the provisos that:
when A is $(Y)_m$: then k+l+m≥1, and if k+l+m=1, then n>1;
when A is U: then k+l≥1.
W, X, and Y are independently selected from compounds having the formula:

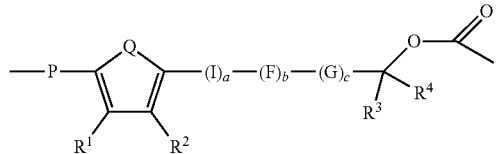

or the formula:

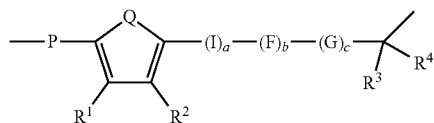

wherein: Q is —$R^5C$=$CR^6$—, S, O, $NR^5$, —$R^5C$=N—, or —N=$CR^5$—
P is $NR^7$, O or S
a, b, and c are independently an integer of 0 (included) to 5 (included);
I, F and G are independently selected from compounds having the formula:

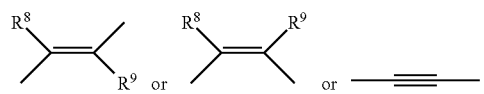

wherein $R^1$, $R^2$, $R^3$, $R^4$, $R^5$, $R^6$, $R^7$, $R^8$, and $R^9$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x2$ are independently selected from a $C_{1-6}$ alkyl group, a $C_{3-20}$ heterocyclyl group or a $C_{5-20}$ aryl group, two or more of the substituents $R^1$, $R^2$, $R^3$, $R^4$, $R^5$, $R^6$, $R^7$, $R^8$, or $R^9$ optionally being connected to one another to form one or more aliphatic or aromatic cyclic structures;

U is selected from compounds having the formula:

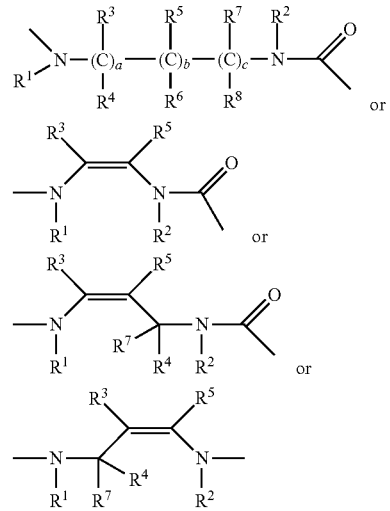

wherein:
a, b and c are independently selected to be an integer of 0 or 1;
provided that a+b+c=2 or 3;
$R^1$ and/or $R^2$ independently represent H, C1-6 alkyl, said alkyl being optionally substituted with one or more of the following groups:
hydroxy (OH), ether ($OR_x$), amino ($NH_2$), mono-substituted amino ($NR_xH$), disubstituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate (CO-$OR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate (OP (=O)(OR$_x$)$_2$), where R$_x$, R$_x^1$ and R$_x^2$ are selected from a C$_{1-6}$ alkyl group, a C$_{3-20}$ heterocyclyl group or a C$_{5-20}$ aryl group; and R$^3$, R$^4$, R$^5$, R$^6$, R$^7$ and R$^8$ independently represent H, C$_{1-6}$ alkyl, C$_{3-20}$ heterocyclyl, C$_{5-20}$ aryl, C$_{1-6}$ alkoxy, hydroxy (OH), amino (NH$_2$), mono-substituted amino (NR$_x$H), disubstituted amino (NR$_x^1$R$_x^2$), nitro (NO$_2$), halogen, CF$_3$, CN, CONH$_2$, SO$_2$Me, CONHMe, cyclic C$_{1-5}$ alkylamino, imidazolyl, C$_{1-6}$ alkylpiperazinyl, morpholino, thiol (SH), thioether (SR$_x$), tetrazole, carboxy (COOH), carboxylate (COOR$_x$), sulphoxy (S(=O)$_2$OH), sulphonate (S(=O)$_2$OR$_x$), sulphonyl (S(=O)$_2$R$_x$), sulphixy (S(=O)OH), sulphinate (S(=O)OR$_x$), sulphinyl (S(=O)R$_x$), phosphonooxy (OP(=O)(OH)$_2$), and phosphate (OP(=O)(OR$_x$)$_2$), where R$_x$, R$_x^1$ and R$_x^2$ are selected from a C$_{1-6}$ alkyl group, a C$_{3-20}$ heterocyclyl group or a C$_{5-20}$ aryl group, and two or more of the substituents R$^1$, R$^2$, R$^3$, R$^4$, R$^5$, R$^6$, R$^7$, or R$^8$ are optionally connected to one another to form one or more aliphatic or aromatic cyclic structures.

E$_A$17. The B7-H3-ADC of E$_A$16, wherein said LM Linker Molecule comprises:
(1) p-aminobenzyloxycarbonyl-p-aminobenzyloxycarbonyl;
(2) p-aminobenzyloxycarbonyl-p-aminobenzyloxycarbonyl-p-aminobenzyloxycarbonyl;
(3) p-aminocinnamyloxycarbonyl;
(4) p-aminocinnamyloxycarbonyl-p-aminobenzyloxycarbonyl;
(5) p-amino-benzyloxycarbonyl-p-aminocinnamyloxycarbonyl;
(6) p-aminocinnamyloxycarbonyl-p-aminocinnamyloxycarbonyl;
(7) p-aminophenylpentadienyloxycarbonyl;
(8) p-aminophenylpentadienyloxycarbonyl-p-aminocinnamyloxycarbonyl;
(9) p-aminophenylpentadienyloxycarbonyl-p-aminobenzyloxycarbonyl;
(10) p-aminophenylpentadienyloxycarbonyl-p-aminophenylpentadienyloxycarbonyl;
(11) p-aminobenzyloxycarbonyl(methylamino)ethyl(methylamino) carbonyl;
(12) p-aminocinnamyloxycarbonyl(methylamino)ethyl (methylamino) carbonyl;
(13) p-aminobenzyloxycarbonyl-p-aminobenzyloxycarbonyl(methylamino) ethyl(methylamino)carbonyl;
(14) p-aminocinnamyloxycarbonyl-p-aminobenzyloxycarbonyl (methylamino)ethyl(methylamino)carbonyl;
(15) p-aminobenzyloxycarbonyl-p-aminocinnamyloxycarbonyl (methylamino)ethyl(methylamino)-carbonyl;
(16) p-aminocinnamyloxycarbonyl-p-aminocinnamyloxycarbonyl (methylamino)ethyl(methylamino)carbonyl;
(17) p-aminobenzyloxycarbonyl-p-aminobenzyl;
(18) p-aminobenzyloxycarbonyl-p-aminobenzyloxycarbonyl-p-aminobenzyl;
(19) p-aminocinnamyl;
(20) p-aminocinnamyloxycarbonyl-p-aminobenzyl;
(21) p-aminobenzyloxycarbonyl-p-aminocinnamyl;
(22) p-amino-cinnamyloxycarbonyl-p-aminocinnamyl;
(23) p-aminophenylpentadienyl;
(24) p-aminophenylpentadienyloxycarbonyl-p-aminocinnamyl;
(25) p-aminophenylpentadienyloxycarbonyl-p-aminobenzyl; or
(26) p-aminophenylpentadienyloxycarbonyl-p-aminophenylpentadienyl.

E$_A$18. The B7-H3-ADC of any one of E$_A$13-E$_A$17, wherein said LM Linker Molecule is conjugated to the side chain of an amino acid of a polypeptide chain of Ab and binds said Ab to a molecule of said cytotoxic drug moiety D.

E$_A$19. The B7-H3-ADC of any one of E$_A$1-E$_A$18, wherein said cytotoxic drug moiety D comprises a cytotoxin, a radioisotope, an immunomodulator, a cytokine, a lymphokine, a chemokine, a growth factor, a tumor necrosis factor, a hormone, a hormone antagonist, an enzyme, an oligonucleotide, a DNA, an RNA, an siRNA, an RNAi, a microRNA, a photoactive therapeutic agent, an anti-angiogenic agent, a pro-apoptotic agent, a peptide, a lipid, a carbohydrate, a chelating agent, or combinations thereof.

E$_A$20. The B7-H3-ADC of E$_A$19, wherein said cytotoxic drug moiety D comprises a cytotoxin and is selected from the group consisting of a tubulysin, an auristatin, a maytansinoid, a calichearmicin, a pyrrolobenzodiazepine, and a duocarmycin.

E$_A$21. The B7-H3-ADC of E$_A$19, wherein said cytotoxic drug moiety D comprises a tubulysin cytotoxin and is selected from the group consisting of tubulysin A, tubulysin B, tubulysin C, and tubulysin D.

E$_A$22. The B7-H3-ADC of E$_A$19, wherein said cytotoxic drug moiety D comprises an auristatin cytotoxin and is selected from the group consisting of MMAE (N-methylvaline-valine-dolaisoleuine-dolaproine-norephedrine) and MMAF (N-methylvaline-valine-dolaisoleuine-dolaproine-phenylalanine).

E$_A$23. The B7-H3-ADC of E$_A$19, wherein said cytotoxic drug moiety D comprises a mavtansinoid cytotoxin and is selected from the group consisting of Mytansine, DM1 and DM4.

E$_A$24. The B7-H3-ADC of E$_A$19, wherein said cytotoxic drug moiety D comprises a calicheamicin cytotoxin and is selected from the group consisting of calicheamicin γ1, calicheamicin β1 Br, calicheamicin γ1Br, calicheamicin α2I, calicheamicin α3I, calicheamicin β1I, calicheamicin γ1I, and calicheamicin Δ1I.

E$_A$25. The B7-H3-ADC of E$_A$19, wherein said cytotoxic drug moiety D comprises a pyrrolobenzodiazepine cytotoxin and is selected from the group consisting of vadastuximab talirine, SJG-136, SG2000, SG2285 and SG2274.

E$_A$26. The B7-H3-ADC of E$_A$19, wherein said cytotoxic drug moiety D comprises a duocarmycin cytotoxin and is selected from the group consisting of duocarmycin A, duocarmycin B1, doucarmycin B2, duocarmycin C1, duocarmycin C2, duocarmycin D, duocarmycin SA, CC-1065, adozelesin, bizelesin, carzelesin (U-80244) and spiro-duocarmycin (DUBA).

E$_A$27. The B7-H3-ADC of any of E$_A$1-E$_A$26, wherein said LM Linker Molecule is covalently linked to said Ab via reduced inter-chain disulfides.

E$_A$28. A pharmaceutical composition that comprises an effective amount of the B7-H3-ADC of any of E$_A$1-E$_A$27 and a pharmaceutically acceptable carrier, excipient or diluent.

E$_A$29. Use of the B7-H3-ADC of any one of E$_A$1-E$_A$27 or the pharmaceutical composition of E$_A$28 in the treatment of a disease or condition associated with or characterized by the expression of B7-H3.

E$_A$30. The use of E$_A$29, wherein said disease or condition associated with or characterized by the expression of B7-H3 is cancer.

E$_A$31. The use of E$_A$30, wherein said cancer is characterized by the presence of a cancer cell selected from the group consisting of a cell of: an adrenal gland tumor, an AIDS-associated cancer, an alveolar soft part sarcoma, an astrocytic tumor, an adrenal cancer, a bladder cancer, a bone cancer, a brain and spinal cord cancer, a metastatic brain tumor, a B-cell cancer, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gastric cancer, a gestational trophoblastic disease, a germ cell tumor, a head and neck cancer, a glioblastoma, a hematological malignancy, a hepatocellular carcinoma, an islet cell tumor, a Kaposi's Sarcoma, a kidney cancer, a leukemia (e.g., an acute myeloid leukemia), a liposarcoma/malignant lipomatous tumor, a liver cancer, a lymphoma, a lung cancer (e.g., a non-small-cell lung cancer (NSCLC)), a medulloblastoma, a melanoma, a meningioma, a mesothelioma pharyngeal cancer, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a renal metastatic cancer, a rhabdoid tumor, a rhabdomyosacoma, a sarcoma, a skin cancer, a small round blue cell tumor of childhood (including neuroblastoma and rhabdomyosarcoma), a soft-tissue sarcoma, a squamous cell cancer (e.g., a squamous cell cancer of the head and neck (SCCHN), a stomach cancer, a synovial sarcoma, a testicular cancer, a thymic carcinoma, a thymoma, a thyroid cancer (e.g., a thyroid metastatic cancer), and a uterine cancer.

$E_A$31. The use of $E_A$30, wherein said cancer is selected from the group consisting: of adrenal cancer, bladder cancer, breast cancer, colorectal cancer, gastric cancer, glioblastoma, kidney cancer, non-small-cell lung cancer (NSCLC), acute lymphocytic leukemia, acute myeloid leukemia, chronic lymphocytic leukemia, chronic myeloid leukemia, hairy cell leukemia, Burkett's lymphoma, diffuse large B cell lymphoma, follicular lymphoma, mantle cell lymphoma, marginal zone lymphoma, mesothelioma pharyngeal cancer, non-Hodgkin's lymphoma, small lymphocytic lymphoma, multiple myeloma, melanoma, ovarian cancer, pancreatic cancer, prostate cancer, skin cancer, renal cell carcinoma, small round blue cell tumors of childhood (including neuroblastoma and rhabdomyosarcoma), squamous cell cancer (e.g., squamous cell cancer of the head and neck (SCCHN), testicular cancer, thyroid cancer (e.g., a thyroid metastatic cancer), and uterine cancer.

$E_B$1. A B7-H3-binding molecule that comprises a Variable Light Chain (VL) Domain that comprises a $CDR_L$1 Domain, a $CDR_L$2 Domain, and a $CDR_L$3 Domain, and a Variable Heavy Chain (VH) Domain that comprises a $CDR_H$1 Domain, a $CDR_H$2 Domain and a $CDR_H$3 Domain, wherein:
(1) said $CDR_H$1 Domain comprises the amino acid sequence of SEQ ID NO:27;
(2) said $CDR_H$2 Domain comprises the amino acid sequence of SEQ ID NO:28; and
(3) said $CDR_H$3 Domain comprises the amino acid sequence of SEQ ID NO:29.

$E_B$2. The B7-H3-binding molecule of $E_B$1, that comprises said VL Domain that comprises a $CDR_L$1 Domain, a $CDR_L$2 Domain, and a $CDR_L$3 Domain, and said VH Domain that comprises a $CDR_H$1 Domain, a $CDR_H$2 Domain and a $CDR_H$3 Domain, wherein:
(1) said $CDR_L$1 Domain comprises the amino acid sequence of SEQ ID NO:23;
(2) said $CDR_L$2 Domain comprises the amino acid sequence of SEQ ID NO:24; and
(3) said $CDR_L$3 Domain comprises the amino acid sequence of SEQ ID NO:25.

$E_B$3. The B7-H3-binding molecule of $E_B$1, that comprises said VL Domain that comprises a $CDR_L$1 Domain, a $CDR_L$2 Domain, and a $CDR_L$3 Domain, and said VH Domain that comprises a $CDR_H$1 Domain, a $CDR_H$2 Domain and a $CDR_H$3 Domain, wherein said domains are selected from the group consisting of:
(1) a $CDR_H$1 Domain comprising the amino acid sequence of SEQ ID NO:27;
(2) a $CDR_H$2 Domain comprising the amino acid sequence of SEQ ID NO:28;
(3) a $CDR_H$3 Domain comprising the amino acid sequence of SEQ ID NO:29;
(4) a $CDR_L$1 Domain comprising the amino acid sequence of SEQ ID NO:23;
(5) a $CDR_L$2 Domain comprising the amino acid sequence of SEQ ID NO:24; and
(6) a $CDR_L$3 Domain comprising the amino acid sequence of SEQ ID NO:25.

$E_B$4. The B7-H3-binding molecule of any one of $E_B$1-$E_B$3, wherein said VH Domain comprises the amino acid sequence of SEQ ID NO:26 or SEQ ID NO:31.

$E_B$5. The B7-H3-binding molecule of any one of $E_B$1-$E_B$4, wherein said VL Domain comprises the amino acid sequence of SEQ ID NO:22 or SEQ ID NO:30.

$E_B$6. A B7-H3-binding molecule that comprises a VL Domain and a VH Domain, wherein said VL Domain comprises the amino acid sequence of SEQ ID NO:20.

$E_B$7. A B7-H3-binding molecule that comprises a VL Domain and a VH Domain, wherein said VH Domain comprises the amino acid sequence of SEQ ID NO:21.

$E_B$8. A B7-H3-binding molecule that comprises a VL Domain and a VH Domain, wherein said VL Domain comprises the amino acid of SEQ ID NO:20 and said VH Domain comprises the amino acid sequence of SEQ ID NO:21.

$E_B$9. The B7-H3-binding molecule of any one of $E_B$1-$E_B$8, wherein said molecule is an antibody or antigen binding fragment thereof.

$E_B$10. The B7-H3-binding molecule of any one of $E_B$1-$E_B$8, wherein said molecule is:
(a) a bispecific antibody; or
(b) a diabody, said diabody being a covalently bonded complex that comprises two, three, four or five polypeptide chains; or
(c) a trivalent binding molecule, said trivalent binding molecule being a covalently bonded complex that comprises three, four, five, or more polypeptide chains.

$E_B$11. The B7-H3-binding molecule of any one of $E_B$1-$E_B$10, wherein said molecule comprises an Fc Domain.

$E_B$12. The B7-H3-binding molecule of $E_B$10, wherein said molecule is a diabody and comprises an Albumin-Binding Domain (ABD).

$E_B$13. The B7-H3-binding molecule of $E_B$11, wherein said Fc Domain is a variant Fc Domain that comprises:
(a) one or more amino acid modifications that reduces the affinity of the variant Fc Domain for an FcγR; and/or (b) one or more amino acid modifications that enhances the serum half-life of the variant Fc Domain.

$E_B14$. The B7-H3-binding molecule of $E_B13$, wherein said modifications that reduces the affinity of the variant Fc Domain for an FcγR comprise the substitution of L234A; L235A; or L234A and L235A, wherein said numbering is that of the EU index as in Kabat.

$E_B15$. The B7-H3-binding molecule of any one of $E_B13$ or $E_B14$, wherein said modifications that that enhances the serum half-life of the variant Fc Domain comprise the substitution of M252Y; M252Y and S254T; M252Y and T256E; M252Y, S254T and T256E; or K288D and H435K, wherein said numbering is that of the EU index as in Kabat.

$E_B16$. The B7-H3-binding molecule of any one of $E_B1$-$E_B15$, wherein said molecule is bispecific and comprises two epitope-binding sites capable of immunospecific binding to an epitope of B7-H3 and two epitope-binding sites capable of immunospecific binding to an epitope of a molecule present on the surface of an effector cell.

$E_B17$. The B7-H3-binding molecule of any one of $E_B1$-$E_B15$, wherein said molecule is bispecific and comprises one epitope-binding site capable of immunospecific binding to an epitope of B7-H3 and one epitope-binding site capable of immunospecific binding to an epitope of a molecule present on the surface of an effector cell.

$E_B18$. The B7-H3-binding molecule of any one of $E_B1$-$E_B15$, wherein said molecule is trispecific and comprises:
(a) one epitope-binding site capable of immunospecific binding to an epitope of B7-H3;
(b) one epitope-binding site capable of immunospecific binding to an epitope of a first molecule present on the surface of an effector cell; and
(c) one epitope-binding site capable of immunospecific binding to an epitope of a second molecule present on the surface of an effector cell.

$E_B19$. The B7-H3-binding molecule of any one of $E_B1$-$E_B8$, wherein said molecule is capable of simultaneously binding to B7-H3 and a molecule present on the surface of an effector cell.

$E_B20$. The B7-H3-binding molecule of any one of $E_B16$-$E_B18$, wherein said molecule present on the surface of an effector cell is CD2, CD3, CD8, TCR, or NKG2D.

$E_B21$. The B7-H3-binding molecule of any one of E16-$E_B20$, wherein said effector cell is a cytotoxic T-cell, or a Natural Killer (NK) cell.

$E_B22$. The B7-H3-binding molecule of any of $E_B16$-$E_B21$, wherein said molecule present on the surface of an effector cell is CD3.

$E_B23$. The B7-H3-binding molecule of $E_B18$, wherein said first molecule present on the surface of an effector cell is CD3 and said second molecule present on the surface of an effector cell is CD8.

$E_B24$. The B7-H3-binding molecule of any one of $E_B16$-$E_B23$, wherein said molecule mediates coordinated binding of a cell expressing B7-H3 and a cytotoxic T cell.

$E_B25$. A pharmaceutical composition that comprises an effective amount of the B7-H3-binding molecule of any of $E_B1$-$E_B24$ and a pharmaceutically acceptable carrier, excipient or diluent.

$E_B26$. Use of the B7-H3-binding molecule of any one of $E_B1$-$E_B24$ or the pharmaceutical composition of $E_B26$ in the treatment of a disease or condition associated with or characterized by the expression of B7-H3.

$E_B27$. The use of $E_B26$, wherein said disease or condition associated with or characterized by the expression of B7-H3 is cancer.

$E_B28$. The use of $E_B27$, wherein said cancer is characterized by the presence of a cancer cell selected from the group consisting of a cell of: an adrenal gland tumor, an AIDS-associated cancer, an alveolar soft part sarcoma, an astrocytic tumor, an adrenal cancer, a bladder cancer, a bone cancer, a brain and spinal cord cancer, a metastatic brain tumor, a B-cell cancer, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gastric cancer, a gestational trophoblastic disease, a germ cell tumor, a head and neck cancer, a glioblastoma, a hematological malignancy, a hepatocellular carcinoma, an islet cell tumor, a Kaposi's Sarcoma, a kidney cancer, a leukemia (e.g., an acute myeloid leukemia), a liposarcoma/malignant lipomatous tumor, a liver cancer, a lymphoma, a lung cancer (e.g., a non-small-cell lung cancer (NSCLC)), a medulloblastoma, a melanoma, a meningioma, a mesothelioma pharyngeal cancer, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a renal metastatic cancer, a rhabdoid tumor, a rhabdomyosacoma, a sarcoma, a skin cancer, a small round blue cell tumor of childhood (including neuroblastoma and rhabdomyosarcoma), a soft-tissue sarcoma, a squamous cell cancer (e.g., a squamous cell cancer of the head and neck (SCCHN), a stomach cancer, a synovial sarcoma, a testicular cancer, a thymic carcinoma, a thymoma, a thyroid cancer (e.g., a thyroid metastatic cancer), and a uterine cancer $E_B29$. The use of $E_B27$, wherein said cancer is selected from the group consisting: of adrenal cancer, bladder cancer, breast cancer, colorectal cancer, gastric cancer, glioblastoma, kidney cancer, non-small-cell lung cancer (NSCLC), acute lymphocytic leukemia, acute myeloid leukemia, chronic lymphocytic leukemia, chronic myeloid leukemia, hairy cell leukemia, Burkett's lymphoma, diffuse large B cell lymphoma, follicular lymphoma, mantle cell lymphoma, marginal zone lymphoma, mesothelioma pharyngeal cancer, non-Hodgkin's lymphoma, small lymphocytic lymphoma, multiple myeloma, melanoma, ovarian cancer, pancreatic cancer, prostate cancer, skin cancer, renal cell carcinoma, small round blue cell tumors of childhood (including neuroblastoma and rhabdomyosarcoma), squamous cell cancer (e.g., squamous cell cancer of the head and neck (SCCHN), testicular cancer, thyroid cancer (e.g., thyroid metastatic cancer), and uterine cancer.

EXAMPLES

Having now generally described the invention, the same will be more readily understood through reference to the following Examples. The following examples illustrate various methods for compositions in the diagnostic or treatment methods of the invention. The examples are intended to illustrate, but in no way limit, the scope of the invention.

Example 1

Generation, Humanization and Characterization of Anti-B7-H3 Antibodies

Figure 7:
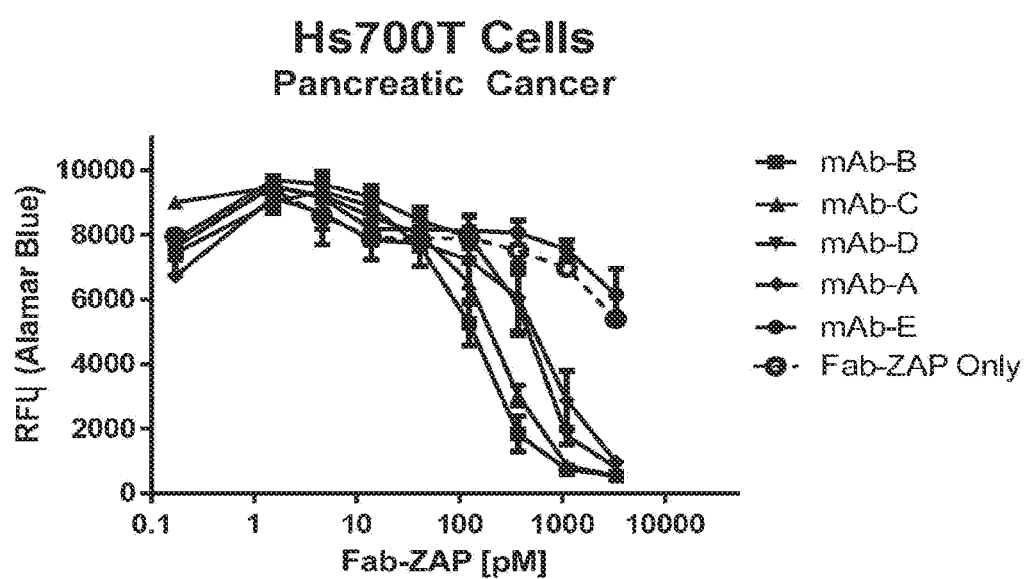
FIG. 7 shows the results of a screen for anti-B7-H3 antibodies capable of internalizing into Hs700T pancreatic cancer cells.
Figure 8A:
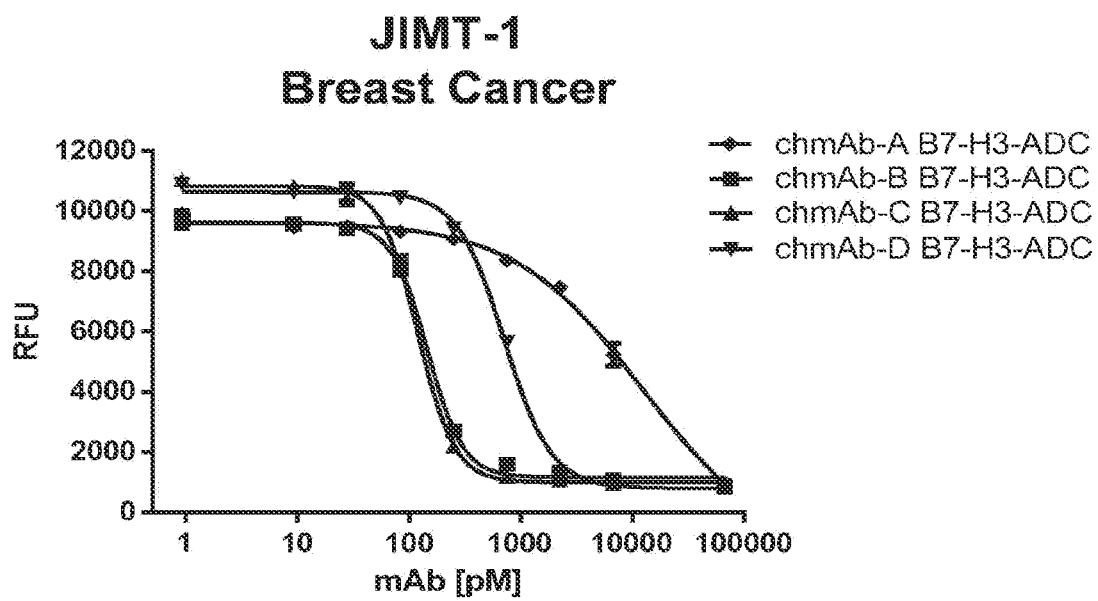
FIGS. 8A-8J shows the results of a study of the ability of the B7-H3-ADC of the present invention to mediate in vitro cytotoxicity against B7-H3 expressing JIMT-1 breast cancer cells (FIG. 8A), MDA-MB-468 breast cancer cells (FIG. 8B), A375.S2 melanoma cells (FIG. 8C), Calu-6 non-small cell lung cancer cells (FIG. 8D), NCI-H1703 non-small cell lung cancer cells (FIG. 8E), NCI-H1975 non-small cell lung cancer cells (FIG. 8F), PA-1 ovarian cancer cells (FIG. 8G), Hs700T pancreatic cancer cells (FIG. 8H), DU145 prostate cancer cells (FIG. 8I), and B7-H3 negative Raji B Cell lymphoma cells (FIG. 8J).
Figure 8B:
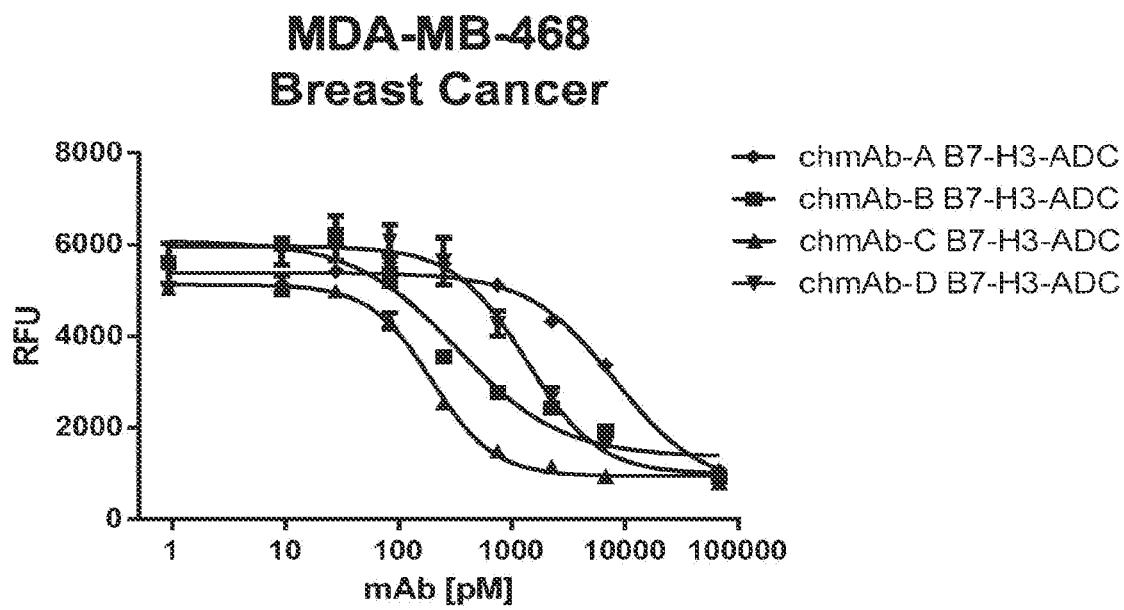
Figure 8C:
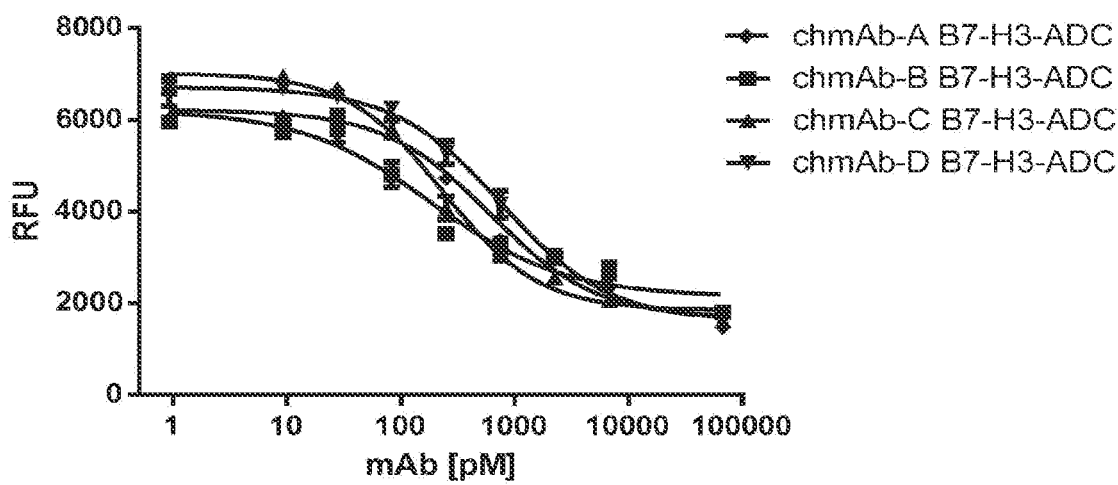
Figure 8D:
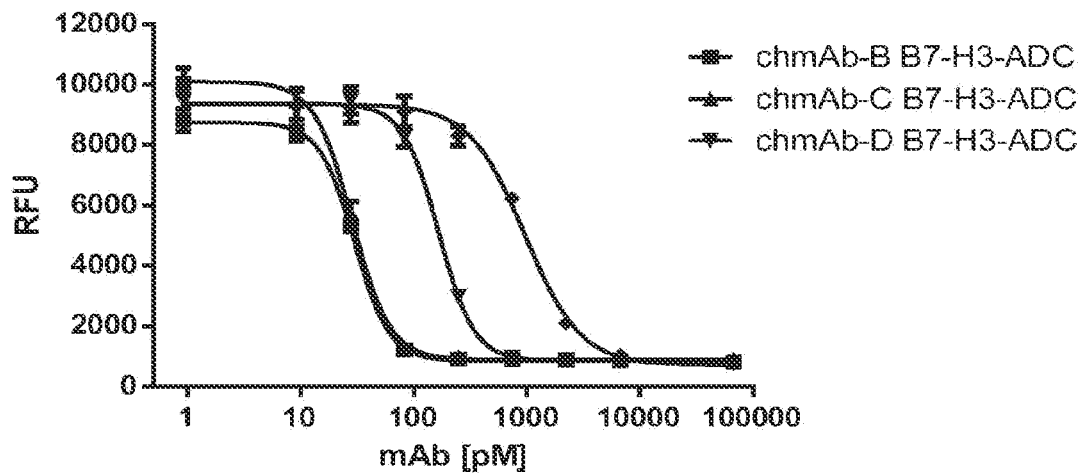
Figure 8E:
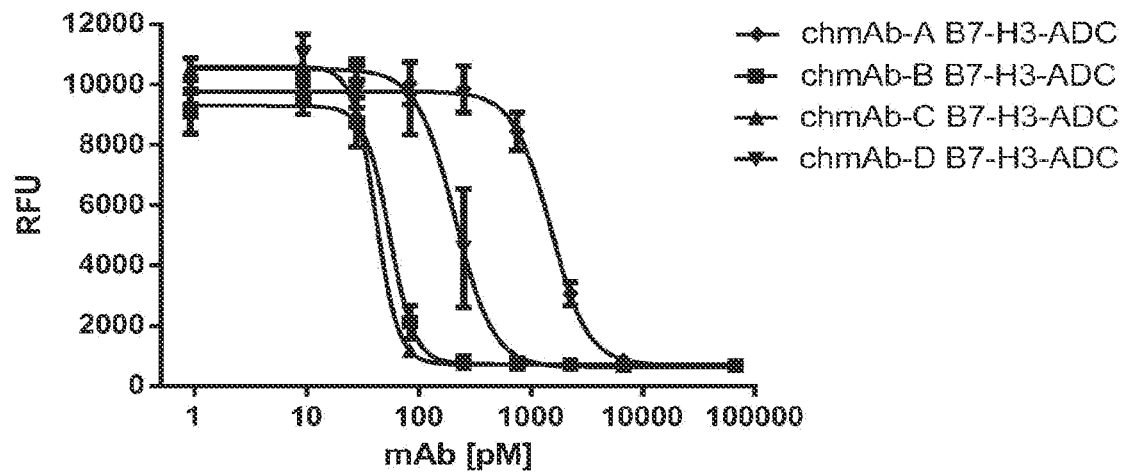
Figure 8F:
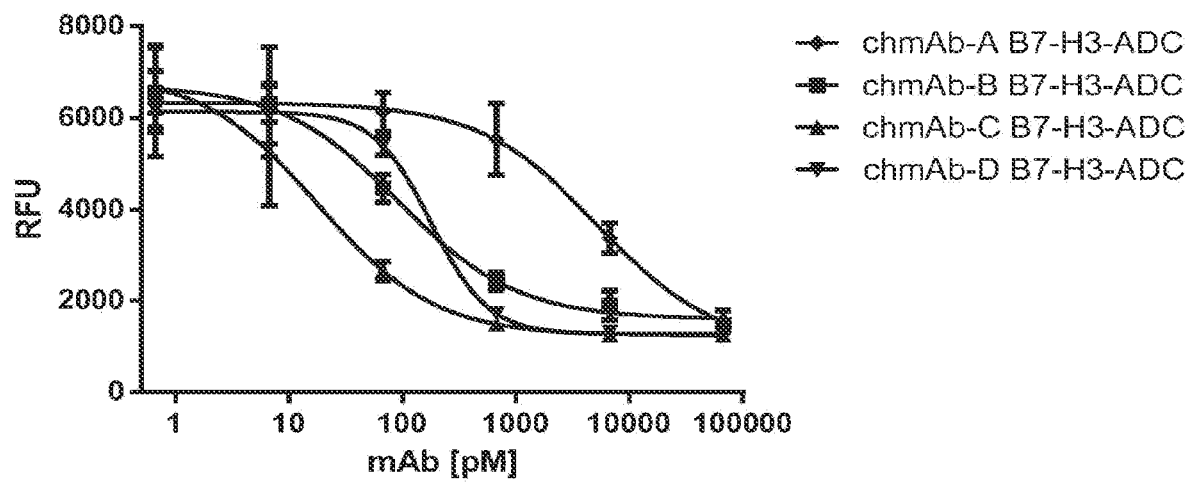
Figure 8G:
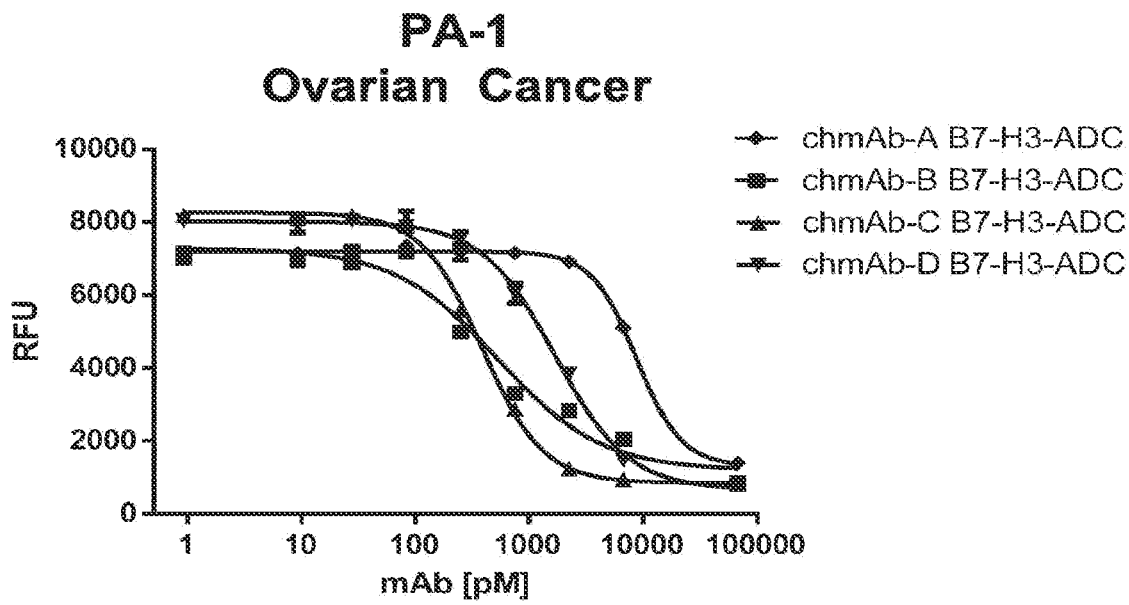
Figure 8H:
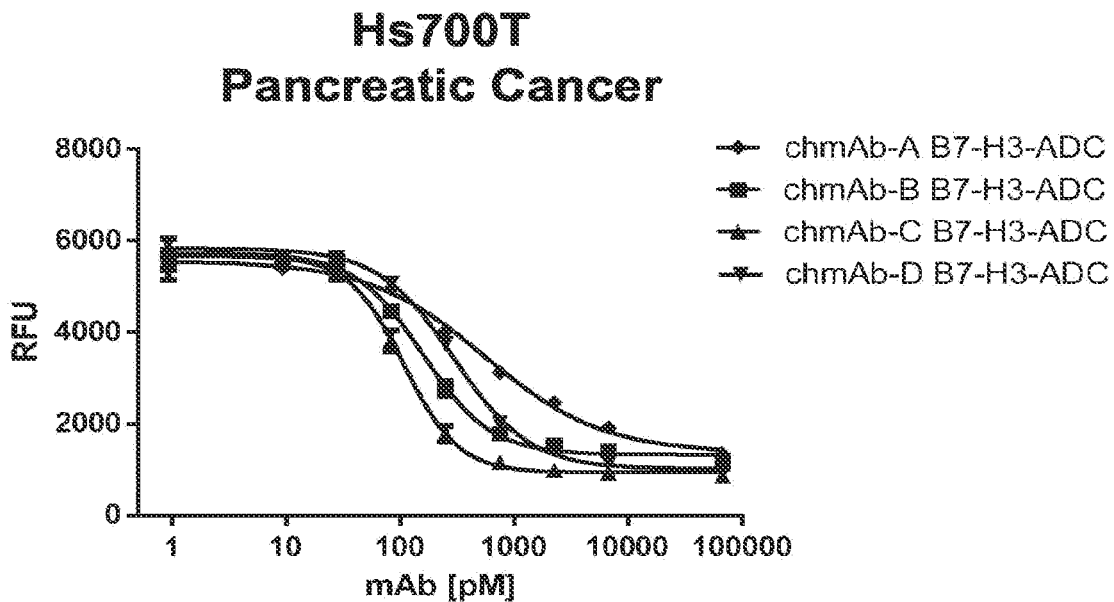
Figure 8I:
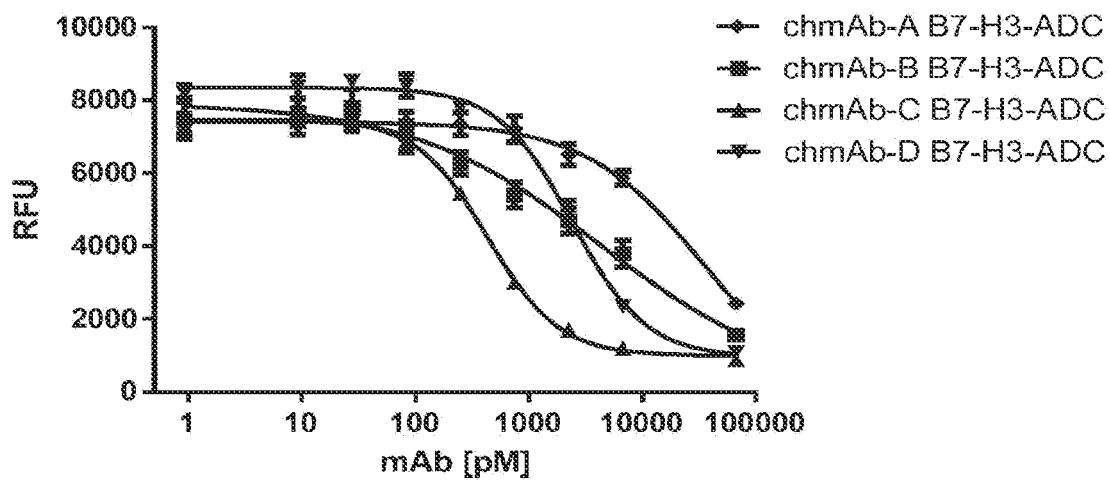
Figure 8J:
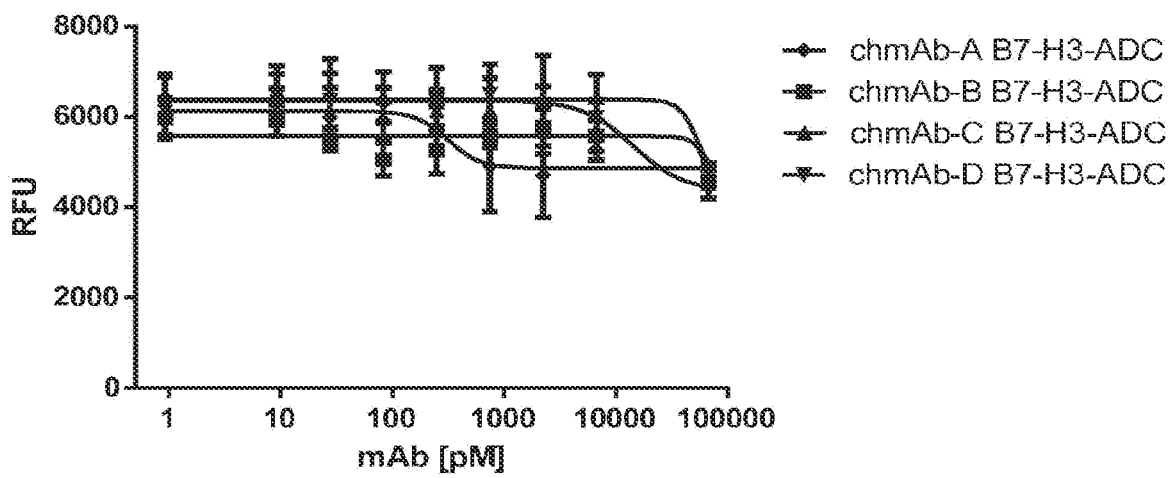

Monoclonal antibodies were generated via immunization of mice with viable human fetal progenitor cells or tumor initiating/cancer step-like cells (CSLCs) as previously described (Loo et al. (2007) "The glycotope-specific RAV12 monoclonal antibody induces oncosis in vitro and has anti-tumor activity against gastrointestinal adenocarcinoma tumor xenografts in vivo" Mol Cancer Ther; 6: 856-65). An IHC screen for cancer-specific mAbs identified a panel of anti-B7-H3 (CD276) reactive mAbs with highly differential tumor-versus-normal tissue binding. A subset of anti-B7-H3 antibodies that were efficiently internalized was identified using an internalization assay performed in a 5 day assay using a saporin-conjugated anti-mouse Fab at 1:1 or 10:1 Fab-ZAP:Test mAb ratio according to the manufacturers protocol (Advanced Targeting Systems). As shown in FIG. 7, a number of anti-B7-H3 antibodies including the anti-B7-H3 antibodies designated "mAb-C," and "mAb-D" were efficiently internalized.

The above-described murine anti-B7-H3 mAbs: mAb-B, mAb-C and mAb-D are used to form humanized VL and VH Domains in which the CDRLS and CDRHs of their domains are fused to human framework domains. The humanized VH and VL domains are then used to generate humanized light chains having a kappa light chain constant region (i.e., SEQ ID NO:1) and IgG1 $CH_1$, hinge, and Fc Domains (i.e., SEQ ID NOs:3, 7, 12). The humanized antibodies were designated "hmAb-B," "hmAb-C," and "hmAb-D."

The amino acid sequences of the humanized VL and VH Domains are provided above. It will be noted that the CDRs of hmAb-B may be modified to generate alternative humanized VL and VH domains as described above. The amino acid sequence of the entire humanized light and heavy chains of hmAb-C and hmAb-D are provided above.

The binding kinetics of the humanized antibodies was investigated using Biacore analysis in which a soluble human or cyno B7-H3 (4Ig)-His tag fusion protein (shB7-H3-His or scB7-H3-His, respectively) was passed over immobilized antibodies. Briefly, each humanized antibody was captured on immobilized a Fab2 goat anti-human Fc surface and was incubated with shB7-H3-His or scB7-H3-his (6.25-100 Nm), and the kinetics of binding were determined via Biacore analysis. The calculated $k_a$, $k_d$ and $K_D$ from these studies using a bivalent binding fit are presented in Table 6. The results demonstrate that the humanized antibodies bind by human and cynomolgus monkey B7-H3 with a range of affinities.

TABLE 6

| Antibody | Human | | | Cyno | | |
| --- | --- | --- | --- | --- | --- | --- |
| | $K_a$ ($\times 10^4$) | $K_d$ ($\times 10^{-4}$) | $K_D$ (nM) | $K_a$ ($\times 10^4$) | $K_d$ ($\times 10^{-4}$) | $K_D$ (nM) |
| hmAb-B | 11.0 | 0.12 | 0.11 | 7.1 | 2.9 | 4.1 |
| hmAb-C | 16 | 34 | 21.3 | 6.4 | 31 | 48.4 |
| hmAb-D | 3.4 | 22 | 62.9 | 1.35 | 77 | 592.3 |

The tissue cross-reactivity of the humanized antibodies was examined by immunohistochemistry (IHC). Table 7 summarizes the findings for several IHC studies performed on normal human tissues, human tumor tissues, human cancer cell lines, and CHO cell lines expressing or not expressing B7-H3 using the humanized anti-B7-H3 antibodies at the indicated antibody concentrations. The scoring criteria for these studies is provided in Table 8.

TABLE 7

| Tissue | Sample ID | hmAb-B 0.313 ug/ml | hmAb-C 0.625 ug/ml | hmAb-D 2.5 ug/ml |
| --- | --- | --- | --- | --- |
| Colon | MG06-CHTN-94F | epi 2+ (c) occasional | lamina propria cells 1+ (c) very rare | – |
| Liver | ILS11103A | hepatocytes 3+ (m) occasional to frequent | hepatocytes 2-3+ (m) rare to occasional | hepatocytes 1+ (m) rare |
| Kidney | ILS11119D | epi 1+ (c) rare | – | – |
| Pancreas | ILS10266 | fibril 3+ (c) rare | endo 1+ (c, m) very rare | – |
| Lung | MG06-CHTN-85-A-2 | pneumocytes 1+ (c) occasional | – | – |
| Heart | MG06-CHTN-76B | endo 2+ (c) rare to occasional | endo 1+ (c) very rare | – |
| Skin | MG03-St.Agn-50B | epi 2+ (c) occasional | squamous epi 1+ (c, m) rare | – |
| Adrenal | MG04-St.Agn-22B-A | 4+ (m, c) frequent | epi 3+ (m, c) occasional to frequent | epi 2+ (c, m) rare to occasional |
| Head and Neck CA (squamous) | VNM00340-D03 | 2 | 2 | 1 |
| | VNM00302-D01 | 3 | 2 | 1 |
| | ILS7068-D04 | 3 | 2 | 1 |
| | ILS2073-D01 | 3 | 3 | 2 |
| Lung CA (NSCLC) | ILS7115-C | 3 | 2 | 1 |
| | ILS7253-C | 2 | 1 | 1 |
| | ILS2153-G | 3 | 2 | 1 |
| | ILS-11149- C | 2 | 1 (BV) only | 1 |
| Hs700T ABC = 2.1e6 | 91812 | 4+ (c, m) frequent | 4+ (m > c) frequent | 2-3+ (m) |
| NCI-H1703 ABC = 8.1e5 | 033115-1 | 3-4+ (c) frequent | 2-3+ (c, m) occasional to frequent | ± |

TABLE 7-continued

| Tissue | Sample ID | hmAb-B 0.313 ug/ml | hmAb-C 0.625 ug/ml | hmAb-D 2.5 ug/ml |
|---|---|---|---|---|
| CHO + B7H3 Cl 31 ABC = 4.9e6 | 32113 | 2+ (c) frequent | 3-4+ (c, m) frequent | 3+ (m, c) |
| CHO + B7H3 Cl 32 ABC = 2.2e5 | 31813 | 3+ (c) frequent | 1-2+ (c) rare to occasional | ± |
| CHO − B7-H3 | 060414-2 | − | − | − | c: cytoplasm
m: membrane
epi: epithelium
Tu: tumor
BV: blood vessel

TABLE 8

| Normal Tissue Scoring Criteria: | | Tumor Scoring Criteria: | |
|---|---|---|---|
| − | negative | 0 (negative): | no staining |
| ± | equivocal | 1 (weak): | 1-100% of specific staining cells with 1+ staining intensity or 1-20% of specific staining cells with 2+ staining intensity |
| 1+ | weak | | |
| 2+ | moderate | 2 (moderate): | 2+ staining intensity in 21-79% of specific staining cells or a 3+ staining intensity in 1-49% of specific staining cells |
| 3+ | strong | | |
| 4+ | very strong | 3 (strong): | 2+ staining intensity in 80-100% of specific staining cells or 3+ staining intensity in ≥50% of specific staining cells. |

These results demonstrate that all the humanized antibodies exhibit binding to numerous B7-H3 positive tumor cells. hmAb-B exhibits the greatest tumor reactivity under the conditions tested but also exhibited normal tissue reactivity to liver hepatocytes and adrenal tissue. hmAb-C exhibits somewhat reduced tumor reactivity as compared to hmAb-B, but also exhibits substantially less reactivity with normal liver hepatocytes, and also reactivity on fewer independent samples. hmAb-D exhibits overall reduced reactivity on tumor and normal tissues. The antibodies show comparable cross-reactivity with cynomolgus monkey tissues although hmAb-D binds with less intensity in these IHC studies. To minimize off target toxicity hmAb-C and hmAb-D may be preferred for generation of B7-H3-ADC molecules of the invention.

Example 2

Production of B7-H3-ADC

The above-described murine anti-B7-H3 mAbs: mAb-A, mAb-B, mAb-C and mAb-D were used to form chimeric antibodies in which the VL Domain of such antibodies was fused to a human Light Chain Kappa Constant Region (SEQ ID NO:1), and in which the VH Domain of such antibodies was fused to human IgG1 CH1-Hinge-CH2-CH3 Constant Region (SEQ ID NOs:3, 7, and 12, respectively). The chimericized antibodies ("chmAb-A," "chmAb-B," "chmAb-C," and "chmAb-D") were converted to B7-H3-ADC via cysteine-conjugation to a B7-H3 binding domain thereof with the cleavable auristatin E linker/payload "vc-MMAE" (Concortis Biosystems), as discussed above.

Example 3

B7-H3-ADCs Exhibit Potent In Vitro Activity

In order to demonstrate the anti-tumor activity of the B7-H3-ADC of the present invention, the above-described B7-H3-ADC (MMAE) were incubated at concentrations ranging from 1-100,000 pM with B7-H3-expressing JIMT-1 breast cancer cells, MDA-MB-468 breast cancer cells, A375.52 melanoma cells, Calu-6 non-small cell lung cancer cells, NCI-H1703 non-small cell lung cancer cells, NCI-H1975 non-small cell lung cancer cells, PA-1 ovarian cancer cells, Hs700T pancreatic cancer cells, DU145 prostate cancer cells, or B7-H3-negative Raji B Cell lymphoma cells. in vitro cytotoxicity was quantified after 7 days. Briefly, B7-H3-ADCs and controls are diluted and plated into microtiter plates, 5000 cells are added to each well and incubated at 37 C for 4-7 days. Alamar Blue Reagent (e.g., BioRad/ThermoFisher/Invitrogen) is added to the plates and read according to the manufacturer's protocol. The number of antibody binding sites present on these cells was determined using a Bangs QFACS™ Kit.

The cytotoxicity curves from this study are presented in FIGS. 8A-8J. The IC50 values were determined and are provided in Table 9. The results of these studies demonstrate that each of the internalizing anti-B7-H3 antibodies tested exhibited dose-dependent cytotoxicity in vitro against B7-H3-expressing tumor cells. The antibodies exhibited a range of potencies. The relative potency in these assays was: chmAb-C>chmAb-B>chmAb-D>chmAb-A.

TABLE 9

| | Cell Line | | | | | | | | |
|---|---|---|---|---|---|---|---|---|---|
| | Breast Cancer | | Melanoma | Non-Small Cell Lung Cancer | | | Ovarian | Pancreatic | Prostate |
| | JIMT-1 | MDA-MB-468 | A375.52 | Calu-6 | NCI-H1703 | NCI-H1975 | Cancer PA-1 | Cancer Hs700T | Cancer DU145 |
| | Antibody Binding Sites per Cell (×10$^5$) | | | | | | | | |
| B7-H3-ADC | 11 | 4.2 | 7.5 | 8.5 | 8.1 | 4.8 | 6.1 | 21 | 2.4 |
| | IC50 (pM) | | | | | | | | |
| chmAb-A B7-H3 ADC | 9100 | 8095 | 703 | 995 | 1517 | 26976 | 8326 | 607 | 20153 |
| chmAb-B B7-H3 ADC | 221 | 352 | 153 | 59 | 90 | 31 | 555 | 159 | 3770 |
| chmAb-C B7-H3 ADC | 124 | 201 | 267 | 30 | 43 | 16 | 409 | 109 | 465 |
| chmAb-D B7-H3 ADC | 735 | 1383 | 887 | 171 | 219 | 162 | 1795 | 303 | 2587 |

Example 4

B7-H3-ADCs Exhibit Potent In Vivo Activity

In order to further demonstrate the anti-tumor activity of the B7-H3-ADC of the present invention, the above-described chmAb-B B7-H3-ADC, chmAb-C B7-H3-ADC, and/or chmAb-D B7-H3-ADC (MMAE) molecules were evaluated for in vivo toxicity in a CD1 nude mouse model using different tumor cell lines. In brief, ~5×10$^6$ tumor cells (suspended in 1:1 media and MATRIGEL®) were subcutaneously implanted into the flank of the CD1 nude mice (Charles River Laboratories). When tumors had reached a volume of approximately 150 mm$^3$, the mice were randomized and B7-H3-ADC or control vehicle was administered intraperitoneally. In these studies, one dose of the B7-H3-ADC or control vehicle was administered (qdx1). Tumors were measured twice weekly by orthogonal measurements with electronic calipers, with tumor volumes calculated as: (length×width×height)/2. The tumor volume (relative to control) was determined ("T/C"). A finding that the tumor volume of treated animals had decreased to ≤5 mm$^3$ during the study period was considered to denote a Complete Response ("CR").

In Vivo Activity Against MDA-MB-468 Breast Cancer Tumor Cells

Figure 9:
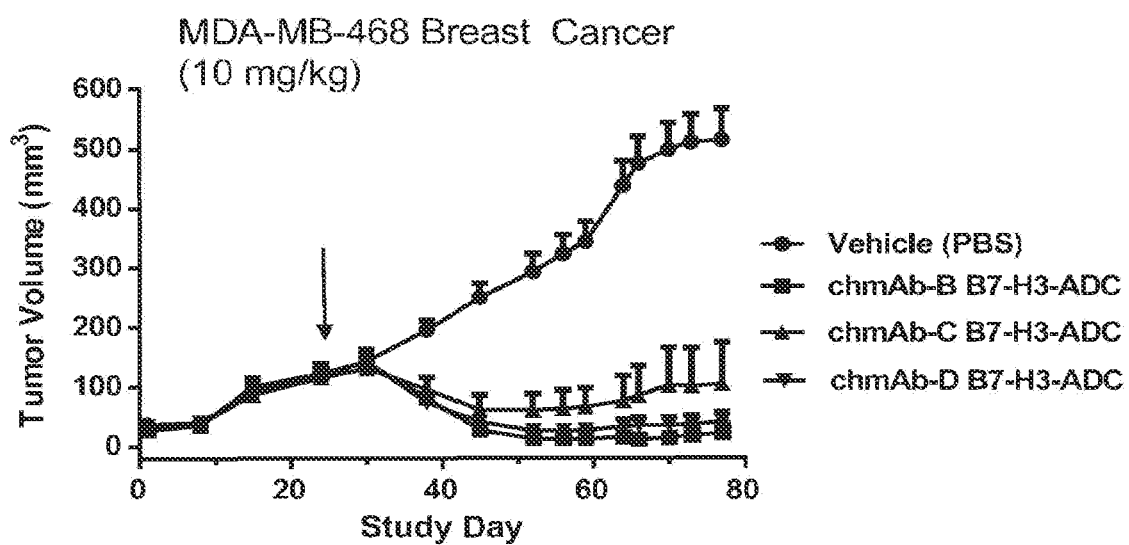
FIG. 9 shows the results of a study of the ability of the B7-H3-ADC of the present invention to mediate in vivo cytotoxicity against MDA-MB-468 breast cancer tumor cells implanted in the mammary fat pad in a CD1 nude mouse model. The tumor growth curves are presented for mice treated intraperitoneally with 10 mg/kg of chmAb-B-vc-MMAE, chmAb-C-vc-MMAE, and chmAb-D-vc-MMAE or vehicle alone on Day 25 (shown by arrow).

The results of this study with respect to mammary fat pad implanted MDA-MB-468 breast cancer tumor cells are presented in Table 10 and in FIG. 9, and show responsiveness against the MDA-MB-468 tumor cells.

TABLE 10

| Treatment (Initial Dose on Day 30) | Dose (mg/kg) | T/C | CR Response |
|---|---|---|---|
| chmAb-B B7-H3 ADC | 10 | 4 | 6/7 Highly Active |
| chmAb-C B7-H3 ADC | 10 | 20 | 4/7 Highly Active |
| chmAb-D B7-H3 ADC | 10 | 8 | 1/7 Highly Active | in vivo Activity Against NCI-H1703 Non-Small Cell Lung Cancer Tumor Cells

Figure 10A:
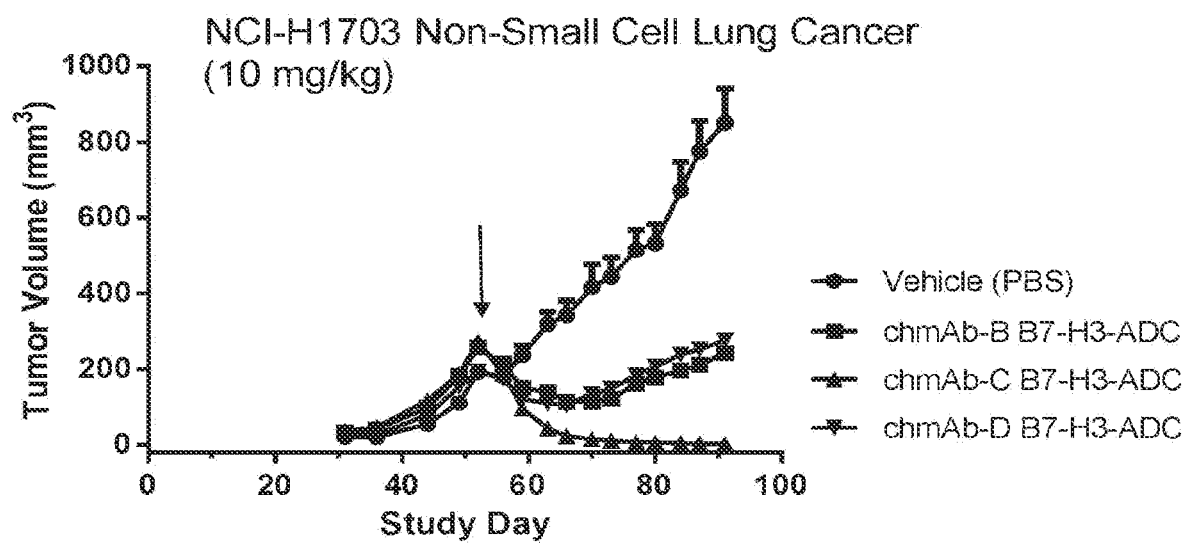
FIGS. 10A-10C shows the results of a study of the ability of the B7-H3-ADC of the present invention to mediate in vivo cytotoxicity against subcutaneously implanted NCI-H1703 non-small cell lung cancer tumor cells in a CD1 nude mouse model. The tumor growth curves are presented for mice treated intraperitoneally with 10 mg/kg (FIG. 10A), 3 mg/kg (FIG. 10B), 1 mg/kg (FIG. 10C) chmAb-B-vc-MMAE, chmAb-C-vc-MMAE, and chmAb-D-vc-MMAE at 10 mg/kg or vehicle alone on Day 52 (shown by arrow).
Figure 10B:
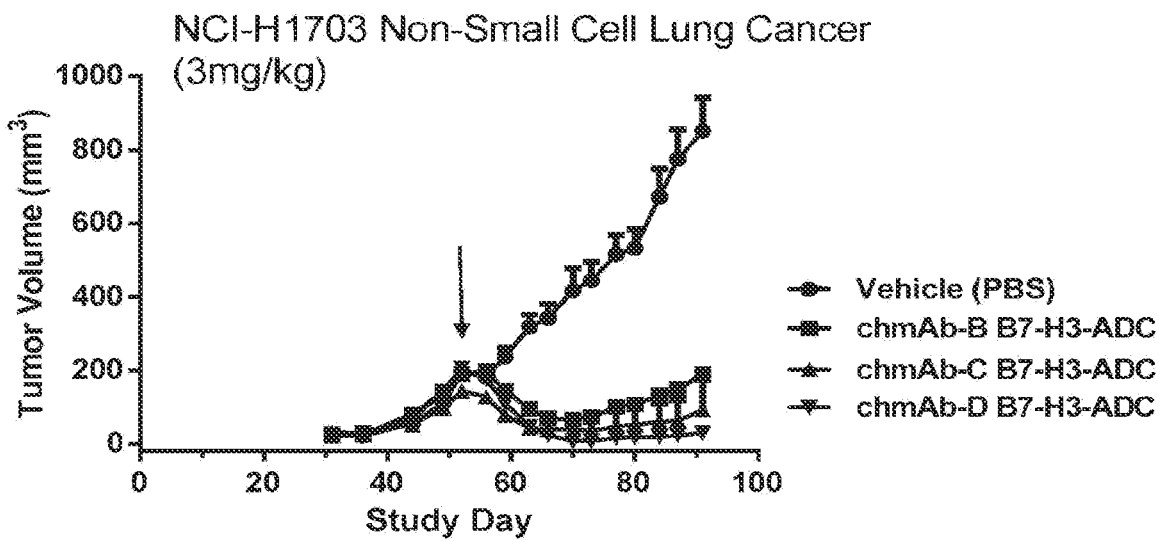
Figure 10C:
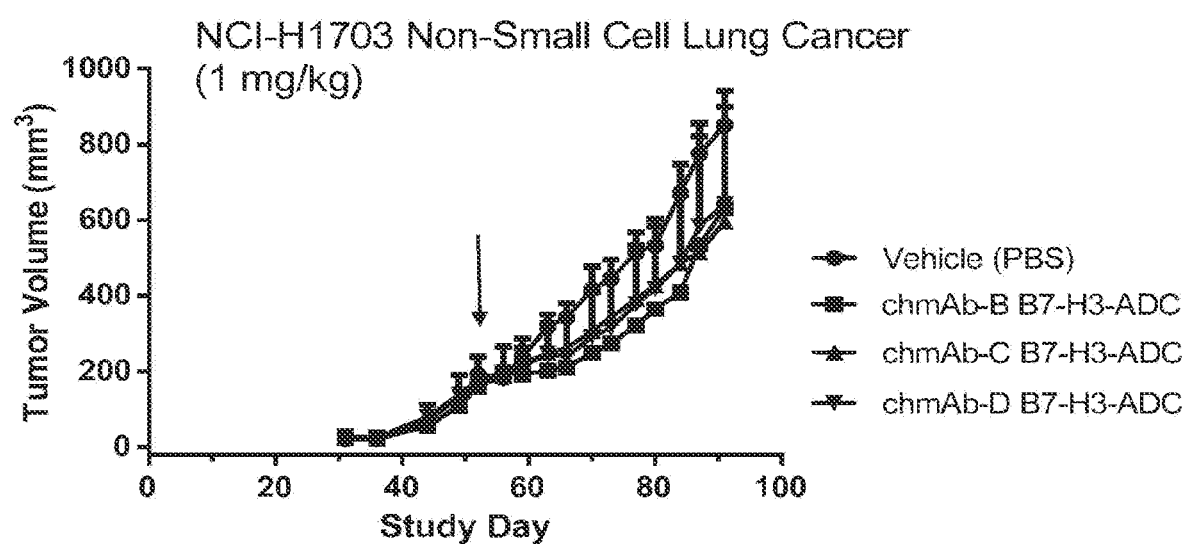

The results of this study with respect to subcutaneously implanted NCI-H1703 non-small cell lung cancer tumor cells are presented in Table 11 and in FIGS. 10A-10C, and show responsiveness against the NCI-H1703 tumor cells.

TABLE 11

| Treatment (Initial Dose on Day 52) | Dose (mg/kg) | T/C | CR Response |
|---|---|---|---|
| chmAb-B B7-H3-ADC | 10 | 28 | 5/7 Highly Active |
| | 3 | 22 | 3/7 Highly Active |
| | 1 | 74 | 0/7 Active |
| chmAb-C B7-H3-ADC | 10 | 0 | 6/7 Highly Active |
| | 3 | 11 | 5/7 Highly Active |
| | 1 | 70 | 0/7 Active |
| chmAb-D B7-H3-ADC | 10 | 32 | 5/7 Highly Active |
| | 3 | 4 | 6/7 Highly Active |
| | 1 | 76 | 0/7 Active |

In Vivo Activity Against PA-1 Ovarian Cancer Tumor Cells

Figure 11A:
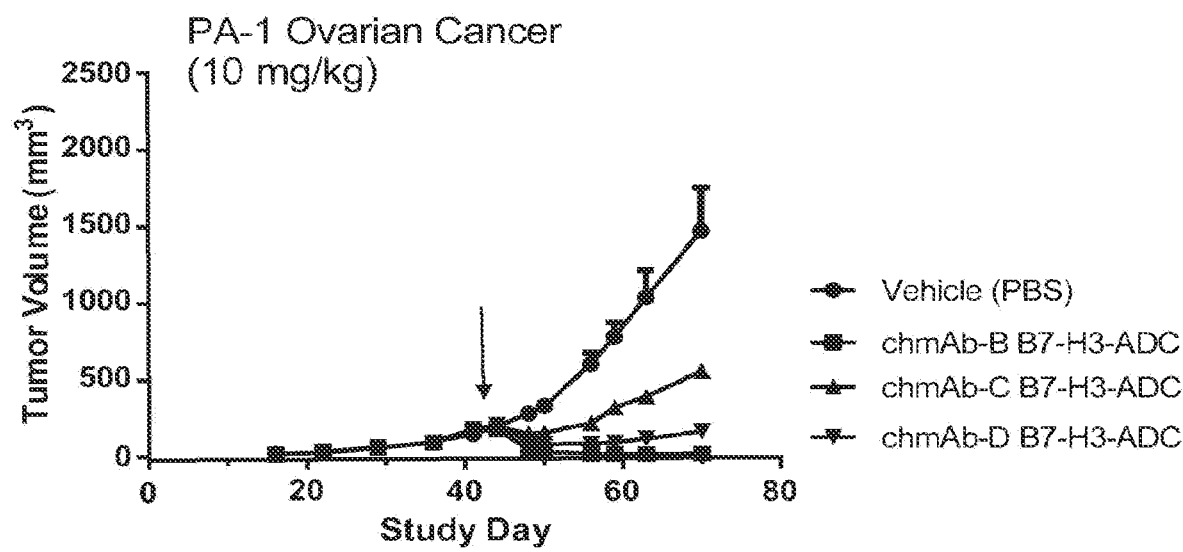
FIGS. 11A-11C shows the results of a study of the ability of the B7-H3-ADC of the present invention to mediate in vivo cytotoxicity against subcutaneously implanted PA-1 ovarian cancer tumor cells in a CD1 nude mouse model. The tumor growth curves are presented for mice treated intraperitoneally with 10 mg/kg (FIG. 11A), 3 mg/kg (FIG. 11B), 1 mg/kg (FIG. 5C) chmAb-B-vc-MMAE, chmAb-C-vc-MMAE, and chmAb-D-vc-MMAE at 10 mg/kg or vehicle alone on Day 42 (shown by arrow).
Figure 11B:
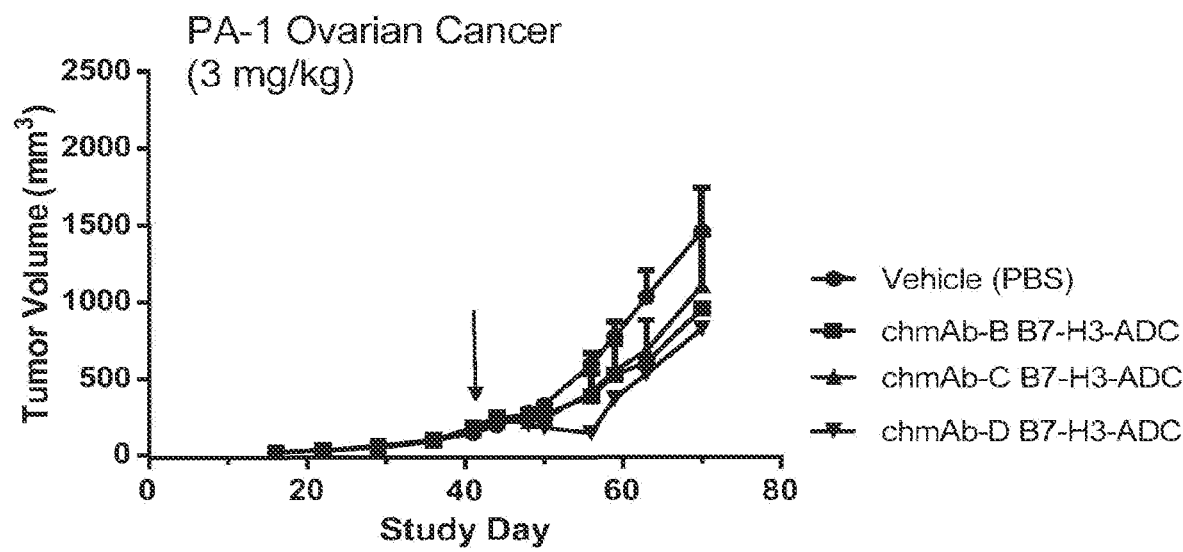
Figure 11C:
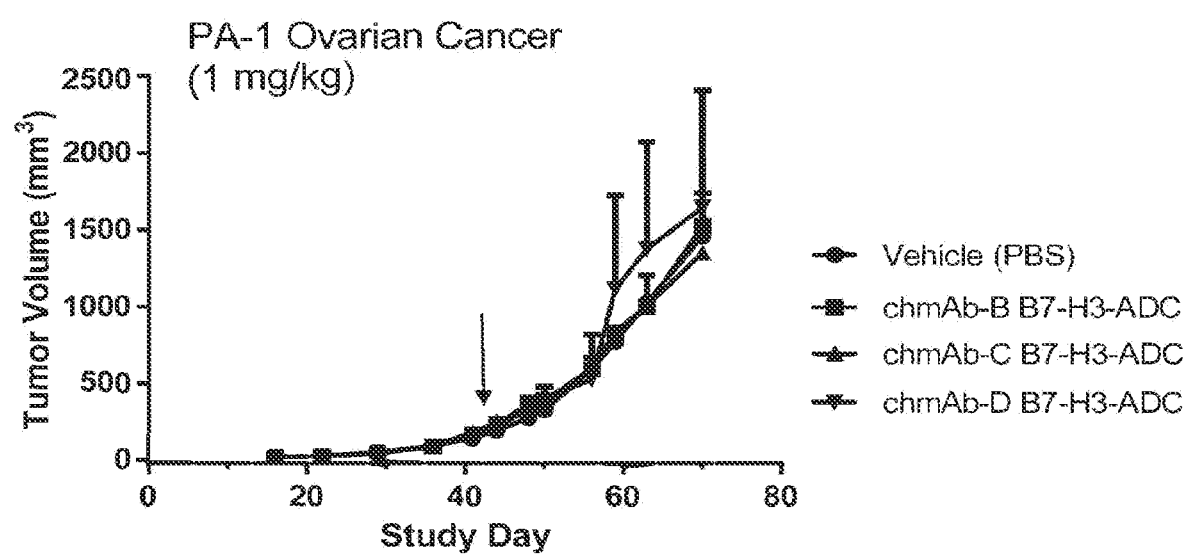

The results of this study with respect to subcutaneously implanted PA-1 ovarian cancer tumor cells are presented in Table 12 and in FIGS. 11A-11C, and show responsiveness against the PA-1 tumor cells.

TABLE 12

| Treatment (Initial Dose on Day 42) | Dose (mg/kg) | T/C | CR Response |
|---|---|---|---|
| chmAb-B B7-H3-ADC | 10 | 0 | 6/7 Highly Active |
| | 3 | 65 | 0/7 Active |
| | 1 | 105 | 0/7 Not Active |
| chmAb-C B7-H3-ADC | 10 | 37 | 3/7 Highly Active |
| | 3 | 76 | 1/7 Active |
| | 1 | 93 | 0/7 Not Active |
| chmAb-D B7-H3-ADC | 10 | 11 | 7/7 Highly Active |
| | 3 | 57 | 1/7 Active |
| | 1 | 113 | 0/7 Not Active |

In Vivo Activity Against Calu-6 Non-Small Cell Lung Cancer Tumor Cells

Figure 12A:
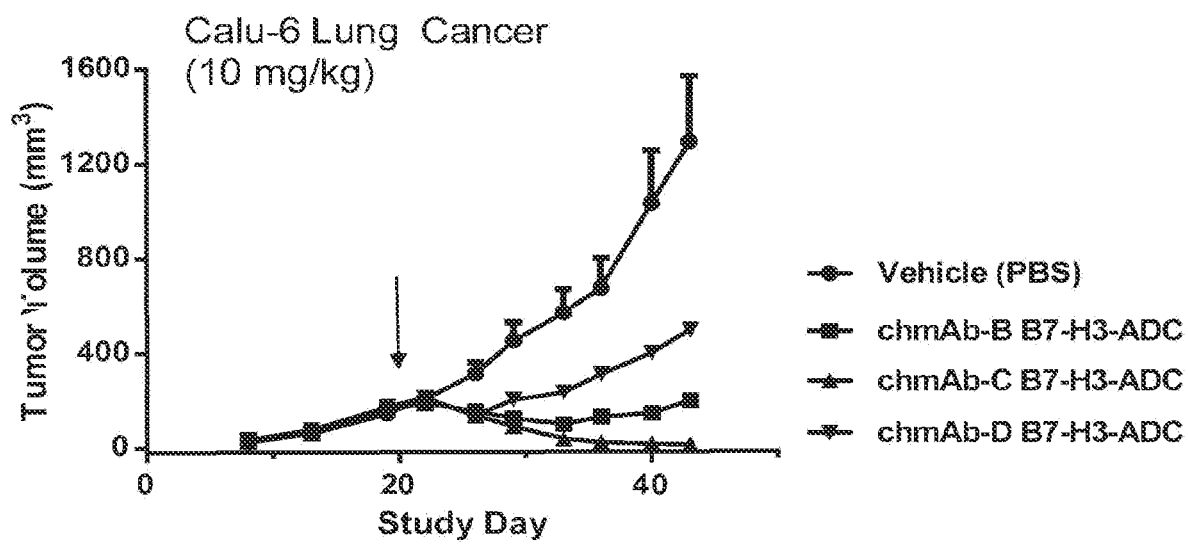
FIGS. 12A-12C shows the results of a study of the ability of the B7-H3-ADC of the present invention to mediate in vivo cytotoxicity against subcutaneously implanted Calu-6 non-small cell lung cancer tumor cells in a CD1 nude mouse model. The tumor growth curves are presented for mice treated intraperitoneally with 10 mg/kg (FIG. 12A), 3 mg/kg (FIG. 12B), 1 mg/kg (FIG. 12C) chmAb-B-vc-MMAE, chmAb-C-vc-MMAE, and chmAb-D-vc-MMAE at 10 mg/kg or vehicle alone on Day 20 (shown by arrow).
Figure 12B:
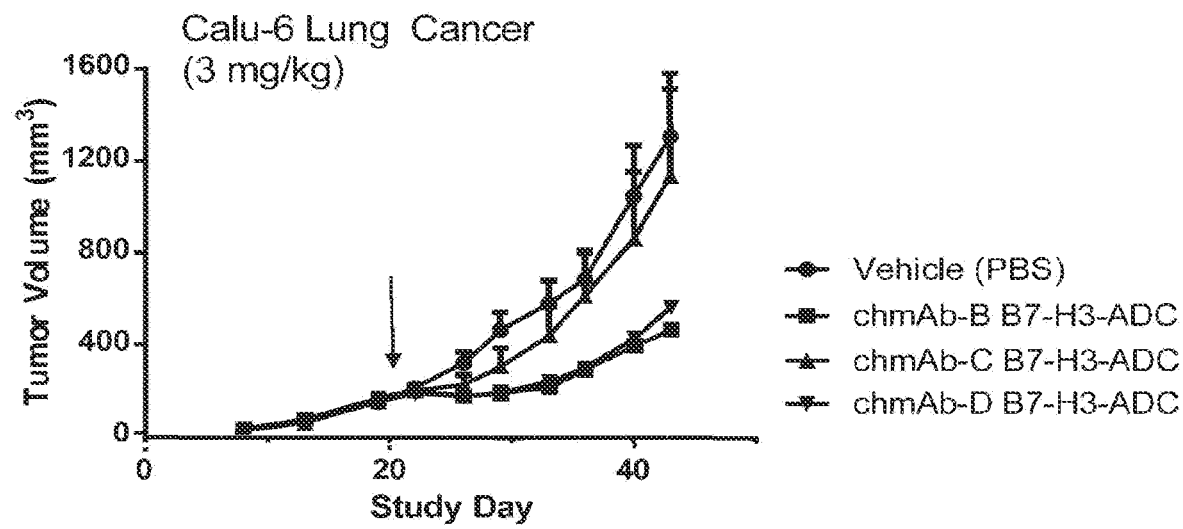
Figure 12C:
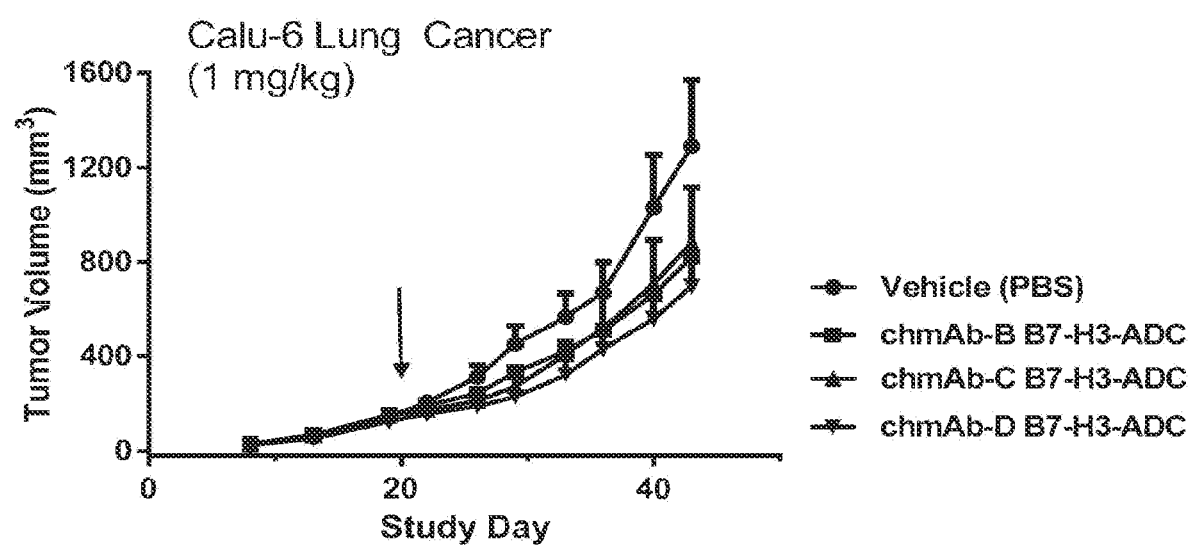

The results of this study with respect to subcutaneously implanted Calu-6 non-small cell lung cancer tumor cells are presented in Table 13 and in FIGS. 12A-12C, and show responsiveness against the Calu-6 tumor cells.

TABLE 13

| Treatment (Initial Dose on Day 20) | Dose (mg/kg) | T/C | CR Response |
|---|---|---|---|
| chmAb-B B7-H3-ADC | 10 | 15 | 3/7 Highly Active |
|  | 3 | 35 | 0/7 Active |
|  | 1 | 64 | 0/7 Active |
| chmAb-C B7-H3-ADC | 10 | 1 | 3/7 Highly Active |
|  | 3 | 87 | 0/7 Not Active |
|  | 1 | 68 | 0/7 Active |
| chmAb-D B7-H3-ADC | 10 | 39 | 2/7 Highly Active |
|  | 3 | 43 | 0/7 Active |
|  | 1 | 54 | 0/7 Active | in vivo Activity Against A375. S2 Melanoma Tumor Cells

Figure 13A:
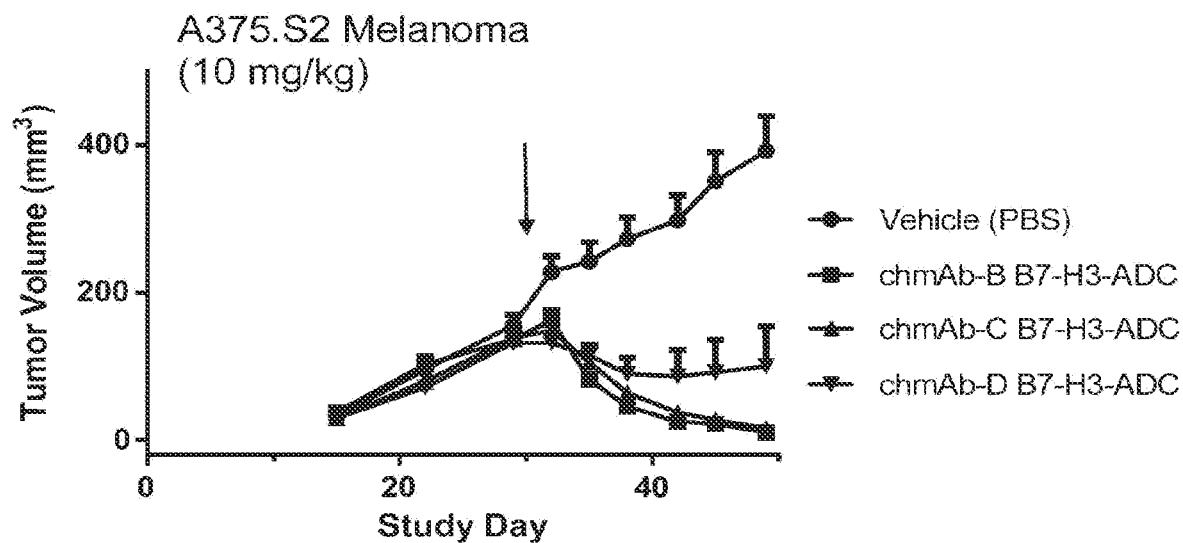
FIGS. 13A-13C shows the results of a study of the ability of the B7-H3-ADC of the present invention to mediate in vivo cytotoxicity against subcutaneously implanted A375. S2 melanoma cells in a CD1 nude mouse model. The tumor growth curves are presented for mice treated intraperitoneally with 10 mg/kg (FIG. 13A), 3 mg/kg (FIG. 13B), 1 mg/kg (FIG. 13C) chmAb-B-vc-MMAE, chmAb-C-vc-MMAE, and chmAb-D-vc-MMAE at 10 mg/kg or vehicle alone on Day 30 (shown by arrow).
Figure 13B:
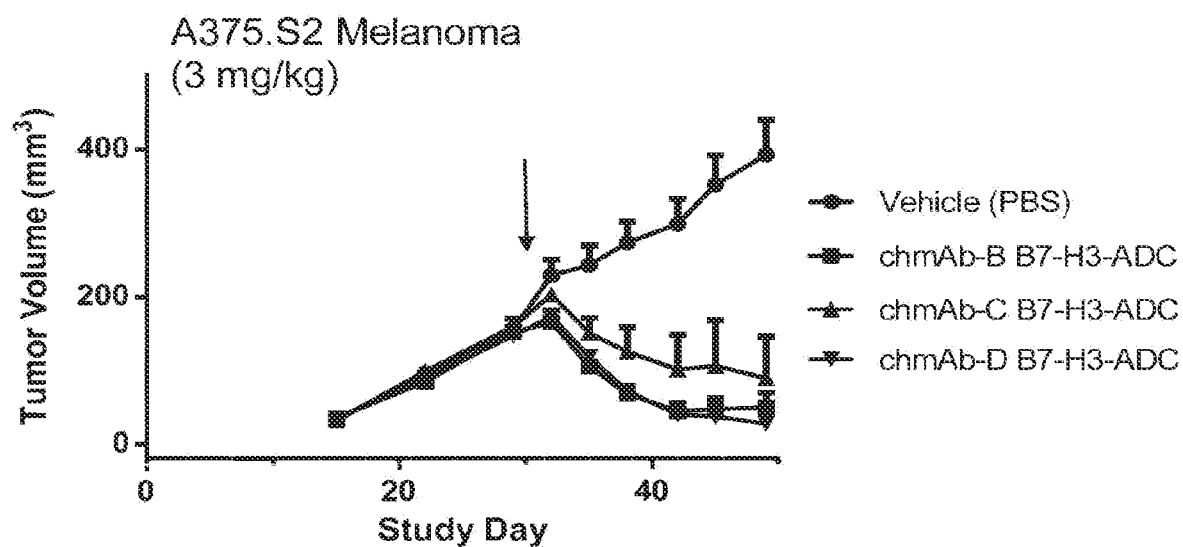
Figure 13C:
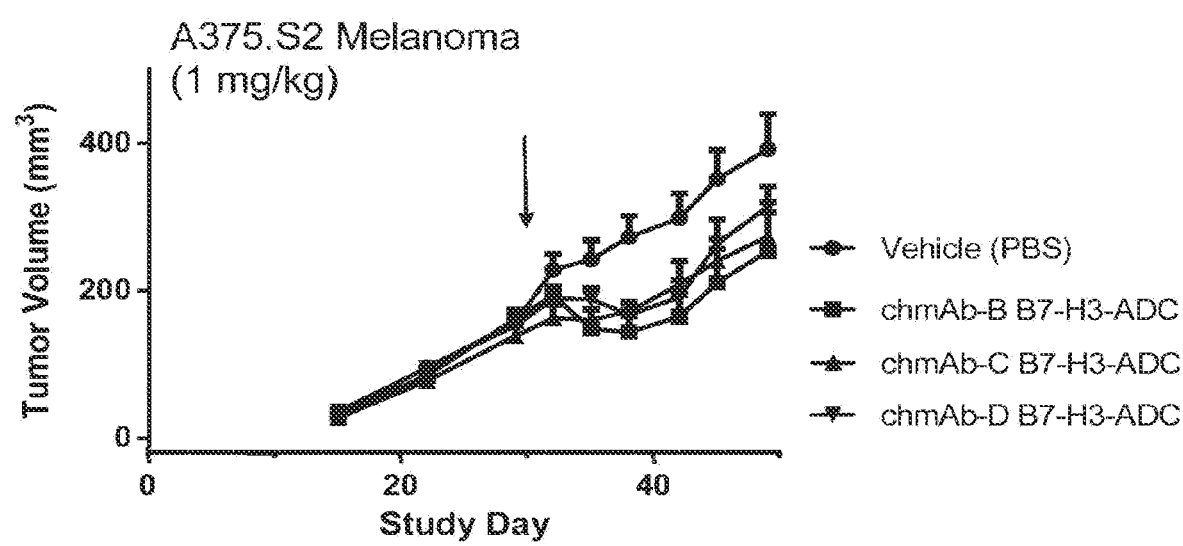

The results of this study with respect to subcutaneously implanted A375. S2 melanoma tumor cells are presented in Table 14 and in FIGS. 13A-13C, and show responsiveness against the A375. S2 melanoma cells.

TABLE 14

| Treatment (Initial Dose on Day 20) | Dose (mg/kg) | T/C | CR Response |
|---|---|---|---|
| chmAb-B B7-H3-ADC | 10 | 3 | 2/7 Highly Active |
|  | 3 | 13 | 0/7 Highly Active |
|  | 1 | 65 | 0/7 Active |
| chmAb-C B7-H3-ADC | 10 | 4 | 1/7 Highly Active |
|  | 3 | 23 | 0/7 Highly Active |
|  | 1 | 70 | 0/7 Active |
| chmAb-D B7-H3-ADC | 10 | 26 | 0/7 Highly Active |
|  | 3 | 7 | 0/7 Highly Active |
|  | 1 | 80 | 0/7 Active |

The results of these studies demonstrate that each of the B7-H3-ADCs tested exhibited significant dose-dependent in vivo anti-tumor activity toward B7-H3-positive tumors in murine xenograft models of breast, lung and ovarian cancers as well as melanoma.

The pharmacokinetics of the above B7-H3-ADC (MMAE) molecules was evaluated in non-tumor bearing CD1 nude mice by administering such molecules intraperitoneally at a single dose of 5 mg/kg. Blood samples were collected over the course of 10 days and sandwich ELISAs were performed on the sera to quantify total antibody and intact B7-H3-ADC concentrations.

Figure 14A:
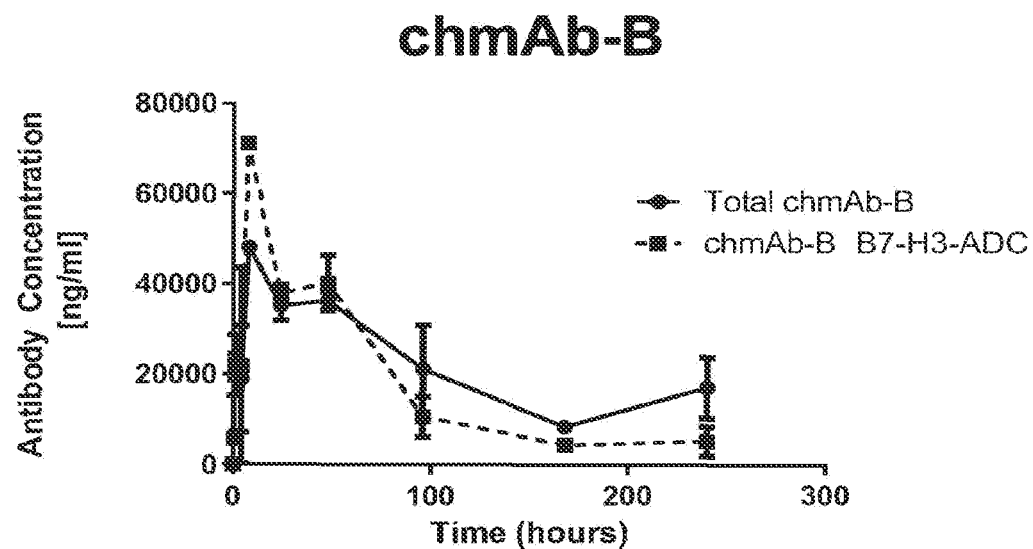
FIGS. 14A-14C shows the results of a study of the pharmacokinetic stability of B7-H3-ADC molecules. The serum antibody concentration cuves are presented for total antibody (circles) and intact B7-H3-ADC (squares) derived from chmAb-B (FIG. 14A), chmAb-C(FIG. 14B), and chmAb-D (FIG. 14C).
Figure 14B:
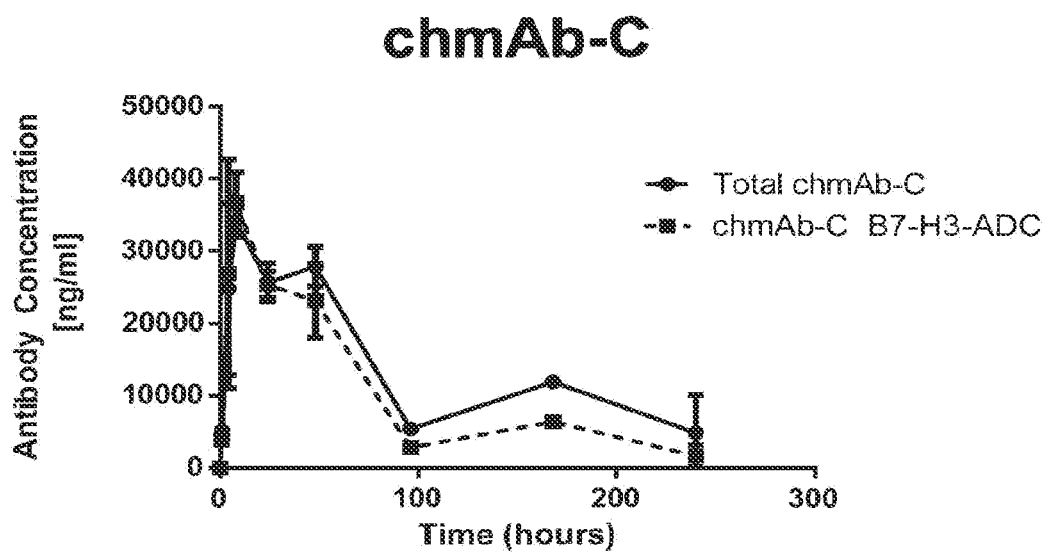
Figure 14C:
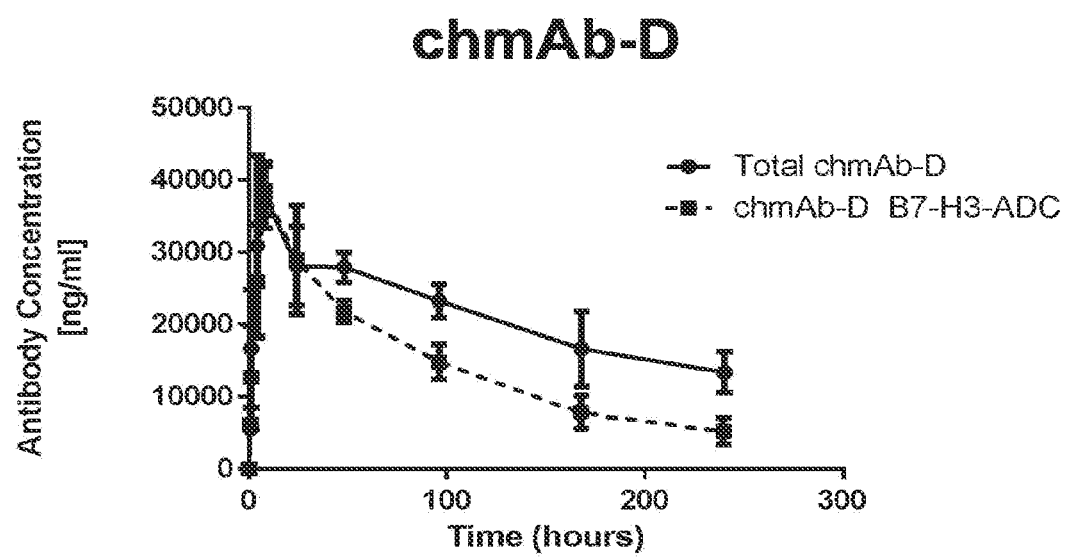

Representative results of this study, with respect to chmAb-B B7-H3 ADC, chmAb-C B7-H3 ADC, and chmAb-D B7-H3 ADC, are presented in FIGS. 14A-14C and in Table 15, and show that the B7-H3-ADC molecules were highly stable, exhibiting half-lives of approximately 2.2-3.6 days. The half-life of the conjugates was comparable to that of the unconjugated molecules, demonstrating that B7-H3-ADC molecules are highly stable in mice.

TABLE 15

| | Total Anti-B7-H3 Antibody | | Intact B7-H3-ADC* | |
|---|---|---|---|---|
| B7-H3-ADC | $T_{1/2}$ (hours) | AUC (hr*ng/mL) | $T_{1/2}$ (hours) | AUC (hr*ng/mL) |
| chmAb-B B7-H3 ADC | 114.1 | 4,796,235 | 58.9 | 4,032,575 |
| chmAb-C B7-H3 ADC | 75.9 | 2,698,831 | 52.6 | 2,201,893 |
| chmAb-D B7-H3 ADC | 177.2 | 5,162,024 | 87.3 | 3,502,158 |

*MMAE conjugate

Example 5

B7-H3-ADC Having Cleavable Linker-Duocarmycin Moiety

A B7-H3-ADC is constructed ("hmAb-C B7-H3-ADC") having an exemplary duocarmycin moiety (DUBA) linked to an amino acid residue of the Ab portion thereof via a cleavable linker conjugated to the antibody via reduced inter-chain disulfides, as described above (see Schemes 9A-9I) and in Elgersma, R. C. et al. (2014) "Design, Synthesis, and Evaluation of Linker-Duocarmycin Payloads: Toward Selection of HER2- Targeting Antibody-Drug Conjugate SYD985," Mol. Pharmaceut. 12:1813-1835 (see, also WO 02/083180; WO 2010/062171; WO 2011/133039; WO 2015/104359; and WO 2015/185142). The average Drug to antibody Ratio (DAR) is about 2-4, typically about 2.7. It will be understood that the exact DAR may vary for each preparation. The order of the steps of the synthesis may be varied as desired. Preferably, the method used will be that of Schemes 9A-9I, as described above, and the linker-DUBA is conjugated to the antibody via reduced inter-chain disulfides.

Example 6

Figure 15A:
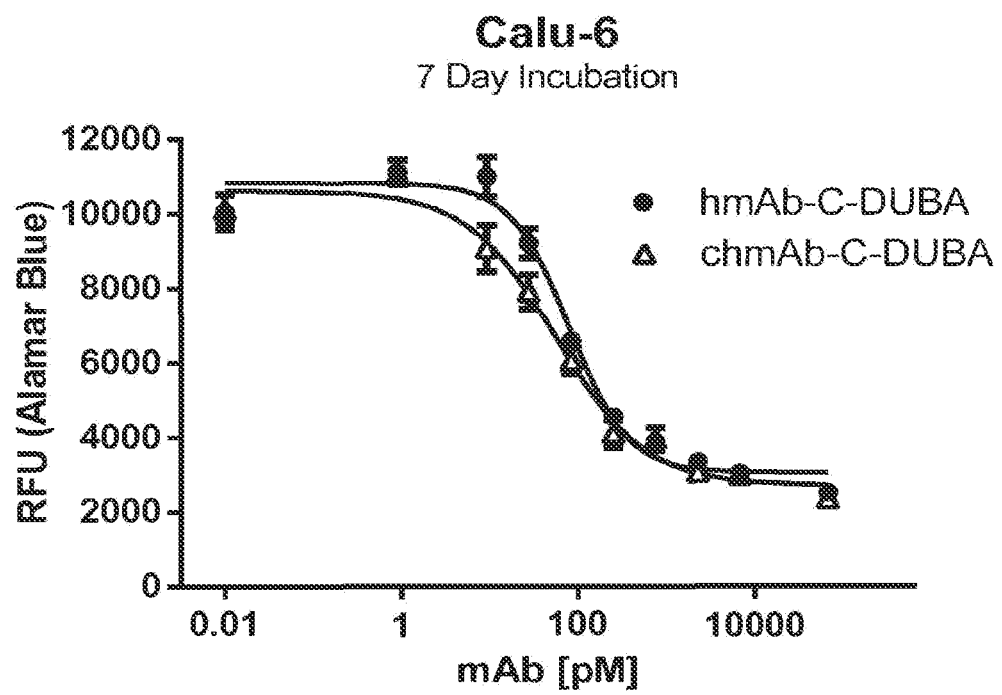
FIGS. 15A-15C show the retention of biological activity by hmAb-C B7-H3-ADC having an exemplary duocarmycin moiety (DUBA) linked to an amino acid residue of the Ab portion thereof via a cleavable linker ("hmAb-C-DUBA").
Figure 15B:
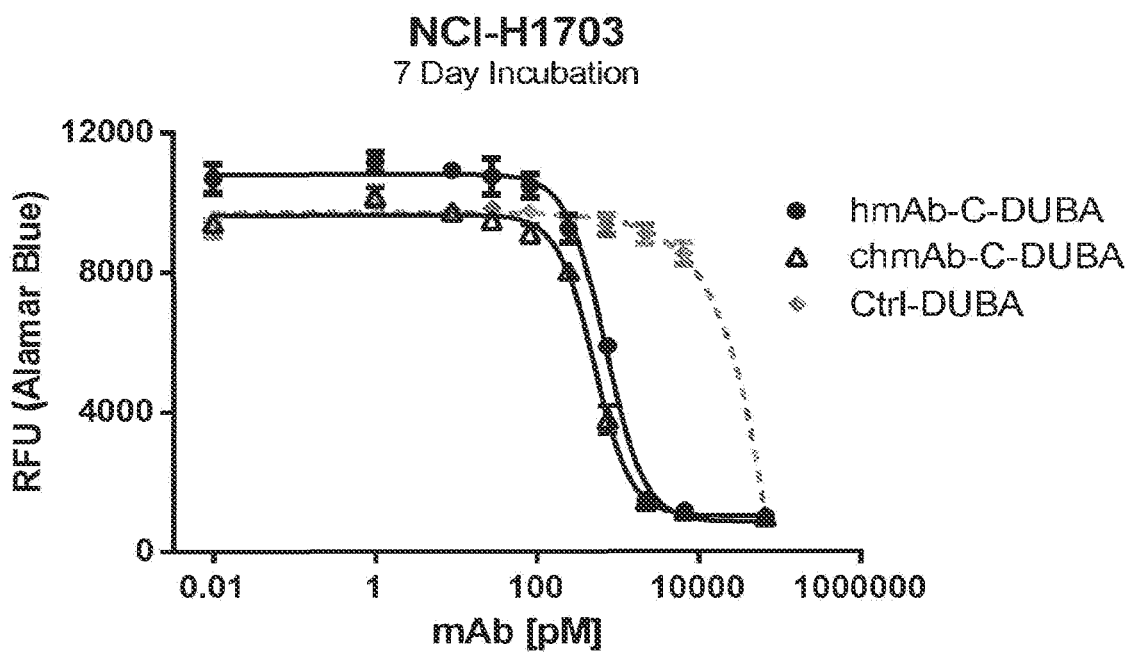
Figure 15C:
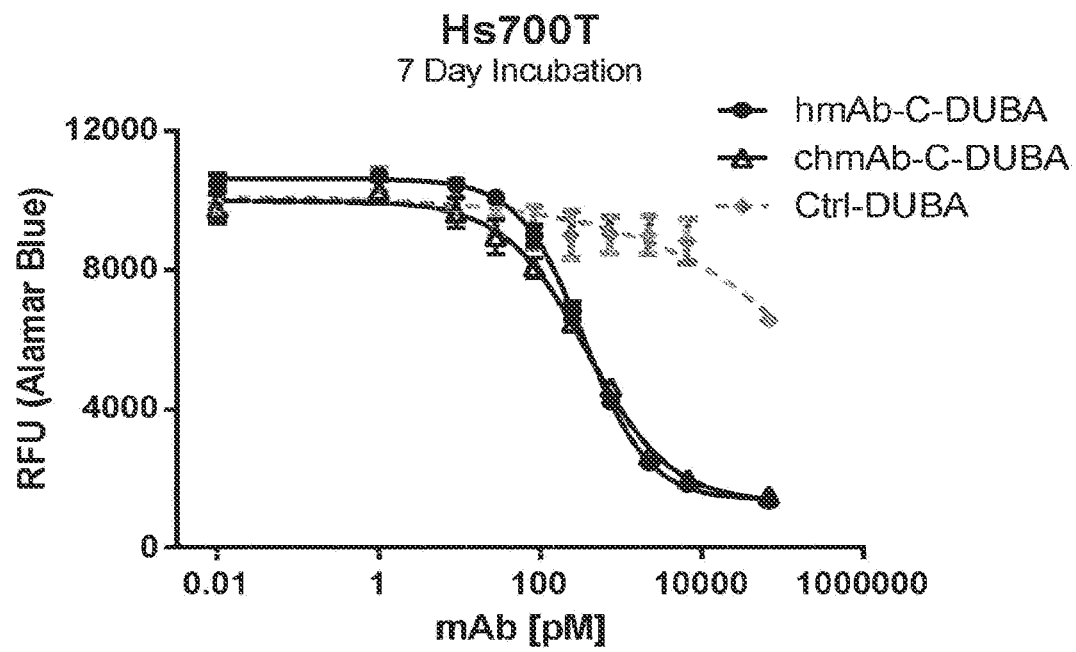

B7-H3-ADC Having Cleavable Linker-Duocarmycin Moiety Retains Biological Activity The above-described hmAb-C B7-H3-ADC (having an exemplary duocarmycin moiety (DUBA) linked to an amino acid residue of the Ab portion thereof via a cleavable linker) ("hmAb-C-DUBA") was incubated with cells for 7 days and viability was determined using an Alamar blue assay essentially as described above. As shown in FIGS. 15A-15C, the hmAb-C-DUBA construct retained biological activity, as evidenced by its cytotoxic activity on B7-H3 postive tumor cells. Similar results were observed for the above-described chmAb-C linked to duocarmycin ("chmAb-C-DUBA").

In this study and additional studies described below, a molecule that binds an unrelated antigen (CD20) conjugated to DUBA ("Ctrl-DUBA") was used as a non-binding control ADC to account for non-specific activity in vivo due to rodent-specific carboxyesterase CES1c present in rodent plasma.

Example 7

B7-H3-ADC Exhibits Potent Anti-Tumor Activity In Vivo

Figure 16:
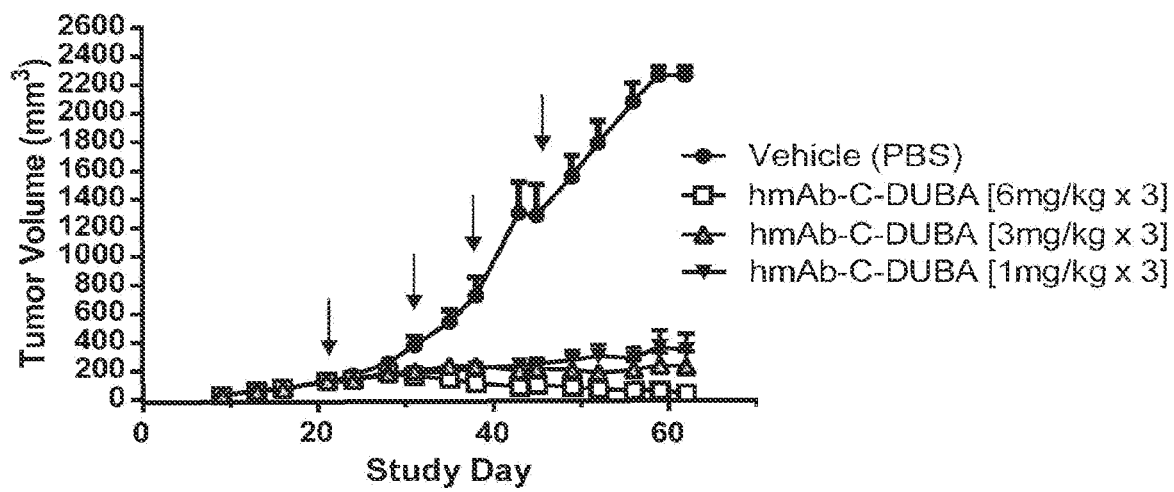
FIG. 16 shows the results of an in vivo study of the efficacy of hmAb-C-DUBA Calu-6 non-small cell lung carcinoma cells. hmAb-C-DUBA was introduced into groups of mice (n=5) that had been subcutaneously inoculated with Calu-6 non-small cell lung carcinoma cells. Doses of hmAb-C-DUBA (1 mg/kg×3, 3 mg/kg×3, or 6 mg/kg×3) were provided intraperitoneally to the mice at Day 24, 31, 38 and 45 (shown by arrows) post inoculation, and the animals were evaluated for tumor volume for up to 62 days.

A multidose study was undertaken in order to assess the in vivo efficacy of the molecule. Calu-6 non-small cell lung carcinoma cells were subcutaneously implanted into groups of mice (n=5) essentially as described above, which then received doses of hmAb-C-DUBA (1 mg/kg×3, 3 mg/kg×3, or 6 mg/kg×3) at Day 24, 31, 38 and 45 (shown by arrows) post inoculation, and the animals were evaluated for tumor volume (essentially as described above) for up to 62 days. As shown in FIG. 16, all three tested doses of hmAb-C-DUBA proved to be effective in reducing or eliminating tumor volume. Calu-6 cells exhibited an IHC score of 2+ and the Antibody Binding Sites per Cell (ABC) is reported in Table 9.

Figure 17:
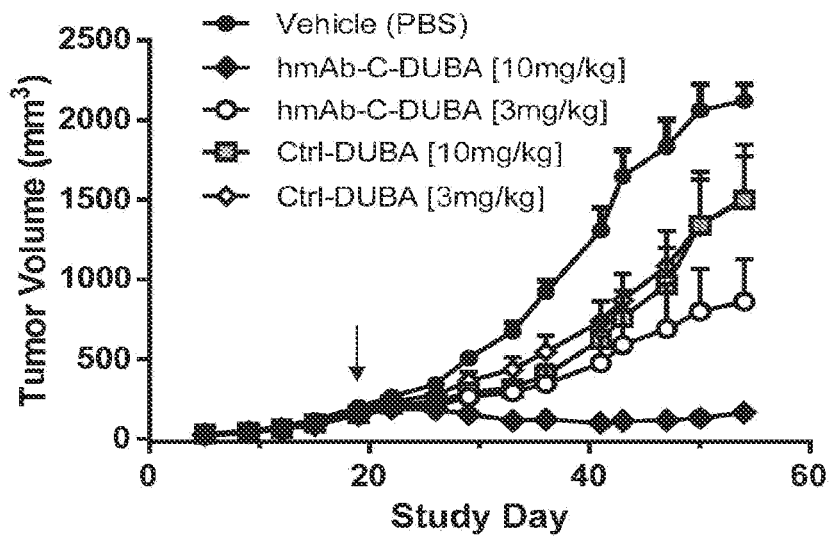
FIG. 17 shows the results of an in vivo study of the efficacy of hmAb-C-DUBA against Calu-6 non-small cell lung carcinoma cells. hmAb-C-DUBA was introduced into groups of mice (n=7) that had been subcutaneously inoculated with Calu-6 non-small cell lung carcinoma cells. A dose of hmAb-C-DUBA or Ctrl-DUBA (3 mg/kg or 10 mg/kg) was provided to the mice at Day 20 (shown by arrow) post inoculation, and the animals were evaluated for tumor volume for up to 55 days.

In a second in vivo study (performed essentially as described above), Calu-6 non-small cell lung carcinoma cells were subcutaneously implanted into groups of mice (n=7), which then received a single dose of hmAb-C-DUBA or Ctrl-DUBA (3 mg/kg or 10 mg/kg) at Day 20 (shown by arrow). Table 16 and FIG. 17 summarize the results, and show that the provision of hmAb-C-DUBA significantly decreased tumor volume.

TABLE 16

| Treatment | Dose - QW (mg/kg) | Tumor Volume Treatment/Control % | Complete Remission |
|---|---|---|---|
| hmAb-C-DUBA | 10 | 8 | 0/7 |
| hmAb-C-DUBA | 3 | 41 | 0/7 |
| Ctrl-DUBA | 10 | 71 | 0/7 |
| Ctrl-DUBA | 3 | 71 | 0/7 |

Figure 18:
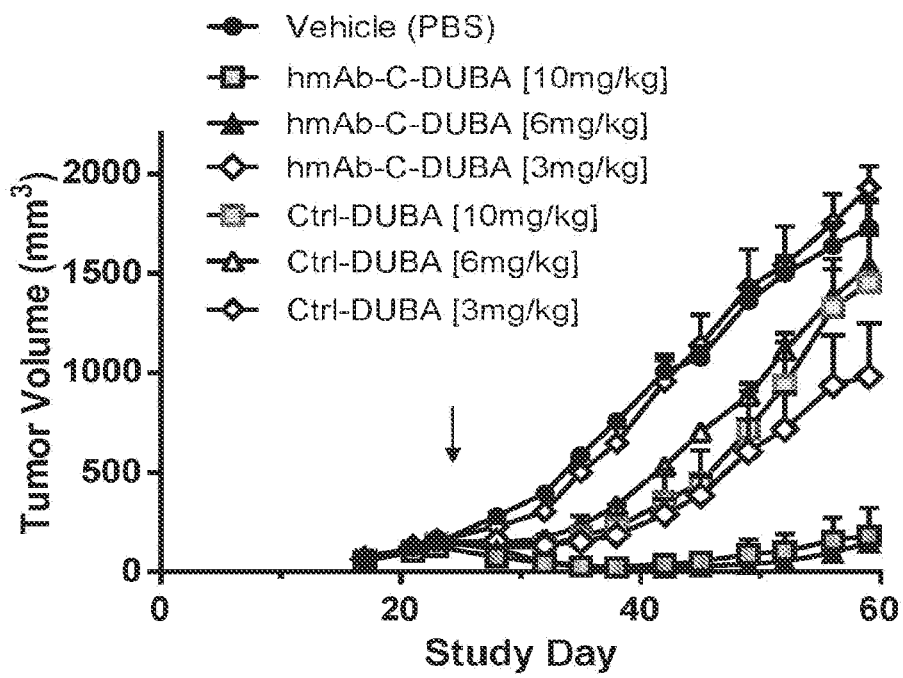
FIG. 18 shows the results of an in vivo study of the efficacy of hmAb-C-DUBA against PA-1 ovarian carcinoma cells. hmAb-C-DUBA or Ctrl-DUBA was introduced into groups of mice (n=6) that had been subcutaneously inoculated with PA-1 ovarian carcinoma cells. A dose of hmAb-C-DUBA or Ctrl-DUBA (3 mg/kg, 6 mg/kg or 10 mg/kg) was provided to the mice at Day 25 (shown by arrow) post inoculation, and the animals were evaluated for tumor volume for up to 60 days.

In a third in vivo study (performed essentially as described above), PA-1 ovarian carcinoma cells were subcutaneously implanted into groups of mice (n=6), which then received a single dose of hmAb-C-DUBA or Ctrl-DUBA (1 mg/kg, 6 mg/kg or 10 mg/kg) at Day 25 (shown by arrow). Table 17 and FIG. 18 summarize the results, and show that the provision of hmAb-C-DUBA significantly decreased tumor volume, and achieved complete remission of up to half the treated animals.

TABLE 17

| Treatment | Dose - QW (mg/kg) | Tumor Volume Treatment/Control % | Complete Remission |
|---|---|---|---|
| hmAb-C-DUBA | 10 | 11 | 3/6 |
| hmAb-C-DUBA | 6 | 9 | 2/6 |
| hmAb-C-DUBA | 3 | 57 | 1/6 |
| Ctrl-DUBA | 10 | 84 | 0/6 |
| Ctrl-DUBA | 6 | 89 | 0/6 |
| Ctrl-DUBA | 3 | 111 | 0/6 |

Figure 19:
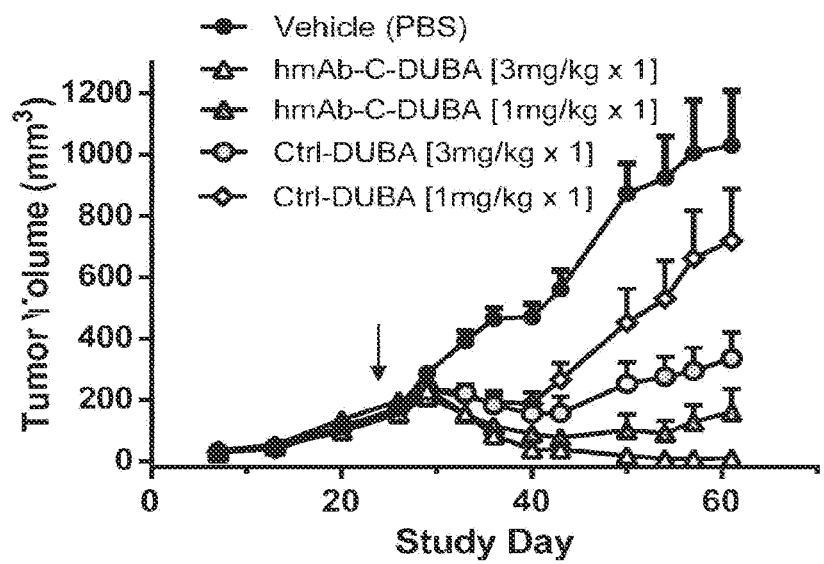
FIG. 19 shows the results of an in vivo study of the efficacy of hmAb-C-DUBA against A375. S2 melanoma cells. hmAb-C-DUBA or Ctrl-DUBA was introduced into groups of mice (n=7) that had been subcutaneously inoculated with A375. S2 melanoma cells. A dose of hmAb-C-DUBA or Ctrl-DUBA (1 mg/kg or 3 mg/kg) was provided to the mice at Day 25 (shown by arrow) post inoculation, and the animals were evaluated for tumor volume for up to 60 days.

Potent in vivo activity was also observed against A375.S2 melanoma cells. Such cells were subcutaneously implanted into groups of mice (n=7) (essentially as described above), which then received a single dose of hmAb-C-DUBA or Ctrl-DUBA (1 mg/kg or 3 mg/kg) at Day 25 (shown by arrow). Table 18 and FIG. 19 summarize the results, and show that the provision of hmAb-C-DUBA significantly decreased tumor volume, and achieved complete remission in 5/7 treated animals at the higher dose tested.

TABLE 18

| Treatment | Dose - QW (mg/kg) | Tumor Volume Treatment/Control % | Complete Remission |
|---|---|---|---|
| hmAb-C-DUBA | 3 | 1 | 5/7 |
| hmAb-C-DUBA | 1 | 16 | 1/7 |
| Ctrl-DUBA | 3 | 33 | 0/7 |
| Ctrl-DUBA | 1 | 70 | 1/7 |

Figure 20A:
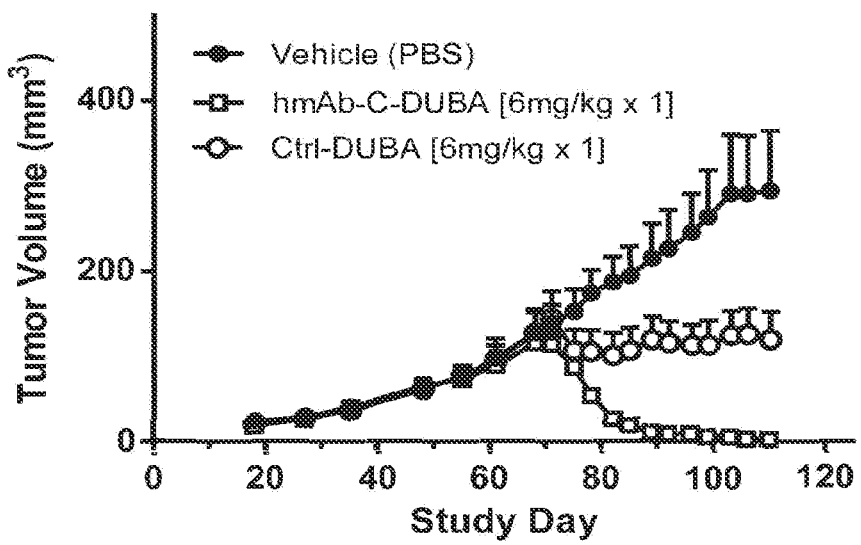
FIGS. 20A-20D show the results of an in vivo study of the efficacy of hmAb-C-DUBA against fat pad xenographs of MDA-MB468 breast carcinoma cells. hmAb-C-DUBA or Ctrl-DUBA was administered intraperitoneally into groups of mice at days 70, 74 and 78 after being inoculated with MDA-MB468 breast carcinoma cells in the mammary fat pad. A dose of hmAb-C-DUBA or Ctrl-DUBA (either a single dose of 3 mg/kg or 6 mg/kg) at Day 70 or three doses of 3 mg/kg at days 70, 74 and 78 (shown by arrows) was provided post inoculation, and the animals were evaluated for tumor volume for up to 110 days.
Figure 20B:
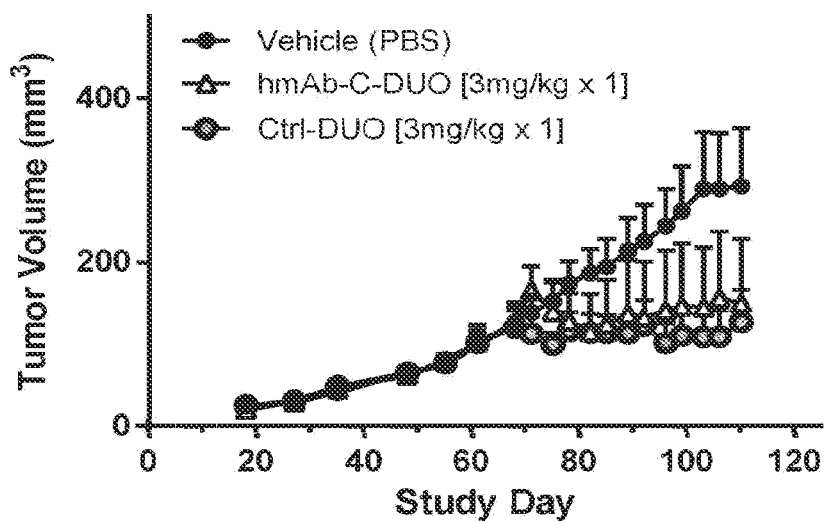
Figure 20C:
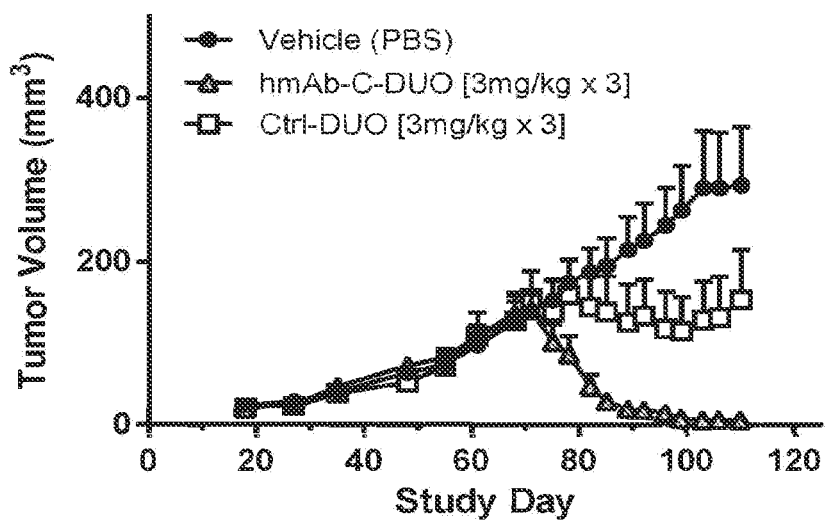
Figure 20D:
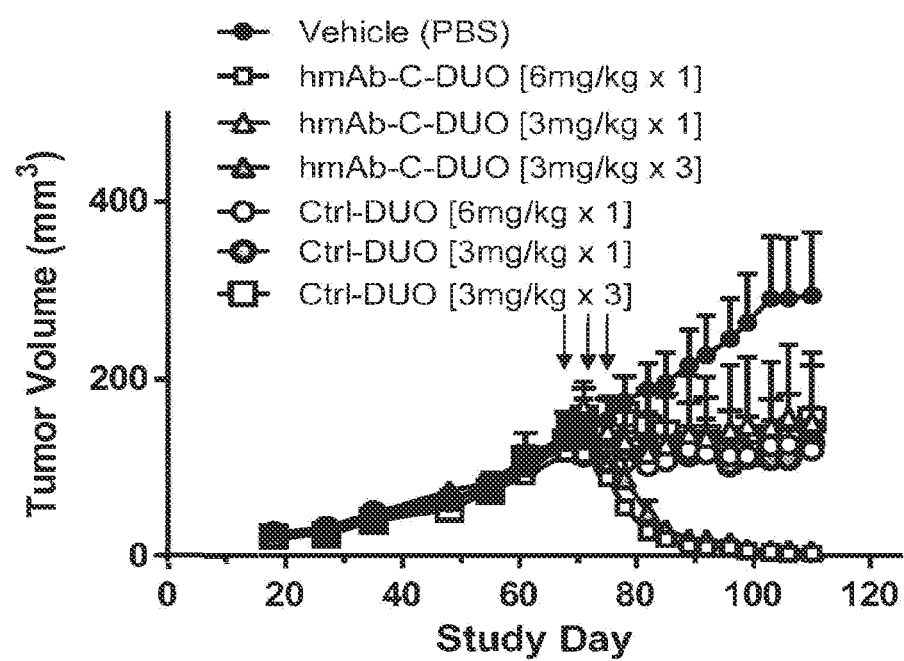

Potent in vivo activity was observed against MDA-MB468 breast carcinoma cells. Such cells were implanted into the mammary fat pads of groups of mice (n=5) (essentially as described above), which then received either a single dose of hmAb-C-DUBA or Ctrl-DUBA (3 mg/kg or 6 mg/kg) at Day 70 or three doses of hmAb-C-DUBA or Ctrl-DUBA (3 mg/kg (shown by arrows). The animals were evaluated for tumor volume (essentially as described above) for up to 110 days. MDA-MB468 cells exhibited an IHC score of 2+, and the ABC is reported in Table 9. Table 19 and FIGS. 20A-20D summarize the results. FIG. 20A shows results for vehicle, hmAb-C-DUBA or Ctrl-DUBA at 6 mg/kg (single dose). FIG. 20B shows results for vehicle, hmAb-C-DUBA or Ctrl-DUBA at 3 mg/kg (single dose). FIG. 20C shows results for vehicle, hmAb-C-DUBA or Ctrl-DUBA at 3 mg/kg (three doses). FIG. 20D shows all of the results on a single graph. The data show that the provision of hmAb-C-DUBA significantly decreased tumor volume, and achieved complete remission in 4/5 treated animals at the higher dose tested, and that provision of replicate doses markedly improved the treatment outcome.

TABLE 19

| Treatment | Dose - QW (mg/kg) | Tumor Volume Treatment/Control % | Complete Remission |
|---|---|---|---|
| hmAb-C-DUBA | 6 | 1 | 4/5 |
| hmAb-C-DUBA | 3 | 51 | 1/5 |
| hmAb-C-DUBA | 3 × 3 doses | 2 | 3/5 |
| Ctrl-DUBA | 6 | 41 | 0/5 |
| Ctrl-DUBA | 3 | 43 | 0/5 |
| Ctrl-DUBA | 3 × 3 doses | 53 | 0/5 |

Figure 21A:
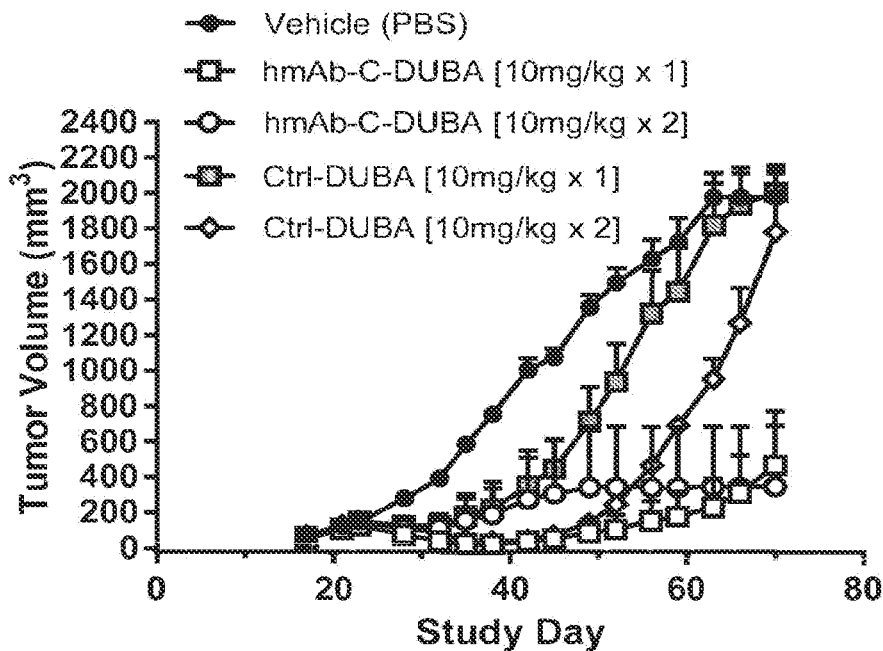
FIGS. 21A-21D show the results of an in vivo study of the efficacy of hmAb-C-DUBA against subcutaneously implanted xenographs of PA-1 ovarian carcinoma cells. hmAb-C-DUBA or Ctrl-DUBA was administered intraperitoneally (either a single dose of 3 mg/kg, 6 mg/kg or 10 mg/kg) at day 24 post-inoculation, or two doses of 10 mg/kg hmAb-C-DUBA or Ctrl-DUBA (at days 24 and 28 post-inoculation) or four doses of 6 mg/kg hmAb-C-DUBA or Ctrl-DUBA (at days 24, 28, 31 and 35 post-inoculation). The animals were evaluated for tumor volume for up to 70 days.
Figure 21B:
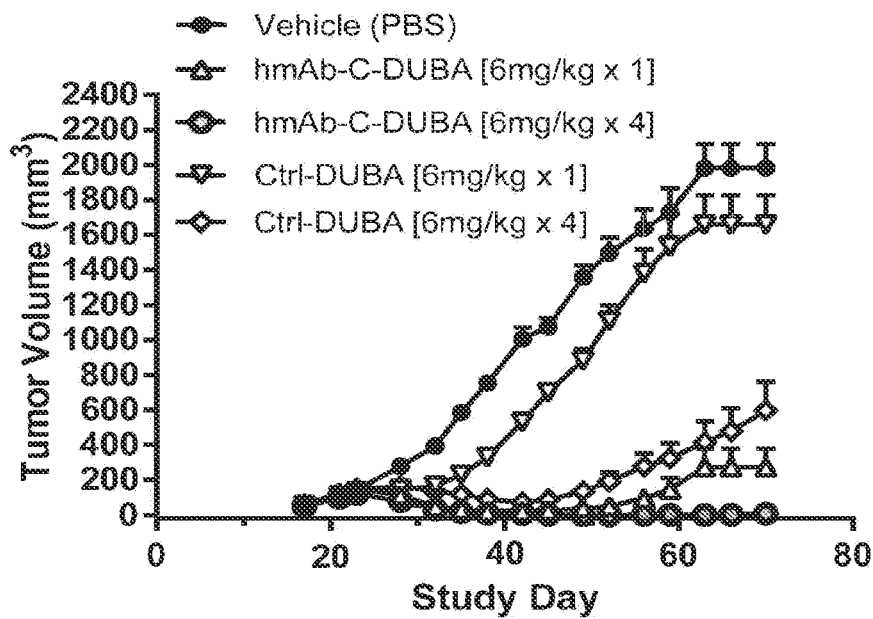
Figure 21C:
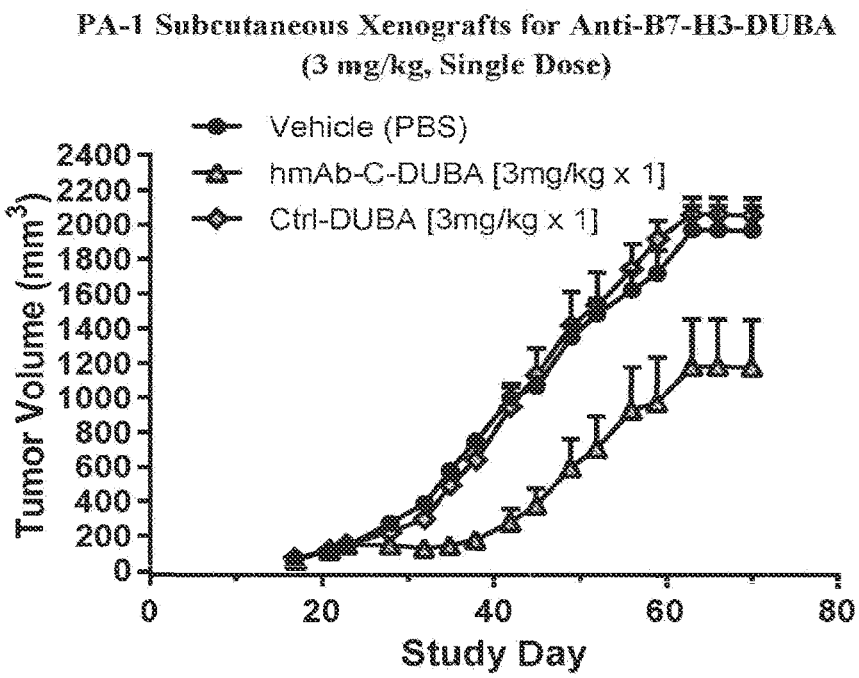
Figure 21D:
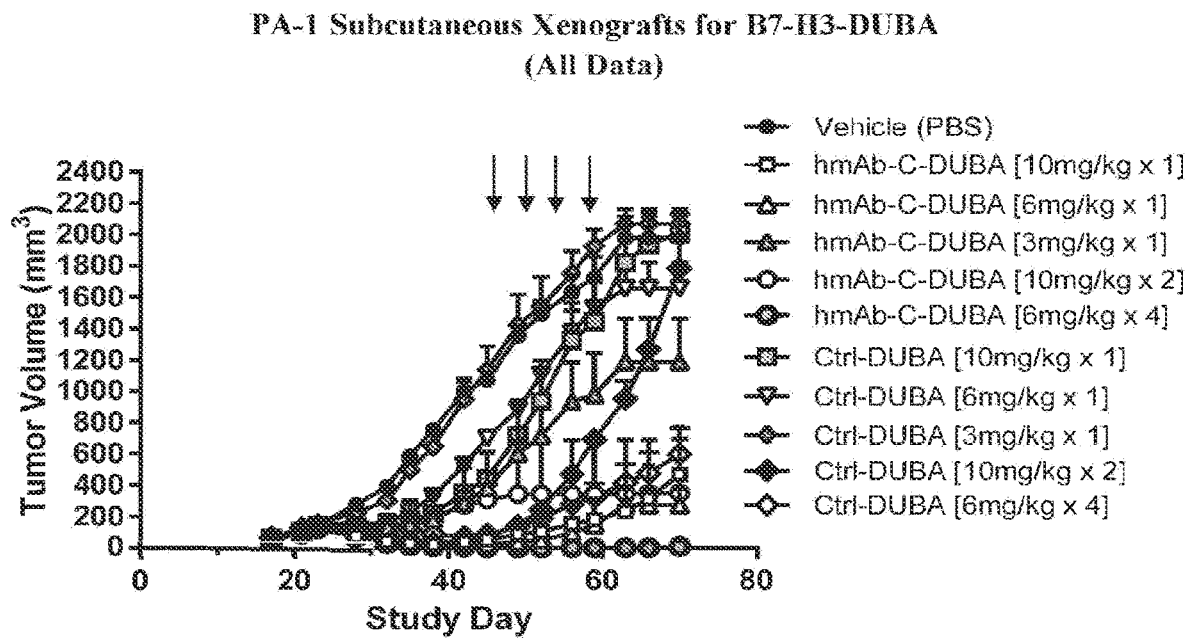

In a further study, xenographs of PA-1 ovarian carcinoma cells (~5×10$^6$ tumor cells suspended in 1:1 media and MATRIGEL®) were subcutaneously introduced into of groups of mice which then received a dose of hmAb-C-DUBA or Ctrl-DUBA (either a single dose of 3 mg/kg, 6 mg/kg or 10 mg/kg) at day 24 post-inoculation, or two doses of 10 mg/kg hmAb-C-DUBA (at days 24 and 28 post-inoculation) or four doses of 6 mg/kg hmAb-C-DUBA (at days 24, 28, 31 and 35 post-inoculation). The animals were evaluated for tumor volume for up to 70 days (essentially as described above). PA-1 cells exhibited an IHC score of 2+, and the ABC is reported in Table 9. FIGS. 21A-21D summarize the results. FIG. 21A shows results for vehicle, hmAb-C-DUBA or Ctrl-DUBA at 10 mg/kg (single or double dose). FIG. 21B shows results for vehicle, hmAb-C-DUBA or Ctrl-DUBA at 6 mg/kg (single or quadruple dose). FIG. 21C shows results for vehicle, hmAb-C-DUBA or Ctrl-DUBA at 3 mg/kg (single doses). FIG. 21D shows all of the results on a single graph. The data show that the provision of hmAb-C-DUBA significantly decreased tumor volume in treated animals.

Example 8

Pharmacokinetics of B7-H3-ADC

Figure 22:
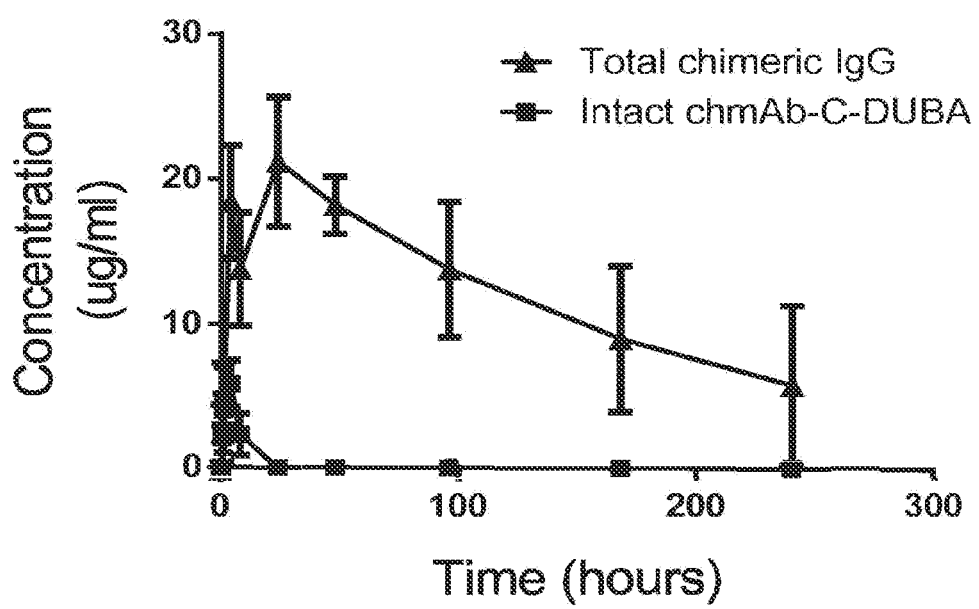
FIG. 22 shows the pharmacokinetics of chmAb-C-DUBA administration in mice. The figure shows total human IgG and intact ADC of chmAb-C-DUBA at 3 mg/kg (n=3).

The pharmacokinetics of the above-described chmAb-C-DUBA was investigated using a log/linear plot of total IgG or intact ADC curve in mice (n=3) that had each received a single intravenous dose of chmAb-C-DUBA (5 mg/kg). The results are shown in FIG. 22.

Figure 23A:
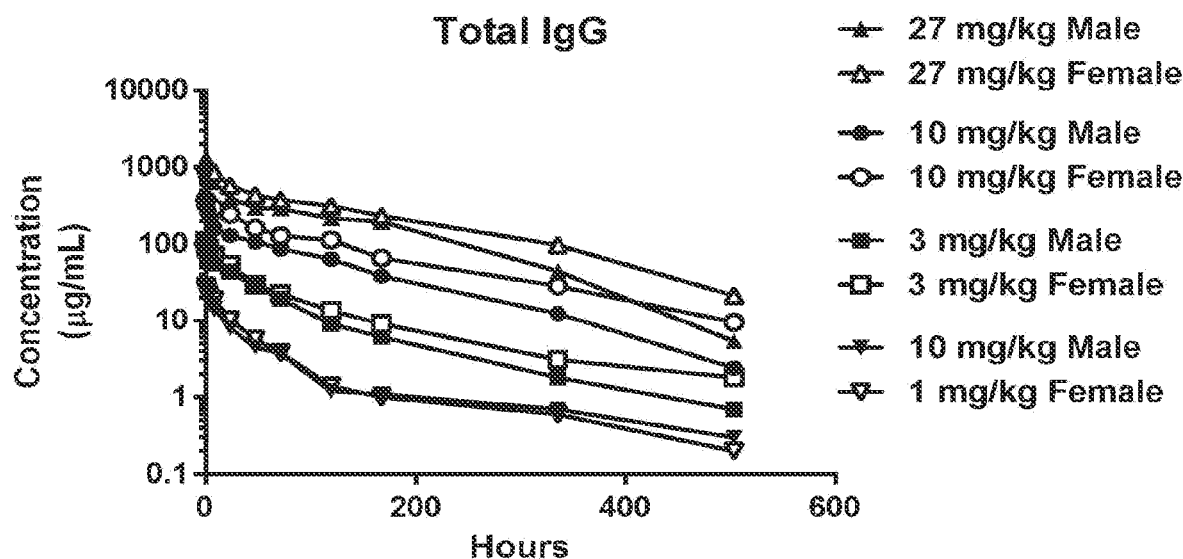
FIGS. 23A-23B show the pharmacokinetics of hmAb-C-DUBA administration in cynomolgus monkeys. The figures show total human IgG (FIG. 23A) and intact ADC (FIG. 23B) of hmAb-C-DUBA at 1 mg/kg (1 male; 1 female), 3 mg/kg (1 male; 1 female), 10 mg/kg (1 male; 1 female) or 27 mg/kg (2 males; 2 females)).
Figure 23B:
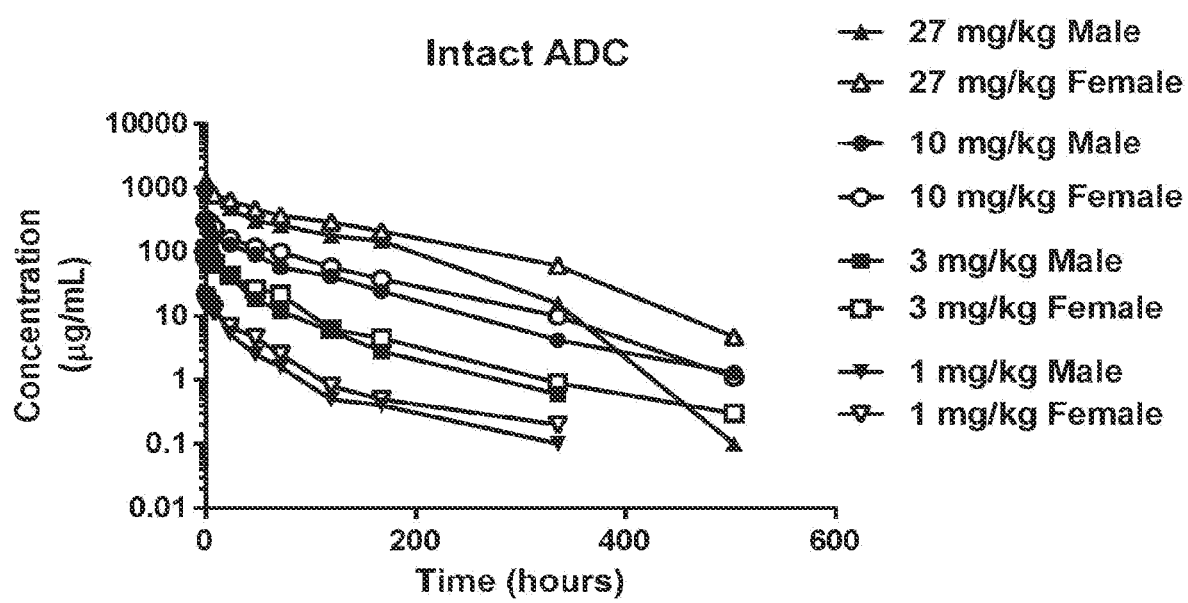

The pharmacokinetics of hmAb-C-DUBA was investigated using a log/linear plot of total IgG or intact ADC curve in cynomolgus monkeys that had each received a single intravenous dose of hmAb-C-DUBA (1 mg/kg (1 male; 1 female), 3 mg/kg (1 male; 1 female), 10 mg/kg (1 male; 1 female) or 27 mg/kg (2 males; 2 females)). The results are shown in FIG. 23A (total IgG) and FIG. 23B (intact ADC).

In these studies, total IgG was determined by ELISA. Briefly, Serum samples, standards and controls were captured on microtiter plates coated with goat anti-human IgG (H+L). Following washing, plates were incubated with peroxidase-conjugated goat anti-human IgG Fc. Following washing, plates were developed with 3, 3', 5, 5'-tetramethylbenzidine (TMB) substrate, the reaction was stopped with phosphoric acid, and the plates were read at 405 nM. Total IgG in the test samples was calculated from the standard curve. Intact ADC was also determined by ELISA. Briefly, Mouse anti-duocarmycin mAb was immobilized onto microtiter plates. Following washing, plates were incubated with peroxidase-conjugated goat anti-human IgG Fc. Following washing, plates were developed with 3, 3', 5, 5'-tetramethylbenzidine (TMB) substrate, the reaction was stopped with phosphoric acid, and the plates were read at 405 nM. Intact ADC in the test samples was calculated from the standard curve.

The pharmacokinetic parameters for the murine 5 mg/kg and the cynomolgus monkey 3 mg/kg and 10 mg/kg doses were deduced by comparing such data and are summarized in Table 20 (wherein AUC Last denotes area under curve from the origin to the last data point). Exposure in mouse of intact ADC is limited due to rodent-specific carboxyesterase CES1c. These data indicate a large therapeutic index in a preclinical setting.

TABLE 20

| Species | Dose (mg/kg) | $T_{1/2}$ (hr) | $C_{max}$ (ng/ml) | AUC Last (hr*µg/ml) |
|---|---|---|---|---|
| Mouse | 5 | ND | 5909 | 45 |
| Cyno | 3 | 62.7 | 113484 | 3798 |
| Cyno | 10 | 57.3 | 330983 | 17978 |

Example 9

Characterization of Anti-B7-H3 Diabodies

The B7-H3×CD3 bispecific two-chain and three-chain diabodies are evaluated to determine their ability to mediate redirected cell killing and/or cytokine release from target cells expressing cell surface B7-H3. Redirected cell killing is examined using a cytotoxic T lymphocyte (CTL) assay. Briefly, B7-H3×CD3 bispecific diabodies (or a negative control diabody that binds an irrelevant antigen instead of B7-H3) are incubated for 24 hours with effector pan T-cells and target B7-H3-expressing tumor cells at an effector to target cell ratio of 10:1. The percentage cytotoxicity (i.e., cell killing) is determined by measuring the release of lactate dehydrogenase (LDH) into the media by damaged cells. Cytokine release is examined using a similar format. Briefly, B7-H3×CD3 bispecific diabodies (or a negative control diabody lacking an B7-H3-binding site) are incubated for 24 hours with effector PBMC cells alone or in the presence of target tumor cells (e.g., SK-MES-1 lung carcinoma cells) at an effector to target cell ratio of 10:1 or 30:1 and the release of IFNγ, TNF-α, and IL-10 cytokines is determined. The analysis shows the ability of the B7-H3×CD3 bispecific diabodies to mediate redirected cell killing and cytokine release.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

---

What is claimed is:

1. An anti B7-H3 antibody drug conjugate (B7-H3-ADC) comprising the formula:

$$Ab\text{-}(LM)_m\text{-}(D)_n,$$

wherein:
Ab is a B7-H3 antibody or B7-H3 binding fragment thereof that binds to B7-H3 and comprises:
  (i) a Variable Light Chain (VL) domain comprising the amino acid sequence of SEQ ID NO:20; and
  (ii) a Variable Heavy Chain (VH) domain comprising the amino acid sequence of SEQ ID NO:21;
D is a cytotoxic drug moiety;
LM comprises at least one bond or a Linker Molecule that covalently links Ab and D;
m is an integer between 0 and n and denotes the number of Linker Molecules of the B7-H3-ADC; and
n is an integer between 1 and 10 and denotes the number of cytotoxic drug moieties covalently linked to the B7-H3-ADC molecule.

2. The B7-H3-ADC of claim 1, wherein said Ab further comprises an Fc domain of a human IgG.

3. The B7-H3-ADC of claim 2, wherein said human IgG is a human IgG1, IgG2, IgG3, or IgG4.

4. The B7-H3-ADC of claim 2, wherein said human IgG is said human IgG1.

5. The B7-H3-ADC of claim 2, wherein said Fc Domain is a variant Fc Domain that comprises:
  (a) one or more amino acid modifications that reduces the affinity of the variant Fc Domain for an FcγR; and/or
  (b) one or more amino acid modifications that enhances the serum half-life of the variant Fc Domain.

6. The B7-H3-ADC of claim 5, wherein said modifications that reduce the affinity of the variant Fc Domain for an FcγR comprise the substitution of L234A; L235A; or L234A and L235A, wherein the numbering is that of the EU index as in Kabat.

7. The B7-H3-ADC of claim 5, wherein said modifications that enhance the serum half-life of the variant Fc Domain comprise the substitution of M252Y; M252Y and S254T; M252Y and T256E; M252Y, S254T and T256E; or K288D and H435K, wherein the numbering is that of the EU index as in Kabat.

8. The B7-H3-ADC of claim 1, wherein at least one of said LM moieties is a Linker Molecule.

9. The B7-H3-ADC of claim 8, wherein said LM Linker Molecule comprises a cleavable linker.

10. The B7-H3-ADC of claim 9, wherein said cleavable linker is a peptidic linker.

11. The B7-H3-ADC of claim 10, wherein said peptidic linker is a valine-citrulline dipeptide linker.

12. The B7-H3-ADC of claim 9, wherein said LM Linker Molecule further comprises a self-eliminating spacer between the cleavable linker and D.

13. The B7-H3-ADC of claim 12, wherein said self-eliminating spacer comprises a para-aminobenzyloxycarbonyl moiety.

14. The B7-H3-ADC of claim 9, wherein said Linker Molecule further comprises a maleimide linker moiety between the cleavable linker and Ab.

15. The B7-H3-ADC of claim 7, wherein LM comprises the formula:

$$[V\text{---}(W)_k\text{---}(X)_l\text{-}A]$$

and said conjugate comprises the formula:

$$Ab\text{-}[V\text{---}(W)_k\text{---}(X)_l\text{-}A]\text{-}D$$

wherein:
V is a cleavable linker,
$W)_k\text{---}(X)_l\text{-}A$ is an elongated, self-eliminating spacer system, that self-eliminates via a 1, (4+2n)-elimination,
W and X are each a 1, (4+2n) electronic cascade spacer, being the same or different,
A is either a spacer group of formula $(Y)_m$, wherein Y is a Y is a 1, (4+2n) electronic cascade spacer, or a group of formula U, being a cyclisation elimination spacer,
k, l and m are independently an integer of 0 (included) to 5 (included),
n is an integer of 0 (included) to 10 (included),
with the provisos that:
  when A is $(Y)_m$: then k+l+m≥1, and
  if k+l+m=1, then n>1;
  when A is U: then k+l≥1;
W, X, and Y are independently selected from compounds having the formula:

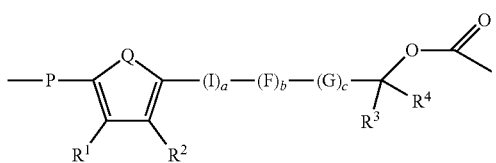

or the formula:

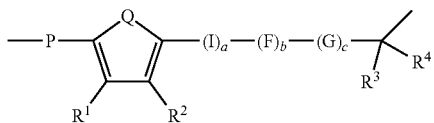

wherein: Q is —R$^5$C═CR$^6$—, S, O, NR$^5$, —R$^5$C═N—, or —N═CR$^5$—

P is NR$^7$, O or S a, b, and c are independently an integer of 0 (included) to 5 (included);

I, F and G are independently selected from compounds having the formula:

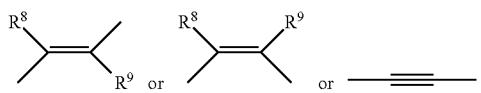

wherein R$^1$, R$^2$, R$^3$, R$^4$, R$^5$, R$^6$, R$^7$, R$^8$, and R$^9$ independently represent H, C$_{1-6}$ alkyl, C$_{3-20}$ heterocyclyl, C$_{5-20}$ aryl, C$_{1-6}$ alkoxy, hydroxy (OH), amino (NH$_2$), mono-substituted amino (NR$_x$H), di-substituted amino (NR$_x^1$R$_x^2$), nitro (NO$_2$), halogen, CF$_3$, CN, CONH$_2$, SO$_2$Me, CONHMe, cyclic C$_{1-5}$ alkylamino, imidazolyl, C$_{1-6}$ alkylpiperazinyl, morpholino, thiol (SH), thioether (SR$_x$), tetrazole, carboxy (COOH), carboxylate (COOR$_x$), sulphoxy (S(═O)$_2$OH), sulphonate (S(═O)$_2$OR$_x$), sulphonyl (S(═O)$_2$R$_x$), sulphixy (S(═O)OH), sulphinate (S(═O)OR$_x$), sulphinyl (S(═O)R$_x$), phosphonooxy (OP(═O)(OH)$_2$), and phosphate (OP(═O)(OR$_x$)$_2$), where R$_x$, R$_x^1$ and R$_x^2$ are independently selected from a C$_{1-6}$ alkyl group, a C$_{3-20}$ heterocyclyl group or a C$_{5-20}$ aryl group, two or more of the substituents R$^1$, R$^2$, R$^3$, R$^4$, R$^5$, R$^6$, R$^7$, R$^8$, or R$^9$ optionally being connected to one another to form one or more aliphatic or aromatic cyclic structures;

U is selected from compounds having the formula:

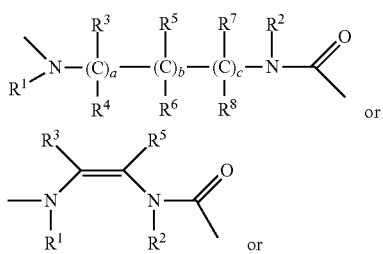

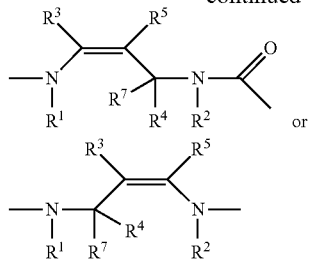

wherein:

a, b and c are independently selected to be an integer of 0 or 1;

provided that a+b+c=2 or 3;

R$^1$ and/or R$^2$ independently represent H, C1-6 alkyl, the alkyl being optionally substituted with one or more of the following groups: hydroxy (OH), ether (OR$_x$), amino (NH$_2$), mono-substituted amino (NR$_x$H), disubstituted amino (NR$_x^1$R$_x^2$), nitro (NO$_2$), halogen, CF$_3$, CN, CONH$_2$, SO$_2$Me, CONHMe, cyclic C$_{1-5}$ alkylamino, imidazolyl, C$_{1-6}$ alkylpiperazinyl, morpholino, thiol (SH), thioether (SR$_x$), tetrazole, carboxy (COOH), carboxylate (COOR$_x$), sulphoxy (S(═O)$_2$OH), sulphonate (S(═O)$_2$OR$_x$), sulphonyl (S(═O)$_2$R$_x$), sulphixy (S(═O)OH), sulphinate (S(═O)ORx), sulphinyl (S(═O)Rx), phosphonooxy (OP(═O)(OH)$_2$), and phosphate (OP(═O)(OR$_x$)$_2$), where R$_x$, R$_x^1$ and R$_x^2$ are selected from a C$_{1-6}$ alkyl group, a C$_{3-20}$ heterocyclyl group or a C$_{5-20}$ aryl group; and R$^3$, R$^4$, R$^5$, R$^6$, R$^7$ and R$^a$ independently represent H, C$_{1-6}$ alkyl, C$_{3-20}$ heterocyclyl, C$_{5-20}$ aryl, C$_{1-6}$ alkoxy, hydroxy (OH), amino (NH$_2$), mono-substituted amino (NR$_x$H), disubstituted amino (NR$_x^1$R$_x^2$), nitro (NO$_2$), halogen, CF$_3$, CN, CONH$_2$, SO$_2$Me, CONHMe, cyclic C$_{1-5}$ alkylamino, imidazolyl, C$_{1-6}$ alkylpiperazinyl, morpholino, thiol (SH), thioether (SR$_x$), tetrazole, carboxy (COOH), carboxylate (COOR$_x$), sulphoxy (S(═O)$_2$OH), sulphonate (S(═O)$_2$OR$_x$), sulphonyl (S(═O)$_2$R$_x$), sulphixy (S(═O)OH), sulphinate (S(═O)OR$_x$), sulphinyl (S(═O)R$_x$), phosphonooxy (OP(═O)(OH)$_2$), and phosphate (OP(═O)(OR$_x$)$_2$), where R$_x$, R$_x^1$ and R$_x^2$ are selected from a C$_{1-6}$ alkyl group, a C$_{3-20}$ heterocyclyl group or a C$_{5-20}$ aryl group, and two or more of the substituents R$^1$, R$^2$, R$^3$, R$^4$, R$^5$, R$^6$, R$^7$, or R$^8$ are optionally connected to one another to form one or more aliphatic or aromatic cyclic structures.

16. The B7-H3-ADC of claim 15, wherein said LM linker molecule comprises:
(1) p-aminobenzyloxycarbonyl-p-aminobenzyloxycarbonyl;
(2) p-aminobenzyloxycarbonyl-p-aminobenzyloxycarbonyl-p-aminobenzyloxycarbonyl;
(3) p-aminocinnamyloxycarbonyl;
(4) p-aminocinnamyloxycarbonyl-p-aminobenzyloxycarbonyl;
(5) p-amino-benzyloxycarbonyl-p-aminocinnamyloxycarbonyl;
(6) p-aminocinnamyloxycarbonyl-p-aminocinnamyloxycarbonyl;
(7) p-aminophenylpentadienyloxycarbonyl;
(8) p-aminophenylpentadienyloxycarbonyl-p-aminocinnamyloxycarbonyl;

(9) p-aminophenylpentadienyloxycarbonyl-p-aminobenzyloxycarbonyl;
(10) p-aminophenylpentadienyloxycarbonyl-p-aminophenylpentadienyloxycarbonyl;
(11) p-aminobenzyloxycarbonyl(methylamino)ethyl(methylamino) carbonyl;
(12) p-aminocinnamyloxycarbonyl(methylamino)ethyl(methylamino) carbonyl;
(13) p-aminobenzyloxycarbonyl-p-aminobenzyloxycarbonyl(methylamino) ethyl(methylamino)carbonyl;
(14) p-aminocinnamyloxycarbonyl-p-aminobenzyloxycarbonyl (methylamino)ethyl(methylamino)carbonyl;
(15) p-aminobenzyloxycarbonyl-p-aminocinnamyloxycarbonyl (methylamino)ethyl(methylamino)-carbonyl;
(16) p-aminocinnamyloxycarbonyl-p-aminocinnamyloxycarbonyl (methylamino)ethyl(methylamino)carbonyl;
(17) p-aminobenzyloxycarbonyl-p-aminobenzyl;
(18) p-aminobenzyloxycarbonyl-p-aminobenzyloxycarbonyl-p-aminobenzyl;
(19) p-aminocinnamyl;
(20) p-aminocinnamyloxycarbonyl-p-aminobenzyl;
(21) p-aminobenzyloxycarbonyl-p-aminocinnamyl;
(22) p-amino-cinnamyloxycarbonyl-p-aminocinnamyl;
(23) p-aminophenylpentadienyl;
(24) p-aminophenylpentadienyloxycarbonyl-p-aminocinnamyl;
(25) p-aminophenylpentadienyloxycarbonyl-p-aminobenzyl;
or
(26) p-aminophenylpentadienyloxycarbonyl-p-aminophenylpentadienyl.

17. The B7-H3-ADC of claim 8, wherein said LM Linker Molecule is conjugated to the side chain of an amino acid of a polypeptide chain of Ab and binds the Ab to a molecule of the cytotoxic drug moiety D.

18. The B7-H3-ADC of claim 1, wherein said cytotoxic drug moiety D comprises a cytotoxin, a radioisotope, an immunomodulator, a cytokine, a lymphokine, a chemokine, a growth factor, a tumor necrosis factor, a hormone, a hormone antagonist, an enzyme, an oligonucleotide, a DNA, an RNA, an siRNA, an RNAi, a microRNA, a photoactive therapeutic agent, an anti-angiogenic agent, a pro-apoptotic agent, a peptide, a lipid, a carbohydrate, a chelating agent, or combinations thereof.

19. The B7-H3-ADC of claim 18, wherein said cytotoxic drug moiety D comprises a cytotoxin and is selected from the group consisting of a tubulysin, an auristatin, a maytansinoid, a calicheamicin, a pyrrolobenzodiazepine, a *Pseudomonas* exotoxin, a Diptheria toxin, a botulinum toxin A, a botulinum toxin B, a botulinum toxin C, a botulinum toxin D, a botulinum toxin E, a botulinum toxin F, a ricin, an abrin, a saporin, and a cytotoxic fragment thereof.

20. The B7-H3-ADC of claim 19, wherein said cytotoxic drug moiety D comprises an auristatin cytotoxin and is selected from the group consisting of MMAE (N-methyl-valine-valine-dolaisoleuine-dolaproine-norephedrine) and MMAF (N-methylvaline-valine-dolaisoleuine-dolaproine-phenylalanine).

21. The B7-H3-ADC of claim 19, wherein said cytotoxic drug moiety D comprises a maytansinoid cytotoxin and is selected from the group consisting of Mytansine, DM1 and DM4.

22. The B7-H3-ADC of claim 8, wherein said LM Linker Molecule is covalently linked to the Ab via reduced interchain disulfides.

23. The B7-H3-ADC of claim 1, wherein said antibody or said B7-H3 binding fragment thereof comprises a human IgG Constant Domain Kappa Domain.

24. The B7-H3-ADC of claim 23, wherein said human IgG Constant Domain Kappa Domain comprises the amino acid sequence of SEQ ID NO:1.

25. The B7-H3-ADC of claim 24, wherein:
Ab is said antibody and said antibody comprises:
  (i) a light chain comprising the Variable Light Chain (VL) domain comprising the amino acid sequence of SEQ ID NO:20 and a CL Kappa Domain of SEQ ID NO:1; and
  (ii) a heavy chain comprising the Variable Heavy Chain (VH) domain comprising the amino acid sequence of SEQ ID NO:21, a $CH_1$ Domain of SEQ ID NO:3, a Hinge Domain of SEQ ID NO:7 and a Fc Domain comprising a $CH_2$—$CH_3$ Domain of SEQ ID NO:12; and
said LM comprises a Linker Molecule comprising a maleimide linker moiety, a valine-citrulline dipeptide linker, and a para-aminobenzyloxycarbonyl moiety.

26. A pharmaceutical composition comprising an effective amount of the B7-H3-ADC of claim 1 and a pharmaceutically acceptable carrier, excipient or diluent.

27. A pharmaceutical composition comprising an effective amount of the B7-H3-ADC of claim 25 and a pharmaceutically acceptable carrier, excipient or diluent.

* * * * *

UNITED STATES PATENT AND TRADEMARK OFFICE
CERTIFICATE OF CORRECTION

| | |
|---|---|
| PATENT NO. | : 11,591,400 B2 |
| APPLICATION NO. | : 17/124972 |
| DATED | : February 28, 2023 |
| INVENTOR(S) | : Deryk Loo et al. |

It is certified that error appears in the above-identified patent and that said Letters Patent is hereby corrected as shown below:

In the Claims

Column 226, Line 34 (Claim 15):
"$R^a$" should be replaced with --$R^8$--.

Column 228, Lines 34-36 (Claim 25):
"a $CH_1$ Domain of SEQ ID NO:3, a Hinge Domain of SEQ ID NO:7 and a Fc Domain comprising a $CH_2$—$CH_3$ Domain" should be replaced with --a CH1 Domain of SEQ ID NO:3, a Hinge Domain of SEQ ID NO:7 and a Fc Domain comprising a CH2—CH3 Domain--.

Signed and Sealed this
Sixth Day of June, 2023

Katherine Kelly Vidal
*Director of the United States Patent and Trademark Office*